(12) United States Patent
Lehtonen et al.

(10) Patent No.: US 10,578,634 B2
(45) Date of Patent: Mar. 3, 2020

(54) AUTOMATED SOLUTION DISPENSER

(71) Applicant: Labminds Ltd, Oxford (GB)

(72) Inventors: Ville Lehtonen, Somerville, MA (US); Michal Wozny, Medford, MA (US); Jochen Klingelhoefer, Somerville, MA (US)

(73) Assignee: Labminds Ltd, Oxford (GB)

( * ) Notice: Subject to any disclaimer, the term of this patent is extended or adjusted under 35 U.S.C. 154(b) by 4 days.

(21) Appl. No.: 15/667,961

(22) Filed: Aug. 3, 2017

(65) Prior Publication Data

US 2018/0080952 A1  Mar. 22, 2018

Related U.S. Application Data

(63) Continuation of application No. PCT/IB2016/000372, filed on Feb. 4, 2016.
(Continued)

(51) Int. Cl.
*G01N 35/10* (2006.01)
*B01F 13/08* (2006.01)
(Continued)

(52) U.S. Cl.
CPC ....... *G01N 35/1016* (2013.01); *B01F 3/1221* (2013.01); *B01F 13/0818* (2013.01); *B01F 13/1055* (2013.01); *B01F 15/0022* (2013.01); *B01F 15/00025* (2013.01); *B01F 15/00155* (2013.01); *B01F 15/00175* (2013.01);
(Continued)

(58) Field of Classification Search
CPC ......... G01N 35/1016; G01N 35/00722; G01N 35/00732; G01N 2035/009; G01N 2035/00534; G01N 2035/0091; G01N 2035/00891; B65B 3/26; B65B 3/04; B01F 15/00025; B01F 3/1221; B01F 15/00318; B01F 15/00155; B01F 15/065;
(Continued)

(56) References Cited

U.S. PATENT DOCUMENTS 2,517,456 A   8/1950   Wherrett
3,058,622 A   10/1962  Ballestra
(Continued)

FOREIGN PATENT DOCUMENTS

CN   1050831 A   4/1991
CN   2423282 Y   3/2001
(Continued)

OTHER PUBLICATIONS

Office Action dated Oct. 4, 2017 for U.S. Appl. No. 14/415,567.
(Continued)

*Primary Examiner* — Matthew W Jellett
(74) *Attorney, Agent, or Firm* — Wilson, Sonsini, Goodrich & Rosati

(57) ABSTRACT

Provided herein are methods and systems of the invention that include the use of an automated solution dispenser to form a solution according to at least one target characteristic. A controller may be operatively connected to the automated solution dispenser, wherein the controller is programmed to direct mixing of one or more solids and one or more liquids to produce the solution. At least a portion of the solution can be dispensed into one or more containers.

21 Claims, 39 Drawing Sheets

Related U.S. Application Data

(60) Provisional application No. 62/113,249, filed on Feb. 6, 2015.

(51) Int. Cl.

| | | |
|---|---|---|
| G05D 11/13 | (2006.01) | |
| B01F 13/10 | (2006.01) | |
| B01F 15/00 | (2006.01) | |
| B01F 15/02 | (2006.01) | |
| B01F 15/06 | (2006.01) | |
| G05D 21/02 | (2006.01) | |
| B01F 3/12 | (2006.01) | |
| B65B 3/04 | (2006.01) | |
| B65B 3/26 | (2006.01) | |
| G01N 35/00 | (2006.01) | |

(52) U.S. Cl.
CPC .... *B01F 15/00318* (2013.01); *B01F 15/0292* (2013.01); *B01F 15/065* (2013.01); *B65B 3/04* (2013.01); *B65B 3/26* (2013.01); *G01N 35/00722* (2013.01); *G05D 11/135* (2013.01); *G05D 21/02* (2013.01); *B01F 2215/0037* (2013.01); *G01N 2035/009* (2013.01); *G01N 2035/0091* (2013.01); *G01N 2035/00534* (2013.01)

(58) Field of Classification Search
CPC .............. B01F 15/0292; B01F 15/0022; B01F 15/00175; B01F 13/1055; B01F 13/0818
See application file for complete search history.

(56) References Cited

U.S. PATENT DOCUMENTS

| | | | |
|---|---|---|---|
| 3,744,768 A | 7/1973 | Kauffman et al. | |
| 3,899,915 A | 8/1975 | Williams, Jr. et al. | |
| 3,936,271 A | 2/1976 | Statter | |
| 4,091,834 A | 5/1978 | Frigato | |
| 4,443,109 A | 4/1984 | Watts | |
| 4,525,071 A | 6/1985 | Horowitz et al. | |
| 4,627,225 A | 12/1986 | Faller et al. | |
| 4,830,508 A | 5/1989 | Higuchi et al. | |
| 4,859,072 A | 8/1989 | Fey et al. | |
| 4,964,185 A | 10/1990 | Lehn | |
| 5,052,486 A | 10/1991 | Wilson | |
| 5,129,418 A | 7/1992 | Shimomura et al. | |
| 5,366,896 A | 11/1994 | Margrey et al. | |
| 5,626,422 A | 5/1997 | Adamo et al. | |
| 5,879,079 A | 3/1999 | Hohmann et al. | |
| 5,882,589 A | 3/1999 | Mariotti | |
| 6,572,255 B2 | 6/2003 | Husher | |
| 6,743,201 B1 | 6/2004 | Doenig et al. | |
| 6,793,387 B1 | 9/2004 | Neas et al. | |
| 6,985,983 B2 | 1/2006 | Pellegrino et al. | |
| 7,134,573 B2 | 11/2006 | Post et al. | |
| 7,226,203 B2 | 6/2007 | Rondeau et al. | |
| 7,344,299 B2 | 3/2008 | Sprinkle | |
| 7,347,613 B2 | 3/2008 | Ditzig et al. | |
| 7,451,941 B2 | 11/2008 | Jackson | |
| 7,510,730 B2 | 3/2009 | Lyons et al. | |
| 7,534,970 B2 | 5/2009 | Tump | |
| 7,810,987 B2 | 10/2010 | Hildreth | |
| 7,860,727 B2 | 12/2010 | Showalter et al. | |
| 7,871,575 B2 | 1/2011 | Baeuerle et al. | |
| 7,972,734 B2 | 7/2011 | Kuroda et al. | |
| 7,991,560 B2 | 8/2011 | Kaushikkar et al. | |
| 8,008,082 B2 | 8/2011 | Howland et al. | |
| 8,041,437 B2 | 10/2011 | Stellari et al. | |
| 8,177,411 B2 | 5/2012 | Borgstadt | |
| 8,668,869 B2 * | 3/2014 | Hirayama | G01N 35/00722 422/105 |
| 8,808,623 B2 * | 8/2014 | Linssen | G16H 15/00 422/67 |
| 9,138,693 B2 | 9/2015 | Aouad | |
| 2001/0006485 A1 | 7/2001 | Kubiak et al. | |
| 2002/0154567 A1 | 10/2002 | Husher | |
| 2003/0060925 A1 | 3/2003 | Bartholomew et al. | |
| 2003/0126195 A1 | 7/2003 | Reynolds et al. | |
| 2003/0198125 A1 | 10/2003 | Linsen et al. | |
| 2003/0227819 A1 | 12/2003 | Villwock et al. | |
| 2004/0151062 A1 * | 8/2004 | Yao | B01F 5/102 366/137 |
| 2004/0157336 A1 | 8/2004 | Petroff et al. | |
| 2005/0087545 A1 | 4/2005 | Petrus et al. | |
| 2005/0169099 A1 | 8/2005 | Sprinkle | |
| 2007/0025179 A1 | 2/2007 | Hildreth | |
| 2007/0078631 A1 * | 4/2007 | Ariyoshi | G06F 19/00 702/189 |
| 2007/0084520 A1 | 4/2007 | Driessen et al. | |
| 2007/0269894 A1 | 11/2007 | Howland et al. | |
| 2008/0190460 A1 | 8/2008 | Berklund et al. | |
| 2008/0279038 A1 | 11/2008 | Bellafiore et al. | |
| 2009/0022007 A1 | 1/2009 | Massarotto | |
| 2009/0092001 A1 | 4/2009 | Hildreth et al. | |
| 2009/0246085 A1 | 10/2009 | Watson et al. | |
| 2009/0268548 A1 | 10/2009 | Hartmann et al. | |
| 2010/0185322 A1 | 7/2010 | Bylsma et al. | |
| 2011/0040593 A1 | 2/2011 | Depreter | |
| 2011/0076159 A1 | 3/2011 | Fulkerson et al. | |
| 2011/0284090 A1 | 11/2011 | Popa et al. | |
| 2012/0041045 A1 | 2/2012 | Harvey et al. | |
| 2012/0147924 A1 | 6/2012 | Hall | |
| 2012/0241045 A1 | 9/2012 | Aouad | |
| 2014/0016432 A1 | 1/2014 | Lehtonen et al. | |
| 2014/0165846 A1 | 6/2014 | Ochoa et al. | |
| 2015/0314246 A1 | 11/2015 | Lehtonen et al. | |

FOREIGN PATENT DOCUMENTS

| | | |
|---|---|---|
| CN | 1410759 A | 4/2003 |
| CN | 1451470 A | 10/2003 |
| CN | 1571921 A | 1/2005 |
| CN | 101019009 A | 8/2007 |
| CN | 200995183 Y | 12/2007 |
| CN | 101152620 A | 4/2008 |
| CN | 101153815 A | 4/2008 |
| CN | 201373768 Y | 12/2009 |
| CN | 201493057 U | 6/2010 |
| CN | 201506693 U | 6/2010 |
| CN | 202237860 U | 5/2012 |
| CN | 202246198 U | 5/2012 |
| DE | 102004053921 A1 | 5/2006 |
| EP | 0289048 A2 | 11/1988 |
| EP | 0958118 A1 | 11/1999 |
| EP | 1559652 A1 | 8/2005 |
| EP | 2665997 A1 | 11/2013 |
| JP | S6388029 A | 4/1988 |
| JP | S63273014 A | 11/1988 |
| JP | S63274441 A | 11/1988 |
| JP | 2004279414 A | 10/2004 |
| JP | 2005344182 A | 12/2005 |
| JP | 2006102667 A | 4/2006 |
| JP | 2008521555 A | 6/2008 |
| JP | 2008537882 A | 10/2008 |
| WO | WO-9417370 A2 | 8/1994 |
| WO | WO-9617543 A1 | 6/1996 |
| WO | WO-03086604 A1 | 10/2003 |
| WO | WO-2010015925 A2 | 2/2010 |
| WO | WO-0244994 A9 | 9/2010 |
| WO | WO-2011162666 A1 | 12/2011 |
| WO | WO-2012098403 A1 | 7/2012 |
| WO | WO-2014015186 A1 | 1/2014 |

OTHER PUBLICATIONS

European search report and opinion dated Feb. 12, 2016 for EP Application No. 13820519.

Hicks, et al. Modification of an automated liquid-handling system for reagent-jet, nanoliter-level dispensing. Biotechniques. Apr. 2001;30(4):878-85.

(56) References Cited

OTHER PUBLICATIONS

International search report and written opinion dated Apr. 19, 2012 for PCT/GB2012/050114.
International search report and written opinion dated Jun. 3, 2016 for PCT/US2016/016633.
International search report and written opinion dated Jul. 1, 2016 for PCT/IB2016/000372.
International search report and written opinion dated Oct. 21, 2013 for PCT/US2013/051157.
International search report with written opinion dated Jun. 3, 2016 for PCT/IB2016/000372.
Office Action dated Feb. 3, 2017 for U.S. Appl. No. 13/980,855.
Office action dated May 5, 2016 for U.S. Appl. No. 13/980,855.
Office action dated Aug. 5, 2014 for CN Application No. 201280014018.6.
UK search report dated May 31, 2011 for GB Application No. 1101075.8.
Office action dated Jun. 7, 2018 for U.S. Appl. No. 14/415,567.
Office action dated Sep. 5, 2018 for U.S. Appl. No. 13/980,855.
U.S. Appl. No. 13/980,855 Office Action dated Dec. 20, 2017.
U.S. Appl. No. 14/415,567 Non-Final Office Action dated Jan. 8, 2019.

\* cited by examiner

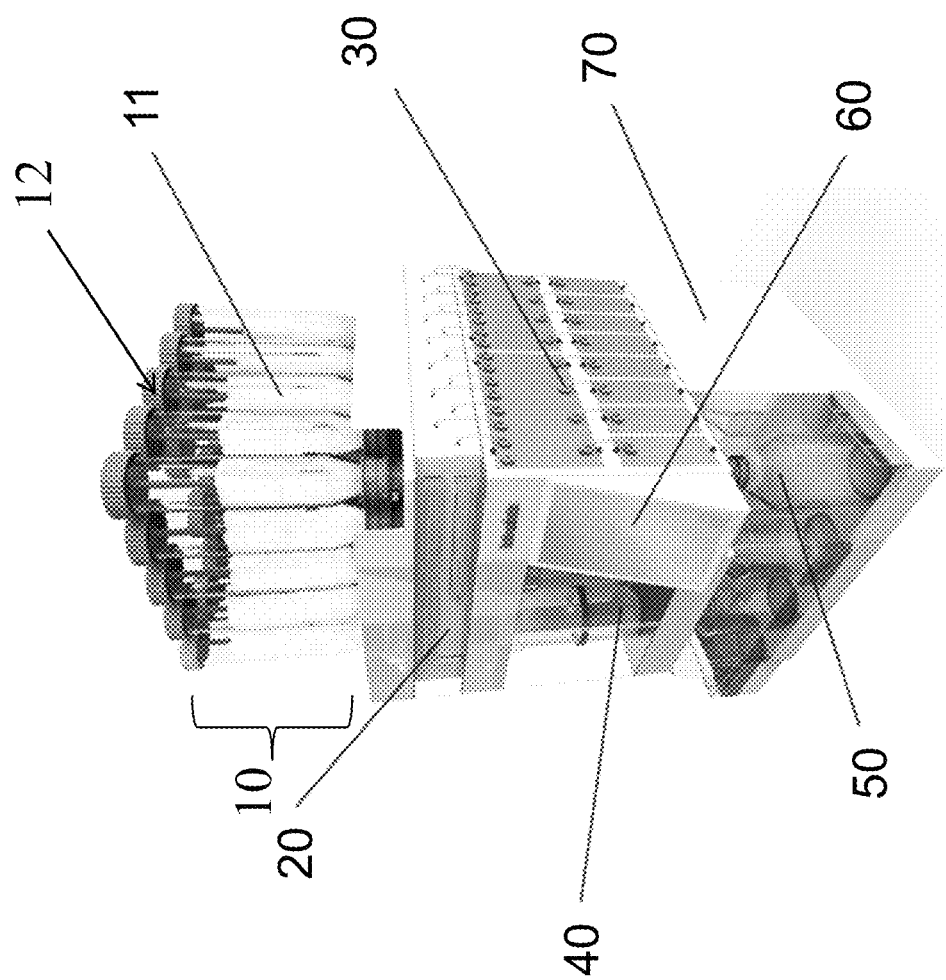

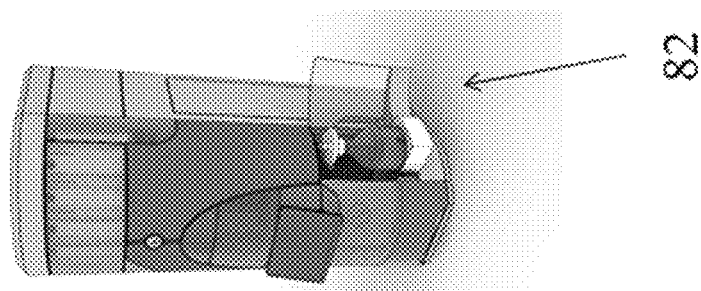
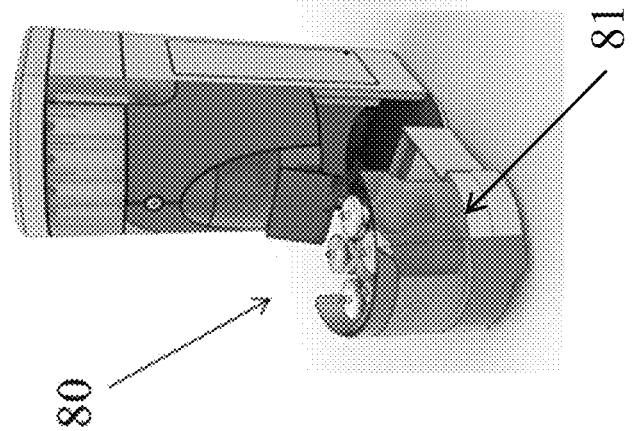
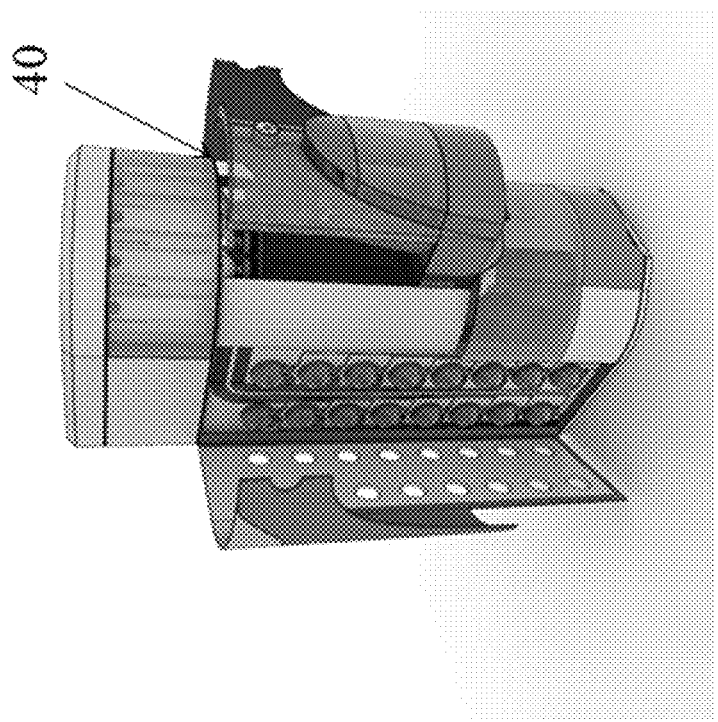
Fig. 1D
Fig. 1E

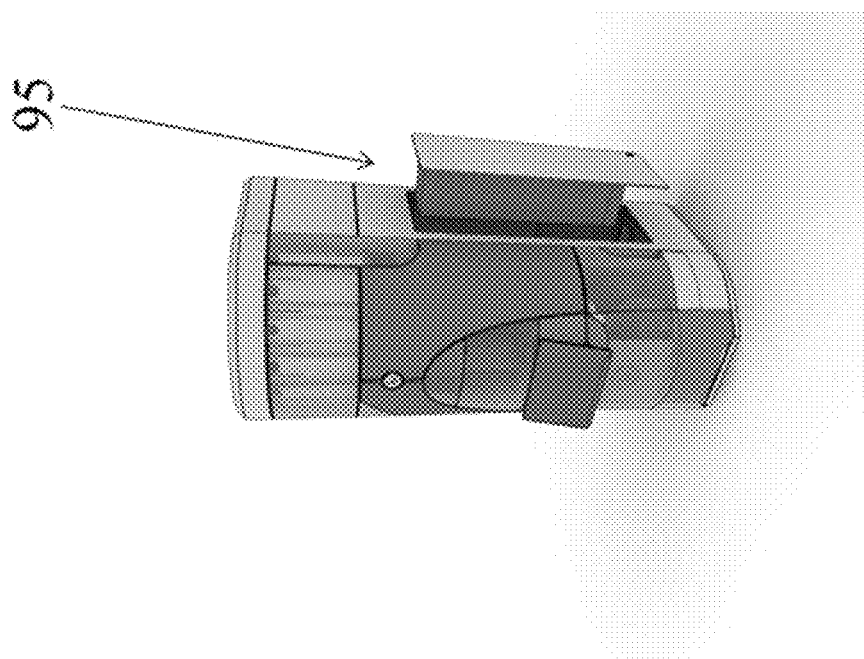
FIG. 1G
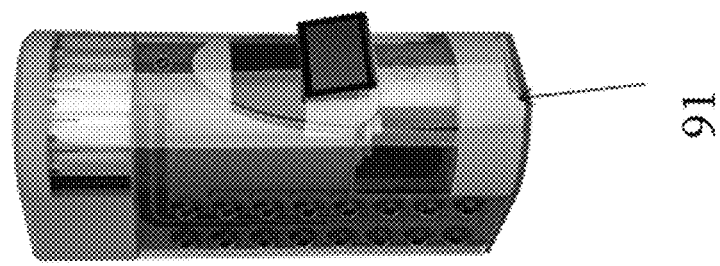
FIG. 1F
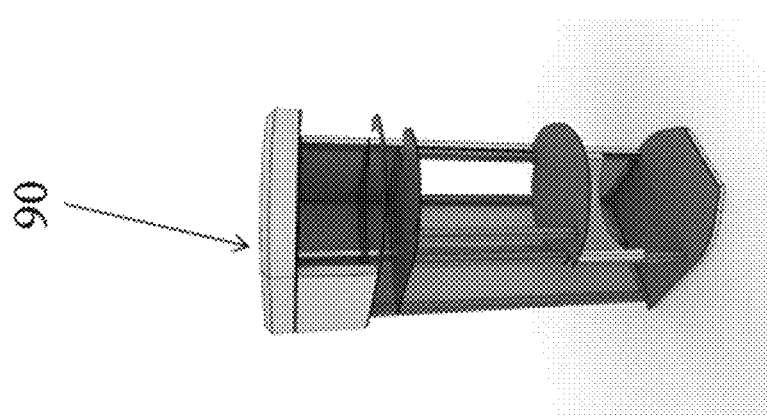

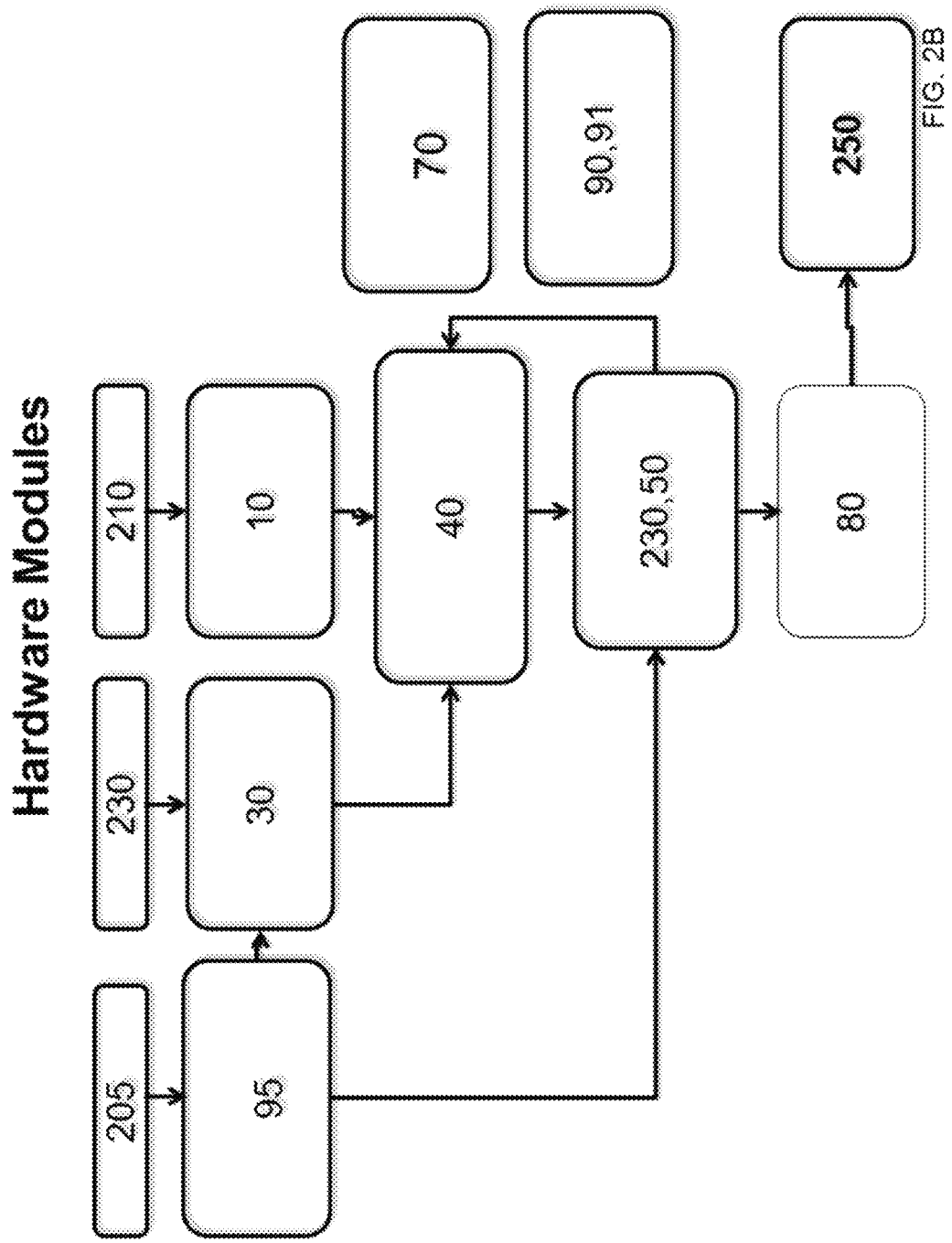

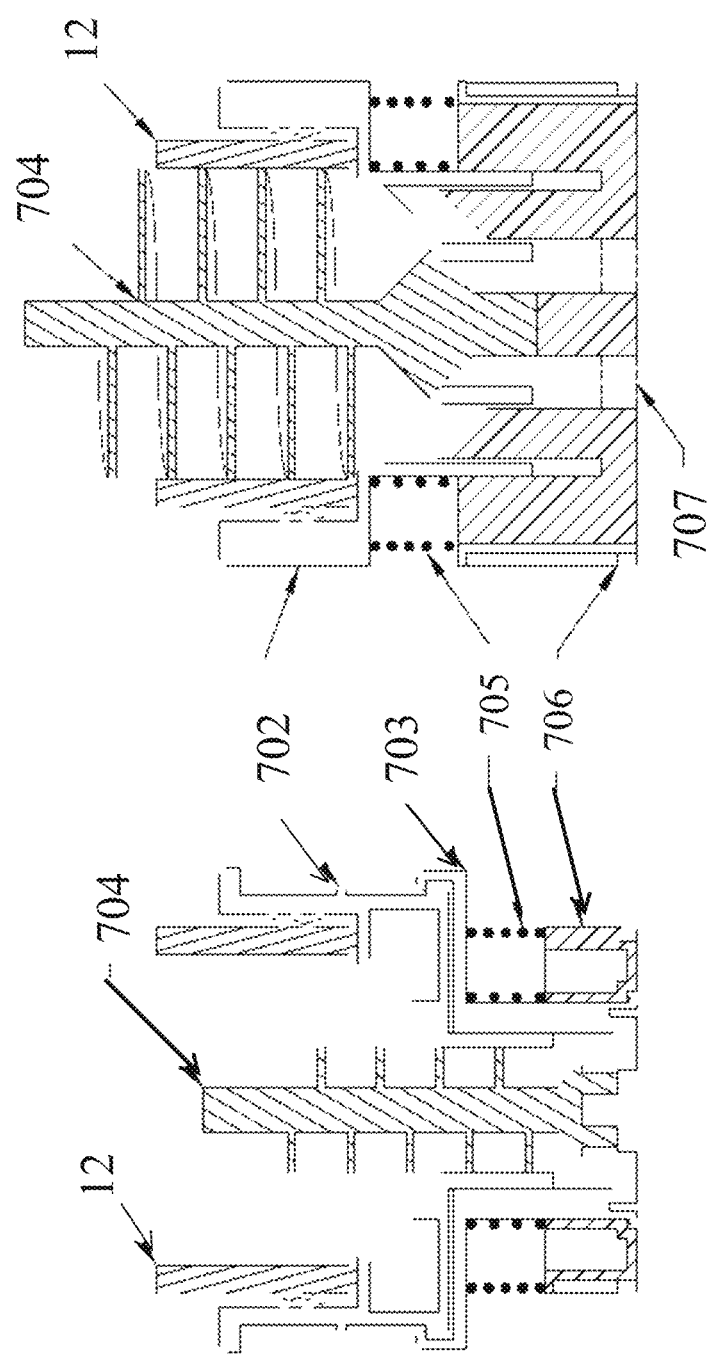

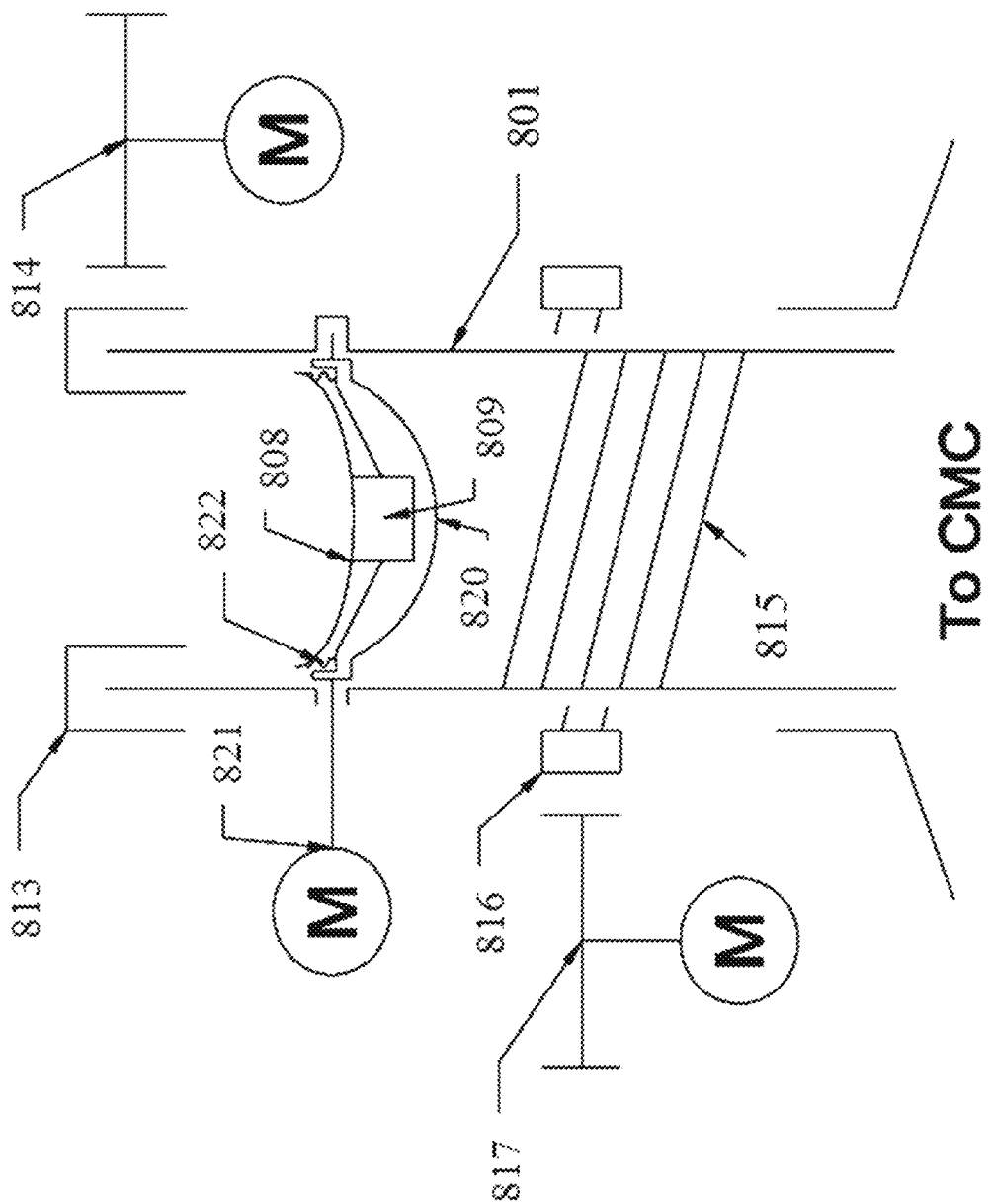

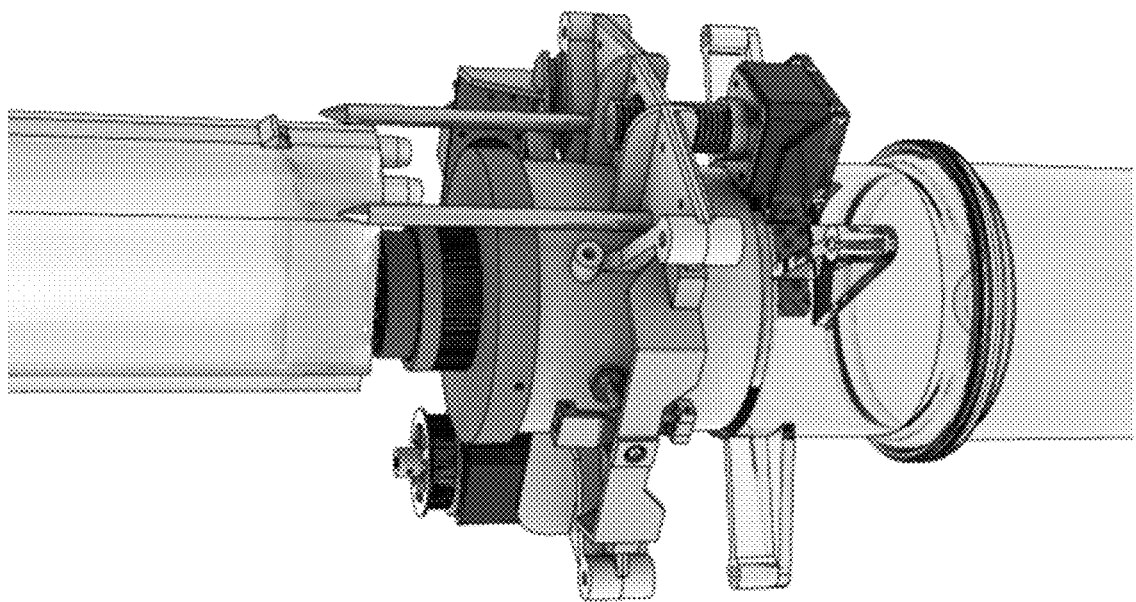

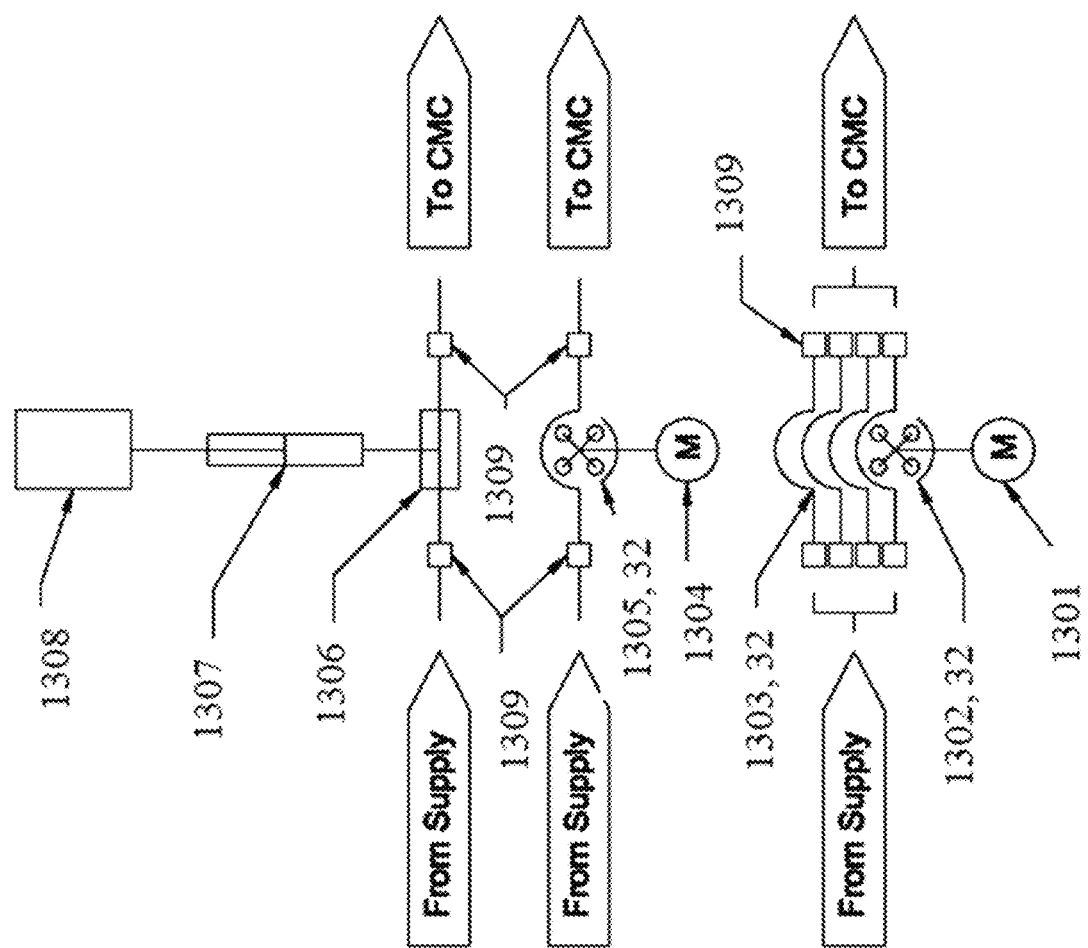

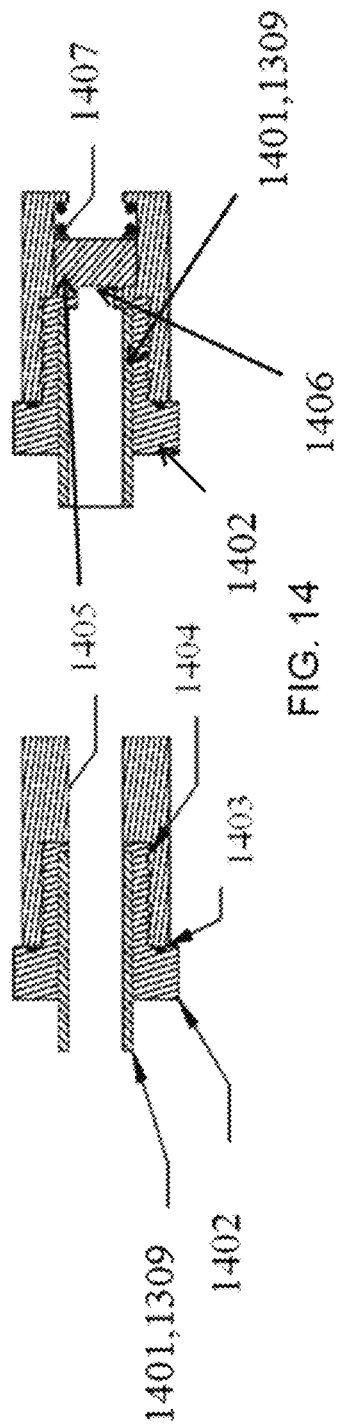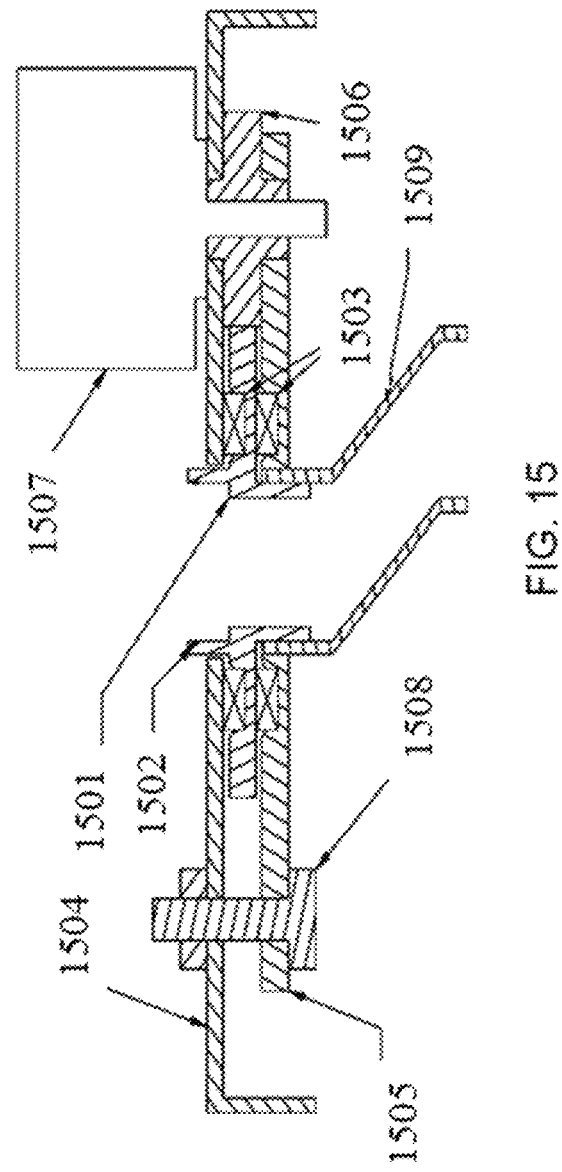

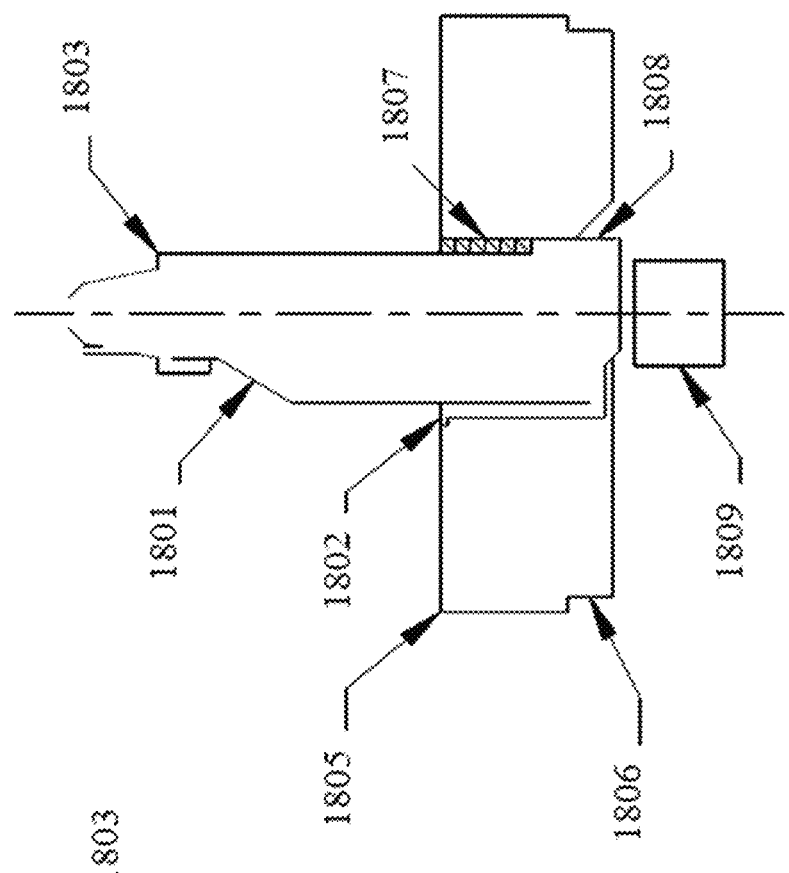
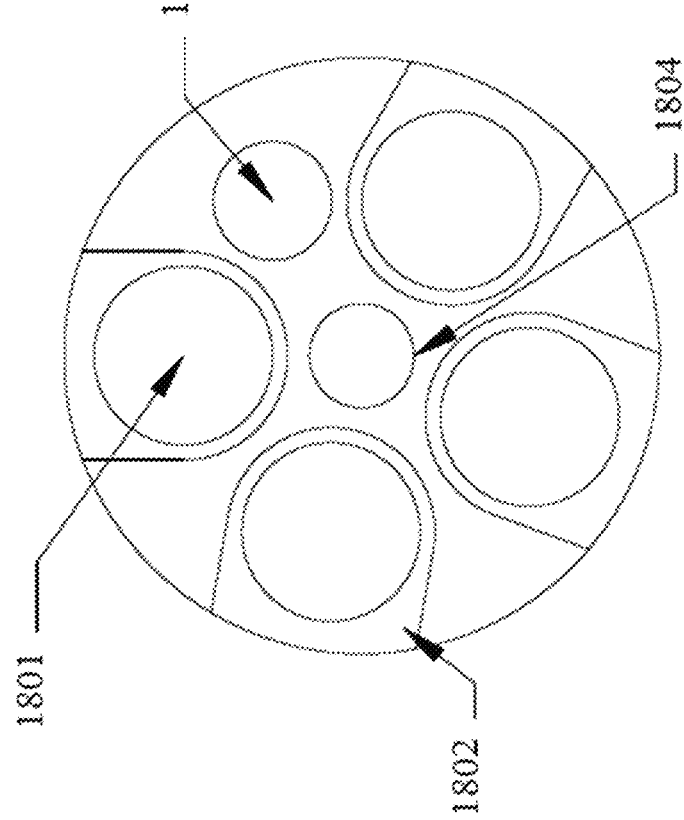
FIG. 18B
FIG. 18A

AUTOMATED SOLUTION DISPENSER

CROSS-REFERENCE

This application is a continuation of PCT/IB2016/000372, filed Feb. 4, 2016, which claims priority to U.S. provisional application 62/113,249, filed on Feb. 6, 2015, each of which are entirely incorporated herein by reference.

BACKGROUND

Solution preparation is one of the most common and time consuming activities in a laboratory environment in the industry and academia. A number of the tasks that can be involved in solution preparation, including measuring, dispensing, mixing, adjusting the pH, adjusting the temperature, degassing, filtering, bottling, labeling, and cleaning before or after solution preparation is mostly done manually requiring a lot of time from laboratory workers. Consistent handling of a wide range of solids, including fine powders, clumpy powders and crystalline solids in an accurate manner is currently often achieved manually. Automation may reduce the time spent by the individual workers for these routine tasks and allow them the use of their time in other tasks. Automation may also enable for reproducibility and consistency within and among laboratories. Automation may also allow for consistent and accurate monitoring of key parameters of the solution, such as temperature and pH, increasing the ease and speed of preparing the solutions and optimizing solution preparation parameters. Further, automation may allow for consistent log keeping for the stock and consumption of solution components, which may ease procurement of the solution components in a timely and efficient manner. In addition, through the use of automation, new sales and restocking systems may be developed. In addition to this, the system will over time yield data which will allow optimization of both solutions and the amounts prepared, creating considerable savings of money to laboratories and savings in chemical use for a green benefit.

SUMMARY

As recognized herein, a solution dispenser that can accurately dose, mix, pH, heat, cool, degas, filter, and bottle solutions with minimal human intervention may be beneficial. Further, an automated solution dispenser that can handle solids of various physical properties, such as fine powder, clumpy powder, and crystalline solids, accurately and consistently, may be useful in various contexts. An automated log keeping for solution preparation for optimizing solution preparation, procurement and stocking of solution components in a semi-automated or fully automated manner may be advantageous.

An aspect of the present disclosure provides a system for preparing a solution. The system may comprise (a) a mixing chamber; (b) an automated solution dispenser that directs at least one solid selected from a plurality of solids and at least one liquid selected from a plurality of liquids in the mixing chamber to form the solution; (c) one or more containers having an internal volume that is sufficient to accommodate at least a portion of the solution; (d) a bottle handling sub-system, wherein the bottle handling sub-system is configured to manipulate the one or more containers; and (e) a controller that is operably coupled to the automated solution dispenser and the bottle handling sub-system. In some embodiments, the controller may be programmed to (i) direct mixing of the at least one solid and the at least one liquid in the mixing chamber to form the solution having at least one target characteristic, (ii) direct the bottle handling sub-system to manipulate at least a subset of the one or more containers to a dispensing position, and (iii) dispense at least a portion of the solution from the mixing chamber into the one or more containers when the one or more containers are at the dispensing position. In some embodiments, the at least one target characteristic may be selected from the group consisting of temperature, pH, chemical composition, weight, conductivity, turbidity, density, capacitance, volume, and viscosity.

In some embodiments, the at least one target characteristic may be at least three target characteristics. In some embodiments, the controller may be operably coupled to a user interface that is programmed to receive an input from a user. In some embodiments, the input may comprise a solution order corresponding to the at least one target characteristic. In some embodiments, the solution may be dispensed into the one or more containers according to the input.

In some embodiments, the system may further comprise a sensor operably coupled to the controller. In some embodiments, the controller may be programmed to receive one or more inputs from the sensor and compares the one or more inputs to a safety value associated with a safety regulation. In some embodiments, the controller may receive the safety value, the safety regulation, or a combination thereof from a user via a user interface operably coupled to the controller.

In some embodiments, the controller may be programmed to present a user with an alarm when the one or more inputs (i) exceeds the safety value, (ii) is within about 20% of the safety value, (iii) violates the safety regulation, or (iv) or a combination thereof. In some embodiments, the controller may be programmed to present the user with the alarm when the one or more inputs is within about 10% of the safety value. In some embodiments, the alarm may be a visual alert, an audible alert, a tactile alert, or any combination thereof. In some embodiments, the controller may discontinue preparing the solution when the one or more inputs (i) exceeds the safety value, (ii) is within about 20% of the safety value, (iii) violates the safety regulation, or (iv) or a combination thereof.

In some embodiments, the one or more inputs may be a measurement of the at least one target characteristic. In some embodiments, the one or more inputs may be a solution volume. In some embodiments, during use, the sensor may detect the internal volume of the one or more containers and the controller may direct the automated solution dispenser to dispense the solution into the one or more containers not to exceed 100% of the detected internal volume.

In some embodiments, the sensor may be a weight sensor, a pressure sensor, an optical sensor, an ultrasonic sensor, an infrared sensor, a barcode sensor, an apriltag sensor, a material composition sensor, or any combination thereof. In some embodiments, the sensor may detect an emission of light, a reflection of light, an absorption of light, a sound emission, or any combination thereof to determine the internal volume of the one or more containers.

In some embodiments, the sensor may identify a characteristic of the one or more containers independent of an external container shape of the one or more containers. In some embodiments, the characteristic may be the internal volume of the one or more containers. In some embodiments, the characteristic may be an amount of liquid in the one or more containers. In some embodiments, the characteristic may be a barcode, an apriltag, a label, or any combination thereof associated with the one or more containers. In some embodiments, the characteristic may be a material composition of the one or more containers.

In some embodiments, the material composition may comprise a glass, a polymer, a metal, a metal alloy, a metal oxide, a ceramic, a stone, or any combination thereof. In some embodiments, the polymer may comprise a polyethylene, a polypropylene, a polystyrene, a polytetrafluoroethylene, a polychlorotrifluoroethylene, a nylon, a bakelite, a polyvinyl chloride, a rubber, or any combination thereof. In some embodiments, the polymer may comprise KEVLAR®, TWARON®, MYLAR®, NEOPRENE®, NOMEX®, ORLON®, RILSAN®, TECHNORA®, ULTEM™, VECTRAN®, VITON®, ZYLON®, TEFLON™ or any combination thereof. In some embodiments, the polyethylene may comprise a low density polyethylene, a high density polyethylene, or a combination thereof. In some embodiments, the polyethylene may comprise a polyethylene terephthalate. In some embodiments, the metal alloy may comprise stainless steel. In some embodiments, the stainless steel may have a crystal structure selected from the group consisting of austenitic, superaustenitic, ferritic, martensitic, duplex, precipitation-hardening martensitic stainless, or any combination thereof.

In some embodiments, the external container shape may be a three dimensional shape. In some embodiments, the external container shape may have at least one curved surface. In some embodiments, the external container shape may have at least one flat surface. In some embodiments, the external container shape may be a curved shape. In some embodiments, the external container shape may be a platonic solid. In some embodiments, the external container shape may be square, rectangular, round, oblong, conical, cylindrical, pyramidal, or amorphous.

In some embodiments, the solution may be dispensed into a first container until the sensor detects that the dispensed solution volume is within about 10% of the internal volume of the first container, after which the solution may be then dispensed into a second container. In some embodiments, the controller may be programmed to receive one or more inputs from the sensor, wherein the one or more inputs may comprise (a) an amount of dispensed solution, (b) an amount of solution remaining to be dispensed, (c) a portion of the internal volume of the container that is filled with the dispensed solution, (d) a portion of the internal volume of the container that is unfilled, or (e) any combination thereof, and wherein the solution may be dispensed into the one or more containers according to the one or more inputs.

In some embodiments, the sensor may be positioned within the internal volume of the one or more containers. In some embodiments, the sensor may be positioned adjacent an opening of the one or more containers. In some embodiments, the sensor may be two sensors, three sensors, or four sensors.

In some embodiments, the controller automatically may calibrate the sensor. In some embodiments, an automatic sensor calibration by the controller may occur (i) at one or more times specified in a user input, (ii) when the sensor senses its own degradation, or (iii) a combination thereof. In some embodiments, the sensor (i) may sense its own degradation, (ii) may restore its sensor activity, or a combination thereof. In some embodiments, a sensor degradation may be detected when the sensor fails to provide a measurement or when the sensor provides a measurement outside a predetermined range.

In some embodiments, the sensor may be a waste sensor. In some embodiments, (i) the waste sensor may detect one or more characteristics of a liquid, a gas, a solution, or any combination thereof, (ii) the controller may compare the one or more characteristics to at least one regulation to provide a comparison, and (iii) the controller may direct the liquid, the gas, the solution, or any combination thereof to be drained or vented to a public draining or venting system, based on the comparison. In some embodiments, the at least one regulation may be a state regulation, a municipal regulation, a federal regulation, or any combination thereof.

In some embodiments, the automated solution dispenser may direct the liquid, the gas, the solution, or any combination thereof to (i) a hazardous waste container or a sewage waste container for collection, or to (ii) a public draining or venting system based on instructions received from the controller. In some embodiments, the hazardous waste container may comprise a classification. In some embodiments, the classification may be non-specific source waste (F list), source-specific waste (K list), discarded commercial chemical product (P list or U list), or any combination thereof. In some embodiments, the controller may direct the automated solution dispenser to neutralize the liquid, the gas, the solution, or combination thereof, based on an input from the waste sensor. In some embodiments, the liquid may be a cleaning fluid. In some embodiments, the automatic solution dispenser may dispense a buffer solution to neutralize the liquid, the gas, the solution, or combination thereof. In some embodiments, the buffer solution may be an acidic solution or a basic solution.

In some embodiments, during use, the sensor may detect an amount of a first solid, an amount of a first liquid, or a combination thereof that is dispensed into the mixing chamber and the controller may compare the amount detected by the sensor to the amount specified in a solution order. In some embodiments, when the amount detected may be different than the amount specified, and wherein the controller may recalibrate by calculating an increased amount or a decreased amount of each of the solid and liquid components specified in the solution order such that a ratio of components of the solution order may be maintained substantially constant. In some embodiments, the system further may comprise a dosing unit operably coupled to the controller, wherein the controller may instruct the dosing unit to supply the increased amount or the decreased amount to the mixing chamber. In some embodiments, the controller may automatically recalibrate. In some embodiments, the controller may inform a user of the recalibration.

In some embodiments, the one or more containers may include two or more containers, and wherein at least two of the two or more containers may have a different external container shape. In some embodiments, the bottle handling sub-system may comprise a conveyor belt; a roller conveyor; an adhesive conveyor; an automated arm, hand, or gripper; a robotic arm, hand, or gripper; a mechanical arm, hand, or gripper; a programmable arm, hand, or gripper; or any combination thereof. In some embodiments, during use, the bottle handling sub-system may select a number of the one or more containers to receive the solution. In some embodiments, a selection of the number may be based on an input received by the controller from a user via a user interface operably coupled to the controller. In some embodiments, the one or more containers may include two or more containers, and wherein the bottle handling sub-system may select the two or more containers to receive the solution. In some embodiments, the system may further comprise a sensor operably coupled to the controller, wherein a selection of the two or more containers may be based on an input received by the controller from the sensor.

In some embodiments, a volume of the solution may be at least about 5 milliliters. In some embodiments, the volume of the solution may be from about 5 mL to about 10 L. In some embodiments, the volume of the solution may be from about 100 mL to about 10 L.

In some embodiments, the internal volume of the one or more containers may be at least about 5 milliliters. In some embodiments, the internal volume of the one or more containers may be from about 5 mL to about 10 L. In some embodiments, the internal volume of the one or more containers may be from about 100 mL to about 10 L. In some embodiments, the internal volume of the one or more containers may be from about 0.25 L to about 2 L.

In some embodiments, at least two of the one or more containers may have the same internal volume. In some embodiments, at least two of the one or more containers may have different internal volumes. In some embodiments, at least two of the one or more containers may have a different external container shape. In some embodiments, at least two of the one or more containers may comprise a different material composition.

In some embodiments, the internal volume for each of the one or more containers may not vary by more than about 25% of 1 L. In some embodiments, the internal volume for each of the one or more containers may not vary by more than about 25% of 0.5 L.

In some embodiments, the one or more containers may be two, three, or four. In some embodiments, the system may further comprise a storage area for the one or more containers.

In some embodiments, the controller may inform a user of a change in a solution order. In some embodiments, the change may be a change in volume of the solution order.

In some embodiments, the system further may comprise one or more lumens that bring the mixing chamber in fluid communication with the one or more containers. In some embodiments, the one or more lumens may include two or more lumens, and wherein diameters of at least two of the two or more lumens may be different. In some embodiments, the one or more lumens may include a first lumen and a second lumen, and wherein a diameter of the first lumen may be from about 0.1× to about 100× greater that a diameter of the second lumen.

Another aspect of the present disclosure provides a system for preparing a solution. The system may comprise (a) a mixing chamber; (b) an automated solution dispenser that directs at least one solid selected from a plurality of solids and at least one liquid selected from a plurality of liquids in the mixing chamber to form the solution; (c) a container having an internal volume and at least one opening, which internal volume is sufficient to accommodate at least a portion of the solution; (d) a filter in fluid communication with the container, wherein the filter removes one or more contaminants from the solution such that the solution is at least about 95% free of the one or more contaminants; and (e) a controller that is operably coupled to the automated solution dispenser and the one or more containers. In some embodiments, the controller is programmed to (i) direct mixing of the at least one solid and the at least one liquid in the mixing chamber to form the solution having at least one target characteristic and (ii) dispense at least a portion of the solution from the mixing chamber into the container. In some embodiments, the at least one target characteristic may be selected from the group consisting of temperature, pH, chemical composition, weight, conductivity, turbidity, density, capacitance, volume, and viscosity. In some embodiments, the at least one target characteristic may be independent of an atmospheric condition.

In some embodiments, the at least one target characteristic may be at least three target characteristics. In some embodiments, the controller may be operatively coupled to a user interface that is programmed to receive an input from a user. In some embodiments, the input may comprise a solution order corresponding to the at least one target characteristic. In some embodiments, during use, the solution may be dispensed into the container according to the input.

In some embodiments, the controller may maintain the at least one target characteristic for at least about 1 day. In some embodiments, the atmospheric condition may comprise a temperature, a pressure, a concentration of a gas, a concentration of a liquid, a humidity, a molarity, a molality, or any combination thereof.

In some embodiments, the contaminant may comprise a solid. In some embodiments, the contaminant may comprise an endotoxin. In some embodiments, the contaminant may comprise a virus or portion thereof, a viral particle, a bacterium or portion thereof, a bacterial particle, a fungus or portion thereof, a fungi particle, or any combination thereof.

In some embodiments, the system further may comprise a seal operatively coupled to the container, wherein the seal may be impermeable to liquid and/or gas. In some embodiments, the seal may be an o-ring seal. In some embodiments, the seal may be disposed between the automated solution dispenser and the at least one opening of the container.

In some embodiments, the system further may comprise a cap adjacent to the at least one opening of the container. In some embodiments, a passive priming element may be positioned between the cap and the seal. In some embodiments, the passive priming element may be a spring.

In some embodiments, the filter may be positioned adjacent to the cap. In some embodiments, the filter may be a vacuum filter. In some embodiments, the system further may comprise a detector that detects a presence or absence of the filter. In some embodiments, the controller may be programmed to refill or replace the filter based on input from the detector, a user, or a combination thereof. In some embodiments, the controller may connect or disconnect the filter based on (i) input from the detector, (ii) input from a user, (iii) instructions in a solution order, or any combination thereof. In some embodiments, the solution may be at least about 96% free of contaminant.

In some embodiments, the system may further comprise a dosing screw that regulates dosing of the at least one solid and/or the at least one liquid into the mixing chamber. In some embodiments, during use, the dosing screw may break, crush, or pulverize a solid prior to dispensing the solid into the mixing chamber. In some embodiments, during use, the dosing screw may break, crush, or pulverize individual particles of the solid that are greater than about 1 centimeter in diameter. In some embodiments, during use, the dosing screw may break, crush, or pulverize individual particles of the solid, such that the individual particles of the solid that are dispensed into the mixing chamber are less than about 1 centimeter in diameter.

In some embodiments, the system further may comprise a seal operatively connected to the automated solution dispenser, wherein the seal may be impermeable to liquid and/or gas. In some embodiments, the seal may be positioned adjacent to the dosing screw.

In another aspect, the disclosure relates to a system for preparing a solution. The solution may comprise: (a) an automated solution dispenser capable of mixing at least one solid and one liquid; and (b) a controller that is operably linked to the solution dispenser, comprising a user interface; wherein the system is capable of (i) mixing the solid and liquid according to a solution order from a user; and (ii) determining a weight of the at least one solid prior to mixing.

The solution may comprise a laboratory solution. The solution may comprise a buffer solution, for example a buffer solution to pH titrate a solution or a buffer solution for running an assay. The solution may comprise a media solution, for example, a media solution for cell or tissue culture. The system may comprise a solids handling system (sometimes referred to as the solid handling system) for storing, manipulating, and/or dosing the at least one solid (sometimes referred to as solid component). The system may also comprise a liquid handling system for likewise storing, handling, and dosing the at least one liquid (sometimes referred to as liquid component). The controller may be equipped to be accessed from a remote location. The system may be configured to accept a solution order. The solution order may be entered from a remote location. The solution order may comprise specifications for solution preparation. The solution order may be linked to stored specifications for solution preparation. The automated solution dispenser may be capable of self-cleaning. The self-cleaning may allow the solution dispenser to create multiple different solutions with sufficiently low cross-contamination, without manual human intervention. Reagents for the preparation of multiple different solutions may be connected to the automated solution dispenser further reducing or eliminating the need for manual human intervention. The system may be capable of monitoring the pH of the solution. The laboratory solution may be a biological solution. In some embodiments, the system is capable of preparing the laboratory solution at least 95%, 99%, 99.5%, 99.9%, or higher accuracy. The volume of the solution may be about 25 milliliters (mL), 50 mL, 100 mL, 250 mL, 500 mL, 1 liter (L), 2 L, 5 L or more. The system may be capable of preparing 2, 3, 4, 5, 10, 15, 25, 50, 100 or more solutions without manual intervention. The automated solution dispenser may be further capable of dosing and mixing at least 2, 3, 4, 5, 10, 15, 25, 50, 100 or more solids. In some embodiments, the system is capable of titrating the solution with an acid or base solution achieving a specified target pH.

The laboratory solution may comprise one or more reagents from the group consisting of Citric Acid, Methanol, Ethanol, Acetonitrile, Hexane, BSA $Na_2HPO_4$, $NaH_2PO_4$, Imidazole, Hexane, Methanol, Ethanol, Acetonitrile, Sodium Citrate, Sodium Acetate, Acetic Acid, Sodium Carbonate, Sodium Bicarbonate, 2-(N-morpholino)ethanesulfonic acid (MES), 2-[Bis(2-hydroxyethyl)amino]-2-(hydroxymethyl)propane-1,3-diol (Bis-Tris), N-(2-Acetamido) iminodiacetic Acid (ADA), 2-(carbamoylmethylamino) ethanesulfonic acid (ACES), 1,4-Piperazinediethanesulfonic acid (PIPES), 3-(N-Morpholino)-2-hydroxypropanesulfonic Acid (MOPSO), 1,3-bis(tris(hydroxymethyl)methylamino) propane (Bis-Tris Propane), N,N-Bis(2-hydroxyethyl)-2-aminoethanesulfonic Acid (BES), 3-morpholinopropane-1-sulfonic acid (MOPS), 4-(N-morpholino)butanesulfonic acid (MOBS), 2-[[1,3-dihydroxy-2-(hydroxymethyl)propan-2-yl]amino]ethanesulfonic acid (TES), 2-[4-(2-hydroxyethyl)piperazin-1-yl]ethanesulfonic acid (HEPES), 3-[bis(2-hydroxyethyl)amino]-2-hydroxypropane-1-sulfonic acid (DIPSO), 3-morpholinopropane-1-sulfonic acid (MOPS), 3-[[1,3-dihydroxy-2-(hydroxymethyppropan-2-yl] amino]-2-hydroxypropane-1-sulfonic acid (TAPSO), 2-Amino-2-hydroxymethyl-propane-1,3-diol (TRIZMA), 4-(2-Hydroxyethyl)piperazine-1-(2-hydroxypropanesulfonic acid) (HEPPSO), 2-hydroxy-3-[4-(2-hydroxy-3-sulfopropyl)piperazin-1-yl]propane-1-sulfonic acid (POPSO), TEA, 4-(2-Hydroxyethyl)-1-piperazinepropanesulfonic acid, 4-(2-Hydroxyethyl)piperazine-1-propanesulfonic acid (EPPS), N-(2-Hydroxy-1,1-bis(hydroxymethyl)ethyl)glycine (Tricine), Glycyl-glycine (Gly-Gly), N,N-Bis(2-hydroxyethyl)glycine (Bicine), N-(2-Hydroxyethyl)piperazine-N'-(4-butanesulfonic acid) (HEPBS), 3-[[1,3-dihydroxy-2-(hydroxymethyppropan-2-yl]amino]propane-1-sulfonic acid (TAPS), 2-Amino-2-methyl-1,3-propandiol (AMPD), N-tris(hydroxymethyl)-4-aminobutanesulfonic acid (TABS), N-(1,1-Dimethyl-2-hydroxyethyl)-3-amino-2-hydroxypropanesulfonic acid (AMPSO), 2-(Cyclohexylamino)ethanesulfonic acid (CHES), N-cyclohexyl-2-hydroxyl-3-aminopropanesulfonic acid (CAPSO), 2-amino-2-methyl-1-propanol (AMP), 3-(Cyclohexylamino)-1-propanesulfonic acid (CAPS), and 4-(Cyclohexylamino)-1-butanesulfonic acid (CABS). In some embodiments, the laboratory solution is specified at a pH between about 2-7 or 7-11. The laboratory solution may be selected from the solutions listed in Groups 1-36. The laboratory solution may comprise a solvent with a dielectric constant in the range of 1-2, 2-3, 3-4, 4-5, 5-10, 10-15, 15-20, 20-30, 30-40, 40-50, 50-60, 60-70, or 70-80.

In some embodiments, the system further comprises a water purifier and/or a filtration system. Consumption, present or estimated future stock level of at least one solid or at least one liquid may be tracked, for example at a remote location. A purchase order may be suggested for a solid or liquid, for a plurality of solids, liquids or a combination of at least one of each. The purchase order may be automatically submitted. The purchase order may be submitted according to one or more reagent ordering criteria introduced by a user. The cloud systems can optimize the timing of purchase orders to optimize logistics of the suppliers.

In some embodiments, instructions for one or more enumerated solutions are programmed into the controller. The one or more enumerated solutions may comprise crystallography screening solutions or solutions for liquid chromatography. Instructions for the one or more enumerated solutions may be provided from a remote location. Instructions for the one or more enumerated solutions may be provided by a user. Instructions for the one or more enumerated solutions may be provided from an authorized system.

The controller may be further configured to give access to a user to control at least one secondary system. The secondary system may comprise at least one component selected from the group consisting of a camera, a light detector, a moveable optical system, a radioactivity detector, a light source, a power supply, a voltage regulator, a voltage meter, an ammeter, a thermocouple, a thermometer, a potentiometer, an oscillator, a heater, a cooler, a pump, a pressure regulator, a chromatography system, an agitator, a shaker, a sonicator, a vacuum source, a scale, a centrifuge, a filtration device, a timer, a monitor, a robotic arm, an automated pipetting system, a positive displacement pump, and a printer. The control of the secondary system may be facilitated by a user installed device driver. The controller may be further configured to give access to a user through an application programming interface. The system may further comprise a user installed computer program, wherein the computer program is capable of manipulating data originating from the automated solution dispenser. The system may also comprise a user installed computer program, wherein the computer program is capable of manipulating data originating from the secondary system. In some embodiments, the automated solution dispenser and the secondary system are obtained from separate providers. The automated solution dispenser and the secondary system may be manufactured by separate producers. In some embodiments, the user is not a member of the entity providing the automated solution dispenser or the entity manufacturing the automated solution dispenser. The solution dispenser may be operably linked to a secondary system and may be able to supply solutions to the secondary system directly. The controller may be configured to facilitate, track, and/or control the transfer of a solution from the solution dispenser to the secondary system. In some embodiments, the computer system and the user installed computer program are obtained from separate providers. The system may further comprise a memory storage unit and/or a database. In some embodiments, at least one operating parameter is stored in the memory storage unit. The controller may be configured to measure at least one operating parameter. The at least one operating parameter may be selected from the group consisting of operating time, temperature, pH, turbidity, volume, capacitance, and composition of solution. The at least one operating parameter may be measured over time. The controller may be capable of outputting the at least one operating parameter.

The system may further comprise at least one controllable inlet port, wherein the at least one controllable inlet port controllably receives at least one component of a solution. In some embodiments, the system further comprises at least one mixing chamber. At least one controllable inlet port may be operably linked to the at least one mixing chamber for delivery of at least one component of a solution. The at least one controllable inlet port may comprise a controllable solids port that is capable of controllably supplying solid components to the at least one mixing chamber from one or more solid sources. The controllable solids port may comprise a solids dispensing system that is engageable with a solids dosing mechanism, wherein the solids dosing mechanism is capable of controllably dispensing a dosed amount of the at least one solid from a solid source. The solids dispensing system, also referred to as the solids delivery system (SDS) may comprise a dosing mechanism driver (DMD) that is moveable in and out of engagement with the solids dosing mechanism (SDM). The solids dosing mechanism, when in engagement, may be driveable for dispensing the dosed amount of the at least one solid by the dosing mechanism driver. The system may further comprising a moveable tube extending from an inlet of the at least one mixing chamber towards the solids dosing mechanism. The moveable tube may comprise an inlet for receiving solids dispensed from a solid source, an outlet coupled to the inlet of the at least one mixing chamber and is configured to allow the at least one solid to pass therethrough. The moveable tube may be moveable in and out of engagement with a portion of the solids dispensing system. Typically the movable tube may be movable in and out of engagement with the solids dosing mechanism. When engaged, the moveable tube may form a path between the solids dispensing system and the at least one mixing chamber through which the at least one solid is capable of passing. The moveable tube may comprise a shape that is capable of preventing solids from attaching to an inner surface of the moveable tube. In some embodiments, at least one wall of the moveable tube is electrostatically charged or coated with a non-stick material such that solids are repelled. In some embodiments, a cleaning system is implemented in a similar configuration to a solids dosing mechanism and can be used to clean parts of the solids dosing mechanism and/or the central mixing chamber. The controllable solids port, SDS, SDM, and DMD may each be part of a larger system known as the solids handling system (SHS), which is sometimes also referred to as the solid handling system. The solids handling system may further comprise a mechanical apparatus such as a roller conveyor, a conveyor belt, an automatic arm or hand, a robotic arm or hand, mechanical arm or hand, programmable arm or hand, or other to handle the one or more stores of solid components or solid reagents to be used in preparing various solutions. The SHS may handle manipulation and selection of the various solid components to be dosed and dispensed by the SDS, SDM, and DMD.

The solids dosing mechanism may further comprise a dosing screw rotatable about a longitudinal axis of the dosing screw, wherein the dosing screw is capable of carrying the at least one solid. The solids dosing mechanism may further comprise a rotatable base coupled to the dosing screw, the rotatable base being rotatable in cooperation with the dosing screw. The solids dosing mechanism may further comprise a solids outlet for receiving the at least one solid from the dosing screw. When rotated about the longitudinal axis, the dosing screw may carry the at least one solid from a solids inlet to the solids outlet. The dosing screw and the rotatable base may be movable along the longitudinal axis of the dosing screw between an open position in which the solids outlet is open, and a closed position in which the solids outlet is closed. The dosing screw and the rotatable base may be coupled to a gear gate for driving the dosing screw. The gear gate may be drivable by the dosing mechanism driver. The dosing screw and the rotatable base may be biased in the closed position. A locking mechanism may be operably linked to seal a disengaged system. A locking mechanism may utilize a passive priming element, such as a spring. In some embodiments, the dosing mechanism comprises a grinder and/or a crusher. In some embodiments, solid containers comprise a grinder and/or a crusher.

In some embodiments of the present disclosure, the SDM and/or the DMD may be used as driving mechanisms for transmitting torque or mechanical force to additional elements of the system described elsewhere in this application or known to the art. For example, either the SDM or the DMD can couple to specialized containers, such as a cleaning container contained within the solids handling system or equipment used to calibrate various sensors used by the system.

The controller may be configured to determine a weight of a dosed amount of the at least one solid dispensed from the solid source at a desired time. In some cases, the desired time may be selected dependent on a rate at which the solids dosing mechanism is driven. The controller may be configured to determine a weight of the dosed amount of the solid from the solid source dependent on a time and rate at which the solid dosing mechanism is driven. The determined weight of the dosed amount of solid from the solid source is tracked to monitor the amount of solid left in the solid source. Alternatively, the weight of the dosed amount of solid is determined by measuring the weight of a solids container (also referred to as a solid container) that stores the solid source. The system may be configured to facilitate ordering more solid when supply of solid left falls below a user defined threshold.

In some embodiments, the solid source is a container (also referred to as a solid container or solids container) containing the at least one solid. The solids dosing mechanism may, controllable solids port, or solids dispensing system be coupleable to the container. The system may further comprise a plurality of such containers, each container may be coupleable to the solid dosing mechanism, controllable inlet port, or solids dispensing system. The plurality of containers may be controllably moveable between at least one dispensing position, in which a container is aligned with the controllable inlet port to enable dispensing of a contained solid, and a storage position in which the container is not aligned with the controllable inlet port. The plurality of containers may be disposed on a turntable having an axis of rotation such that the containers are movable between the dispensing and storage positions. The containers may be further movable to an access port for facilitating removal and installation of the containers from or onto the turntable.

The at least one controllable inlet port may comprise a controllable liquid inlet port for controllably supplying liquid to the at least one mixing chamber from one or more liquid sources. The one or more liquid sources may comprise a continuous supply, a reservoir internal to the system or a reservoir external to the system. The controllable liquid inlet port may comprise one or more pumps coupled to the controller. The controller may be configured to control the one or more pumps such that the one or more pumps are capable of dispensing a desired amount of liquid from the one or more liquid sources. The one or more pumps may comprise a peristaltic pump, a syringe pump, a piston pump, a reciprocating pump, a diaphragm pump, a screw pump, a rotating lobe pump, a gear pump, a plunger pump, or other suitable pump. In some embodiments, the controllable liquid inlet port controllably supplies liquid to the at least one mixing chamber using vacuum or gravity.

The at least one mixing chamber may comprise one or more cleaning nozzles disposed in at least one wall of the at least one mixing chamber, the nozzles being coupled to at least one spray inlet port and being arranged to spray received cleaning fluid inside the at least one mixing chamber.

The system may further comprise at least one sensor. The at least one sensor may sense at least one characteristic of the solution. The at least one sensor may sense at least one characteristic of at least one component of a solution prior to mixing.

The at least one sensor may be coupled to a weighing device configured to determine a loss in weight of the container upon dispensing of the at least one solid from the container. The controller may be configured to controllably supply the solid to the mixing chamber until a target weight of the at least one solid is reached based on the loss in weight of the container. The at least one sensor may be coupled to a solids weighing device that is capable of receiving, weighing and dispensing the at least one solid from the solids dosing mechanism into the at least one mixing chamber. The solids weighing device may comprise a moveable receptacle for receiving the at least one solid; a weighing device coupled to the moveable receptacle for weighing the dispensed solid; and a dispensing mechanism for dispensing the at least one solid upon weighing into the mixing chamber. The weighing device may comprise a load cell or a force compensated electromagnet.

The dispensing mechanism may be configured to move the moveable receptacle to a receiving position when receiving the at least one solid from the solids dosing mechanism, and configured to move the moveable receptacle to a dispensing position when dispensing the at least one solid into the mixing chamber. The at least one sensor may comprise a weighing device configured to determine a gain in weight of the at least one mixing chamber upon receipt of a solid into the at least one mixing chamber. The controller may be configured to controllably supply the solid to the mixing chamber until a target weight of the solid is reached.

The at least one sensor may comprise a solution sensor capable of sensing one or more characteristics of the solution. The controller may be configured to controllably supply the at least one solid to the at least one mixing chamber until a target characteristic of the solution is detected. The characteristic of the solution may be selected from the group consisting of pH, temperature, chemical composition, weight, flow rate, conductivity, turbidity, density, capacitance, and viscosity. The at least one sensor may measure cleanliness.

The system may perform at least one self-cleaning cycle. The controller may initiate an additional self-cleaning cycle based on cleanliness. In some embodiments, at least one inlet port is controlled to input a cleaning fluid into the at least one mixing chamber. At least one outlet port may be controlled to dispense a cleaning fluid from the at least one mixing chamber. The at least one mixing chamber may comprise one or more cleaning nozzles disposed in at least one wall of the at least one mixing chamber, the nozzles being coupled to at least one spray inlet port and being arranged to spray a cleaning fluid inside the chamber. The controller may be configured to implement the self-cleaning cycle, wherein at least one spray inlet port is controlled to input a cleaning fluid into the at least one mixing chamber, and a controllable outlet valve is controlled to dispense the cleaning fluid. At least one spray inlet port may be coupled to one or more cleaning nozzles arranged to spray a cleaning fluid inside the at least one mixing chamber. At least one spray inlet port may be coupled to a spray ball comprising a plurality of nozzles arranged to spray a cleaning fluid inside the at least one mixing chamber. At least one inlet port may be coupled to a pump for supplying the cleaning fluid. The cleaning fluid may be supplied under pressure. The at least one spray inlet port may be coupled to a detergent source for dispensing detergent into the cleaning fluid. The detergent source may comprise an injection pump. The cleaning cycle may clean a flowable path from one or more inlet ports coupled with the at least one mixing chamber through to an output of one or more outlet ports. In some embodiments of the present disclosure the cleaning cycle incorporates a container such as one of the solid containers. The solids dosing mechanism (SDM) and/or the dosing mechanism driver (DMD) of the solids dispensing system (SDS) may couple to a one of the solid containers or a specialized cleaning container (in the same fashion as a standard solid container). Either the solid container or the specialized cleaning container may comprise a drivable cleaning nozzle. The SDM or the DMD may supply torque to the drivable cleaning nozzle such that the drivable cleaning nozzle rotates while spraying the cleaning fluid to more effectively clean all nearby portions of the system. The specialized cleaning container may have a spray inlet or spray nozzle for cleaning one or more downstream components of the system. The nozzle may be rotatable as explained above or instead the SDM or DMD may rotate the bottle itself to accomplish rotating the cleaning fluid spray. Such rotation is typically, but not necessarily about the long axis of the solid bottle or cleaning bottle.

A controllable drying system may be coupled to the controller. The controller may implements a drying cycle in the at least one mixing chamber by controlling the controllable drying system. The controller may implement a drying cycle in a flowable path from one or more inlet ports coupled with the at least one mixing chamber through to an output of one or more outlet ports, by controlling the controllable drying system. The controllable drying system may comprise a fan, a vacuum, a heat source or a source of substantially dry air.

The system may further comprise a heating system and/or a cooling system. A sensor may be configured to measure a temperature of the solution. The controller may be configured to control the heating and/or cooling system to control the temperature of the solution based on a target temperature and the temperature of the solution. A target temperature may be used to optimize the time it takes for various reagents to dissolve.

The system may further comprise at least one outlet port. The at least one outlet port may be coupled to the at least one mixing chamber. The system may further comprise a controllable outlet port valve capable of controlling flow of the solution through the at least one outlet port. In some embodiments, the mixing chamber may comprise a beaker with or without a bottom valve. The beaker may be tipped, for example by a robot, to pour the solution to a bottle. The beaker may be removed and can be replaced with a second clean beaker. Alternatively, the beaker may be replaced after cleaning. In some embodiments, the mixing chamber comprises a bottle. The bottle may be removed for the delivery of the prepared solution.

The system may further comprise at least one agitation system enabling agitation of the solution. The agitation may be implemented using a method selected from a group consisting of stirring, shaking, and sonicating.

In some embodiments, the controller may be coupled to at least one controllable inlet port, at least one input sensor, at least one agitation system, at least one sensor, and/or at least one outlet port valve. The controller may be configured to initiate mixing and dispensing of the solution.

The controller may be configured to measure and store at least one operating parameter of the automated solution dispenser during operation and store the at least one operating parameter in the memory storage.

In another aspect, the disclosure relates to a method comprising the use of an automated solution dispenser, wherein at least one solid or liquid is delivered from an intermediate vendor, wherein the intermediate vendor supplies the at least one solid or liquid. The intermediate vendor may supply the at least one solid or liquid at a price margin over a primary vendor price. The delivery of the at least one solid or liquid may be triggered by a consumption or stock alert for the at least one solid or liquid. The consumption stock alert may be generated when a present or estimated future stock level of the at least one solid or liquid falls below a preset threshold value. The laboratory solution may comprise one or more of Citric Acid, Methanol, Ethanol, Acetonitrile, Hexane, BSA, $Na_2HPO_4$, $NaH_2PO_4$, Imidazole, Hexane, Methanol, Ethanol, Acetonitrile, Sodium Citrate, Sodium Acetate, Acetic Acid, Sodium Carbonate, Sodium Bicarbonate, MES, Bis-Tris, ADA, aces, PIPES, MOPSO, Bis-Tris Propane, BES, MOPS, TES, HEPES, DIPSO, MOBS, TAPSO, TRIZMA, HEPPSO, POPSO, TEA, EPPS, Tricine, Gly-Gly, Bicine HEPBS, TAPS, AMPD, TABS, AMPSO, CHES, CAPSO, AMP, CAPS, or CABS.

In yet another aspect, the disclosure relates to a method comprising preparing a laboratory solution using the automated solution dispenser, wherein the at least one solid or liquid comprises one or more of Citric Acid, Methanol, Ethanol, Acetonitrile, Hexane, BSA, Na2HPO4, NaH2PO4, Imidazole, Hexane, Methanol, Ethanol, Acetonitrile, Sodium Citrate, Sodium Acetate, Acetic Acid, Sodium Carbonate, Sodium Bicarbonate, MES, Bis-Tris, ADA, aces, PIPES, MOPSO, Bis-Tris Propane, BES, MOPS, TES, HEPES, DIPSO, MOBS, TAPSO, TRIZMA, HEPPSO, POPSO, TEA, EPPS, Tricine, Gly-Gly, Bicine, HEPBS, TAPS, AMPD, TABS, AMPSO, CHES, CAPSO, AMP, CAPS, or CABS. The laboratory solution is prepared at a pH between about 2-7 or 7-11.

In a further aspect, the disclosure relates to a method comprising preparing a laboratory solution using the automated solution dispenser, wherein the laboratory solution is selected from the solutions listed in Groups 1-36.

In a yet further aspect, the disclosure relates to a method comprising preparing a laboratory solution using the automated solution dispenser, wherein the laboratory solution comprises a solvent with a dielectric constant in the range of 1-2, 2-3, 3-4, 4-5, 5-10, 10-15, 15-20, 20-30, 30-40, 40-50, 50-60, 60-70, or 70-80.

The automated solution dispenser may comprise a water purifier. At least some of the water within the prepared laboratory solution may be purified by the water purifier. The automated solution dispenser may further comprise a filtration system. One or more of the components of the prepared solution may be filtered, for example by the integrated filtration system.

Some embodiments of the present disclosure entail systems and methods for calibrating the one or more sensors of the system. The system may use sensor references (standards) within or outside the system to calibrate the various sensors used by the system during operation. Such standards may comprise standard weights having verified known weights for calibrating scales, reference pH solutions with known pH values for calibrating pH sensors, or standard materials, having predetermined and verified properties including but not limited to conductivity, turbidity, particle sizes, radioactivity, density, volume or temperature. The standard materials may include solid phase materials or liquid phase materials, for example a standard weight for calibrating a weight sensor maybe a piece of platinum, lead or copper having a known weight or a standard weight. A pH standard solution is an example of a liquid phase standard material. The standard materials may also include a combination of solid and liquid phase materials. For example a temperature sensor in the Central Mixing Chamber (CMC) may be calibrated by introducing a dry ice and ethanol bath into the CMC. Such a bath will remain at $-78°$ C. until all the dry ice sublimates providing a reference temperature for calibrating the temperature sensor. Solid and liquid standards may be handled by the solid handling system and the liquid handling system respectively. For instance the dry ice and ethanol bath may be introduced to the CMC by loading the system with a container of dry ice, whereby the solids handling system will transfer a quantity of the dry ice to the CMC. The ethanol similarly can by introduced to the CMC via the liquid handling system. In some cases, a user of the system may manually introduce the reference materials into the system for calibration. For example, the user may manually load a standard weight on the weighing tray of the solids weighing system. The user may also load solid containers onto the solids handling system having known weights in order to calibrate weight sensors that are tasked with monitoring the weights of the solids containers. The system may utilize cleaning cycles before, during, or after calibration procedures.

Some embodiments of the present disclosure provide a system and method for calibrating weight sensors used by the system. In some embodiments the system comprises one or more weight sensors (scales) for measuring the weight of the solids containers. Such measurements may be used by the system to facilitate accurate dosing of the solids reagents stored in the one or more solids containers to the CMC. Such measurements may also be used to track the amount of solids reagents currently stored by the solids handling system and the rate at which the various solids reagents are consumed. This information may be used to anticipate and/or generate replacement orders of solid reagents. To ensure accurate operation of these scales the system may periodically calibrate the one or more scales.

The system may further comprise a solids container, configured to hold a reference weight having a known weight, for calibrating the one or more scales, this container may be referred to as scale calibration container. The scale calibration container having the reference weight being uncoupleable and coubleable to the scale calibration container, the coupling and decoupling controlled by rotation of a motor (such as a motor of the SDM), and wherein the scale calibration container facilitates calibration of a scales by coupling and decoupling the reference weight in between weighing of the scale calibration container by the scale. The reference weight, contained in the scale calibration container or held by the scale calibration container, may have a hook configured to hook and unhook to the scale calibration container. The scale calibration container may be configured to interface with a motor (sometimes referred to as a solids dosing motor) of the solids handling system such that rotating the solids dosing motor will lower the reference weight into a solid cup of the solid handling system. Further rotation of the solids dosing motor may fully unhook the reference weight from the scale calibration container. After unhooking the reference weight from the scale calibration container, further rotation of the solids dosing motor may re-hook the reference weight to the scale calibration container and raise the reference weight into the scale calibration container. In some cases, the scale calibration container may couple the SDM or the DMD such that the SDM or the DM D supplies the torque used to lower, raise, hook, and/or unhook the reference weight.

Various embodiments of the present disclosure may evaluate a status of the various sensors of the system. These sensors may include pH sensors, weight, sensors, conductivity sensors, turbidity sensors, or any other sensors described in the various embodiments of the present disclosure elsewhere in this application. The system may store measurement histories of any of the sensors comprising readings from the sensors during the operation of the sensor. The measurement histories may be stored in the system's database for access and statistical processing, which in turn may be used to evaluate the operable status of any given sensor. The system may then take appropriate action such as ordering a replacement sensor if any sensor is operating outside of specified parameters.

Various embodiments of the present disclosure may evaluate a status of the various sensors of the system. These sensors may include pH sensors, weight, sensors, conductivity sensors, turbidity sensors, or any other sensors described in the various embodiments of the present disclosure elsewhere in this application. The system may store measurement histories of any of the sensors comprising readings from the sensors during the operation of the sensor. The measurement histories may be stored in the system's database for access and statistical processing, which in turn may be used to evaluate the operable status of any given sensor. The system may then take appropriate action such as ordering a replacement sensor if any sensor is operating outside of specified parameters.

Some embodiments may be directed at mixing solutions that comprise multiple solid and or multiple liquid components. The number of solid components (reagents) and/or liquid components (reagents) may comprise 2, 3, 4, 5, 10, 25, 50, 100, or more. The number of solid components and/or liquid components may also be in the range of 2-100, 2-10, 10-20, 20-30, 30-40, 40-50, 50-60, 60-70, 70-80, 80-90, 90-100, greater than 100. All of the solid and/or liquid components may be stored within the system by the Solids Handling System (SHS) or Liquid Handling System (LHS). Addition of additional solid or liquid components to the solution may happen while the solution is being mixed from other solid or liquid components. In some embodiments the user may add additional solid or liquid components (not presently contained by the system) to the system to be handled by the SHS or LHS and subsequently introduced to the solution being created, while the solution is being created or while the solution is being mixed. While the solution is being mixed, the user may add solid or liquid components to the system which will not be introduced to the currently being prepared solution. The user may do this to prepare the system for a subsequently to be creates solution.

In some cases, the systems and methods provide for inventory management. The system's computerized hardware and software may take data from the various sensors of the system (scales, cameras, radio frequency identification (RFID) scanners) to keep track of and manage the stores of various solid and liquid reagents and components used to prepare the solutions. In some embodiments this data is used along with workflow data to manage the inventory of various reagents held within the system.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the present disclosure are utilized, and the accompanying drawings (also "figure" and "FIG." herein), of which:

FIG. 1A illustrates and overview of an automated solution dispenser according to some embodiments of the present disclosure. FIG. 1D depicts an embodiment of the central mixing chamber. FIG. 1E depicts an embodiment of the bottle handling sub-system. FIG. 1F depicts an embodiment of the support and casing structures. FIG. 1G depicts an embodiment of the water purification module.

FIGS. 2A-B illustrates exemplary workflows for the automated solution dispenser.

FIG. 7A and FIG. 7B illustrate a dosing system according to some embodiments of the present disclosure FIG. 8A and FIG. 8B illustrate a solids platform weight scale and dosing driver according to some embodiments of the present disclosure.

FIG. 12 illustrates another aspect for the solids handling system of an automated solution dispenser according to an embodiment of the present disclosure.

FIG. 13 illustrates the liquid handling system according to some embodiments of the present disclosure FIG. 14 illustrates examples of mechanical seals according to some embodiments of the present disclosure.

FIG. 15 illustrates a pivot pipe according to some embodiments of the present disclosure.

FIG. 18A and FIG. 18B illustrates at top and side view, respectively, of a bottle handling sub-system according to some embodiments of the present disclosure.

DETAILED DESCRIPTION

Figure 1C:
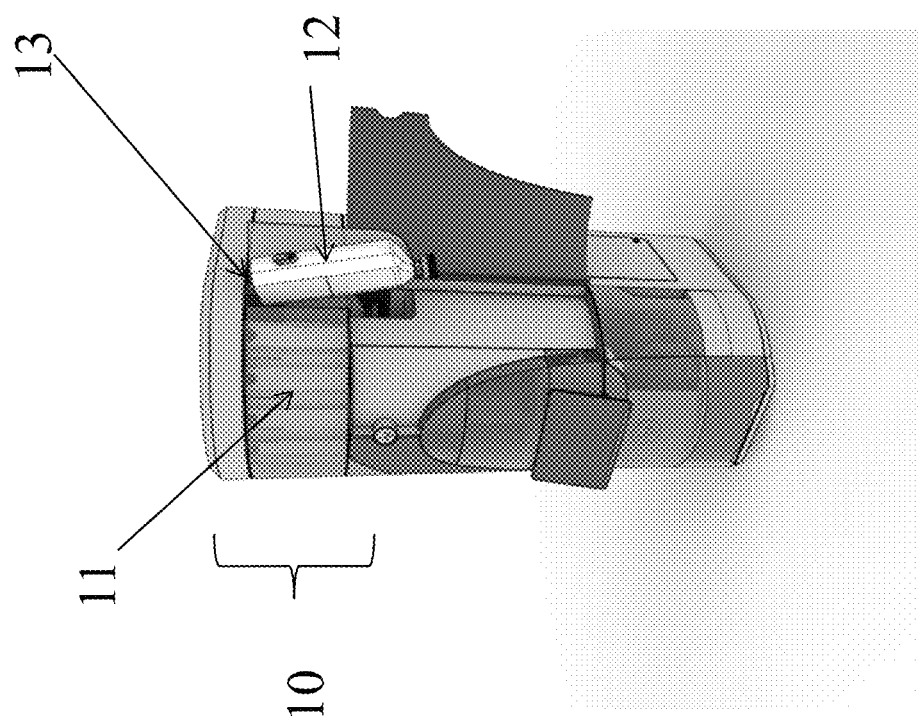
FIG. 1C depicts an embodiment of the solids handling system.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "solution," as used herein, generally refers to a mixture of two or more substances. A solution may be a homogenous or heterogeneous mixture of two or more substances. A solution may be stable. A solution may comprise one phase or multiple phases. A solution may include an emulsion or slurry. A solution may comprise a solute that may be dissolved into a solvent to form the solution. A solution may be a laboratory solution. A solution may be a stock solution from which a needed aliquot may be taken. A solution may be a buffer solution. A buffer solution may be an alkaline solution or an acidic solution. A buffer solution may be (i) a buffer solution used to titrate the pH of another solution, (ii) a buffer solution used in an assay such as an immunoassay or a gel electrophoresis, (iii) a buffer solution used to then create a chemical reaction with another solution or substance, (iv) a buffer solution to lyse or disrupt a cell or tissue sample. A solution may be a media solution, such as a solution used to culture cells or tissues. A solution may be a solution prepared to fix or to permeabilize cells or tissues. A solution may be a solution into which cells or tissues can be frozen or preserved. A solution may be a solution to disrupt protein-protein bonds or bonds within a single protein. A solution may be a solution to stain a cell or tissue sample, such as a histochemical stain. A solution may comprise a buffering agent, a chelating agent, an oxidizing agent, a neutralizing agent, a detergent agent, a nutritive agent, a contaminant inhibiting agent—such as an antibiotic, a denaturing agent, an anticoagulating agent, a cell permeabilizing agent, a catalyst—such as an agent to catalyze a reaction, a chaotropic agent, porogen agent, a dehydrating agent, or others. A solution may be prepared for a laboratory use, a clinical use, a research use, a medical use, a diagnostic use, or others. One or more solids selected from a plurality of solids may be selected to form the solution. One or more liquids selected from a plurality of liquids may be selected to form the solution.

The term "target characteristic," as used herein, generally refers to a target value of characteristic for a solution being prepared. For example a target characteristic may be a final solution volume of 50 liters. A sensor may intermittently measure the solution volume and a controller may compare the sensor input to the target value of 50 liters. The controller may indicate by an alarm when the target characteristic is reached. A target characteristic may be input by a user, for example, a user may input the target characteristic into a user interface. A target characteristic may be determined based on known solution compositions. For example, a solution order may request one liter of a 1 M NaOH solution and the controller may determine a target characteristic of weight (i.e., grams of NaOH) that is needed to complete the solution order. A target characteristic may be a temperature, a pH, a chemical composition, a weight, a conductivity, a turbidity, a density, a capacitance, a volume, a viscosity, or others, or any combination thereof. A sensor may detect a characteristic and a controller may determine whether the measured characteristic matches the target characteristic. A chemical composition may be a molality of solution, a molarity of solution, a normality of solution, a concentration of a component, a molar fraction of a component, a volume fraction of a component, a mass fraction of a component, or any combination thereof. A chemical composition may be a relative amount of different chemical elements that constitute a solution. A target characteristic can be maintained by the automated solution dispenser system at least about 1 hour (hr), 2 hr, 4 hr, 6 hr, 8 hr, 10 hr, 12 hr, 18 hr, 24 hr, 2 days, 3 days, 4 days, 5 days, 6 days, 1 week or more. A system can maintain a target characteristic at least about 1 hr. A system can maintain a target characteristic at least about 4 hr. A system can maintain a target characteristic at least about 8 hr. A system can maintain a target characteristic at least about 1 day. A system can maintain a target characteristic at least about 2 days. A system can maintain a target characteristic at least about 5 days. A system can maintain a target characteristic at least about 1 week.

The term "safety value," as used herein, generally refers to any value set by or informed by a safety regulation. A safety value may be a volume of a substance that can be stored in a container. A safety value may be a ratio of two substances that may be collected in the same container. A safety value may be a time allotment that a substance may be stored prior to discarding. One or more inputs from a sensor may be compared to a safety value, such as by a controller. A safety value may be input by a user into a user interface of the system. An alarm may alert the user when one or more inputs i) exceed a safety value, ii) is within about 1%, 2%, 3%, 4%, 5%, 6%, 7%, 8%, 9%, 10%, 15%, 20% of the safety value, iii) violates the safety regulation, or iv) a combination thereof. An alarm may alert the user when one or more inputs is within about 1% of the safety value. An alarm may alert the user when one or more inputs is within about 5% of the safety value. An alarm may alert the user when one or more inputs is within about 10% of the safety value. An alarm may alert the user when one or more inputs is within about 15% of the safety value. An alarm may alert the user when one or more inputs is within about 20% of the safety value. The controller may discontinue preparing the solution when one or more inputs i) exceed a safety value, ii) is within about 1%, 2%, 3%, 4%, 5%, 6%, 7%, 8%, 9%, 10%, 15%, 20% of the safety value, iii) violates the safety regulation, or iv) a combination thereof. The controller may discontinue preparing the solution when one or more inputs is within about 1% of the safety value. The controller may discontinue preparing the solution when one or more inputs is within about 5% of the safety value. The controller may discontinue preparing the solution when one or more inputs is within about 10% of the safety value. The controller may discontinue preparing the solution when one or more inputs is within about 15% of the safety value. The controller may discontinue preparing the solution when one or more inputs is within about 20% of the safety value.

The term "safety regulation," as used herein, generally refers to guidelines provided to maintain user and societal safety with respect to the generation, storage, and disposal of a hazardous material such as a liquid, a gas, or a solution. A safety regulation may be a federal regulation, a state regulation, a county regulation, a municipal regulation, company-specific regulation or any combination thereof. A safety regulation may provide guidelines of proper disposal of a hazardous substance. A safety regulation may provide guidelines of neutralization of a hazardous substance. A safety regulation may provide guidelines for appropriate storage and/or transport of a hazardous substance. A safety regulation may limit the amounts of a particular substance that may be collected in a particular container. A safety regulation may limit the ratio of two substances that may be collected in the same container. A safety regulation may prevent two substances from being stored in the same container. A safety regulation may be input by a user to a user interface.

The term "contaminant," as used herein, generally refers to any liquid, gas, or solid that contaminates a solution. A contaminant may comprise a solid, a liquid, and a gas. A contaminant may comprise a solid and a liquid. A contaminant may comprise a solid and a gas. A contaminant may comprise a gas and a liquid. A contaminant may comprise a solid. A contaminant may comprise a liquid. A contaminant may comprise a gas. A contaminant may be a liquid, gas, or solid that has not been prescribed in the solution order. A contaminant may be an endotoxin. A contaminant may be a virus or portion thereof, a viral particle, a bacterium or portion thereof, a bacterial particle, a fungus or portion thereof, a fungi particle, or any combination thereof. A contaminant may be a gaseous component, such as air, such as a non-degassed solution. A contaminant may be a solid particle, such as a mineral. A contaminant can be a physical, chemical, biological, or radiological substance. A contaminant may be sediment or organic material. A contaminant can be nitrogen, bleach, salt, pesticide, metal, or others. An automated solution dispenser system may comprise one or more filters or one or more seals to reduce or eliminate contaminants. A solution may be at least about 80%, 85%, 90%, 95%, 96%, 97%, 98%, or about 99% free of contaminant. In some cases, a solution may be at least about 80% free of contaminant. In some cases, a solution may be at least about 85% free of contaminant. In some cases, a solution may be at least about 90% free of contaminant. In some cases, a solution may be at least about 95% free of contaminant. In some cases, a solution may be at least about 96% free of contaminant. In some cases, a solution may be at least about 97% free of contaminant. In some cases, a solution may be at least about 98% free of contaminant. In some cases, a solution may be at least about 99% free of contaminant.

The term "atmospheric condition," as used herein, generally refers to an ambient condition that is external to an internal environment of an automated solution dispenser system. The automated solution dispenser system may be a closed system, such as comprising seals or liquid and gas-tight fittings. A system as disclosed may maintain internal conditions that are independent of ambient conditions. An atmospheric condition may include a temperature, a pressure, a humidity, a concentration of a gas, liquid, or solid or others. For example, a solution prepared by the automated solution dispenser system may maintain a constant temperature of 98 degrees Fahrenheit independent of atmospheric temperature. A solution may maintain a temperature for at least about 0.5, 1, 2, 3, 4, 5, 6, 7, 8, 9, 10 days or longer.

Various embodiments of the present disclosure relate to systems and methods for solution preparation. Many embodiments comprise a system for automatically preparing the solution, the system may be referred to as the system or is sometimes referred to as an automated solution dispenser. In any of the embodiments the solution may be a laboratory solution. In some embodiments, the ingredients for the solution comprise solids, such as loose powder, clumpy powder or crystalline solids. According to some embodiments of the present disclosure, solution preparation is fully or partially automated. In some embodiments, a controller computer or computer system with a software component enables coordination of multiple processes through the system. Multiple users can be coordinated to share the system. In some embodiments, a software component allows incorporation of primary and secondary hardware components into the system. In some embodiments, a software developer is enabled to incorporate additional software components to a core software component of the system using for example an application programming interface (API) to the core software component. Additional software components may be configured to control components of the automated solution dispenser and/or secondary systems.

In various embodiments, the disclosure provides an automated solution dispenser for dispensing a solution having a list of characteristics, such as pH, temperature, chemical composition. The dispenser can comprise one or more of any of the components comprising a mixing chamber, a controllable inlet port to the chamber, an input sensor, an agitator, a solution sensor, an outlet port coupled to the mixing chamber, a controllable outlet port valve, and a controller. The controller can be coupled to one or more controllable inlet ports, one or more input sensors, one or more agitators, one or more solution sensors, and/or one or more outlet port valves. In various embodiments, the controller is configured to measure the received components, mix the received components into a solution and dispense the solution. In some embodiments, an inlet port facilitates controllable entry into the mixing chamber of the components to be mixed into a solution. An input sensor may be utilized to determine a quantitative input of the components to be mixed into the solution. One or more solution sensors may detect one or more characteristics of the solution. An outlet port valve may be used for controlling the flow of solution through the output port. In various embodiments, the agitator is operably linked to the mixing chamber. Components, methods and systems are provided to measure any received components, mix the received components into a solution and dispense the solution. In various embodiments, the controllable inlet port comprises a controllable liquid inlet port for controllably supplying liquid to the mixing chamber from one or more liquid sources. The liquid source may comprise a continuous supply, a reservoir internal to the solution dispenser or a reservoir external to the solution dispenser. The controllable liquid inlet port may comprise one or more pumps coupled to the controller. In some embodiments, the controller is configured to control one or more pumps to dispense a desired amount of liquid from the one or more liquid sources. The pump may comprise a peristaltic pump, a syringe pump, a piston pump, a reciprocating pump, a diaphragm pump, a screw pump, a rotating lobe pump, a gear pump, or a plunger pump. In some embodiments, the controllable liquid inlet port may utilize gravity or vacuum to transfer liquids, for example to supply liquids to the central mixing chamber. In some embodiments, a controllable inlet port comprises a controllable solids port for controllably supplying solid components to the mixing chamber from one or more solid sources.

According to some embodiments of the present disclosure, the systems described herein comprise a central mixing chamber, a flush and verification system, a liquid handling system, a control system such as a controller, a pivot pipe system, a plug valve system, a solid handling system, a bottle handling sub-system, a bottle marker/labeler, a filtering system, and a water purifier. In some embodiments, the system is configured to implement a cleaning cycle. Methods for cleaning the system can be preconfigured into the system. Methods and systems for cleaning cycles are described in further detail elsewhere in this application. In some embodiments, at least one inlet port is controlled to input a cleaning fluid into the mixing chamber, and the controllable outlet valve is controlled to dispense the cleaning fluid.

The outlet port of any of the automated solution dispensers described may be coupled to a controllable directing mechanism for directing a dispensed solution to a desired station. The controller may be configured to control the directing mechanism to dispense a solution to a desired station. Program modes of the automated solution dispenser may include instructions to control the dispensing of solutions. In some embodiments, the station comprises a drain, a bottle handling station, a pH sensor storage liquid recycle station, a filtering and bottling station, a degassing and bottling station, an analyzing and bottling station, or any combination thereof. In various embodiments, the solution sensor comprises a temperature sensor. In some embodiments, the controller may be configured to direct a heater (such as a heating coil, a boiler, a hot plate, a radiator, or others), or a cooler (such as a coolant, a water bath, an icebox, a refrigerator or others) to control the temperature of the solution based on a target temperature.

In some embodiments, the automated solution dispenser comprises a memory storage component such as i) a primary storage such as a computer processing unit (CPU), ii) a secondary storage such as flash memory, floppy disks, iii) a tertiary storage such as Cloud storage, iv) off-line storage such as a flash memory device or external hard drive, or v) any combination thereof. The controller can be configured to measure and store a plurality of operating parameters of the automated solution dispenser during operation and store the parameters in the memory storage component. In various embodiments, the operating parameters comprise one or more of operating time, target temperature, target pH, and target composition of solution. The controller can be configured to output one or more of the operating parameters. The one or more operating parameters can be printed to a label for affixing to a container containing a solution dispensed by the automated solution dispenser.

In various embodiments, the controller is configured to implement a storage cycle when the automated solution dispenser is not in use. The storage cycle may comprise controlling an inlet port to input a storage solution into the mixing chamber, wherein the storage solution is selected to preserve a solution sensor.

The controller may be configured to implement a calibration cycle to calibrate a solution sensor. The calibration cycle can comprise one or more of the steps of controlling an inlet port to input a solution having a known characteristic into the mixing chamber, reading an output of a solution sensor, comparing the reading with the known characteristic, and adjusting the solution sensor based on a difference between the read output and the known characteristic. Further calibration cycles can be implemented to calibrate sensors outside the mixing chamber. For example, weight sensors for the dosing of solids can be calibrated similarly with known amounts of solids. Weight sensors may be calibrated using a special solid container, using torque supplied by the Solids Dosing Mechanism (SDM) or the Dosing Mechanism Driver (DMD) will lower a reference weight on to a weighing platform. Once the system detects the reference weight, it will calibrate itself. The reference weight can then be raised back up using torque supplied by the SDM or DMD.

Various embodiments of the present disclosure allow for tracking reagent use and/or stock level locally or at a remote location. Reagents can be supplied according to stock levels. For example, alerts can be created when the stock level of a particular reagent falls below a certain level. The rate of reagent use can be taken into account to determine an estimated time of depletion for a particular reagent. The alert may be sent to a user of the system for purchasing of reagents. Alternatively, preapproved purchasing decisions can be automatically carried out through a connected supplier site. A networked vendor can ship desired reagents automatically or upon user approval with or without a margin above third party suppliers. Deliveries of orders from multiple user locations can be organized, for example by location. Logistical optimization of order deliveries can allow for savings and overall enhancement in speed, allowing for greater customer satisfaction. In some embodiments, savings from the logistical optimization are reflected in purchase prices as discounts to users.

Systems and methods of the present disclosure further allow for tracking the solution making parameters from one or more automated solution dispensers. Data collected during the preparation of a solution can be compiled to refine the solution making instructions for a given solution recipe, for example 2 molar (M) GdnHCl at pH 5.

FIG. 1A illustrates an automated solution dispenser according to some embodiments of the present disclosure. A solid storage rack 11, part of the solids handling system 10, stores one or more solids containers 12 allows for easy reagent restocking. In some cases, the solid storage rack may comprise a cooling system. A solid dosing module 20, comprising a solid dosing mechanism, can dose solids in a fast and accurate way, for example with milligram accuracy or better. The solid dosing module can have a closed system. Systems and methods described herein allow for the prevention of cross contamination. The liquid handling module 30, also referred to as the liquid handling system (LHS), with open flow paths can handle and dose liquids with milliliter accuracy or better. The liquid handling module can be installed with easy access to a pumping system. A filtering module can be permanently or temporarily linked to the liquid handling module. In some cases, a filter can be provided in a cap that can be fitted on a bottle. A mixing chamber 40, also referred to as the central mixing chamber (CMC). In some cases, the mixing chamber can be used to mix liquids, solids, or a combination thereof. The mixing process can be monitored using a sensor device described herein. In some cases, the solution can be monitored to ensure that a desired concentration of one or more components is maintained in the solution. In some cases, the solution can be monitored to ensure that one or more characteristics of a solution meet a predetermined threshold value associated with a safety regulation. In some cases, a volume of the solution can be monitored. In various embodiments, systems and methods of the present disclosure include self-cleaning capabilities of the mixing chamber and/or any lines feeding or leaving the mixing chamber.

In some cases, an internal volume of a container can be about 0.1 liter (L), 0.2 L, 0.3 L, 0.4 L, 0.5 L, 0.6 L, 0.7 L, 0.8 L, 0.9 L, 1.0 L, 1.5 L, 2 L, 2.5 L, 3 L, 3.5 L, 4 L, 4.5 L, 5 L, 5.5 L, 6 L, 6.5 L, 7 L, 7.5 L, 8 L, 8.5 L, 9 L, 9.5 L, or 10 L. In some cases, an internal volume of a container can be about 0.1 L. In some cases, an internal volume of a container can be about 0.5 L. In some cases, an internal volume of a container can be about 1 L. In some cases, an internal volume of a container can be about 5 L. In some cases, an internal volume of a container can be about 10 L.

In some cases, an internal volume of a container can be from about 5 mL to about 10 L. In some cases, an internal volume of a container can be from about 100 mL to about 10 L. In some cases, an internal volume of a container can be from about 0.25 L to about 2 L. In some cases, an internal volume of a container can be from about 1 L to about 10 L. In some cases, an internal volume of a container can be less than about 1 L. In some cases, an internal volume of a container can be more than 1 L.

In some cases, a volume of a solution can be about 5 milliliter (mL), 25 mL, 50 mL, 100 mL, 250 mL, 500 mL, 1 liter (L), 2 L, 3 L, 4 L, 5 L, 6 L, 7 L, 8 L, 9 L, or about 10 L. In some cases, a volume of a solution can be from about 100 mL to about 10 L. In some cases, a volume of a solution can be from about 5 mL to about 10 L. In some cases, a volume of a solution can be from about 0.25 L to about 2 L. In some cases, a volume of a solution can be from about 1 L to about 10 L. In some cases a volume of a solution can be less than about 1 L. In some cases, a volume of a solution can be more than 1 L.

A volume of a solution can be dispensed into a single container. A portion of a volume of a solution can be dispensed into a single container. A volume of a solution can be dispensed into multiple containers, such as two, three, four containers or more. A solution can be dispensed into a container until the dispensed solution volume is equivalent to about 80%, 85%, 90%, 95%, 96%, 97%, 98%, 99% or 100% the internal volume of the container.

The delivery system 50 can allow for the delivery of the prepared solutions into one or more bottles. The delivery system can be configured to permit delivery of the prepared solution into one or more bottles with a predetermined volume. In some cases the bottle volume can be at least about 0.1 liter (L), 0.2 L, 0.3 L, 0.4 L, 0.5 L, 0.6 L, 0.7 L, 0.8 L, 0.9 L, 1.0 L, 1.5 L, 2 L, 2.5 L, 3 L, 3.5 L, 4 L, 4.5 L, 5 L, 5.5 L, 6 L, 6.5 L, 7 L, 7.5 L, 8 L, 8.5 L, 9 L, 9.5 L, or 10 L. The bottle can have a square, round, rectangular, oblong or an amorphous cross section. A plurality of bottles can be lined up for sequential and/or automatic processing of user provided orders. In some cases, two or more bottles in the plurality of bottles can have different volumes. In some cases, two or more bottles in the plurality of bottles can have different shaped cross sections. The delivery system can comprise a sensor configured to detect the volume of the bottle which is being filled with a solution by the bottle handling sub-system. The delivery system can fill a bottle with a detected volume with a correct amount of solution such that the solution fills at least about 50%, 60%, 70%, 80%, 90%, 95%, 99%, 99.9%, or 100% of the volume of the bottle. In some cases a sensor configured to detect the volume of the bottle can comprise a weight sensor. In some cases a sensor configured to detect the volume of the bottle can comprise a pressure sensor. In some cases a sensor configured to detect the volume of the bottle can comprise an optical sensor. In some cases, the sensor can read a marking (e.g., barcode, apriltag) provided on the bottle to determine the volume of the bottle. Occasionally, the sensor may sense the volume depending on the emission, subsequent reflection and absorption (i.e. receipt) of light or sound emitted by the sensor. The sensor may take into account the time that elapses from the emission of light or sound, to the reception of the light or sound respectively. The sensor can comprise and ultrasonic sensor. The sensor can comprise an infrared (IR) sensor. The infrared sensor can detect bottles formed from materials that are different than glass, or have an internal coating that is different than a glass internal coating (e.g. plastic, ceramic, metallic, polymeric, or any combination thereof). One or more sensors can be provided to detect a bottle and/or a volume of a bottle. The one or more sensors can be located above, below, to the side of a bottle. The one or more sensors can be adjacent to a bottle. The delivery system can ensure correct allocation of prepared solutions into the plurality of bottles.

The one or more bottles containing the prepared solutions may be handled by a bottle handling module 80, also referred to as a bottle handling sub-system. The bottle handling sub-system may be configured to move and/or manipulate the one or more bottles of prepared solution such that a user may retrieve the one or more bottles. The bottle handling sub-system can be configured to move and/or manipulate one or more bottles with different volumes. The bottle handling sub-system can be configured to move and/or manipulate one or more bottles with different cross sections. The bottle handling sub-system may move a container vertically, horizontally, diagonally, circularly, or a combination thereof. A bottle handling sub-system may invert a container one or more times. A bottle handling sub-system may move a container at various angles with respect to a holder of the container. A bottle handling sub-system may move a container from a storage area of the system to an area to form a solution. A bottle handling sub-system may operatively connect a container to the automated solution dispenser. A bottle handling sub-system may move a container to a storage area of the system. A bottle handling sub-system may adjust a position of a container, such as a vertical or horizontal adjustment. A user interface, such as the touch screen user interface 60 may be provided to allow users to enter solution orders and perform administrative tasks, including but not limited to user registration, job tracking, prioritization of orders, tracking and/or ordering of solution components. A controller such as an integrated computer 70 can provide direct customer support, automatic process adherence, and/or automatic restocking of solution components. The integrated computer can further communicate with secondary devices, e.g. other laboratory equipment, and/or computers. A secondary computer can obtain and provide data to the integrated computer, e.g. send solution orders, follow solution preparation through collected parameters, obtain queue information, or access any other information available in the integrated computer. The integrated computer can control secondary laboratory equipment and/or follow their use. For example, the integrated computer can send orders to secondary laboratory equipment for operation through a device driver and/or collect equipment status information, data, or any other available information from the laboratory equipment. Connections to and from secondary laboratory equipment and secondary computers can be achieved using connectivity solutions described elsewhere in this application. Device drivers and/or other software that is used to interact with secondary laboratory devices may be provided by a different vendor/user than the automated solution dispenser and/or the controllers described herein.

Figure 1B:
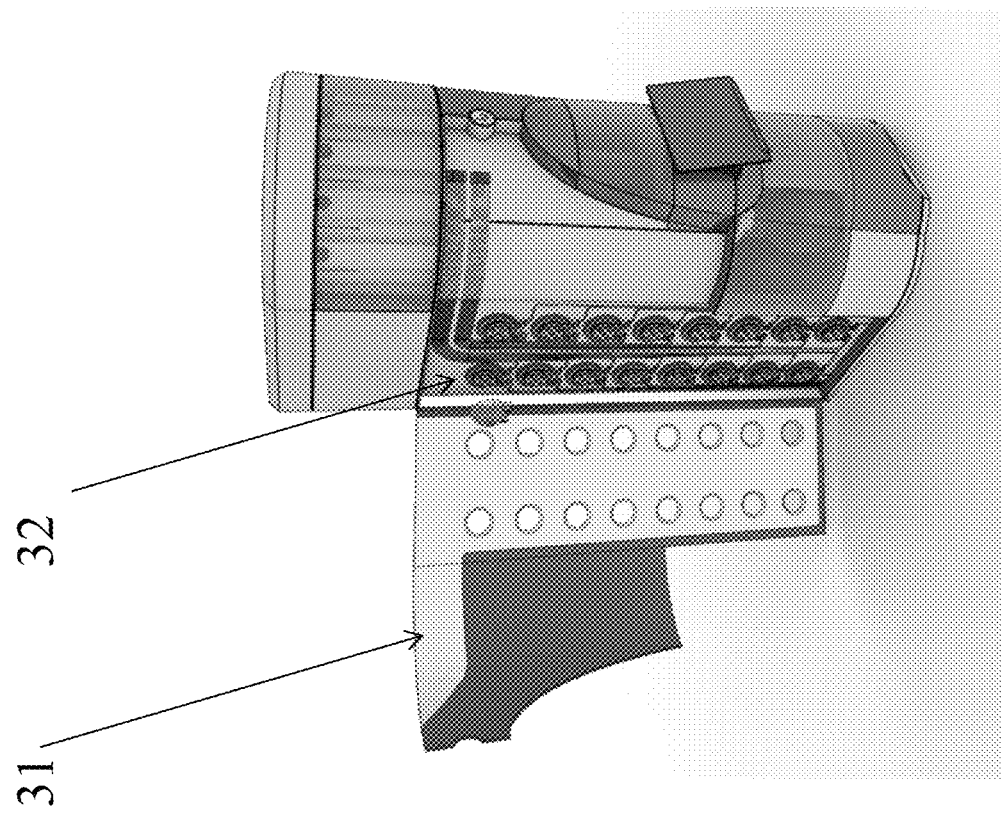
FIG. 1B depicts an embodiment of the liquid handling system.

FIG. 1B, shows the liquid handling module with access door 31 open revealing one or more peristaltic pumps 32 used by the liquid handling module to facilitate transfer and dosing of liquids within the automated solution dispenser system.

FIG. 1C, shows an access door for the solids handling system in the open position revealing a loading port 13 wherein a user may load or unload solids containers 12 into the solid storage rack 11 of the solids handling system 10. Here a solids container 12 is shown being removed from the automated solution dispenser system. In any of the embodiments described herein the solids storage rack may comprise a conveyor line of solids containers or a turntable (solids turntable) wherein there is a mechanical apparatus such as a roller conveyor, a conveyor belt, an automatic arm or hand, a robotic arm or hand, mechanical arm or hand, programmable arm or hand, or other of automatically moving and/or manipulating the solids containers to different positions throughout the solids handling system.

FIG. 1D shows the area that houses central mixing chamber 40. In some embodiments of the present disclosure the Central Mixing Chamber (CMC) 40 may be movable into a maintenance position which facilitates easy access to the CMC 40. In FIG. 1D, a module of the present disclosure containing the CMC is shown moved into a maintenance position.

FIG. 1E shows the bottle handling sub-system 80. In some embodiments the bottle handling sub-system is housed in a slidable module that allows the bottle handling sub-system to move with respect to the rest of the automated solution dispenser to facilitate easy access for maintenance. The bottle handling sub-system is shown in the maintenance positions 81. FIG. 1E also shows the bottle handling sub-system in a normal operating position with an access door open, revealing a removal port where a user may remove an individual bottle 82 from the bottle handling sub-system 80.

FIG. 1F, shows a core support structure 90, that houses and integrates the various modules, systems, or sensors of the automated solution dispenser, such as the solid handling module, liquid handling module, user interfaces, controller (i.e., integrated computer), CMC, delivery system, at bottle handling sub-system, a cleaning system (also referred to as Flush Verification System), and various sensors. Any other module, system, or sensor described in this application may also be housed in the core support structure. Casings 91 may cover the various modules, systems, or sensors integrated into the core support structure.

FIG. 1G, shows an area in the core support structure that may accommodate an integrated water purification system 95.

Figure 2A:
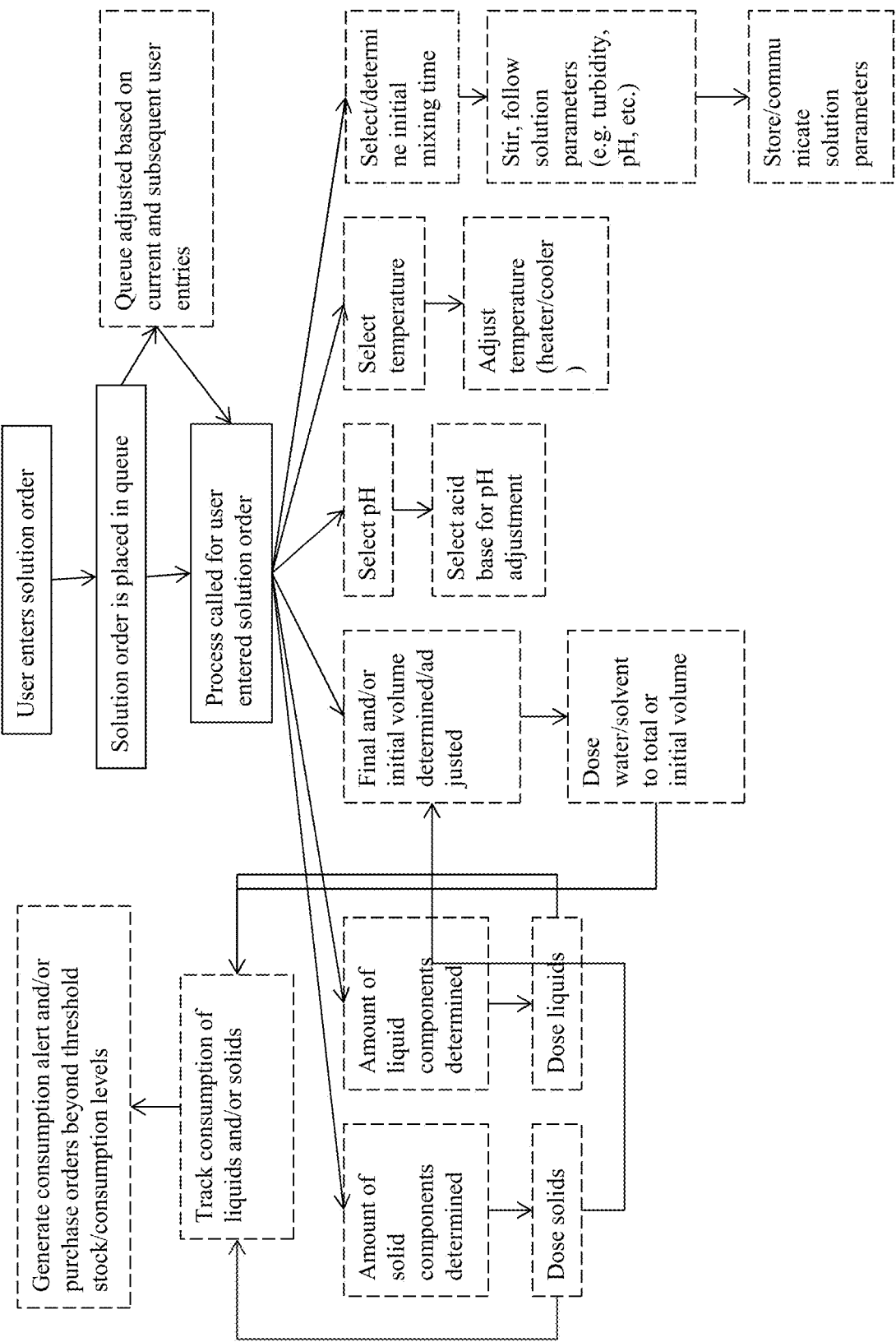

FIG. 2A illustrates exemplary workflows for the automated solution dispenser. Accordingly, a solution order is entered by a user. The solution order is placed in a queue of solution orders. The placement of the solution order in the queue can be adjusted based on various criteria. For example, orders can be prioritized according to user instructions and/or user's priority settings allowing priority to certain users. The user order can be called from the queue to process the order. The solution orders can be entered into the queue with a time stamp and the order can be scheduled to be executed at the requested time interval in the time stamp. The time stamp can comprise a time point, for example 7:30 am PST every Monday, for starting or finishing the solution order. Alternatively, the time stamp can comprise a time interval with start and end points defining acceptable times for the completion of the solution. In another implementation, the time stamp may comprise a time point along with an allowance range, for example 7:30 am PST±30 min, defining an acceptable time interval for the solution preparation. A number of parameters can be pre-determined for the solution preparation, including but not limited to amounts of solid components, amounts of liquid components, total/initial volume, or mixing time. An suitable initial pH value is selected which may or may not be the same as the final pH value. A suitable temperature for the solution preparation can be selected. The selected temperature can be adjusted with heater/cooler components described herein or any other suitable heater/cooler components. The temperature can be measured once, multiple times and can be monitored over time or as a function of other solution parameters as desired.

Solution components that are consumed can be tracked locally or remotely by communicating the consumed amounts to a remote computer, for example via a computer network. The local controller, a remote computer, or combination can generate alerts for consumable levels and/or for purchase orders. In some embodiments, consumables are automatically ordered and shipped based on tracked or historical consumption rates.

The liquid handling systems and solid handling systems are capable of handling and dosing liquids and solids respectively. In some embodiments, consumable tracking can be performed after dosing to obtain an accurate measure of actual consumed amounts.

In some embodiments, water and/or solvents arc added to an initial level and further supplemented to reach an intermediate or final amount during solution preparation. Liquids used in solution preparation can be passed through a filtration system before and/or after solution preparation. In some embodiments, solutions can be degassed after dispensing into a suitable container.

FIG. 2B illustrates exemplary configurations for hardware components and associated systems. In some cases, water mains 205 may be connected to a water purification module such as the integrated water purification system 95 or an external water purification system such as an industry standard microfiltration system or other water purification system. The water from the water mains may be directed by the flush (also referred to as flush verification system) and dispensing system. The flush verification system and dispensing system may be used to run cleaning cycles or may be used to create solutions in the CMC 40. In some cases, water from the water mains 205, water from a water purification system 95, or a combination thereof may be directed to the liquid handling system 30. Liquid handling system 30, accepts liquid components of the solution to be prepared by the automated solution dispenser. Such liquid components 230 may comprise water, solvents, acids, bases, or any liquid reagent required to prepare a solution ordered by the user. The liquid components 230 may be stored internally within the automated solution dispenser, externally in storage tanks, or may be drawn from an external continuous supply.

The liquid handling system, dispensing system and, flush verification system (FVS) are all fluidly connected to the central mixing chamber to facilitate, solution creation in the CMC, cleaning of the CMC and downstream system components, and dispensing the prepared solution. The FVS 230 and dispensing system (delivery system) 50 may direct cleaning fluid and prepared solution to a desired station such as a drain for cleaning fluid or the bottle handling sub-system 80 for bottling of the prepared solution. The CMC 40 is also connected via a controllable solids inlet to the Solid handling system 10 which stores, handles, doses, and dispenses solid components for preparing the user specific solution. The solid components 210, also referred to as solid reagents, may be stored in solids containers as described elsewhere. Solutions prepared from liquid and solid components in the CMC are passed to the dispensing system, via fluid connections. The dispensing system then transfers the prepared solution to an appropriate bottle in the bottle handling sub-system to form the complete solution. The bottle handling sub-system 80 manages the bottled prepared solution and may label the bottle for tracking and usage. The integrated controller 70, along with the core support structure 90, the casing 91, the supporting electronics such as sensors, computer hardware, logic controllers and user interfaces facilitates the coordination of the different hardware modules in creating the complete solution 250.

Figure 3:
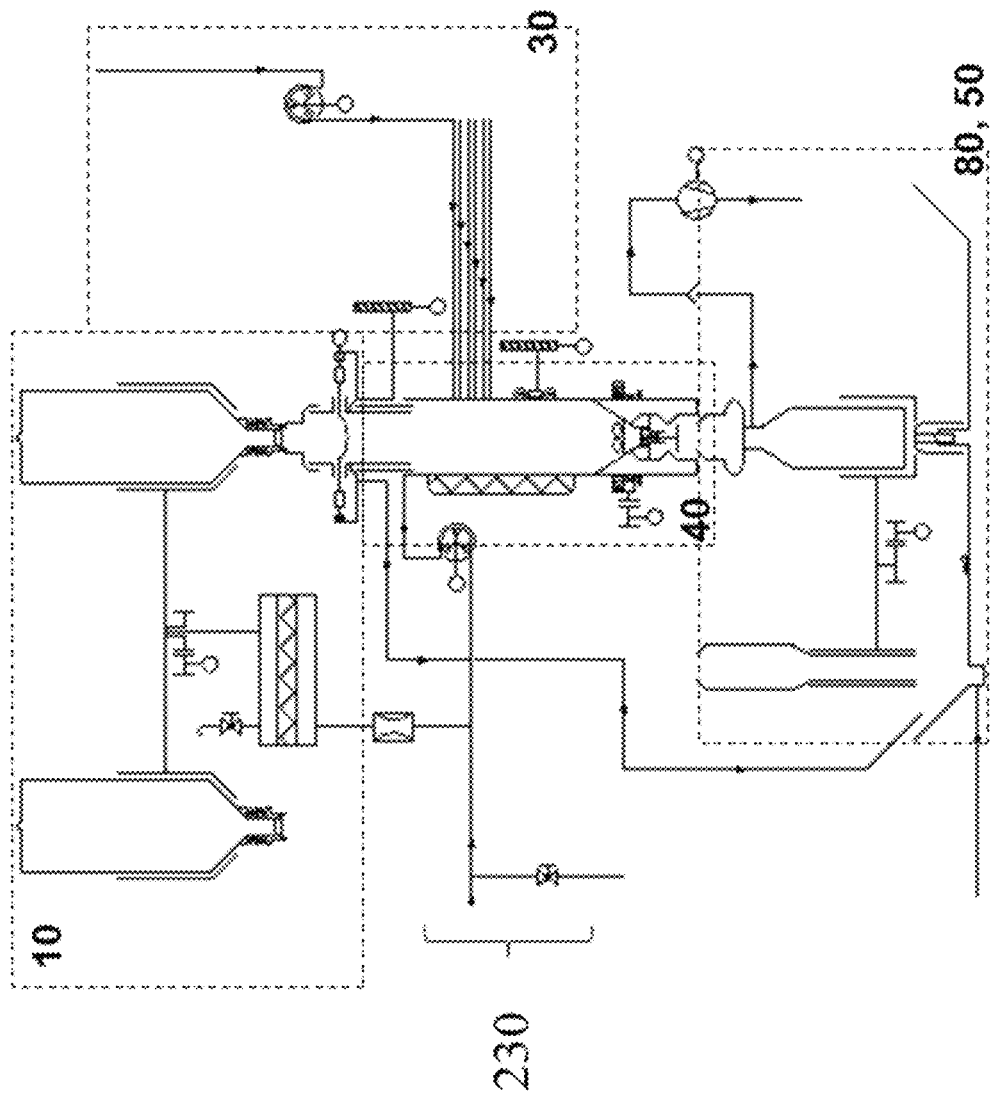
FIG. 3 illustrates an overview of an automated solution dispenser according to some embodiments of the present disclosure.

FIG. 3 illustrates an overview of an automated solution dispenser according to some embodiments of the present disclosure. Accordingly, a CMC 40 collects and holds the dispensed liquids and solids, mixes them, adjusts the pH value of the solution with help of the Liquid Handling System (LHS) 30 and/or Solid Handling System (SHS) 10, and/or adjusts the temperature of the solution according to the user's specification. The resulting solution can be discharged. A Flush and Verification System (FVS) 230 may be integrated to allow the cleaning of the CMC, for example in preparation for the next solution. A variety of Bottle Handling Sub-Systems (BHS) 80 may be used to supply and/or correctly position an empty bottle or other suitable container for discharge from the CMC. Details of the subsystems of the automated solution dispenser are described in further detail herein.

1. Solid Handling

Solid handling is already a major hurdle in automated solution preparation for powders, but solids with coarser nature, such as clumpy powders or crystalline solids provide particular difficulties in solid handling. In various embodiments, the disclosure provides a solution to this difficult problem providing an instrument that is capable of handling solids of all natures, including powder, clumpy powder and crystalline. The automated solid dispensers described herein can dose solids in batch mode. Batches of various volumes can be handled, including, for example, 25 mL, 50 mL, 100 mL, 250 mL, 500 mL, 1 L, 2 L, 5 L, 10 L or more. Solid dosing may be adjusted to address the requirements of various solution volumes. Biological batch solutions require a wide range of solid amounts to be measured, at the same time requiring high precision. In various embodiments, the automated solution dispensers described herein are capable of measuring solids of various physical properties of a wide range of amounts, such as 1-10 microgram (µg), 2-20 µg, 3-30 µg, 5-50 µg, 10-100 µg, 50-500 µg, 250-1000 µg, 1-10 milligram (mg), 2-20 mg, 3-30 mg, 5-50 mg, 10-100 mg, 50-500 mg, 250-1000 mg, 1000-15000 mg, 15000-50000 mg, or any other range having any of these values as end points, e.g. 2-500 µg, 10 µg-50 mg, etc. Automated solution dispensers according various embodiments are designed with high precision in solid handling. Thus, in some embodiments, the automated solution dispensers are capable of measuring solids with 5%, 3%, 2%, 1%, 0.5%, 0.1%, 0.05%, 0.01%, 0.005%, or higher precision. In some cases, solids are measured with less than 5% precision. In some cases, solids are measured with less than 1% precision. In some cases, solids are measured with less than 0.05% precision. In some cases, solids are measured with less than 0.01% precision. In some cases, solids are measured with less than 0.005% precision.

Dosing devices according to various embodiments are particularly suitable for aliquoting from a collection of chemical compounds or for fractionation from storage flasks. Automated solution dispensers are equipped to be able to handle powders or small solids of very different grain sizes and different appearances, for example talc, lactose, cornstarch, or sand. In many cases, solids of powder nature may comprise powders or small solids, such as those with a grain size smaller than the thread or the radius of a dosing screw described herein.

In many embodiments, the disclosure relates to the use of a Solid Handling System (SHS). The SHS can be utilized to accurately dose chemicals in various solid forms, e.g. loose solid/powder forms or crystalline forms. Solids often need to be specially handled for various reasons, including industrial scale packing in specific containers. Solids further present particular challenges related to their accurate weighing, aliquoting, solubility, which may depend on a number of factors including but not limited to temperature, pH, solvent, additional reagents mixing method and time. The solution preparation protocols can be designed to account for these variables. For example, a solid can be solubilized at a favorable pH and/or temperature before switching the solution to the desired and/or final values. Additional solubility impeding reagents can be only added subsequent to the solubilization of a limited solubility solid. Information regarding maximum solubility levels can be stored for a wide range of reagents in various solvents, and at various pH and temperature values. Solution preparation protocols can take into account appropriate solvent levels in accordance with the solid's solubility at present conditions. The solubilization can be monitored, for example by following turbidity of the solution, and subsequent steps, such as switching to less favorable conditions for solubility can be timed upon sufficient solubilization of the solid. Various solution preparation parameters, such as turbidity, connectivity, pH, temperature, can be collected and can be assessed over time. Thus, optimal time intervals for various steps in the solution preparation protocols can be refined from collected data during solution preparation. Key information regarding the behavior of a given reagent in a solution can be linked to the reagent and can be stored either locally or remotely.

In various embodiments, a controllable solids port is operably linked to the solution dispenser. The solids port can enable the automation of the solution creation. In some embodiments, some or all types of solids, e.g. crystalline, loose powder, clumpy powder etc., are handled without user intervention. Difficulties involving the manipulation, transfer and weighing of solids of sticky, clumpy, crystalline, or otherwise coarse solids can be resolved according to the methods and systems described herein. For example, a dosing screw can facilitate removal of a sticky solid from the dosing mechanism A lumen, such as tubing may be shaped to prevent dispensed solids from attaching to an inner surface of the tube and/or be electrostatically charged or coated with a non-stick material to repel dispensed solids. Proper transfer of solids can play a very important role in the accuracy of the total amount of solids in the prepared solution. Systems and methods of the present disclosure described herein comprise measures to reduce reagent losses in transfer and increase the accuracy of the composition of the prepared solution.

The controllable solids port can comprise a solids dispensing system. The solids dispensing system can engage with a solids dosing mechanism for controllably dispensing a dosed amount of a solid from a solid source. In some embodiments, the solids dispensing system comprises a dosing mechanism driver. The dosing mechanism driver can be in moveable configuration in and out of engagement with the solids dosing mechanism. When engaged, the solids dosing mechanism can be designed to be driven to dispense a dosed amount of the solid by the dosing mechanism driver.

The solution dispensing system may comprise a moveable tube extending from an inlet of the mixing chamber towards the solid dosing mechanism. An inlet of the tube can be configured for receiving solids dispensed from a solid source. An outlet coupled to the inlet of the mixing chamber can be configured to allow solids received from the solid source to pass therethrough. The moveable tube can be moveable in and out of engagement with the solids dosing mechanism. When engaged, the tube may form a path between the solid dispensing mechanism and the mixing chamber through which solids are allowed pass. The tube may be shaped to prevent dispensed solids from attaching to an inner surface of the tube. A wall of the tube may be electrostatically charged or coated with a non-stick material to repel dispensed solids. A dedicated water system can be added to clean the solids off the surfaces.

Figure 29:
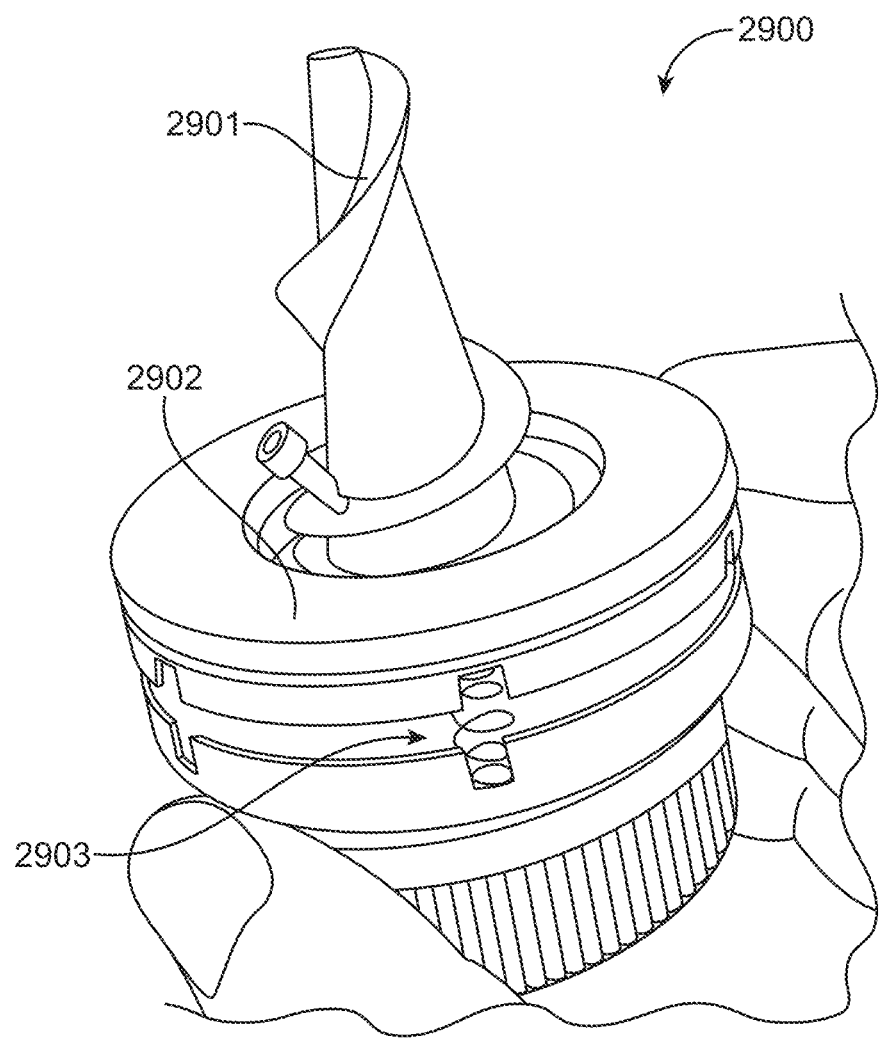
FIG. 29 shows a dosing screw of a solid handling system.
Figure 30:
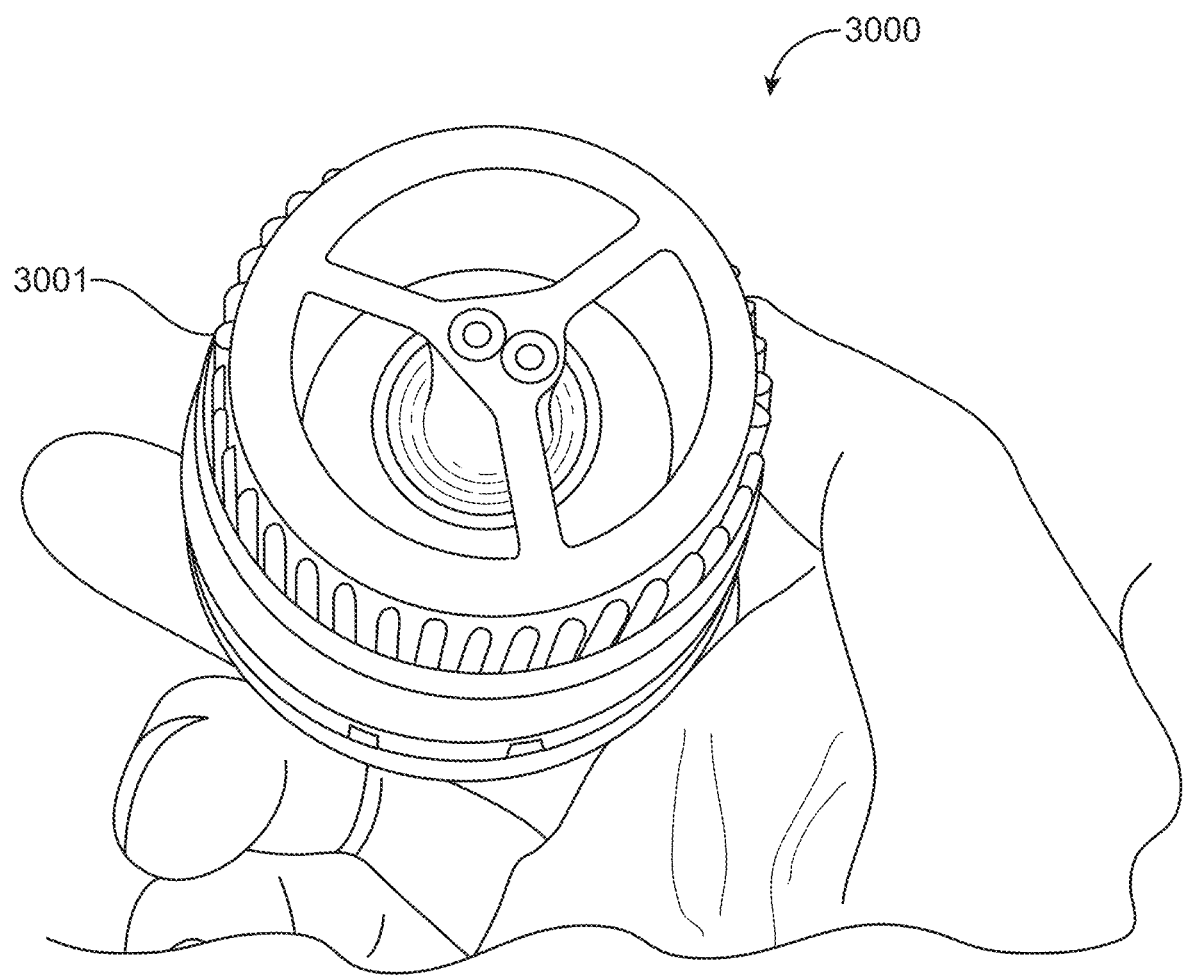
FIG. 30 shows a view of the dosing screw opposite the threaded mechanism.

In some embodiments, the solids dosing mechanism comprises one or more inlets for receiving a solid. In some embodiments, the solids dosing mechanism comprises one or more dosing screws. The dosing screw may be rotatable about its longitudinal axis for carrying the received solid. In some embodiments, the solids dosing mechanism comprises one or more rotatable bases coupled to one or more dosing screws. The rotatable base may be rotatable in cooperation with the dosing screw. FIG. 29 shows one side of a dosing head 2900 that can be rotated to provide a solid to the solid dispensing system. The dosing screw can crunch the solid to break up clumps. The dosing screw can comprise a threaded mechanism 2901 configured to move solid material towards a solution when the dosing screw is turned (e.g., rotated). The dosing screw can deliver a solid at a predeterminate rate based on the rotation rate of the screw. The dosing screw can reduce flow disturbances in the flow of the solid such that a consistent flow of solid material is provided to the solid dispensing system. In some cases, the dosing screw can be sealed such that water vapor, gas, or other contaminants are separated from the solid delivery system. This can be achieved via pressing an o-ring 2902, pressing a spring 2903, or a combination thereof. FIG. 30 shows the other side of the dosing screw 3000 opposite the threaded crushing mechanism. In some cases, the dosing screw can crush, break, pulverize, grind, mill, squash, press, mash, mince, macerate a solid. The dosing screw can crush the solid prior to the automated solution dispenser dispensing the solid into the mixing chamber. The dosing screw may crush particles of a solid that are greater than about 1 centimeter (cm), 5 cm, 10 cm, 50 cm, 100 cm, 250 cm, 500 cm in diameter. A dosing screw may crush particles of a solid that are greater than about 1 cm in diameter. A dosing screw may crush particles of a solid that are greater than about 5 cm in diameter. A dosing screw may crush particles of a solid that are greater than about 10 cm in diameter. A dosing screw may crush particles of a solid that are greater than about 50 cm in diameter. A dosing screw may crush particles of a solid that are greater than about 100 cm in diameter. A dosing screw may crush particles of a solid that are greater than about 250 cm in diameter. The dosing screw may crush particles such that individual solid particles dispensed into the mixing chamber are less than about 0.5 cm, 1 cm, 5 cm, 10 cm, 50 cm in diameter. A dosing screw may crush particles such that individual solid particles dispensed into the mixing chamber are less than about 0.5 cm in diameter. A dosing screw may crush particles such that individual solid particles dispensed into the mixing chamber are less than about 1 cm in diameter. A dosing screw may crush particles such that individual solid particles dispensed into the mixing chamber are less than about 5 cm in diameter. A dosing screw may crush particles such that individual solid particles dispensed into the mixing chamber are less than about 10 cm in diameter. In some cases, as shown in FIG. 30, an o-ring seal 3001 may be attached to the exterior of the dosing screw, 3000 to further allow isolation of the interior environment within the bottle, from the ambient exterior environment. In some embodiments, the solids dosing mechanism comprises one or more outlets for receiving the carried solids from the dosing screw. When rotated about its longitudinal axis, the dosing screw can be configured to carry a received solid from the inlet to the outlet. The dosing screw and rotatable base can be configured to be movable along the longitudinal axis of the dosing screw between an open position in which the outlet is open, and a closed position in which the outlet is closed. The dosing screw and rotatable base can be configured to be coupled to a gear gate for driving the dosing screw and rotatable base. The gear gate can be drivable by the dosing mechanism driver.

In some embodiments, the dosing screw and the gear gate are directly coupled. A conical surface on the screw can mate with a matching surface on an adaptor part, which can seal the solid bottle. The gear gate can be engaged and pushed up facilitating opening.

The dosing screw and rotatable base may be designed to be biased in the closed position. Such a configuration enables solid sources comprising the dosing mechanism to be removed from the system without solids contained within a solid source spilling out. In some embodiments, the controller is configured to determine a weight of a dosed amount of solid dispensed from a solid source dependent on a time and rate at which the solid dosing mechanism is driven. In some cases, when too much (i.e. surplus) or too little (i.e. shortfall) of a predetermined amount of solid is dispensed, the system can automatically recalibrate a solution order by increasing or decreasing other components to be added to the solution such that a correct ratio of components is maintained (such as a ratio that may be specified in a solution order). The solid source may be a container containing a solid to be dispensed. In some embodiments, the solid dosing mechanism is designed to couple with the container. The automated solution dispenser may comprise one or more containers. The container may be designed to couple with a solid dosing mechanism. The one or more containers may be controllably moveable between a dispensing position in which a container is aligned with the controllable inlet port to enable dispensing of a contained solid, and a storage position in which the container is not aligned with the controllable inlet port. In some embodiments, the one or more containers are disposed on a turntable having an axis of rotation such that the containers are movable between the dispensing and storage positions. For example, a conveyor belt can move containers between various positions.

In various embodiments, the input sensor comprises a weighing device configured to determine a loss in weight of the container upon dispensing of a solid into the mixing chamber from the container, and wherein the controller is configured to controllably supply the solid to the mixing chamber until a target weight of the solid is reached based on the determined loss in weight of the container. In some embodiments, the input sensor comprises a solids weighing device for receiving, weighing and dispensing a dispensed solid from the solids dosing mechanism into the mixing chamber. The solids weighing device may comprise a moveable receptacle for receiving the dispensed solid, a weighing device coupled to the moveable receptacle for weighing the dispensed solid, and/or a dispensing mechanism for dispensing the weighed solid into the mixing chamber. In some embodiments, the weighing device comprises a load cell or a force compensated electromagnet.

The dispensing mechanism may be configured to move the receptacle to a receiving position when receiving a solid to be weighed from the solid dosing mechanism. In some embodiments, the dispensing mechanism is configured to move the receptacle to a dispense position when the weighed solid is to be dispensed into the mixing chamber.

In some embodiments, the input sensor comprises a weighing device configured to determine a gain in weight of the mixing chamber upon receipt of a solid into the mixing chamber from a solid source. Accordingly, the controller can be configured to controllably supply the solid to the mixing chamber until a target weight of the solid is reached based on the determined gain in weight of the mixing chamber.

In some embodiments, the input sensor comprises a solution sensor for sensing one or more characteristics of the solution. Accordingly, the controller can be configured to controllably supply the solid to the mixing chamber until a target characteristic of the solution is detected.

Figure 4:
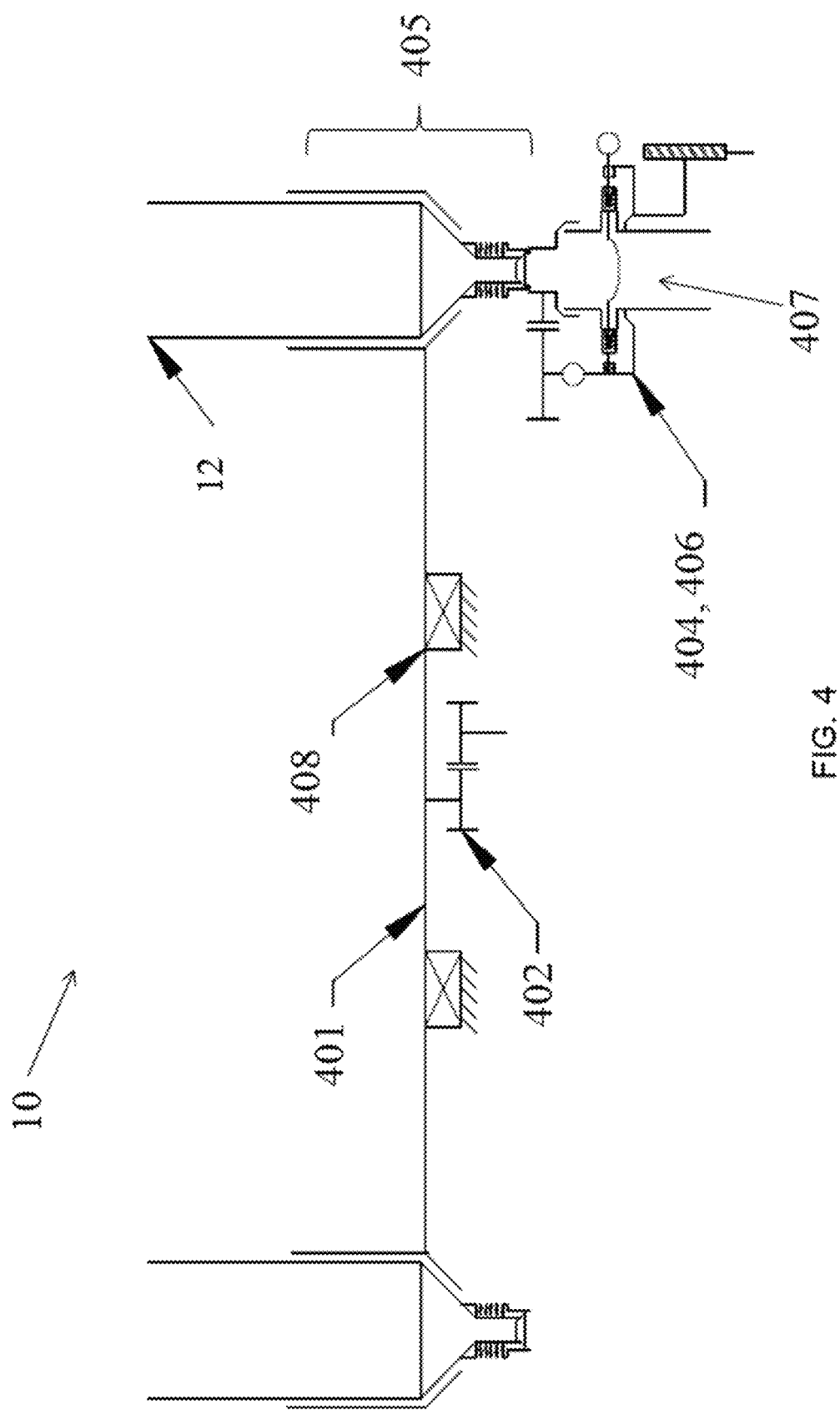
FIG. 4 illustrates a solids handling system according to some embodiments of the present disclosure.

Referring to FIG. 4, an embodiment of a SHS 10 is illustrated, comprising a Solids Turn-Table (STT) or equivalent 401, a table driving mechanism 402, a solids container 12, a Solids Dosing Mechanism (SDM) 405, a Solid Delivery System (SDS) 404, a Dosing Mechanism Driver (DMD) 406, a Solids Weighing Scale (SWS) 407 and support bearings 408. Accordingly, solids of various forms can be handled, including solids in crystalline form, loose powder and clumpy powder forms. The solids can be held in the solid container 12. The solids container can be a custom/purpose made container or an original solids container. Specialized containers can be supplied for use with the automated solution dispenser. In some embodiments, reagents can be purchased and delivered in specialized containers for the automated solution dispenser. Each container can have a SDM 405 mounted on the bottom of the container. The containers can be located on a STT 401 or equivalent device that enables the desired solids container to be aligned with a desired central mixing chamber's (CMC) solids inlet. Once the container is in position, the SDS 404 can rise up and engage the SDM 405. In the process, the DMD 406 can be connected to the SDM 405. The DMD 406 can drive the SDM 405 and dose the solids in controlled amounts. The solids can be dispensed onto the SWS 407, which can be located directly underneath the SDM. Once the right amount (mass) is dispensed, the SWS can deliver the solids into the CMC.

The SWS can be incorporated into the various aspects of the solid handling. For example it can be designed to measure the decreasing weight of the solid's container.

Figure 5:
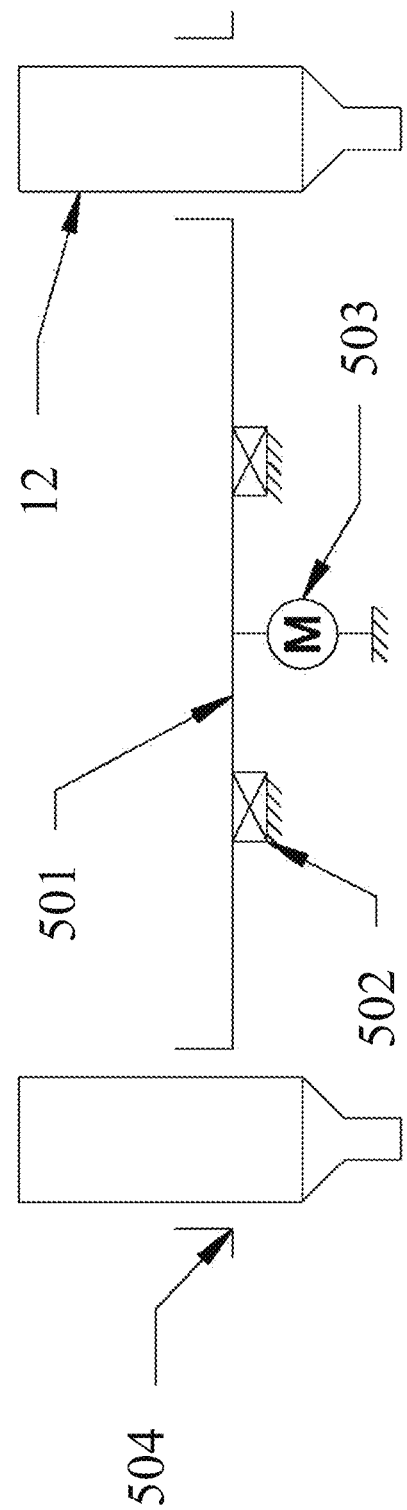
FIG. 5 illustrates a turn table for the solid handling system according to some embodiments of the present disclosure.
Figure 6:
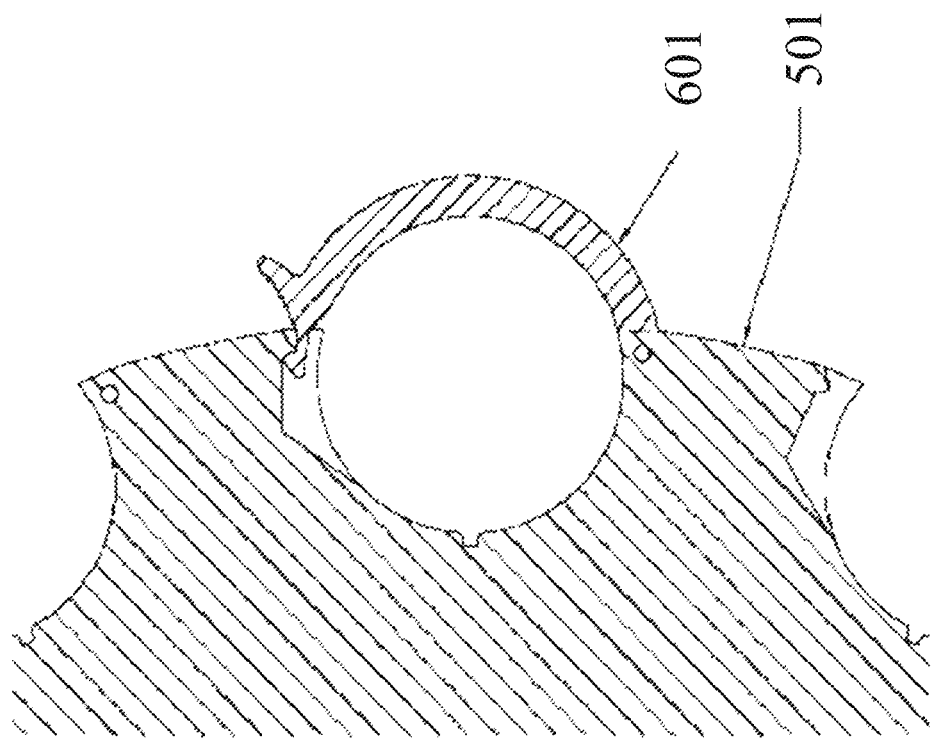
FIG. 6 illustrates the turn table of FIG. 8 in more detail.

Referring to FIGS. 5 and 6, an embodiment of the STT for the SHS is illustrated. The STT can be a turn table 501 with the containers 12 attached at the circumference. The containers 12 can be held in place with a clip 601, slotted in place 504, suspended of the table, or they can be attached using any other suitable method used in the art. The turn table 501 can supported on thrust bearing 502 or equivalent. The turn table 501 can be rotated by a motor 503, which can be mounted on the central axis.

In some embodiments, a conveyor system is implemented to fit more bottles in the same foot print area. The turn table can be also be driven indirectly by a belt system. Referring to FIG. 7A, an embodiment of the SDM is illustrated. Accordingly, the SDM comprises an adapter piece 702. The adapter piece can be designed to screw on to the container 12 that holds the solids. The rotating base 703 can be designed to fit within the adapter 702. The base can be configured to hold the dosing screw 704. The rotating base 703 with the dosing screw 704 can be designed to be able to freely rotate around the adaptor. The gear gate 706 can be designed with a slotted groove that fits on the rotating base 703, allowing the gear gate to move up and down. The springs 705 can be configured to hold the gear gate in the closed position (for example downward). The gear gate can be opened when the SDS engages the SDM. The gear gate 706 has a set of gears on the outer diameter for the DMD with and through which rotational drive and control can be provided. FIG. 7B illustrates another embodiment of the SDM with parts 701-706. Accordingly, the dosing screw and the gear gate directly coupled. A conical surface on the screw can mate with a matching surface on the adaptor part, which can seal the solid bottle. It can be opened when the engage the gear gate is engaged and pushed up. FIG. 7B illustrates an SDM outlet 707.

The gear gate 706 may serve various purposes including but not limited to providing rotational drive and control to the rotating base 703 and the dosing screw 704 and closing the container and internal workings of the SDM when the container is not engaged, thus allowing the container to be stored with solids in any position without leaking any solids.

When the dosing screw 704 is rotating, the exposed screw may be configured to grab onto the solids and carry the solid into the closed section of the screw. Once solid reaches the bottom of the screw, it can be free to fall out of the screw and out through the open gate. If the solid sticks to the screw, the motion of the solids above may push the stuck solid out. In some embodiments, a multi-variable flow-through screw that can be selected by controlling the height of the gear gate is incorporated.

Figure 8A:
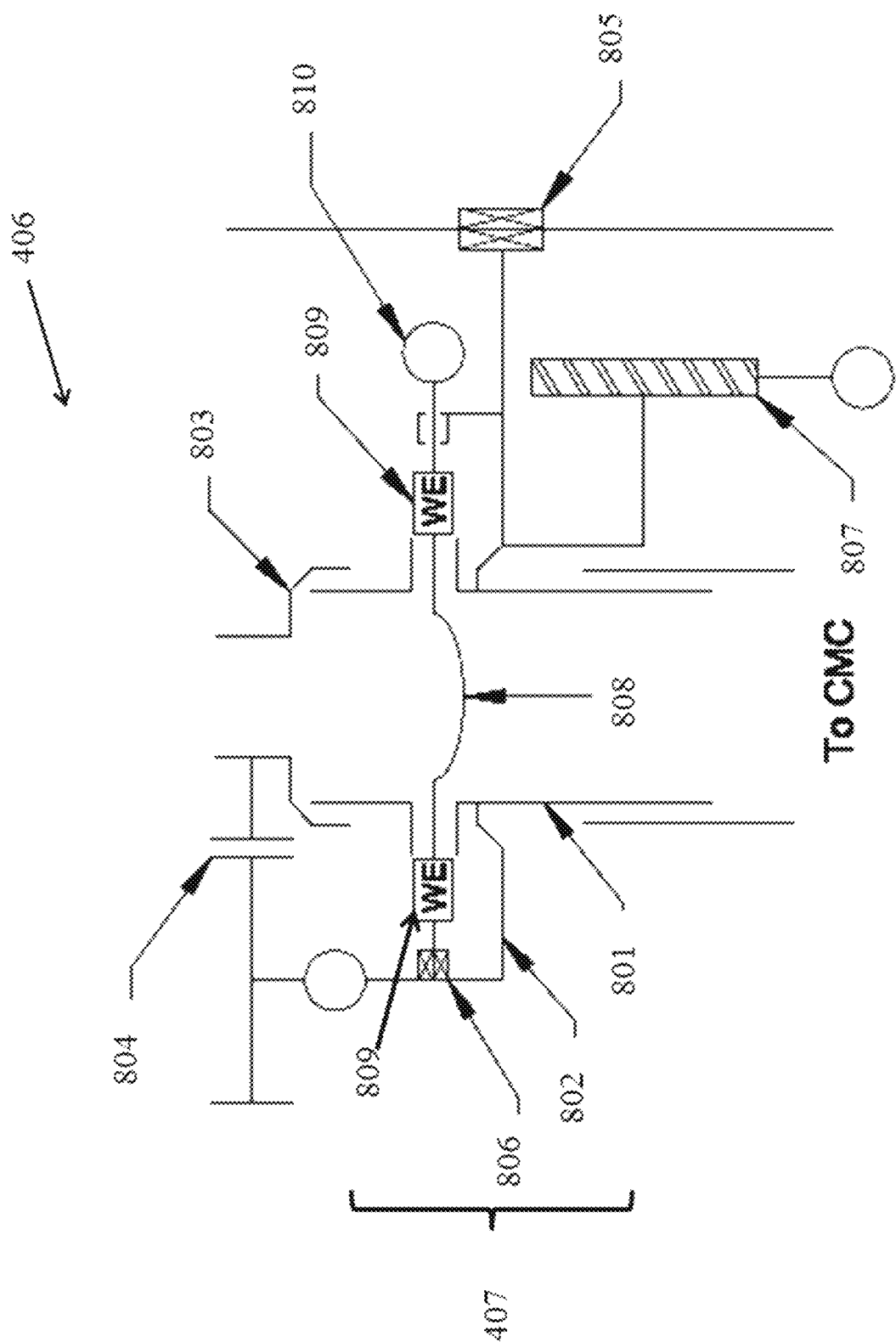

Referring to FIGS. 8A and 8B, the DMD 406 may comprise a delivery tube 801, which can house the SWS 407. A gear cog 803 can be placed on top of the delivery tube. The gear cog 803 can be positioned to mate with the gear gate 706 and the gears can be designed to be self-aligning. The gear cog can be driven by a motor (e.g. stepper, DC, etc.) via a gear, belt or equivalent. A lead screw can be mounted on the tube platform 802 can drive the tube up and down. A linear guide (with bearing) 805 can be utilized to ensure that assembly moves up and down smoothly. Alternatively, the threaded section of the tube 815 can form part of the lifting system. A lead gear 816 can engage the tube threads 815 and can be driven by a driving cog under the drive of a motor 817. This driving cog can rotate the lead gear 816, which in turn can drive the tube 801 up or down via the tube threads 815. A solid dosing gear/belt connection 804 may be formed between the solid dosing actuator 814 and the solid dosing gear 813. A solid dosing gear 813 may engage one or more solid container dosing heads and may direct dosing of one or more solids employing the solid dosing actuator 814. A linear actuator 807 may drive the solid engagement function.

In some embodiments, the SWS comprises a weight dish 808, which is attached to one or more weight sensors 809 such as one on each side, for example one being mounted on bearing 806, the other being mounted on a motor 810. The motor 810 may be configured to rotate the whole SWS, dispensing the solid into the CMC. In some embodiments, the weight sensor can be housed in a rotating case 820. The casing can have a rotating axis 821, which can rotate the weight dish, sensor and case. This rotation can be driven by a motor, solenoid or equivalent. The axis 821 can be left hollow for the weight sensor 809 wires. A barrier 822 can be placed to protect the sensor from liquid and solid ingress on a suitable surface. The barrier can be designed to not restrict the movement of the dish or hold any load.

Solids might have the tendency to attach themselves to the tube 801 walls. The tube shape can be designed to eliminate or minimize this issue. Other solutions include, but are not limited to lining the tube with a passive/active electrostatic barrier, non-stick paint or material, etc. In various embodiments, the inside of the tube 801 up to and including the SWS can be cleaned by the spray nozzle during a cleaning cycle. Tube designs may consider solid attachment tendencies and ease of cleaning together.

In some embodiments, other linear actuator systems can be used instead of the lead screw, to raise the platform.

Figure 9:
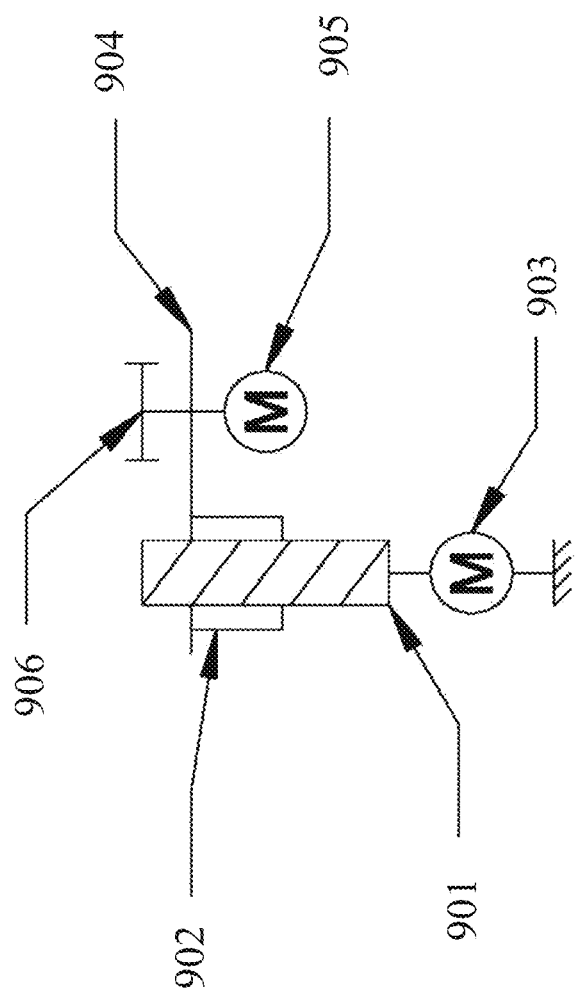
FIG. 9 illustrates an example solids platform and dosing driver according to some embodiments of the present disclosure.

FIG. 9 illustrates the DMD according to some embodiments of the present disclosure. Accordingly, the DMD consists of a gear cog 906 mounted on a motor 905. The gear cog 906 can be designed to mate with the gear gate 706. The gears can be designed to be self-aligning. The DMD can be mounted on the raising platform 904 of the SDS. The platform 904 can be raised by a lead screw assembly. This assembly may consist of a screw nut 902 attached to the platform 904, which is set on the lead screw 901. The lead screw can be rotated by the motor 903 that either rises or lowers the platform, which in turn either engages or disengages the SDM.

Figure 10A:
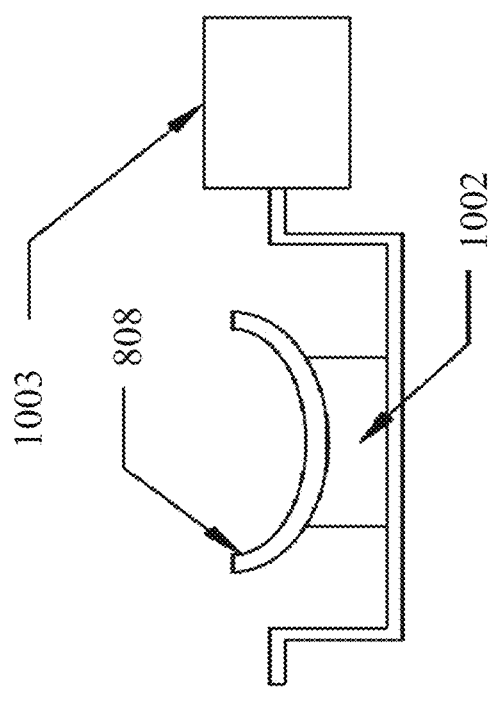
FIG. 10A and FIG. 10B illustrate example weights scale according to some embodiments of the present disclosure.
Figure 10B:
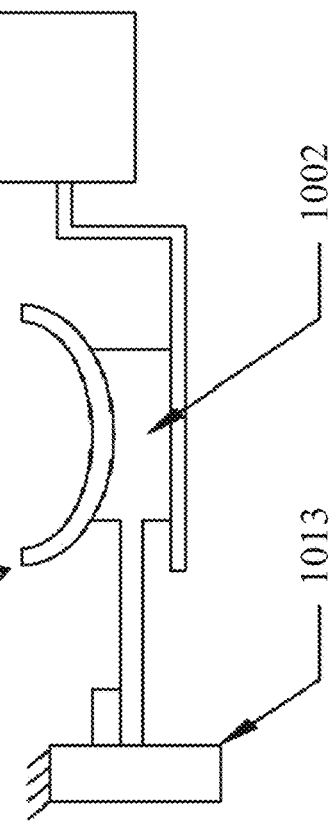

Referring to FIG. 10A and FIG. 10B, accurate dosing and application can be achieved using the SWS 407, in another example. The SWS can measure solids dosed from a selected container 12. In various embodiments, the SWS consists weighting dish 808, a scales mechanism 1002, 1013 (for example a load cell or force compensated electromagnet) and a flipping mechanism 1003. The flipping mechanism 1003 can be either independent (dedicated driver) or the dependent 1013 (a set of guides or mechanical linkages) of the raising platform 904. The SWS can move up and down, for example along the axis of the CMC's solid's inlet, and in the process can rotate so that the weighting dish 808 is facing upwards to receive the solids from the SDM at the up position. The weight dish 808 may rotate when it moves down allowing the solids in the weighing dish to be deposited into the CMC. Subsequently, the dish may be able to close the CMC's solid inlet.

Figure 11:
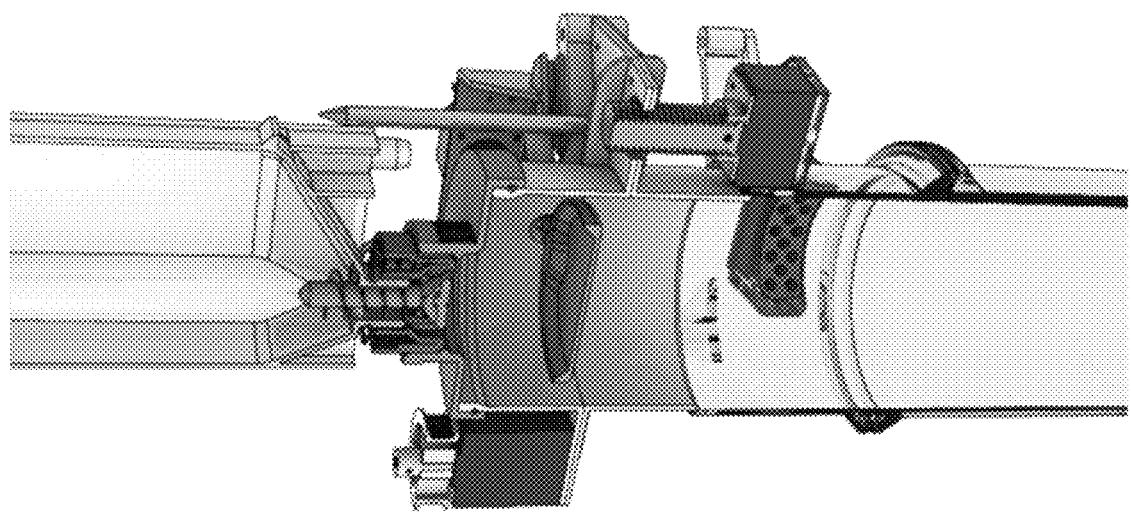
FIG. 11 illustrates portions of the solids handling system of an automated solution dispenser according to an embodiment of the present disclosure.

Surfaces of the present disclosure may comprise electrostatically charged surfaces or non-stick coatings adapted to prevent solid and liquid solution components from sticking to various surfaces. Such electrostatically charged surfaces and/or non-stick coatings are especially useful for the Solid Handling System and the Central Mixing Chamber, any portion of which may comprise such electrostatically charged surfaces and/or non-stick coatings. For example, portions of the SDS, SDM, controllable solids port, SWS, delivery tube, any weighing device or any sensor, the CMC, or LHS may comprise electrostatically charged surfaces or non-stick coatings. This list of examples is not intended to be limiting FIGS. 11 and 12 illustrate the solids handling components of an automated solution dispenser according to an embodiment of the present disclosure. As mentioned above, the automated solution dispensers according to various embodiments are designed to dose multiple solids with varying properties, such as crystalline, fine powder, clumpy powder, etc. In some embodiments, the solids are loaded into a bottle that can be mounted on a carousel or turntable. The carousel or turntable can be replaced by or used in conjunction with a conveyor system. Bottles can be equipped with a dosing screw. Dosing screws, according to various embodiments, may vary according to the type of the solids. Dosing screw properties may depend on dosing requirements and solid properties. For example, the dosing screw's surface properties, pitch and/or radius can be adjusted according to solid requirements, such as coarseness/grain size, amount to be weighed, stickiness, etc.

In various embodiments, a gear gate can be utilized for example to seal the bottle/solid container. The gear gate may engage with the bottle/container by keeping it closed with a passive priming element such as a spring, gravity, or magnetic interaction. The gear gate may be opened by engaging an engagement platform, for example via a lead screw or equivalent mechanism. The gear gate can be driven by a stepper motor, for example via a belt, to dose the solid.

The solids are dosed onto "scale dish", in various embodiments. The dish can be mounted on one or more load cells that calculate the amount dosed. In some cases, two load cells are utilized. In some embodiments, once the correct amount of solid is dosed, a motor tips the scale dish. In some cases, motor also tips the load cell(s) and deposits the dosed solid into the CMC. A cleaning apparatus, such as a water jet can be utilized to clean the "scale dish" of any solids. Cleaning can further ensure that all the solids go into the CMC. In some embodiments, solids are transferred without the use of cleaning apparatus, such as the cleaning water jet. In some embodiments, the scale dish is rotated, while keeping the load cell(s) static (non-rotating).

In various embodiments, there is no limit to the number of solids that can be dosed into the CMC. A common measuring system, such as the system comprising load cell(s) measuring the solid weight as described above, can be utilized to handle a variety of solids. The dosing screw dosing solids from the bottle/container can be adaptive to have an accurate dosing system with a variety of solids. Parameters, such as the solid's grain size, density, total amount to be measured, precision, or stickiness can be taken into account to select an optimized dosing screw for each application. Accordingly, two different dosing screws can be utilized to measure the same solid, depending on the application.

In some embodiments, two pins align the bottle with an engagement platform. A bottle vibrator can engage with the bottle/container via this setup. The bottle vibrator can be utilized to loosen clumps of solids inside containers.

In some embodiments, the speed of dosing may be varied at different stages of dosing. A stepper motor can be used to power dosing. The speed can be adjusted, regularly or as otherwise necessary. In some embodiments, the dosing is slowed down towards the end. Dosing can be slowed down gradually or in one or multiple steps. For example, to accomplish a 10 gram dosing, the solid can be dispensed at max speed until perhaps 8.5 gram. Dosing can then be slowed down until at 9.9 gram, after which the dosing can be slowed down further. The variable speed allows the solid dosing be performed at a relatively high speed for the majority of the dosing, while the slower dosing in the end allows for equilibration of the scale(s), as well as for executing dosing stop commands at a precise timing. During the equilibration stage for the scale(s) (load cell(s)) can stabilize, accounting for environmental factors, such as particle impacts, general movement in the room, air conditioning or any other environmental disturbance, allowing for an accurate reading. In various embodiments, the system is capable of calculating the flow throughput, and optimizing the number of rotations needed for the next dosing. Further, the system may be capable of noting and/or recording the variations in flow throughput, density of the material, or any other suitable parameters during and/or after a dosing. The information can be utilized for the selection of an optimized dosing screw for subsequent applications with the solid.

Accordingly, in various embodiments, solid can be dosed with a precision of 5%, 3%, 2%, 1%, 0.5%, 0.1%, 0.05%, 0.01%, 0.005%, or higher precision. In some embodiments, dosing is not slowed down significantly opting for speed. Any overdosing can be compensated by increasing the other desired components of the final solution, such as liquids, proportionately.

In various embodiments, the dosing screws have two main variable parameters: the thread pitch and diameter of the inner shaft. These parameters can be optimized for varying types of solids and for the desired throughputs. For example, a screw with a small pitch might find it hard to "grab" clumpy (hygroscopic) solids, while a large pitch screw will have a hard time controlling the flow of a fine and loose solid. For a further example, a slow throughput screw will take time to dose a large amount, while a high throughput screw will require a high degree of control to dose a very small amount of solid.

In some embodiments, a grinder attachment may be utilized in concert with the dosing screw, for breaking up the solid prior to dosing. The grinder may break down solids employing a peppermill-type mechanism.

The disclosure, in various embodiments allows for better handling of hygroscopic solids, since the solids can be kept better away from air. Hygroscopic solids pose an additional concern while dosing, as they may have a tendency to stick to bottle walls and not come down through the dosing mechanism. In some embodiments, the dosing screw keeps the solids loose enough to avoid sticking. In some embodiments, a vibrating mechanism is utilized to loosen the wall bond. Alignment pins on the "solid platform" may be designed to power the vibrating mechanism.

As mentioned before, this system measures the solids dispensed from the solid containers. In another embodiment of the present disclosure, the solid container is weighed as the solid is being dosed. The automated solution dispenser may be designed to allow for the variation.

2. Liquid Handling

Liquid Handling System

Liquids constitute a major component of the solutions prepared by the automated solution dispenser. Thus, various embodiments of the present disclosure employ a Liquid Handling System (LHS) in order to accurately deliver a specified amount of liquid. Various liquid materials handled by the LHS include but are not limited to acids and bases at various concentrations, water, pH calibration liquids, pH sensor storage solution, stock solutions (for example: chemicals that are only available in liquid form) and other liquid components, for example those that require to be added in liquid form for safety, dosing accuracy or other restrictions.

The LHS can be equipped to draw liquids from a variety of liquid sources (supplies), including, continuous supply, such as water from the water mains, water from a purifier, internal supply, such as integrated tanks, and external supply, such as storage bottles.

FIG. 13 illustrates components of the LHS according to some embodiments of the present disclosure. Accordingly, the liquid can be drawn in through, for example using one or more peristaltic pumps 32. The liquid can be further pumped in controlled amounts into the CMC. In various embodiments of the present disclosure, the pump's configuration can be a single pump per CMC or one pump serving multiple CMCs. In the case of multiple CMCs, the liquid path may be controlled by either a single valve/selector or through a series of valves. The pumps can be driven by either a geared/non-geared stepper motor 1301 and 1304, a geared/non-geared DC motor 1301 and 1304, or a linear driver 1308. An injector or T-junction 1306 may be utilized to feed a liquid from within a syringe pump into a feed line.

In various embodiments, positive displacement type pumps may be employed, including but not limited to a single peristaltic pump 1305, multiple channel peristaltic pump 1302 and 1303, syringe pump, or piston/plunger pump 1307, reciprocating pump, diaphragm pump, screw pump, rotating lobe pump, rotary gear pump, progressive cavity pump, gear pump, hydraulic pump, vane pump, and/or regenerative (peripheral) pump.

The pumps according to the embodiments of the present disclosure can be self-priming, gravity-primed by placing the pump underneath the liquid source, or the liquid source, such as the water main line, can be pressurized. A dosing valve can be utilized or an alternative method of dosing specific amounts of liquids can be employed. In some embodiments, the pumps can primed by using software logic, for example rolling back a full tube of a known length known and then bringing it back in. Visual confirmation may be utilized for priming. Less conservatively, a little liquid, for example about 1-2 mL, may be wasted. In some cases, upon asking user permission, enough volume may be pumped to be noticeable to level sensing.

Figure 31:
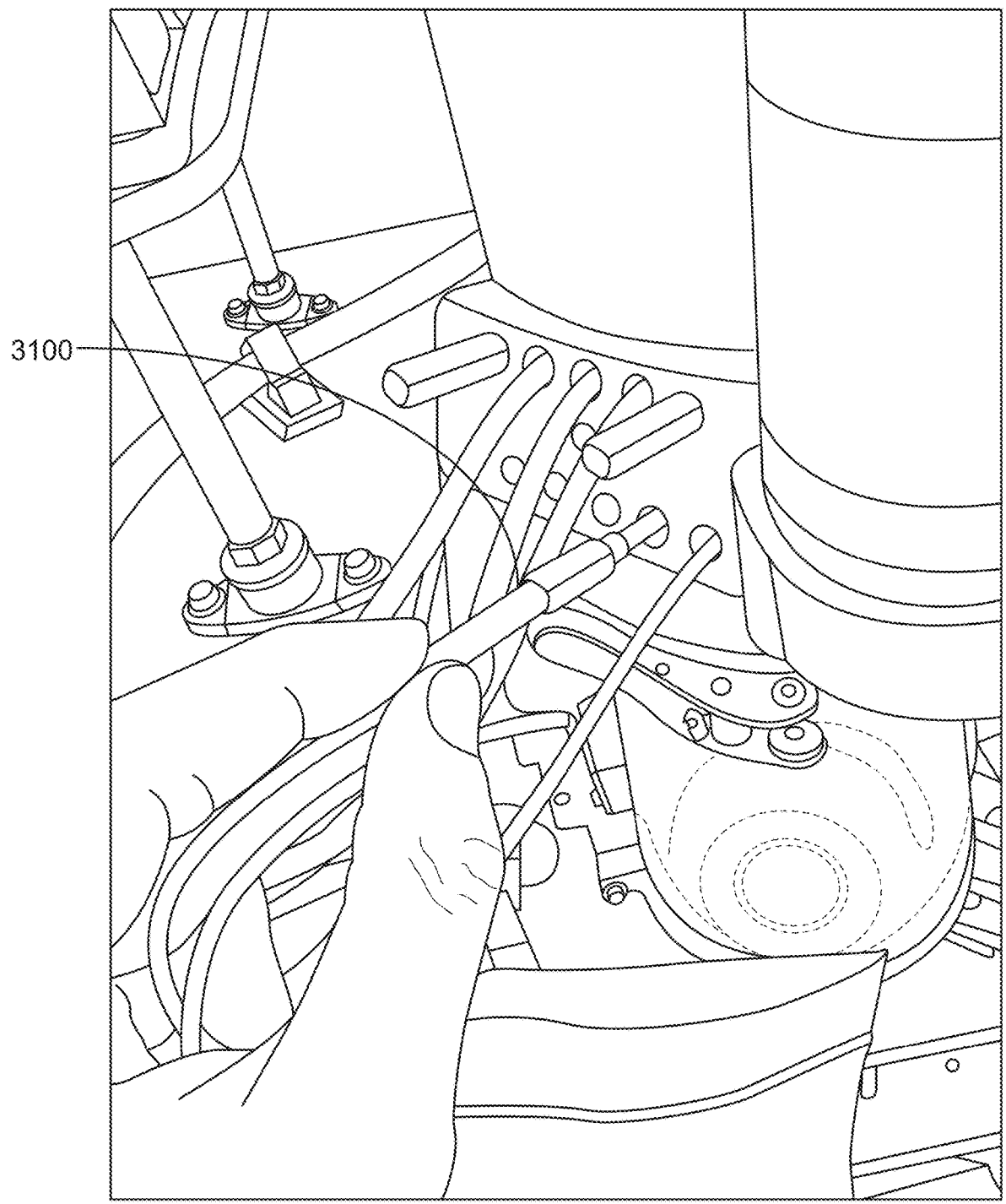
FIG. 31 shows a tube adapter.

In some embodiments, the liquid sources, pumps, and CMC are all connected by lumens, such as tubes 1309, as shown in FIG. 13. The tube material can be selected such that it is suitable for the liquid contained within. The tube connections can vary according to various embodiments, and include, without limitation, sealed and mechanically sealed connections, standard compression fittings, and barbed fittings. In some cases, the LHS can comprise one or more tubes with different diameters. In some cases a first tube can have a diameter that is 0.1×, 0.25×, 0.5×, 0.75×, 1.25×, 1.5×, 1.75×, 2×, 5×, 10×, 25×, 50×, 75×, or 100× the diameter of a second tube (× designates "times"). In some cases, a first tube can have a diameter from about 0.1× to about 100× the diameter of a second tube. In some cases, a first tube can have a diameter that is at least about 2× the diameter of a second tube. In some cases, a first tube can have a diameter that is at least about 10× the diameter of a second tube. In some cases, a first tube can have a diameter that is at least about 50× the diameter of a second tube. In some cases, a first tube can have a diameter that is at least about 100× the diameter of a second tube. FIG. 31 shows a tube adapter 3100 that can be provided to connect tubes of different sizes. The tube adapter can connect to an inlet of the CMC. The tube adapter can connect to two or more tubes of identical or different diameters simultaneously. The tube adapter can form an air (i.e. gas) tight seal with one or more connected tubes. The tube adapter can form a liquid tight seal with one or more tubes. The tube adapter can form a solid tight seal with one or more tubes.

Sealed connections may utilize a permanent adhesive and/or sealant that is resistant to the liquids handled by lumens of the system, such as a plastic tubing. Mechanical Seals (MS) are illustrated according to various embodiments of the present disclosure in FIG. 14. Accordingly, the lumen such as a tubing 1401 is set in the tube holder 1402, which can be screwed 1404 or twist-locked into the base 1405. An o-ring 1403 can ensure that there is no leakage, and can be installed on any tube holder 1402 and base 1405 interface. Alternatively, a valve 1406 can be incorporated in the base 1405. The valve can be opened by the tube holder 1402. The valve 1406 can be closed by a spring 1407 when the tube holder 1402 is removed. In some embodiments, common/standard fittings are utilized.

A lumen may be a tubing, such as a plastic tubing. A lumen may be flexible. A lumen may be rigid. A lumen may be in fluidic communication with a dosing screw, a mixing chamber, one or more containers, a solids dosing mechanism, a liquids dosing mechanism, or any combination thereof. A lumen may comprise two lumens, three lumens, four lumens, five lumens, six lumens, seven lumens, eight lumens, nine lumens, ten lumens, or more. A lumen may be comprise a conduit and i) one or more openings at a first end, ii) one or more openings at a second end, iii) one or more openings therebetween the first and second end, or iv) any combination thereof. A lumen may be impermeable to a liquid and/or a gas. A lumen may direct a flow of a liquid, a solid, a gas, a solution or any combination thereof.

In some embodiments, the systems and methods of the present disclosure comprise the use of an incorporated or auxiliary filtering system. The filtering system components may filter liquids before or after the solution stage, for example, the filtering system may filter the solution before it is dispensed and/or bottled.

A water purifier can be incorporated or operably linked to the automated solution dispenser. The water purifier may deionize and/or filter feed/input water to obtain a desired water quality, for example "ultrapure" or Type 1 water as for example laid out by International Standards Organization (ISO) 3696. Purified water is commonly used to prepare liquid solutions and/or clean materials and components used in the preparation process. The addition of a water purification system can be advantageous in an automated solution preparation system, reducing the need for multiple pieces of laboratory equipment and in some cases, fitting multiple functionalities in a confined space, eliminating the need of proximity and/or complicated connections or in the alternative, manual stocking of purified water by the automated solution dispenser.

In some embodiments, a pivot pipe can be utilized to discharge the contents of the central mixing chamber to the correct station for bottling and/or for flushing. Accordingly, the pivot pipe may be configured to switch between at least two stations, a drain station for dispensing the waste from one or more of the cleaning cycles utilizing flush verification system and a bottling station. More stations can be included enabling for separating waste or bottling multiple solutions to a plurality of bottles in an automated fashion. Additional stations may also allow for pH sensor storage liquid recycling, filtering, filtering, degassing, and analyzing. In some embodiments, stations may incorporate multiple tasks, such as bottling followed by filtering, degassing, or analyzing a solution preparation.

FIG. 15 illustrates the use of a pivot pipe according to some embodiments of the present disclosure. Accordingly, a gear holder 1501 interfaces with the CMC outlet, with an o-ring 1502 creating a seal preventing the CMC discharge from leaking out. The gear holder 1501 can have two thrust bearings 1503 on the top and bottom of the gear holder 1501, and have a bottom plate 1505 that can be bolted 1508 to the top supporting plate 1504. The thrust bearing 1503 can be set in grooves ensuring correct positioning and allowing the gear holder to rotate freely. The gear holder 1501 can have a set of gears on the outer diameter and can interface with the pivot cog 1506. The pivot cog can be mounted on motor 1507 that controls the rotation and position of the gear holder. A curved rigid pipe 1509 can be attached to the gear holder 1501, and can rotate with it. The liquid from the CMC can flow through the rigid pipe 1509 to a selected station. Limit switches can be used to confirm the position of the rigid pipe 1509 discharge.

In some embodiments, alternative systems, including linear or disposable system, enable the correct positioning of a flexible or rigid pipe. A plug valve design can be used and may eliminate the need of the pivot pipe. The CMC may be sealed with a plug that can be closed with spring action. A bottle carousel may comprise discharge bottles and a drain station. The engagement of the discharge bottles and/or the drain station may be configured to open the CMC and discharge the liquid inside.

3. Self-Cleaning

In some embodiments, a controller is configured to control the dispenser to implement a cleaning cycle. The cleaning cycle can comprise controlling at least one inlet port to input a cleaning fluid into the mixing chamber. The cleaning cycle can also comprise controlling the controllable outlet valve to dispense the cleaning fluid. In various embodiments, the cleaning cycle enables automated batch processing of solutions forgoing any user intervention requirement between different solutions being made. The cleaning cycle can reduce any cross-contamination between the solutions being created to a substantially negligible amount suitable for the batch processing of the solutions. In some embodiment, a cleanliness threshold can be set. The cleaning cycle can be configured to address a cleanliness threshold. The configuration can be a preset process. Alternatively, the configuration may comprise iterative application of cleaning cycles and cleanliness measurements.

In some embodiments, the automated solution dispenser comprises a cleanliness measuring sensor coupled to a controller. The controller can be configured to measure cleanliness and do one or more further cleaning cycles in response to the sensed cleanliness of the cleaning fluid after a cleaning cycle. The cleanliness measuring sensor can enable the automated cleaning cycle to determine whether or not the cleaning cycle just performed has been successful or not. If not, the cycle can be repeated until the cleanliness measurement sensor indicates that the cleaning solution is clean enough to indicate that the automated solution dispenser is clean. In some embodiments, the cleanliness measuring sensor comprises a conductivity sensor or turbidity sensor.

A cleaning water line may go through the STT to a solid bottle position. The solid tube may engage with a cleaning bottle. A cleaning nozzle may be used and may be placed in the position of an SDM, altering the SDM set-up for a cleaning set-up. The nozzle can be rotated, for example up to 360° C. to clean the CMC. The cleaning and/or flushing liquids may comprise detergent and may be pre-heated. In some embodiments, the cleaning and/or flushing liquids are pre-heated to over 50° C., 60° C., 70° C., 90° C., 95° C., 99° C., or more. In some embodiments, cleaning and/or flushing liquids are supplied at ambient temperature. Detergent concentrations may be adjusted in a series of dilutions. In some embodiments, the cleaning and/or flushing liquids are devoid of detergents.

In some embodiments, at least one input port is coupled to one or more cleaning nozzles arranged to spray received cleaning fluid inside the chamber. At least one input port may be coupled to a spray ball comprising one or more of nozzles arranged to spray received cleaning fluid inside the chamber. In some embodiments, the mixing chamber comprises a plurality of cleaning nozzles disposed in a wall of the mixing chamber, the nozzles being coupled to at least one input port and being arranged to spray received cleaning fluid inside the chamber. The input may be coupled to a pump for supplying cleaning fluid. The input may also be coupled to a detergent source for dispensing detergent into the cleaning fluid. The detergent source can comprise an injection pump. In some embodiments, the cleaning cycle cleans a flowable path from the inlet port of the mixing chamber through to an output of the outlet port. Cleaning each part of the system involved in creating the solution in turn reduces the risk of cross-contamination between solution producing cycles.

In some embodiments, the automated solution dispenser comprises a controllable drying module coupled to the controller. The controller can control the drying module to implement a drying cycle. The mixing chamber and/or the inlet port can be dried during the drying cycle. In some embodiments, the controllable drying module comprises a fan or a source of substantially dry air. The drying cycle can prevent droplets of cleaning fluid left over from the cleaning cycle(s) (or any residual humidity) from cross-contaminating with, or otherwise affecting, the solution made after the cleaning cycle. The controller can be further configured to control the dispenser to implement a cleaning cycle in which at least one inlet port is controlled to input a cleaning fluid into the mixing chamber, and the controllable outlet valve is controlled to dispense the cleaning fluid.

In embodiments comprising the cleaning cycle, the automated solution dispenser according to the disclosure further comprises a cleanliness measuring sensor coupled to the controller and wherein said controller is configured to measure cleanliness and do one or more further cleaning cycles in response to the sensed cleanliness of the cleaning fluid after a cleaning cycle. Preferably, the cleanliness measuring sensor comprises a conductivity sensor or turbidity sensor.

In some embodiments, the at least one input is coupled to a pump for supplying cleaning fluid under pressure. The input may be coupled to a detergent source for dispensing detergent into the cleaning fluid. The detergent source may comprise an injection pump.

Thus, in various embodiments, the cleaning cycle cleans a flowable path from the inlet port of the mixing chamber through to an output of the outlet port. Furthermore, the automated solution dispenser may comprise a controllable drying module coupled to the controller, and wherein the controller controls the controllable drying module to implement a drying cycle to dry the mixing chamber and/or inlet port. The controllable drying module may comprise a fan or a source of substantially dry air.

Flush and Verification System (FVS)

In some embodiments, a Flush and Verification System (FVS) provides the device with an automated system to clean the CMC and the ability to verify the cleanliness of the CMC. This can be achieved by providing pressurized water and measuring the conductivity, or equivalent, of the water leaving the CMC to measure the cleanliness. In some cases, detergent can be added to the CMC.

Figure 16:
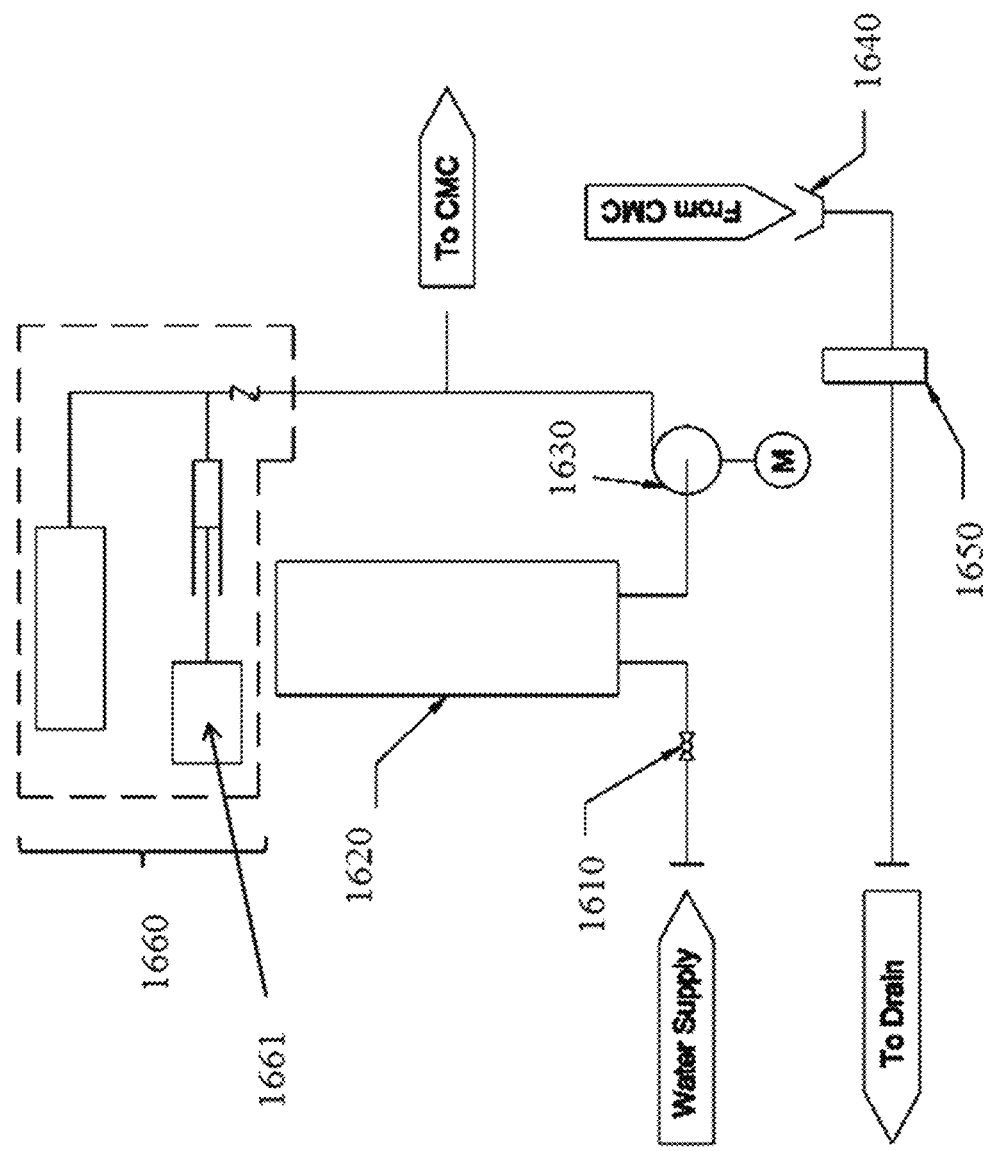
FIG. 16 illustrates a flush and verification system according to some embodiments of the present disclosure.

FIG. 16 illustrates the FVS according to some embodiments of the present disclosure. In an illustrative example, the FVS comprises a Hot Water Generator. In some cases, the FVS comprises a Hot Water Generator Storage (HWGS) 1620, a pressure pump 1650, piping, tubing, fittings, a cleanliness sensor like conductivity meter or equivalent 1650, an detergent tank 1660, an injection pump 1661, or any combination thereof. In some embodiments, the injection pump is placed before the tank. In some embodiments, pressurized water can be provided externally making the pressure pump auxiliary or redundant.

According to various embodiments, the FVS is connected to the water supply, and can be isolated by using the inlet valve 1610. Accordingly, leakage can be prevented if the supply is accidentally disconnected, without following the draining procedure. In various embodiments, the water flows into the Hot Water Generator (HWG). In some cases, the water flows into the HWG, the Hot Water Generator Storage (HWGS) 1620, or a combination thereof. The HWGS can be a custom-made water tank with an installed electrical heater, or a flow through heater. Depending on the water supply source specification, it may be possible to replace the HWGS 1620 with a flow through heater without storage. In some embodiments, insufficient supply water triggers the hot outlet of the HWGS 1620 to be connected to the pressure pump 1630 inlet, and the pump outlet to be connected to the CMC. When the water supply is sufficient, the hot outlet of the HWGS can be connected to the CMC. The pump 1630 can be sized to provide the sufficient pressure and flow to clean the CMC, and may be chosen to accommodate various CMC sizes and cleaning nozzle designs. Pumps may be chosen to meet the flow and pressure requirements and to be able to handle the hot water safely.

In some embodiments, the water from the CMC flows into the drain station 1640, which is connected to the drains. In the line, a conductivity sensor 1650, or equivalent, can be mounted to test the cleanliness of the water exiting the CMC.

In some cases, a liquid, a solution, a solid, a waste material and/or a liquid that has been used to flush (i.e. clean) the CMC can be directed to a drain or a waste container based on the type of liquid, solid or solution that is or has been contained in the CMC. The waste container may be a hazardous waste container. The waste container may be a hazardous waste container of a particular waste classification, or waste class. Waste classification may include non-specific source waste (F list), source-specific waste (K list), discarded commercial chemical products (P list and U list), or any combination thereof. The discarded commercial chemical products may be hazardous wastes (P list), toxic wastes (U list), or a combination thereof. One or more properties of the liquid, solid or solution can be monitored to determine if the liquid, solid or solution that has been used to flush the CMC can be flushed down the drain, or retained in a waste container. In some cases the pH of the liquid or solution can be monitored to determine if the liquid or solution can be flushed down the drain or retained in a (hazardous) waste container. One or more predetermined properties of the solution can be compared to one or more known regulations that dictate which types of solutions can be flushed down the drain (or directed to waste) and which types of solutions may be disposed of as hazardous waste. The hazardous waste may have various hazardous waste classes, for example, as delineated above. A user or an instrument can be alerted when a hazardous waste container is full. An alert to a user may be a visual alert, an audible alert, a tactile alert, or combination thereof. In some cases, the system can neutralize hazardous waste by adding one or more solutions (e.g., buffer solution) such that a hazardous waste material is rendered safe to flush down the drain.

The detergent feature 1660 may comprise a detergent source, an injection pump and a check valve. The feature can be implemented by installing a check valve on the connections between the hot water tank and pressure pump. The detergent can be stored either in an internal tank or an external tank/bottle, and can be connected to an injection pump. The injection pump can be configured to force the detergent into the water line between the check valve and the pump. In many cases, the detergent needs to overcome the water pressure. The check valve can prevent the detergent from flowing into the hot water tank. The detergent tank and injection pump can be combined into a syringe that can be replaced by a user once it needs a refill.

4. Sensors

Various sensors can be utilized as components of the automated solution dispenser. One or more sensor calibration parameters can be stored locally on a memory storage device or in a certain location in the cloud, which is in communication with the sensor. In some cases, a sensor (e.g., pH sensor) can be calibrated by cleaning the sensor with a cleaning solution (e.g. water). The cleaning solution can comprise deionized water. After cleaning the sensor the sensor can be placed in a solution with a known condition to be measured by the sensor. In some cases, the known condition can comprise a pH, temperature, conductivity, or any other measureable property of the solution. In some cases, a series of solutions with different known conditions can be measured sequentially to calibrate the sensor. These data may be retrieved by a user or by the CMC. The stored memory parameters may constitute historic data of the calibration parameters. Similarly, data routinely received by the sensor can be stored as operative historic data on a memory storage device or in the cloud. Such operative historic data may be retrieved automatically, or by a user. The sensors may be coupled to or implemented in any various systems and components of the automated solution dispenser described elsewhere in the application. In some cases, degradation of one or more sensors can be detected automatically. Degradation of one or more of the sensors can be detected when a sensor stops providing a measurement. Degradation of one or more sensors can be detected when a sensor provides a measurement outside or a predetermined range. The degradation parameters may similarly be stored on a memory storage device, or in a certain location in the cloud, and retrieved by the CMS or by a user. The sensor calibration, operative or degradation data may be used separately or in any combination to initiate manual or automatic calibration or replacement of the sensor.

Examples of such systems and components include but are not limited to, the solids handling system, the liquid handling system, the bottle handling sub-system, and central mixing chamber. Such sensors are described herein:

(a) pH sensor: A variety of pH sensors can be used in accordance with the disclosure, including, but not limited to glass membrane electrodes, pHFETs, metal/metal oxide pH sensors, liquid membrane electrodes, electrodes modified with pH-sensitive polymers, potentiometric pH sensors, ion selective electrodes, fiber optic pH probes, optical and fluorescence pH sensors, or miniaturized pH sensors. In some cases, a pH sensor can be calibrated automatically at a predetermined interval. In some cases, a pH sensor may be calibrated automatically based on present or historic data of at least one of the following: calibration, operation or deterioration of the sensor.

(b) Temperature sensor and control (e.g. by a controlled immersion heater or heating through the walls of the container): Any suitable temperature sensor can be used, including but not limited to a mercury thermometer, alcohol thermometer, Beckmann differential thermometer, bi-metal mechanical thermometer, Coulomb blockade thermometer, liquid crystal thermometer, phosphor thermometry, pyrometer, quartz thermometer, thermocoupler, resistance thermometer, or a silicon bandgap temperature sensor.

(c) Level sensor: The level of fluids or fluidized solids can be measured using level sensors in various embodiments of the present disclosure. Level sensors can comprise any suitable sensor, including, but not limited to ultrasonic or pulse-wave ultrasonic, capacitance, optical interface microwave, magnetic and mechanical float, pneumatic, conductive, magneto restrictive, magneto resistive, resistive chain, hydrostatic pressure, air bubbler, gamma ray sensors, vibrating point sensors, admittance-type sensors, and rotating paddle sensors. In some embodiments, optical, ultrasound or capacitance sensors are preferred. For example, a light sensor can detect when the liquid surface hits the target level. Cameras may be used alongside computer vision computing techniques which allow the system to visually track various levels of fluids or fluidized solids.

(d) Turbidity sensor: Turbidity can be measured by light attenuation, absorption, or scattering. Turbidity sensors can be useful both for following solids going into solution during the solution preparation process and the completeness of the cleaning cycles by checking the flushed cleaning fluids. Cameras may be used alongside computer vision computing techniques which allow the system to visually monitor turbidity in various elements of the system.

(e) Conductivity sensor: The electrical conductivity of a solution containing electrolytes can be measured by determining the resistance of the solution. The resistance can be measured using a conductivity meter. Flat/cylindrical electrodes or induction based measurements can be performed. In some cases, the conductivity measurement can be improved by a temperature correction. In many cases, conductivity can be used as a direct or indirect measure of the total dissolved solids. Conductivity sensors can be useful both for following solids going into solution during the solution preparation process and the completeness of the cleaning cycles by checking the flushed cleaning fluids.

(f) Weight sensor: The weight of the solid and liquid ingredients, as well as final solutions according to the disclosure can be determined using any suitable scales, weight sensors, or load cells. Mechanical load cells, including hydraulic and pneumatic load cells, strain gauge load cells, including bending beam, shear beam, and canister load cells, helical, fiber optic, and piezo-resistive load cells and force compensated electromagnets are within the scope of the present disclosure.

(g) Cleanliness sensor: In various embodiments, a conductivity and or turbidity sensor can be utilized to obtain a cleanliness readout, e.g. by monitoring the conductivity of the CMC discharge.

5. Central Mixing Chamber

One or more central mixing chambers (CMCs) can be incorporated to the systems and methods of the present disclosure for collecting, mixing and dispensing liquids and/or solids. Additionally, CMCs allow for the pH and temperature adjustment of solutions or solution components in the CMC. In some cases, adjustments can be made with the help of the Liquid Handling System (LHS) and/or the Solid Handling System (SHS). Contents of the CMC may be discharged into waste or a container/bottle, for example using a Pivot Pipe System (PPS), or a plug valve system. In some embodiments, the mixing chamber may comprise a beaker with or without a bottom valve. The beaker may be tipped, for example by a robot, to pour the solution to a bottle. The beaker may be removed and can be replaced with a second clean beaker. Alternatively, the beaker may be replaced after cleaning. In some embodiments, the mixing chamber comprises a bottle. The bottle may be removed for the delivery of the prepared solution. Systems and methods of the present disclosure allow for the cleaning of CMCs for use with multiple solution orders.

In various embodiments, the CMCs comprise one or more of a mixing chamber, a liquid inlet, a solid inlet, a pH sensor, a temperature sensor, a temperature controller, for example comprising an immersion heater and/or a cooler, a stirrer/agitator, for example a magnetic stir bar driven by an external rotating magnetic field, a liquid level sensor, for example an ultrasound level sensor, a turbidity sensor, and a controlled outlet.

Figure 17:
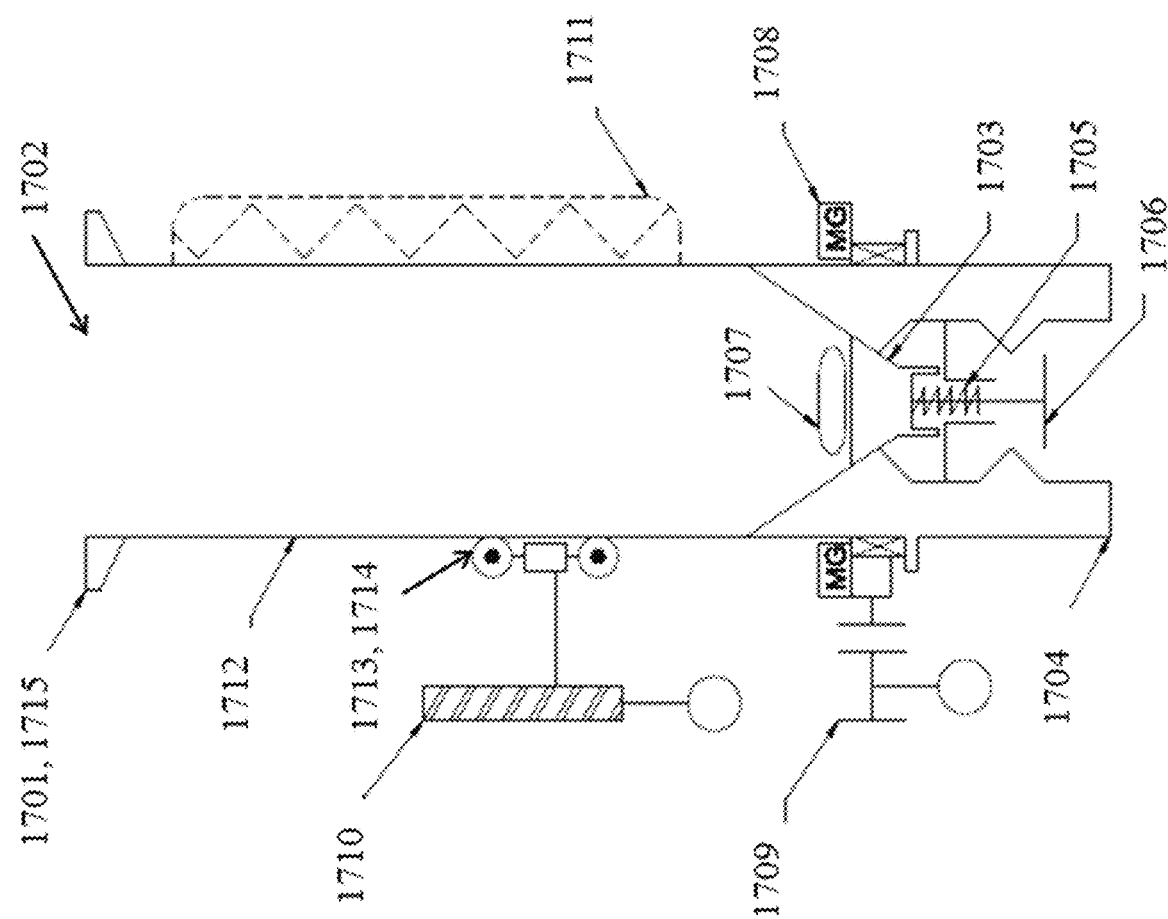
FIG. 17 illustrates a central mixing chamber according to some embodiments of the present disclosure.

Referring to FIG. 17, an exemplary overview of a CMC is illustrated. Accordingly, the liquid 1701 and solid inlets 1702 are located in the top section of the CMC, where each liquid has its own inlet 1701. The solids can have a common inlet port 1702. Some or all of the liquid inlets can be mounted on a manifold 1715 that is attached to the top section to the CMC. The manifold can be removable for ease of replacing the liquid tube.

In some embodiments, the liquid tubes can be equipped to use a nozzle (needles) allowing control of the size of liquid drops that enter the CMC at a time and increasing the accuracy of the liquid dosing. The liquid inlet can hold the liquid tube in place and when necessary can have a sealed connection, for example with a sealant, or a mechanical seal.

In some embodiments, the mechanical seal is in the form of a threaded connection with o-ring seals, or as a compression fitting. The liquid inlet can be either let directly into the CMC or through a nozzle.

In some embodiments, a cleaning nozzle ring is located in the top section of the CMC, and surrounds the common solid inlet. The cleaning nozzle provides the cleaning and flushing liquid to clean the CMC between each solution creation. All exposed internal surfaces of the CMC are cleaned to prevent cross contamination between sequential preparations of solutions. A nozzle can be a hollow ring that has spray nozzles on the inside (directed towards the solid inlet) and/or on the outside (directed towards the exposed internal CMC surface) through which pressurized water, e.g. hot water is delivered to all the CMC surfaces.

In some embodiments, the solid inlet and cleaning nozzle are separated, and use a spray ball nozzle, for example a static or dynamic spray ball nozzle. The cleaning nozzle can be incorporated into the CMC wall, such that the nozzle center becomes the solids inlet and may also reach the liquid inlets.

The bottom of the CMC may comprise the Valve & Outlet section the instrumentation/sensor section below it, and/or the stirrer/agitator section on the bottom. It is possible to swap sections for alternative configurations. The Valve & Outlet section may comprise a spring closed valve 1703 & 1705. The valve 1703, when in the closed position, can hold the liquid solution within the CMC. When the valve is open the liquid can be directed through the outlet to the drain, to the Bottle Handling Sub-System (BHS), or to a Filtering System (FS) of the device. With the plug valve design, the plug can be opened directly or indirectly by a linear actuator, e.g. a solenoid. The valve is opened when either the bottle or drain connection pushes against the stem 1706. This pushed the plug up, against the spring 1705. When the bottle or drain connection disconnects the spring ensures that the valve close and seals the CMC.

The volume of the solution in the CMC can be measured by a level sensor 1712. The level/volume of the CMC can be mathematically determined. The instrumentation section 1710 may allow a pH sensor 1713 to penetrate the CMC wall, which may be sealed either with a sealant or a mechanical seal. This section can also house a temperature sensor 1714 and can be designed with room for any additional sensors, such as other sensors mentioned in this application. The instruments can be located below or above the stirrer section, preventing instrumentation from possible damage from the rotating stirrer 1707. The mechanical seal can be in the form of a threaded connection with o-rings or a compression fitting.

The stirrer can comprise of two parts, an external driver 1708 and 1709 and the internal stirrer 1707. The internal stirrer can be a magnetic bar, located within the CMC. The external driver 1708 and 1709 can be located outside of the CMC and can provide a rotating magnetic field, for example a rotating magnetic field around the CMC's centerline. The magnetic field interact can with the internal stirrer's permanent magnetic field, causing it to rotate about the CMC. An example of the external driver, as shown in the drawings, is a set of synchronized electromagnets that are timed to induce a rotating electromagnetic field. In some embodiments, one or more magnets can be rotated the magnets to generate the stirring effect.

In some embodiments, one or more magnets are mounted on a bearing or a race-rail that can be rotated, for example around the CMC's centerline using a motor or other suitable actuator and a coupling, for example a belt, gear, etc. A heating and cooling arrangement can be implemented to control the temperature of the solutions being created, 1711, as shown in FIG. 17.

The material selected for the CMC and all the wetted surfaces can be chosen to be compatible with the range of chemicals being handled, for example glass or polyethylene terephthalate (PET). The CMC can be sized to hold the maximum desired liquid solution volume plus any additional space required to enable uniform mixing, for example the total CMC volume can be 1.25 times the maximum desired liquid solution volume.

The CMC components can comprise various degrees of integration. For example the valve and/or the cleaning nozzle can be either integrated into the CMC body or be a separate component.

An alternative to the cleaning nozzle is to seal the CMC and flood/flush the CMC repeatedly until clean.

In some embodiments, load cells can be mounted on the legs to measure the weight of the CMC and solution. Alternatively, the CMC can be mounted on a canter lever with integrated load-cells and/or strain gauges. It is further possible to mount all the legs on a single load-cell/scale.

6. User Interface

Systems and methods of the present disclosure may allow for the use of user interfaces facilitating the interaction of users with the computer systems described herein.

In various embodiments, direct manipulation interfaces allow users to manipulate objects presented to them, using actions that correspond at least loosely to the physical world. Graphical user interfaces (GUI) that accept input via devices such as computer keyboard and mouse and provide articulated graphical output on the computer monitor, including but not limited to object-oriented user interfaces (OOUIs) and application oriented interfaces are commonly used and are well suited for various embodiments of the present disclosure. Smaller mobile devices such as personal digital assistants (PDAs) and smart phones may typically use the WIMP ("window, icon, menu, pointing device") elements with post-WIMP environments, utilizing space constraints and the availability of input devices. Further examples of suitable user interfaces include:

- Web-based user interfaces or web user interfaces (WUI) that accept input and provide output by generating webpages, which are transmitted via the Internet and viewed by the user using a web browser program, for example those that utilize Java, Ajax, Adobe Flex, Microsoft .NET, or similar technologies to provide real-time control in a separate program, eliminating the need to refresh a traditional Hyper Text Markup Language (HTML) based web browser;
- Touch screen displays that accept input by touch of fingers or a stylus, including those that are used as a combined input output device;
- Command line interfaces, where the user provides the input by typing a command string with the computer keyboard and the system provides output by printing text on the computer monitor;
- Conversational Interface Agents that personify the computer interface in the form of an animated person, robot, or other character and present interactions in a conversational form;
- Crossing-based interfaces, in which the primary input task consists in crossing boundaries;
- Gesture interfaces, which accept input in a form of hand gestures, or mouse gestures sketched with a computer mouse or a stylus;
- Motion tracking interfaces that monitor the user's body motions and translate them into commands;
- Multi-screen interfaces, which employ multiple displays to provide a more flexible interaction;
- Text user interfaces, which output text, but accept other form of input in addition to or in place of typed command strings;
- Voice user interfaces, which accept input and provide output by generating voice prompts and accepting verbal input;
- Natural-Language interfaces, which can be used for search engines and on webpages and wherein a user can type in a question and wait for a response;
- Zooming user interfaces, in which information objects are represented at different levels of scale and detail, and where the user can change the scale of the viewed area in order to show more detail.

7. Sequential Processing/Prioritizing/Tracking of Orders

Various embodiments of the present disclosure relate to sequential processing or prioritizing of solution orders. For example, orders can be submitted with a timing limitation, such as within 3 hrs, by 5 pm, on Monday, at 10 am, between 1-5 am etc. The software running the hardware can accordingly prioritize the orders to maximize fulfillment of timing requests. In some embodiments, orders can be submitted with a priority stamp. Orders can also be manually reordered by an authorized user. In some embodiments, users can be given VIP status of varying degrees. Accordingly, the orders can be prioritized based on the status of the submitting users.

Users may be informed about the status of the solution preparation process or other processes controlled by the controller. For example, users may receive one or more updates comprising information about the solution preparation they ordered. For another example, users may receive updates from any secondary laboratory instruments that are networked to the controller of the automated solution dispenser. Updates about the automated solution dispenser and/or secondary laboratory instruments may be sent via a communication such as email, Short Message Service (SMS) application, Rich Text Summary (RSS) feed.

The system can detect if a component (e.g., solid or liquid) of a solution is over (i.e. in surplus) or under (i.e. deficiently) dosed. The system can automatically adjust amounts of other components in the solution to compensate for the component that is under or over dosed. In some cases the adjustment can result in an increase or decrease in total volume of solution generated by the system. Users may be informed about a change expected solution volume by the controller. In some cases, a user or the CMC can abort (e.g. discarding) a solution order if the expected volume is unacceptable to the user, or unacceptable according to predetermined standards.

8. Bottle Handling

Systems and methods of the present disclosure may allow for an automated recognition system for bottles/containers, including consumable bottles and solution bottles. A bottle handling sub-system (BHS), as exemplified in FIG. 18A and FIG. 18B can ensure that the right bottle is placed in the right position of the bottling station. In many embodiments, the BHS also has the Bottle Labeling system that marks the bottles with the necessary information.

Figure 32:
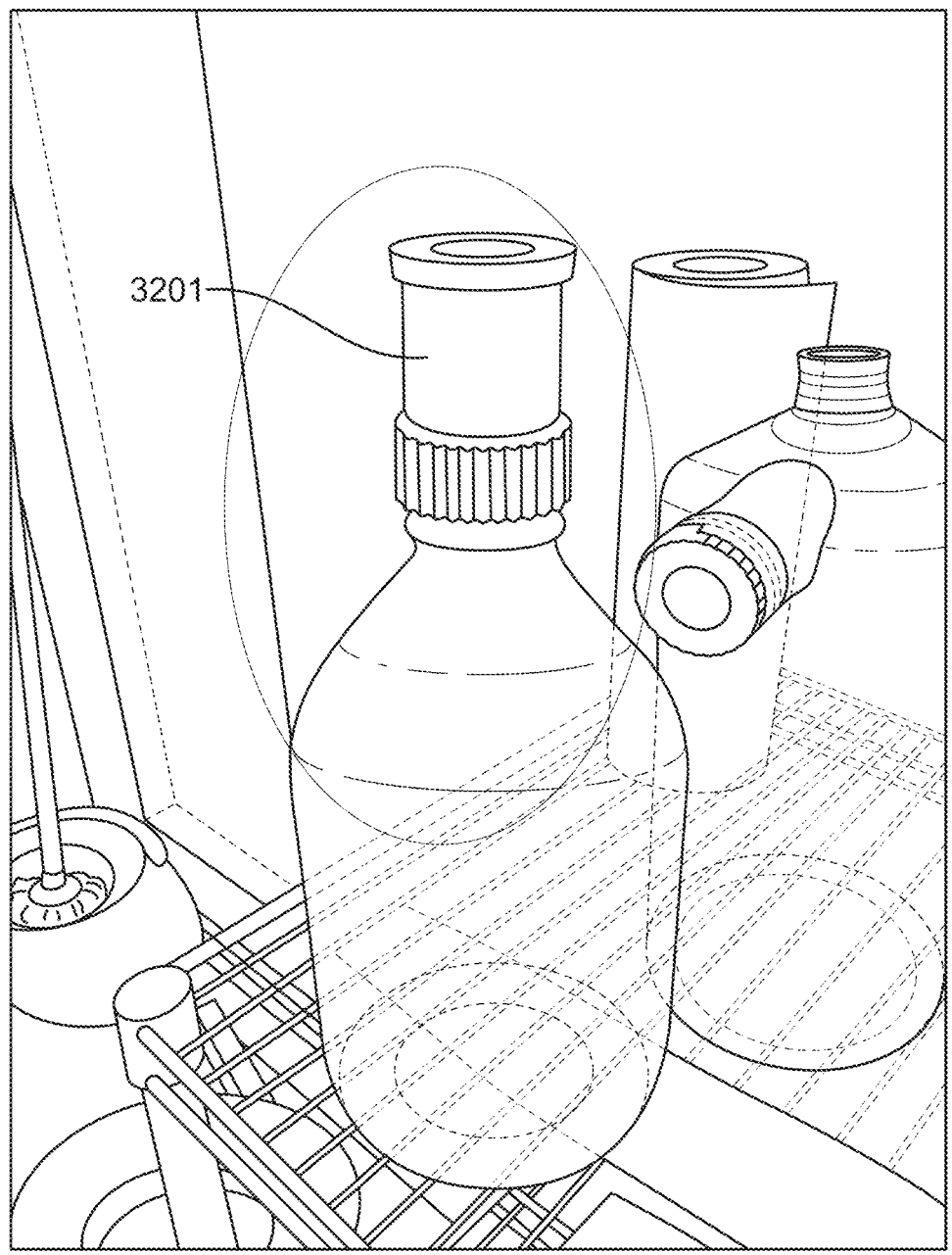
FIG. 32 shows a bottle with a straight bottle adapter.
Figure 33:
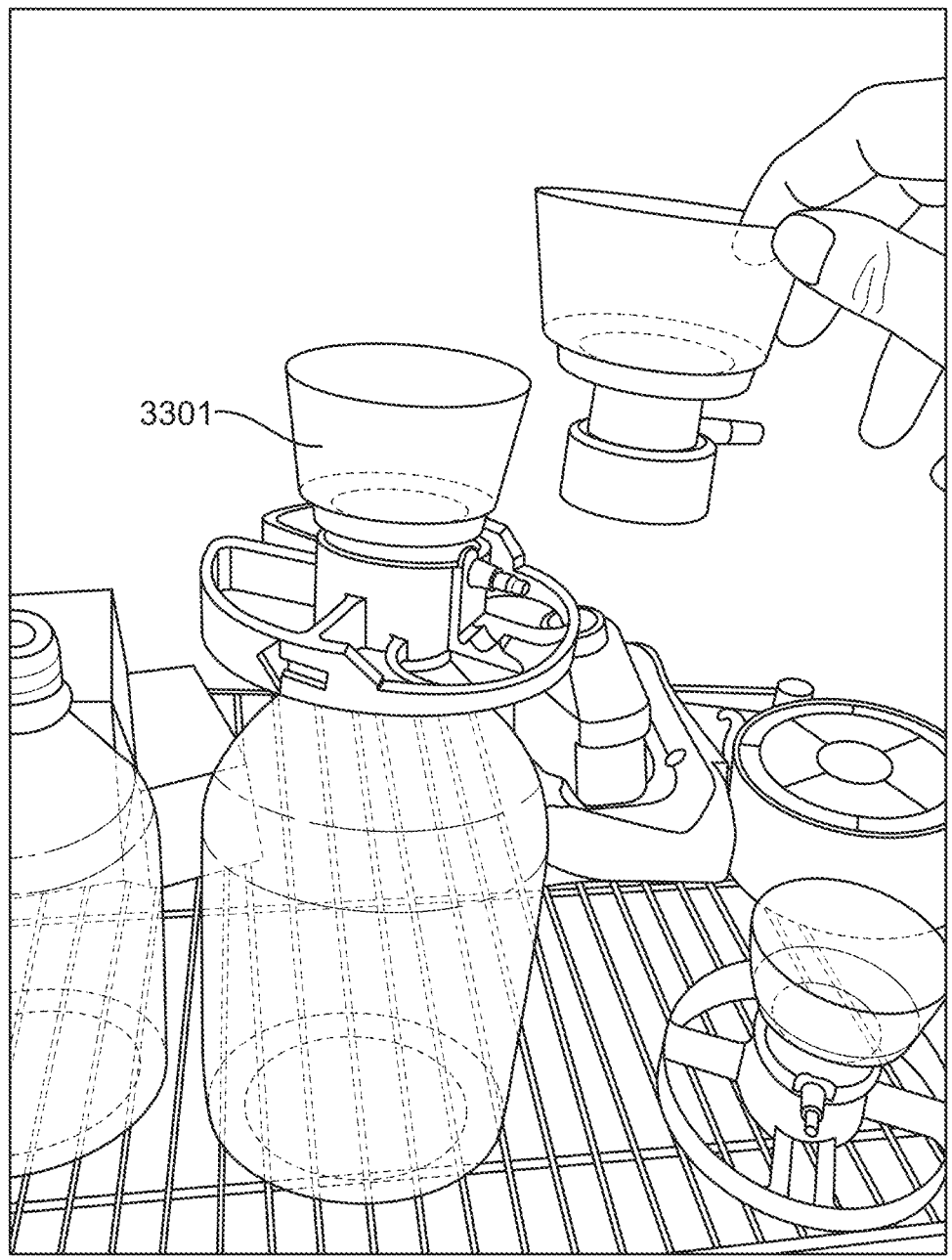
FIG. 33 shows a bottle with a filter cap.

A bottle can comprise a lid with an automatic vacuum filter cap. FIG. 32 depicts a bottle with a custom straight bottle adapter 3201 that can be accepted by the bottle handling sub-system. The custom straight bottle adapter 3201 may not comprise a filter. In some cases, as shown in FIG. 33 the bottle can comprise a vacuum filter cap 3301. The vacuum filter cap can be connected to a vacuum pump to filter a solution in the bottle. The bottle handling sub-system can automatically detect whether a bottle has a custom straight bottle adapter or a vacuum filter cap. The bottle handling sub-system can determine that a cap is a custom straight bottle adapter or a vacuum filter cap based on a dimension (e.g., width) of the cap. In some cases, the filter cap can be wider than the custom straight bottle adapter.

A Bottle Labeling System can provide labels that can be attached to the solution bottles. Alternatively, the labels can be automatically applied to the bottles or the information can be applied directly to the bottle, for example using an ink-jet.

The bottle labeling can be accomplished by optical machine-readable representations of data and radio-frequency identification (RFID) systems. Generally, a label comprises coded identification information. Simple examples of barcodes can vary widths and spacings of parallel lines—also known as linear or one-dimensional barcodes. Two dimensional or matrix barcodes can involve the use of rectangles, dots, hexagons and/or other geometric patterns. Examples of commonly used barcodes include, but are not limited to GTIN-12, EAN-13 (GTIN-13), Code 93, Code 128, Codablock, PDF417, Data Matrix 2D, Aztec Code, EZcode, High Capacity Color Barcode, DataGlyphs, QR Code, MaxiCode, and ShotCode. In some embodiments, the bottle labeling is achieved by RFID. Tags utilizing various mechanisms can be attached to containers. Some suitable tags require no battery and can be powered by the electromagnetic fields used to read them. A radio-frequency electromagnetic coil can modulate an external magnetic field transferring coded identification information when queried by a reader device. Alternatively, a local power source may allow the tags to emit radio waves. The identification information may comprise one or more of a unique tag serial number, a stock number, lot number, batch number, production date, expiration date, or material safety data sheet (MSDS) information.

Barcode readers that are suited for optical recognition of barcodes are commonly built from a light and a photo sensor. Barcodes can be physically moved across a barcode scanner to aid in reading the barcode. Barcode readers may be incorporated or operably linked to primary computer systems operating the automated solution dispenser. In some embodiments, auxiliary computer systems, e.g. hand-held mobile devices, may be linked to a barcode reader. The barcode read-out can be transmitted to other computers linked in a network. Quick Response (QR) codes read by a camera akin to systems available on mobile phones. Reading this QR code may result in a unique ID that can be used to either retrieve all the solution data or to replicate it. This can be useful for sharing solution data between multiple users. One user may permit another user to access solution data via the unique ID and networked automated solution dispensers. This may allow the other user to duplicate a given solution created by the first user (with proper permissions) at a different laboratory than the laboratory of the first user. For example a researcher at first location (such as Oxford University) may share a solution via the unique ID with another researcher at a second location that is far away (such as Stanford University).

Two-way radio transmitter-receivers, often known as interrogators or readers can send a signal to an RFID tag and read the tag's response. The RFID reader can transmit the observation to the primary computer systems operating the automated solution dispenser or auxiliary computer systems. The RFID read-out can be transmitted to other computers linked in a network. In some embodiments, one or more computer systems in the network run an RFID software or middleware.

In some cases, the bottle handling sub-system comprises a single bottle station. In some cases, the bottle handling sub-system comprises a fully automated system. In some cases, the bottle handling sub-system comprises a multi-bottle platform. In various embodiments, a bottle handling sub-system comprises a bottle position/location, a position verification module, and/or a bottle type (no bottle, empty bottle, full bottle) verification module. In some embodiments, BHS comprises an RFID/Barcode reader and bottle storage.

In various embodiments, bottle/containers 1801 are placed in one or more holders 1802 that may be placed in the bottle carousel 1805, as shown in FIG. 18. The carousel can contain multiple bottles and a drain connection 1803. A drive mechanism, for example one that is belt driven, 1806 may be configured to rotate the carousel and open its bearings 1804 to deliver the right outlet to the discharge position. The bottle or drain connection can be pushed up by the engage mechanism 1809. The weight of the bottle may be configured to bring the engage mechanism down, when the engage mechanism disengages. In case of the drain connection, a spring 1807 may be configured to push the bottle or engage mechanism down. The bottle/container may be passed along a reader 1804, for example a barcode reader or an RFID reader, which is equipped to verify the solution that goes into the bottle. The bottle holder 1802 can be replaced, allowing for the carousel to accept different size bottles. Various sensors can be utilized to determine the position of the carousel. The bottles can have an inline filter that connects to a vacuum system when the engagement mechanism 1809 engages the bottle with the CMC, allowing the discharged solution to be vacuum-filtered. A drain tube 1808 may engage with a bottle engage mechanism 1809 to form a seal with a drain port of the CMC, such as a bottom drain port.

At the filling station, the position of the bottle is verified in various embodiments. The system can be configured such that engagement is prevented in the absence of a bottle or drain connection. Further, the bottles can be checked for any contents and empty bottles can be verified. In some embodiments, confirmation of the empty bottle leads to granting permission to the automated solution dispenser or the computer system operating it to fill the bottle with a new solution. Safety precautions may be implemented to prevent discharge from the CMC in the absence of a bottle or drain connection.

A bottom carousel or container belt may open upon listing a desired bottle. The bottle may pass through a hole in the carousel or belt. The bottles may be placed in the right spot right now in a similar fashion to a CD changer being transferred on a bottle carrier. In some embodiments, bottles can be placed manually, either exclusively or in addition to automated bottle handling. Labels can be entered manually or using the automated labeling methods described herein.

9. Mixing Methods

In various embodiments, the automated solution dispenser prepares solutions using one or more of the following steps:
  i. Flush and verify cleanliness of CMC.
  ii. Dose the solution components: Solution components can be dosed in series or in parallel. In many cases, components include, but are not limited to water, any components available as stock solutions, solids, e.g. fine powders, clumpy powders, crystalline solids, liquids, e.g. acids, bases organic liquids. Water can be dosed so that once dosing is complete, an estimated 70%, 80%, 90%, 95% or more of the end volume has been filled. In some embodiments, larger volumes are required or preferred, for example for chemical reasons, e.g. solubility limits of solution components.
  iii. Stir: Solution may be stirred intermittently or during the entire period. Stirring may be stopped once the dosing of one or more components is completed or once one or more components are determined to be sufficiently or completely dissolved. Magnetic stirrers can be utilized.
  iv. Fill up to 95%, 98%, 99%, 99.5%, or 99.9% of the final volume. The correct ratio of liquid components may be maintained.
  v. Adjust pH: pH adjustment can be accomplished by titrating with liquid or solid components until a target pH is reached. Solution may be stirred during the pH adjustment.
  vi. Top off the solution to 100% of final volume while maintaining the correct ratio of liquid components.
  vii. Transfer the solution: The solution may be prepared in a solution chamber (i.e. the central mixing chamber) and upon completion of the solution preparation, transferred into an output container, such as a bottle or other container.
  viii. Print a label for the container: The output container may be labeled using any of the bottle labeling methods described herein. The label may include sufficient information about the contents of the bottle, such as the composition and pH of the solution, the preparation date, an expiration date, batch and lot information for the components, Material Safety Data Sheet (MSDS) data, user name, or any other desired information.
  ix. Store information about the solution preparation: Key parameters regarding solution preparation collected during the solution preparation process may be stored in the primary computer system operably linked to the automated solution dispenser or in any other networked computer system. The stored parameters may include information regarding the temperature, turbidity, conductivity, pH, and/or time during the different stages of the solution preparation. Parameters from multiple preparations of the same or similar solutions can be compiled to optimize solution preparation for a single solution or a family of similar solutions.
  x. Final cleaning cycle: Clean the CMC in preparation for a new solution.

In some embodiments, a pH sensor or pH-meter is permanently stored in the CMC. A premade storing solution can be pumped into the CMC to safely store the pH sensor/meter. Before a new solution is made, the CMC and the pH sensor/meter can be drained and cleaned. In some embodiments, suitable pH instruments are stored in a dry environment.

A pH calibration step may be performed in previously indicated intervals or as desired. Laboratory accepted standard solutions may be used for pH calibration. A spot check calibration may utilize one verified pH solution to check the calibration at a single reading. A complete calibration may utilize two or more verified pH solutions to calibrate the pH sensor/meter.

In some embodiments, the final volume can be adjusted during or after the dosing of one or more components. For example, a hard to dose solid may be dosed within a permitted range from the original specification, such as 90-110%, 95-105%, 98-102%, 99-101% of the original amount. The final volume of the solution and the amounts of additional solids and liquids can be proportionally adjusted. Solid dosing within a small range of a specified amount can take a longer time, as dosing may be slowed down to allow for small additions of solids, increasingly approaching a target amount. Final volume adjustments of solutions based on approximate dosed amounts of solids within a certain range of a target value may allow for increased speed and efficiency in preparing solutions. In some embodiments, solids that are harder to dose arc dosed within a permitted range from the original specification, such as 90-110%, 95-105%, 98-102%, 99-101% of the original amount, followed by the dosing of solids that are easier to dose proportionally adjusted according to the actual dosed amount of the first solid.

10. Computer Systems

Figure 19:
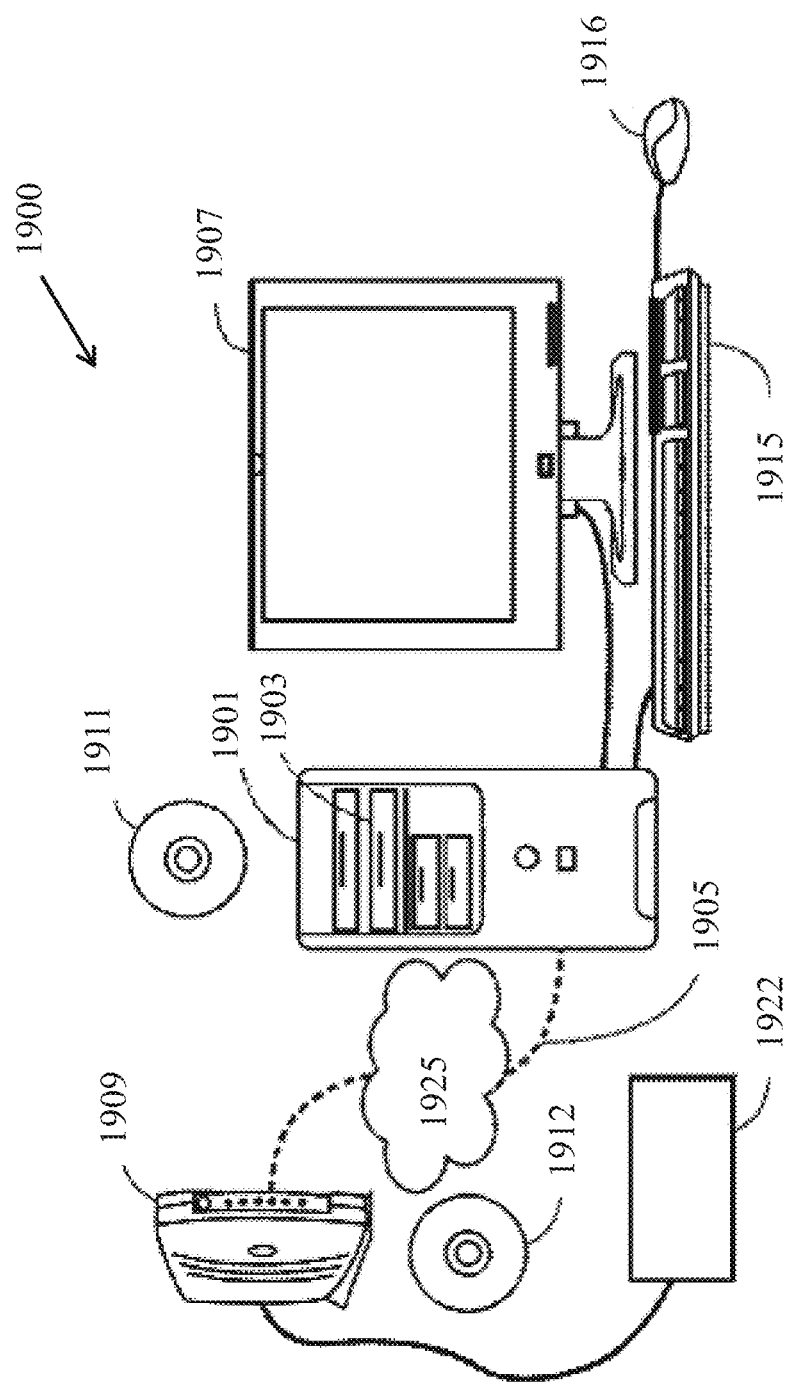
FIG. 19 illustrates various components of a generalized computer system according to some embodiments of the present disclosure.

The computer system 1900 illustrated in FIG. 19 may be understood as a logical apparatus that can read instructions from media 1911 and/or a network port 1905, which can be connected to server 1909 having fixed media 1912. The system, such as shown in FIG. 19 can include a CPU 1901, disk drives 1903, input devices such as keyboard 1915, mouse 1916, monitor 1907, or any combination thereof. Data communication can be achieved through the indicated communication medium 1925 to a server at a local or a remote location. The communication medium 1925 can transmit and/or receive data. For example, the communication medium 1925 can be a network connection, a wireless connection or an internet connection. Such a connection can provide for communication over the World Wide Web. It is envisioned that data relating to the present disclosure can be transmitted over such networks or connections for reception and/or review by a party 1922 as illustrated in FIG. 19.

Figure 20:
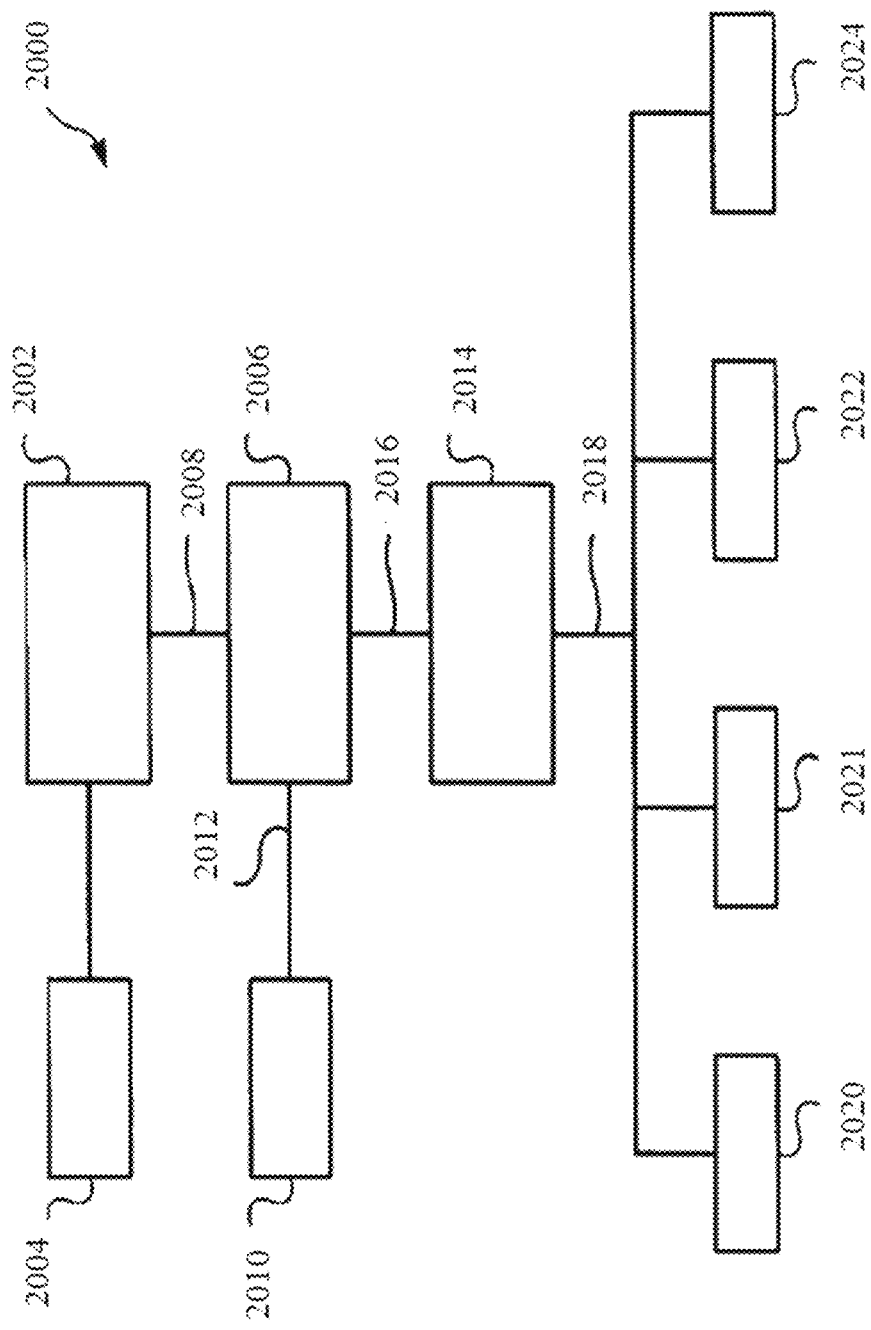
FIG. 20 is a block diagram illustrating an example architecture of a computer system that can be used in connection with example embodiments of the present disclosure.

FIG. 20 is a block diagram illustrating architecture of a computer system 2000 that can be used in connection with example embodiments of the present disclosure. As depicted in FIG. 20, the example computer system can include a processor 2002 for processing instructions. Non-limiting examples of processors include: Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some embodiments, multiple processors or processors with multiple cores can also be used, whether in a single computer system, in a cluster, or distributed across systems over a network comprising a plurality of computers, cell phones, and/or personal data assistant devices.

As illustrated in FIG. 20, a high speed cache 2004 can be connected to, or incorporated in, the processor 2002 to provide a high speed memory for instructions or data that have been recently, or are frequently, used by processor 2002. The processor 2002 is connected to a north bridge 2006 by a processor bus 2008. The north bridge 2006 is connected to random access memory (RAM) 2010 by a memory bus 2012 and manages access to the RAM 2010 by the processor 2002. The north bridge 2006 is also connected to a south bridge 2014 by a chipset bus 2016. The south bridge 2014 is, in turn, connected to a peripheral bus 2018. The peripheral bus can be, for example, Peripheral Component Interconnect (PCI), PCI-X, PCI Express, or other peripheral bus. The north bridge and south bridge are often referred to as a processor chipset and manage data transfer between the processor, Random Access Memory (RAM), and peripheral components on the peripheral bus 2018. In some alternative architectures, the functionality of the north bridge can be incorporated into the processor instead of using a separate north bridge chip.

In some embodiments, the system 2000 of FIG. 20 can include an accelerator card 2022 attached to the peripheral bus 2018. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 2024 and can be loaded into RAM 2010 and/or cache 2004 for use by the processor. The system 2000 of FIG. 20 may include an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with example embodiments of the present disclosure.

In this example, the system 2000 of FIG. 20 may also include network interface cards (NICs) 2020 and 2021 connected to the peripheral bus for providing network interfaces to external storage, such as Network Attached Storage (NAS) and other computer systems that can be used for distributed parallel processing.

Figure 21:
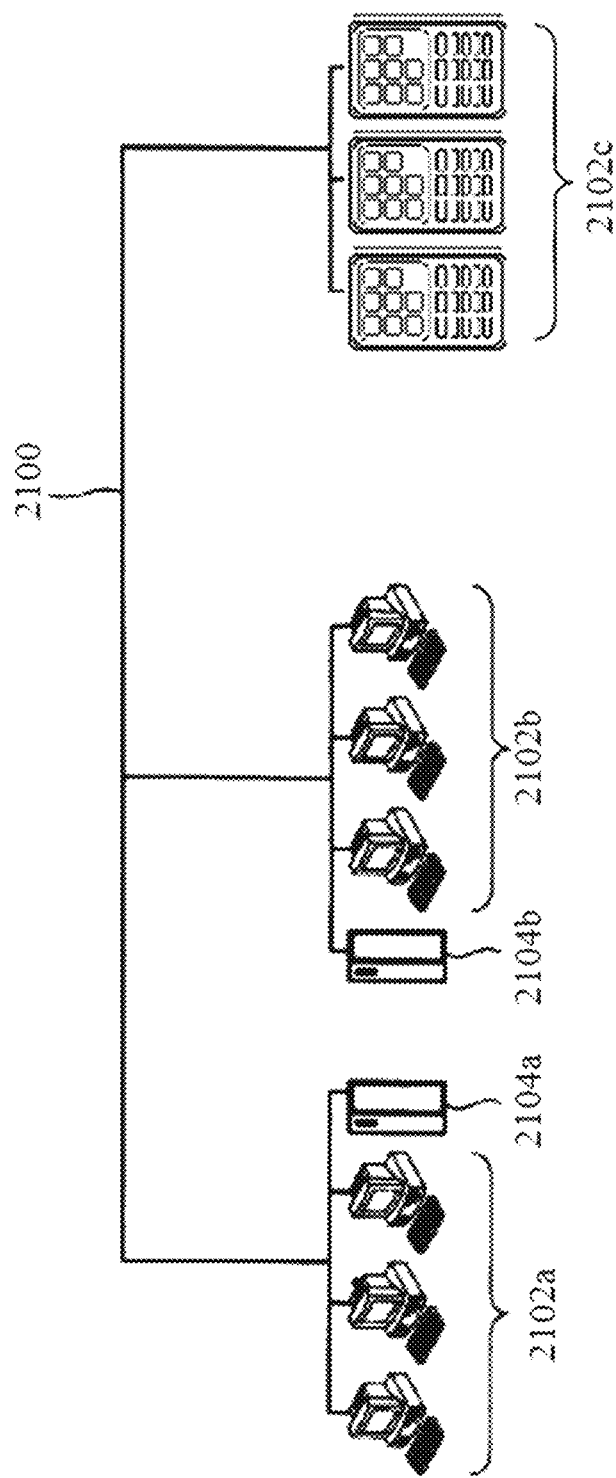
FIG. 21 is a diagram illustrating a computer network that can be used in connection with example embodiments of the present disclosure.

FIG. 21 is a diagram showing a network 2100 with a plurality of computer systems 2102a, and 2102b, a plurality of cell phones and personal data assistants 2102c, and Network Attached Storage (NAS) 2104a, and 2104b. In example embodiments, systems 2102a, 2102b, and 2102c can manage data storage and optimize data access for data stored in Network Attached Storage (NAS) 2104a and 2104b. A mathematical model can be used for the data and be evaluated using distributed parallel processing across computer systems 2102a, and 2102b, and cell phone and personal data assistant systems 2102c. Computer systems 2102a, and 2102b, and cell phone and personal data assistant systems 2102c can also provide parallel processing for adaptive data restructuring of the data stored in Network Attached Storage (NAS) 2104a and 2104b. FIG. 21 illustrates an example only, and a wide variety of other computer architectures and systems can be used in conjunction with the various embodiments of the present disclosure. For example, a blade server can be used to provide parallel processing. Processor blades can be connected through a back plane to provide parallel processing. Storage can also be connected to the back plane or as Network Attached Storage (NAS) through a separate network interface.

In some example embodiments, processors can maintain separate memory spaces and transmit data through network interfaces, back plane or other connectors for parallel processing by other processors. In other embodiments, some or all of the processors can use a shared virtual address memory space.

Figure 22:
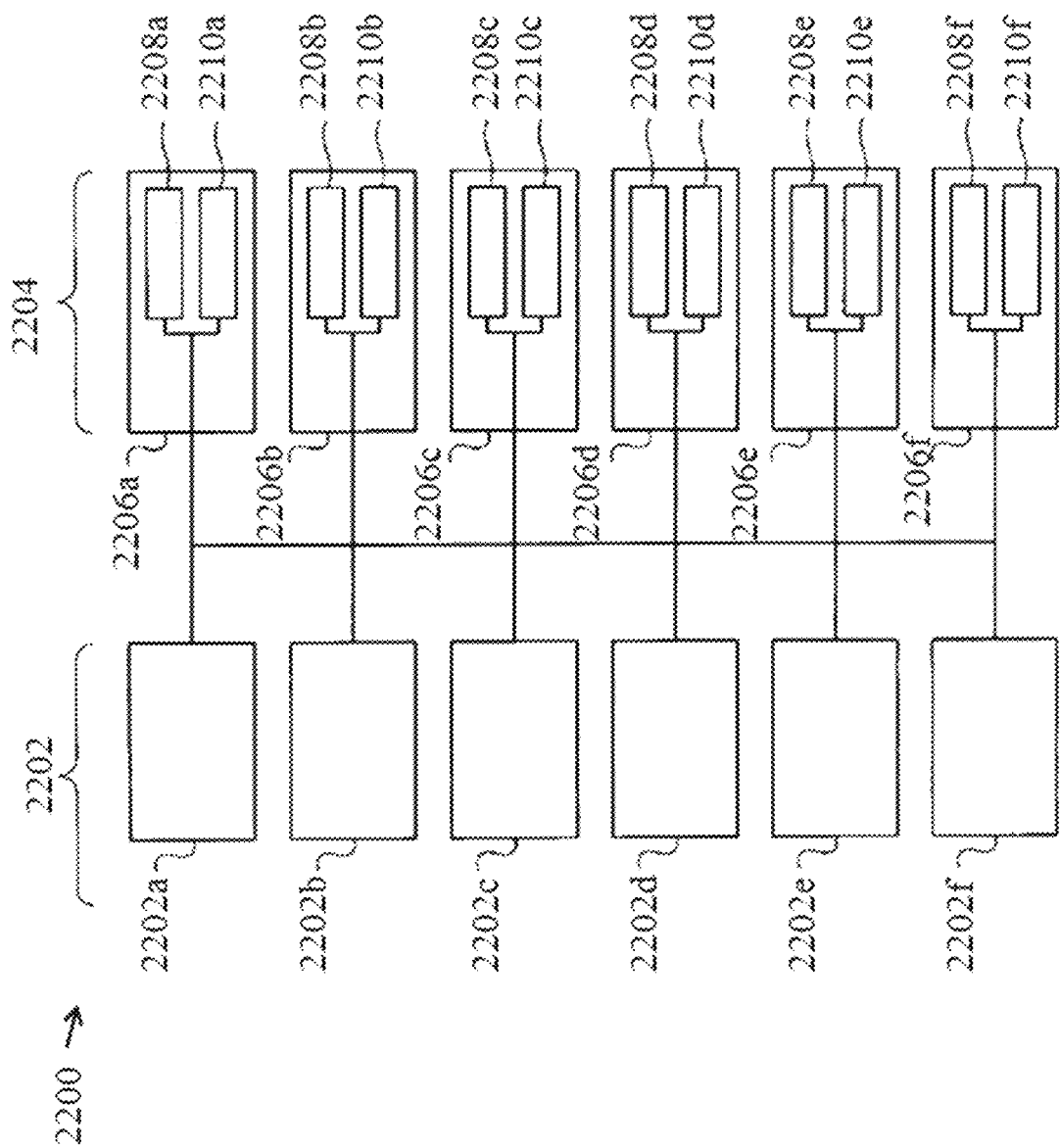
FIG. 22 is a block diagram illustrating another example architecture of a computer system that can be used in connection with example embodiments of the present disclosure.

FIG. 22 is a block diagram of a multiprocessor computer system 2200 using a shared virtual address memory space in accordance with an example embodiment. The system includes a plurality of processors 2202a-f that can access a shared memory subsystem 2204. The system incorporates a plurality of programmable hardware memory algorithm processors (MAPs) 2206a-f in the memory subsystem 2204. Each MAP 2206a-f can comprise a memory 2208a-f and one or more field programmable gate arrays (FPGAs) 2210a-f. The MAP provides a configurable functional unit and particular algorithms or portions of algorithms can be provided to the FPGAs 2210a-f for processing in close coordination with a respective processor. For example, the MAPs can be used to evaluate algebraic expressions regarding the data model and to perform adaptive data restructuring in example embodiments. In this example, each MAP is globally accessible by all of the processors for these purposes. In one configuration, each MAP can use Direct Memory Access (DMA) to access an associated memory 2208a-f, allowing it to execute tasks independently of, and asynchronously from, the respective microprocessor 2202a-f. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example embodiments, including systems using any combination of general processors, co-processors, FPGAs and other programmable logic devices, system on chips (SOCs), application specific integrated circuits (ASICs), and other processing and logic elements. In some embodiments, all or part of the computer system can be implemented in software or hardware. Any variety of data storage media can be used in connection with example embodiments, including random access memory, hard drives, flash memory, tape drives, disk arrays, Network Attached Storage (NAS) and other local or distributed data storage devices and systems.

In example embodiments, the computer system can be implemented using software modules executing on any of the above or other computer architectures and systems. In other embodiments, the functions of the system can be implemented partially or completely in firmware, programmable logic devices such as field programmable gate arrays (FPGAs) as referenced in FIG. 22, system on chips (SOCs), application specific integrated circuits (ASICs), or other processing and logic elements. For example, the Set Processor and Optimizer can be implemented with hardware acceleration through the use of a hardware accelerator card, such as accelerator card 2022 illustrated in FIG. 20.

Figure 24:
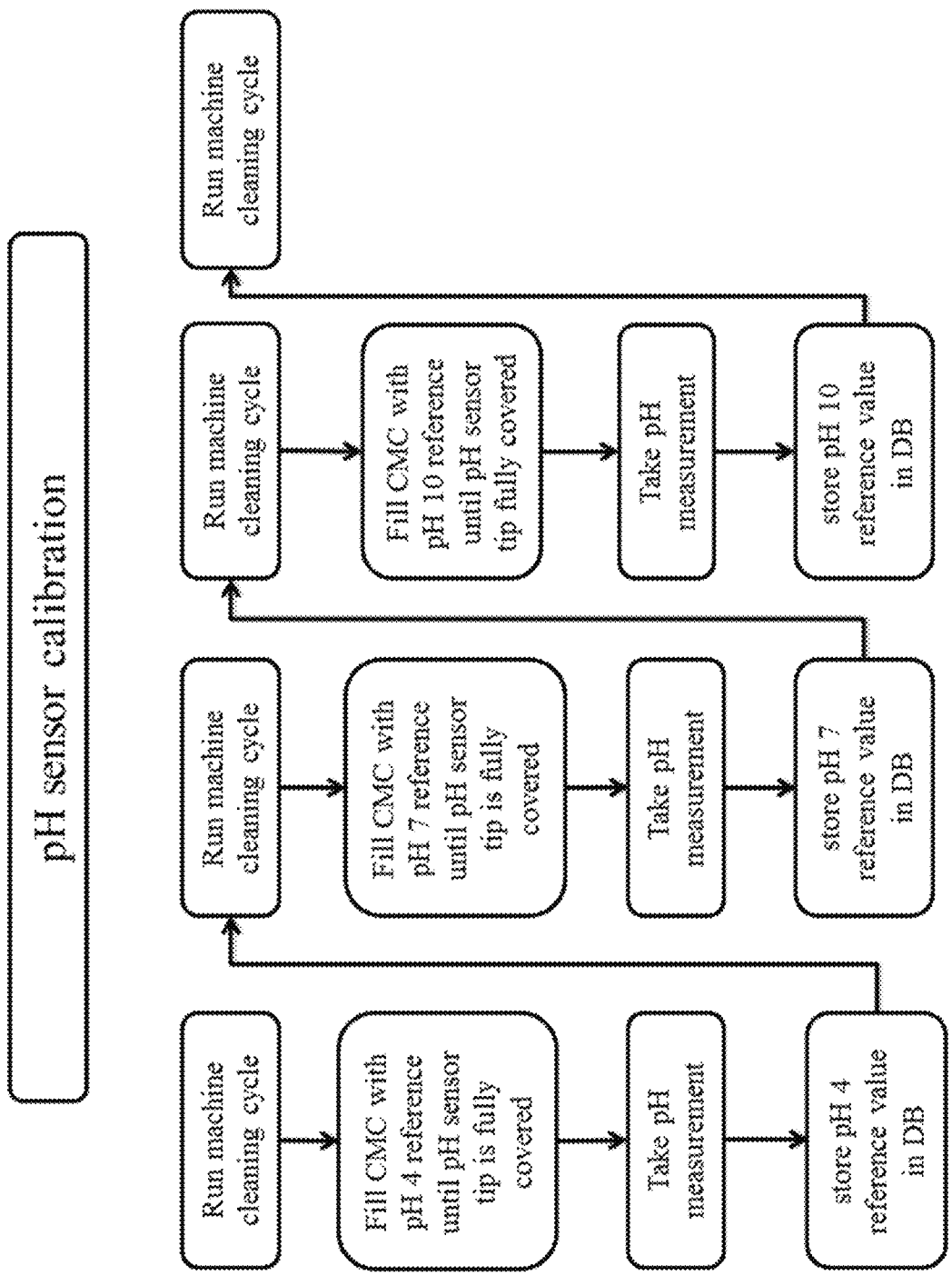
FIG. 24 shows a flow diagram illustrating a process for systems and methods of pH sensor calibration according to some embodiments of the present disclosure.

In some embodiments, the system may calibrate one or more of the various sensors described above. For example, in embodiments having a pH sensor the system may calibrate the pH sensor using one or more pH standard solutions. FIG. 24 illustrates a flow diagram in an example of such a calibration process. The system may first run a cleaning cycle. The cleaning cycle may be run multiple times until a cleanliness sensor signals that the system is clean enough for pH calibration. The liquid handling system will then pump a first pH standard solution through the system to immerse the pH sensor tip in the first pH standard solution. Typically, but not necessarily, the first pH standard solution will have a pH of 4. The pH sensor then takes a pH measurement and stores the reading in a database for sensor calibration measurements maintained by the system, this reading will then correspond the pH of 4 or whatever the pH of the first reference is known to be. The system will then run one or more cleaning cycles as before to ensure the system is clean enough to take a calibration measurement of the next pH reference solution. A second pH reference solution is then pumped through the system until the pH sensor tip is immersed in the second pH reference solution. The second pH reference solution will typically, but not necessarily have a pH of 7. Once again the pH sensor takes a measurement and the value measured is stored in the database for sensor calibration measurement, this reading will correspond to a pH of 7 or whatever the pH of the second reference is known to be. The system will then run one or more cleaning cycles as before to ensure the system is clean enough to take a calibration measurement of the next pH reference solution. A third pH reference solution is then pumped through the system until the pH sensor tip is immersed in the third pH reference solution. The third pH reference solution will typically, but not necessarily have a pH of 10. Once again, the pH sensor takes a measurement and the value measured is stored in the database for sensor calibration measurements, this reading will correspond to a pH of 10 or whatever the pH of the third reference is known to be. The system analyzes the measurements made of the pH reference solutions to calibrate the pH sensor This process may be performed once or repeated until the pH sensor is deemed to be satisfactorily calibrated. Having satisfactorily calibrated the pH sensor the system runs another cleaning cycle in preparation for subsequent solution making operations. In this example, three pH reference solutions are used to calibrate the pH sensor, however, fewer or more pH reference solutions (i.e. 1, 2, 4, or more) reference solutions can be used.

Figure 25:
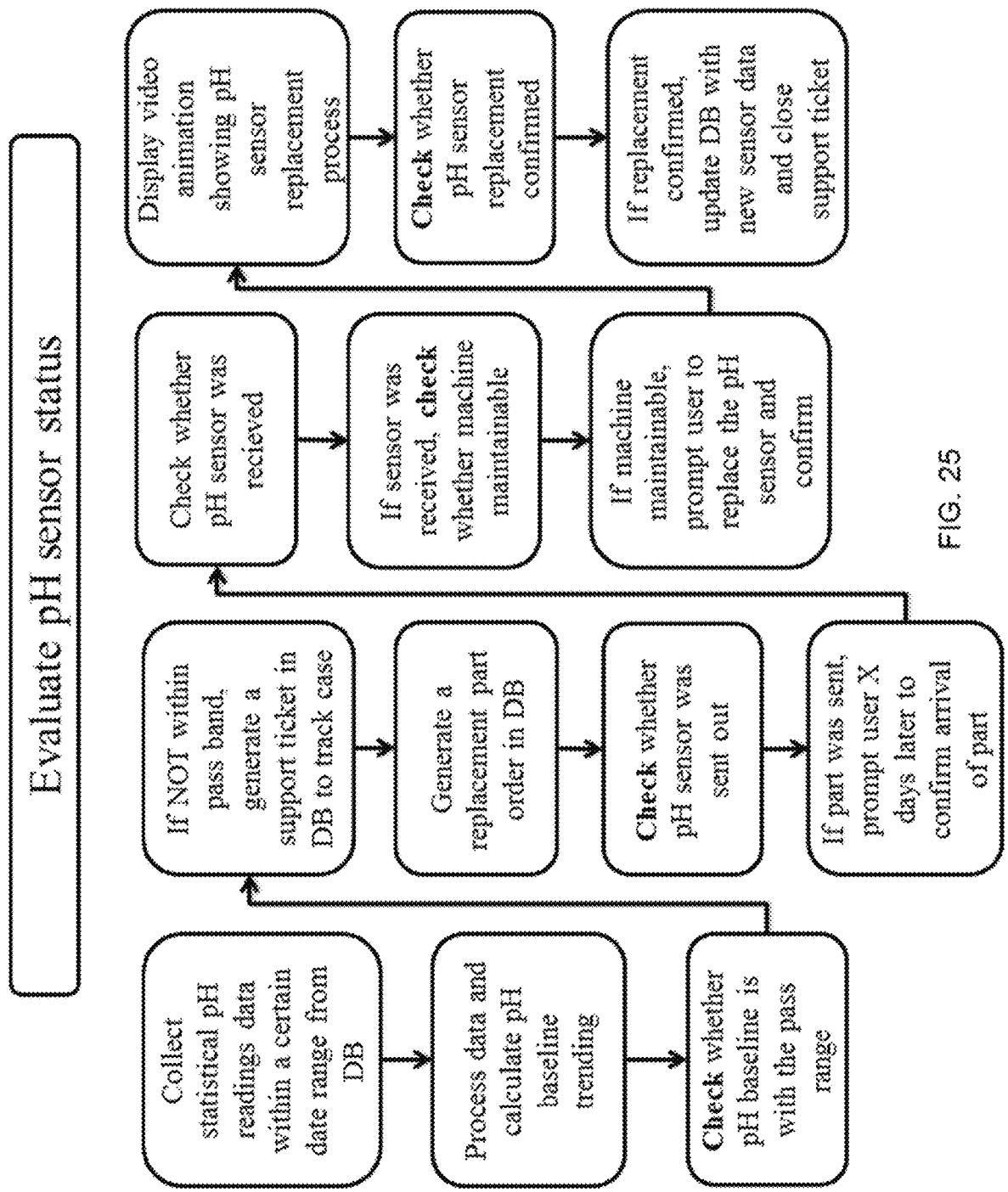
FIG. 25 shows a flow diagram illustrating a process for systems and methods of sensor status evaluation according to some embodiments of the present disclosure.

Some embodiments of the present disclosure further provide systems and method for evaluating a status of the various sensors of the system. These sensors may include pH sensors, weight, sensors, conductivity sensors, turbidity sensors, or any other sensors described in the various embodiments. The system may store measurement histories of any of the sensors comprising readings from the sensors during the operation of the sensor. The measurement histories may be stored in the system's database for access and statistical processing, which in turn may be used to evaluate the operable status of any given sensor. The system may then take appropriate action such as ordering a replacement sensor if any sensor is operating outside of specified parameters. An example is shown in FIG. 25, the system may collect statistical pH readings data from a pH sensor, the collected data may be from a period of time spanning a date range. The system may then process the data and calculate a baseline trend for measurements from the pH sensor. The system may then check if baseline readings or trends fall within a pass range. If the baseline readings or trends do fall within a pass range then the sensor is deemed to be operating within its specified operating parameters. If the sensor's baseline readings or trends fall outside the pass range then the sensor is deemed to be operating outside its specified operating parameters and system generates a support ticket in the system's database for tracking progress in replacing the pH sensor. The system then may also generate a replacement part order. The system may then check to see if the pH sensor has been sent out to the user of the system via an internet connection to the replacement sensor supplier. If the part has been sent, the system may prompt the user after a certain amount of time (typically the 1-7 days) to check to see if the replacement pH sensor has been received. If the sensor has been received the system will check to see if the maintenance can be performed at that time. If maintenance can be performed, the system may display a video animation that instructs the user on how to replace the pH sensor. The system may then check to see if the pH sensor has been replaced. If the sensor has been replaced the system will update its database with data on the new sensor and close the support ticket. In this example a pH sensor has been used for illustrative purposes, however the same process can be applied to replace any of the system's sensors.

As mentioned above, some embodiments of the present disclosure comprise systems and method for calibrating sensors used by the system. In some embodiments the system comprises one or more weight sensors (scales) for measuring the weight of the solids containers. Such measurements may be used by the system to facilitate accurate dosing of the solids reagents stored in the one or more solids containers to the CMC. Such measurements may also be used to track the amount of solids reagents currently stored by the solids handling system and the rate at which the various solids reagents arc consumed. This information may be used to anticipate and/or generate replacement orders of solid reagents. To ensure accurate operation of these scales the system may periodically calibrate the one or more scales. The system may further comprise a solids container, configured to hold a reference weight having a known weight, for calibrating the one or more scales, this container may be referred to as scale calibration container. The reference weight, contained in the scale calibration container or held by the scale calibration container, may have a hook configured to hook and unhook to the scale calibration container. The scale calibration container may be configured to interface with the solids dosing motor such that rotating the solids dosing motor will lower the reference weight into a solid cup of the solid handling system. Further rotation of the solids dosing motor may fully unhook the reference weight from the scale calibration container. After unhooking the reference weight from the scale calibration container, further rotation of the solids dosing motor may re-hook the reference weight to the scale calibration container and raise the reference weight into the scale calibration container.

Figure 26:
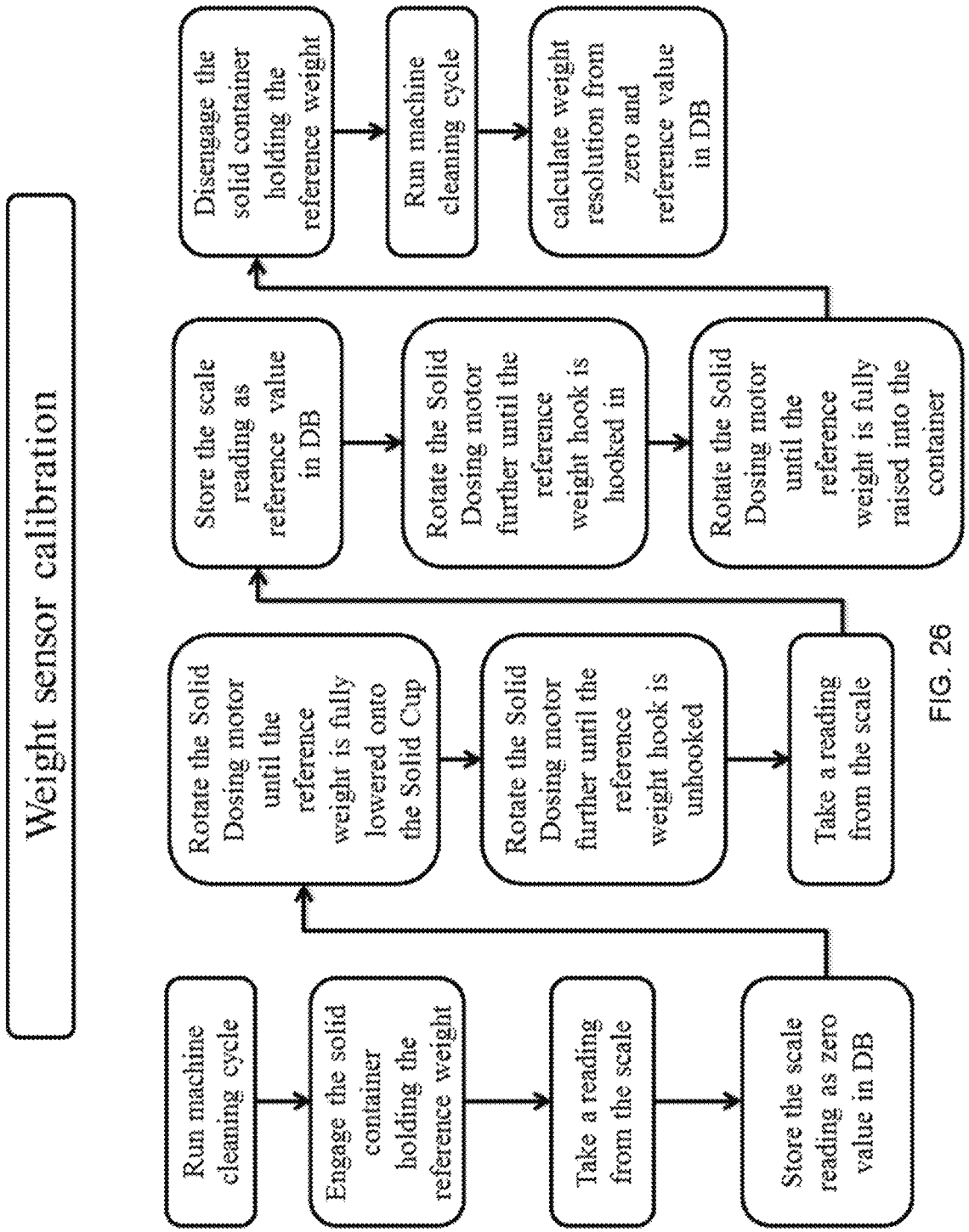
FIG. 26 shows a flow diagram illustrating a process for systems and methods of weight sensor according to some embodiments of the present disclosure.

An example of such a weight sensor calibration process that some embodiments of the present disclosure may perform is illustrated in FIG. 26. To calibrate the one or more scales the system may first run a cleaning cycle to remove any solid contaminants from the system. A user may load the scale calibration container if it is not already one of the solids containers being stored by the solids handling system. The solids handling system will then engage the scale calibration container. The scale being calibrated may then measure the weight of the scale calibration container with the reference weight. This measurement is stored by the system's database as a zero value for the container. The system may then rotate the solids dosing motor to lower the reference weight into the solid cup. The system may then further rotate the solid dosing motor to unhook the reference weight from the scale calibration container. The scale being calibrated may then measure the weight of the scale calibration container and store the measured value in the system's database as a reference value. The system may then further rotate the solids dosing motor to rehook the reference weight to the scale calibration container and to raise the reference weight into the scale calibration container. The system may then manipulate the scale calibration container to disengage it from the solids dosing motor. The solids handling system may then move the scale calibration container to a storage position or prompt a user to remove the scale calibration container. The system may then run another cleaning cycle to remove any solid contaminants and prepare the system for subsequent operations. Using the zero value and reference value stored by the database, the weight resolution of the scale can be calculated and the scale calibration may be completed.

Figure 27:
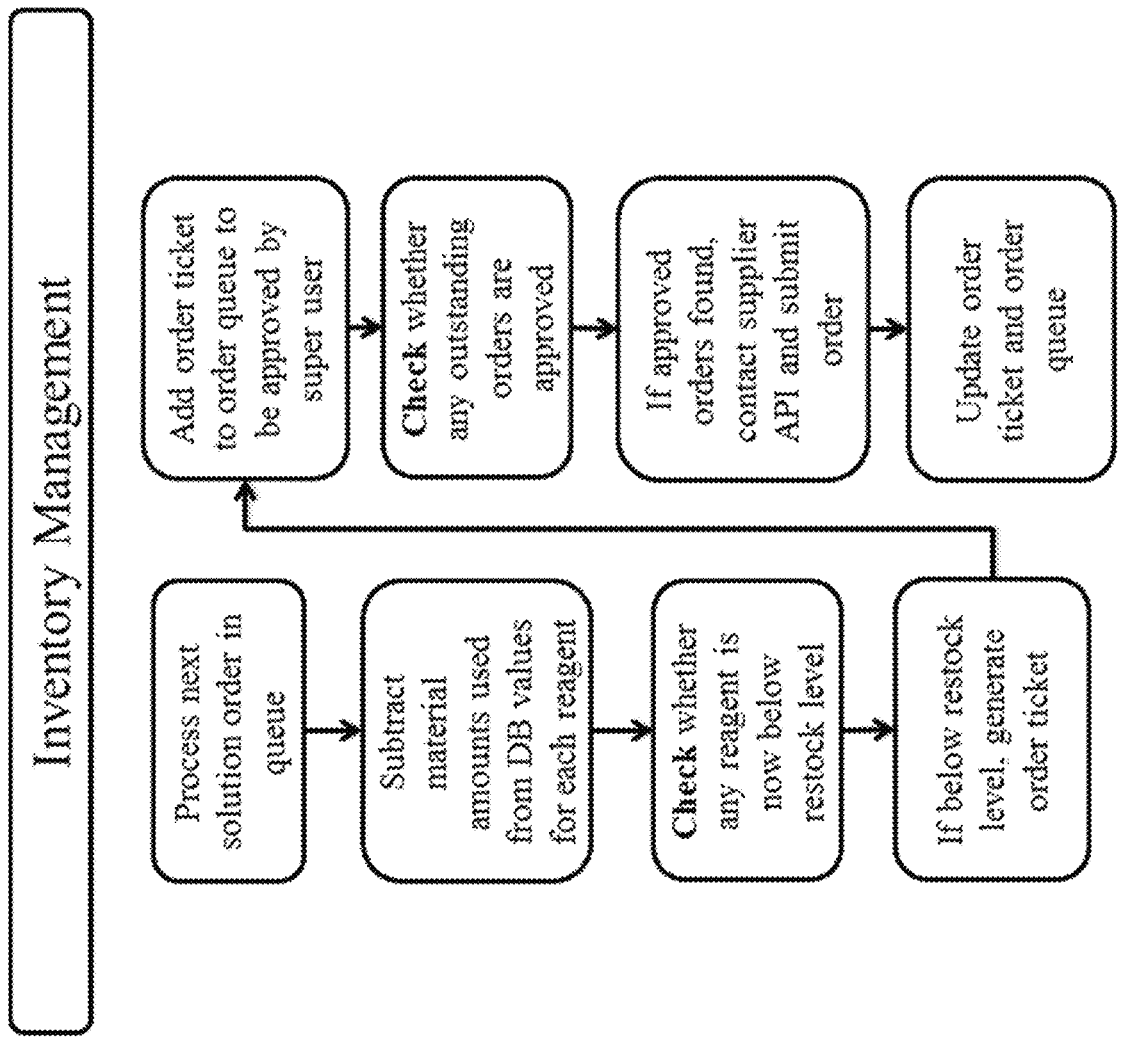
FIG. 27 shows a flow diagram illustrating a process for systems and methods of inventory management according to some embodiments of the present disclosure.

In some cases, system and methods of the present disclosure provide for inventory management. The system's computerized hardware and software may take data from the various sensors of the system (scales, cameras, RFFD scanners) to keep track of and manage the stores of various solid and liquid reagents and components used to prepare the solutions. In some embodiments this data is used along with workflow data to manage the inventory of various reagents held within the system. FIG. 27 shows a flow diagram illustrating inventory management in some embodiments of the present disclosure. In this example, the system may receive a number of solution orders specifying solutions to be made by the system. These solution orders may be stored the system's memory (i.e. the system's database) and executed in a queue. During or after the creation of each solution specified by the solution orders, the system monitors with weight sensors and/or flow sensors the amount of reach reagent consumed to create each solution. The measured amount of each reagent consumed is used to update the system's database, which may store information on how much of each reagent the system has in stock. The system may then check the database to see if the amount of any reagent is below a pre-set restock level. If the amount of any reagent is below the restock level the system may generate an order ticket for that reagent. The order ticket may be a prompt to the user informing the user that more of the reagent needs to be ordered. The order ticket may also be an actual order or pre filled order form that is communicated automatically to a supporting vendor via a computer network or a supplier Application Programming Interface (API). The order ticket may be added to a queue to be approved by the system's user or a manager of the system before being sent to a supplier. The system may then check the order queue for outstanding approved order tickets, if an outstanding order ticket is approved the system can contact the reagent supplier via a networked computer system or supplier API and submit the order for the replacement reagent. The system may then update the order ticket and order queue.

Figure 28A:
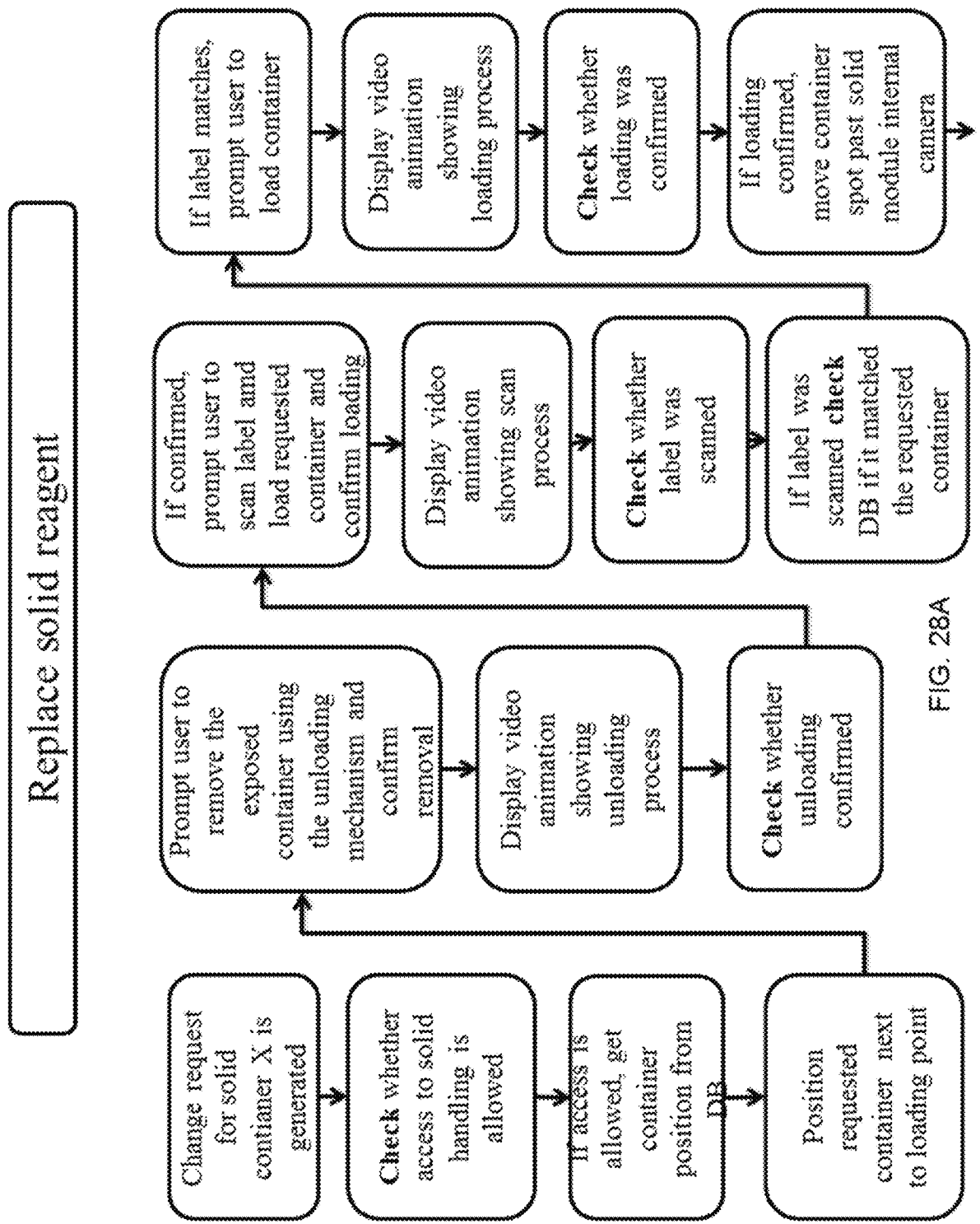
FIGS. 28A-28B show a flow diagram illustrating a process for systems and methods of solid reagent replacement according to some embodiments of the present disclosure.
Figure 28B:
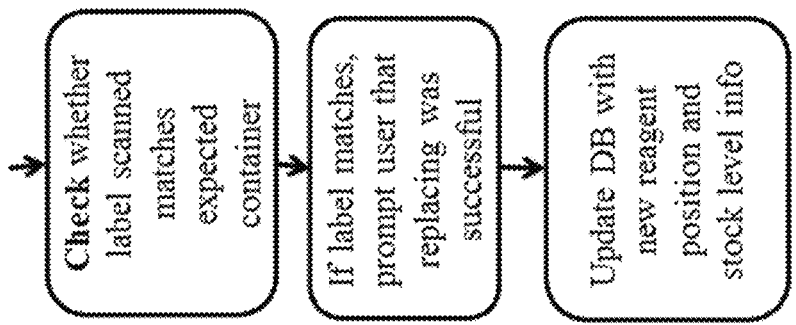

Some embodiments of the present disclosure comprise systems and methods for replacing solid reagents. In any of the embodiments of the present disclosure described herein the solids handling system may comprise a solids turn table or a solids conveyer system that stores one or more solids containers containing solid reagents for use in preparing the laboratory solutions. FIG. 28A and FIG. 28B, show a flow chart illustrating a process for replacing solid reagents used by some embodiments of the present disclosure. At times the one or more containers will need to be replaced or changed out, this may be done to replenish the store of solid reagent inside the container or change the solid reagents available to the system for automatically preparing solutions. At this time, the user or system will generate a change request for one of the one or more containers stored by the solids handling system. The system will then check if access to solids handling is allowed, the solids handling system might be busy performing a higher priority task, or the system may be in a cleaning cycle. In this case the change request will be added to a queue of tasks to be completed. If access is granted, the system will retrieve the container's position from the system's database. The database stores the respective positions of the one or more solids containers in the solids handling system. Using the retrieved position, the solids handling system moves the container to a loading point wherein the solids container can be exposed for access by a user of the system. The system may then prompt the user, via the user interface, to remove the solids container for which the change request has been generated. To aid the user the system user interface may show a video animation that shows the unloading process. The system then checks confirmation of the unloading of the solids container. If such confirmation is received by the system, the system prompts the user to load a new solids container, which may be the just removed container, having been refilled or a completely new container having a different reagent. In some embodiments all the solids containers have labels which the system uses to track the location and contents of the one or more solids containers stored by the solids handling system. Consequently the system may prompt the user to scan the label of the new solids container in order to update the systems database and to track the contents and whereabouts of the one or more solids containers. The system database may have a roster of all stocked containers and their contents. The system may check to see that the label of the new solid container has been scanned and then may check the system database to see if the label of the new solids container matches that of the requested container. If the label of the new solids container matches the requested container the system will prompt the user to load the new solids container into the loading point of the solids handling system. To aid the user the system may display a video animation showing the loading process to the user. The system then checks confirmation of the loading of the new solids container. Once loading of the new solids container is confirmed the solids handling system may move the new solids container to a storage position in the solids handling system. During this process the solids handling system may move the new solids container past a camera or a scanner, such as an RFID or barcode scanner, which scans the label of the new solids container to verify that the correct new solids container with the correct reagent has been loaded into the solids handing system. If the label corresponds to the requested new solids container, the system may prompt the user that the container replacement is successful and update the system database with the location of the new solids container, the reagent stored in the new solids container and the amount of the reagent stored in the new solids container.

11. LABOS

Controller

A Controller or Control System (CS) is operably linked to the automated solution dispensers described herein according to various embodiments of the present disclosure. In many embodiments, the CS is physically connected to the automated solution dispenser. The CS can receive from and send data to the automated solution dispenser. The CS can be further linked to a computer network, as described in further detail elsewhere in this application. In various embodiments, the CS can be accessed remotely through a wireless or wired network. The CS can be linked to a cloud. The cloud can manage various aspects of the CS, such as data updates and the CS can communicate data back to the cloud for automated solution dispenser related activities, including but not limited to ingredient usage, maintenance schedule, instrument use, user access or any other suitable data. The CS can further connect to additional instruments, such as laboratory instruments. In some embodiments, the CS controls at least 1, 2, 3, 4, 5, 8, 10, 15, 20, or more laboratory instruments. The CS can be physically or remotely connected to the additional laboratory instruments.

The controller or control system (CS) can be used in various ways to control the operation of some or all systems in the device. An exemplary CS may comprise low level circuitry, comprising the hardware driver, for example a stepper motor controller, power relays, etc.; sensor information post-processing circuitry, for example current loop driver, low noise amplifier, etc.; one or more microcontroller(s)/microprocessor(s) to control the low level circuitry; a user interface, for example a touchscreen user interface; and/or a central processing unit (CPU), running program code and hosting a database structure.

One aspect to the disclosure relates to a controller capable of operating some or all systems of a solution dispenser system. In some embodiments, a low level circuitry component of the controller comprises a driver for the hardware (e.g. stepper motor controller, power relays, etc). Sensor information from the system can be processed in a post-processing circuitry component, e.g. current loop driver, low noise amplifier, etc. In various embodiments, the controller comprises a microcontroller or microprocessor that is capable of controlling any low level circuitry components. In some embodiments, the controller can be accessed using a user interface, for example a graphical user interface, a touchscreen user interface etc. A central processing unit (CPU) can be operably linked to the various components of the system. In some embodiments, the CPU runs a program code. In some embodiments, the controller hosts a database structure. The database structure can be designed enabling the storage of operating parameters, user instructions, recipes for different solutions, schedule of solution preparation, past usage, information on the solution components, e.g. label information, material safety datasheets etc., consumption of solution components, current stock of solution components, ordering information for solution components, system maintenance schedules, alert schedules/rules, e.g. for preparation of solutions, consumption/current stock of solution components etc., or priority information for users. In various embodiments, the database structure links the stored information in an operationally advantageous manner. For example, the past usage of one or more solution comprising a particular solution component can be used to generate a rule of consumption rate for the particular solution component. The database structure can link this information with the current stock level of a component to compute future levels of consumption.

The controller or control system (CS) can connect secondary devices with auxiliary software. The auxiliary software may be provided by a separate entity/third party then the controller and/or the automated solution dispenser. For example, the auxiliary software may be provided by the same vendor as the secondary device. The auxiliary software may enable the controller to take control of a secondary device, contain its state, store its events and allow sharing of the information related to the secondary device with the same or different auxiliary software. The shared information can be used by the same or difference auxiliary software when controlling another secondary device. Multiple auxiliary software can be introduced and installed, for example to run a single type of secondary device, or alternatively to run multiple secondary devices.

12. LABM1ND/Cloud Computing

Figure 23A:
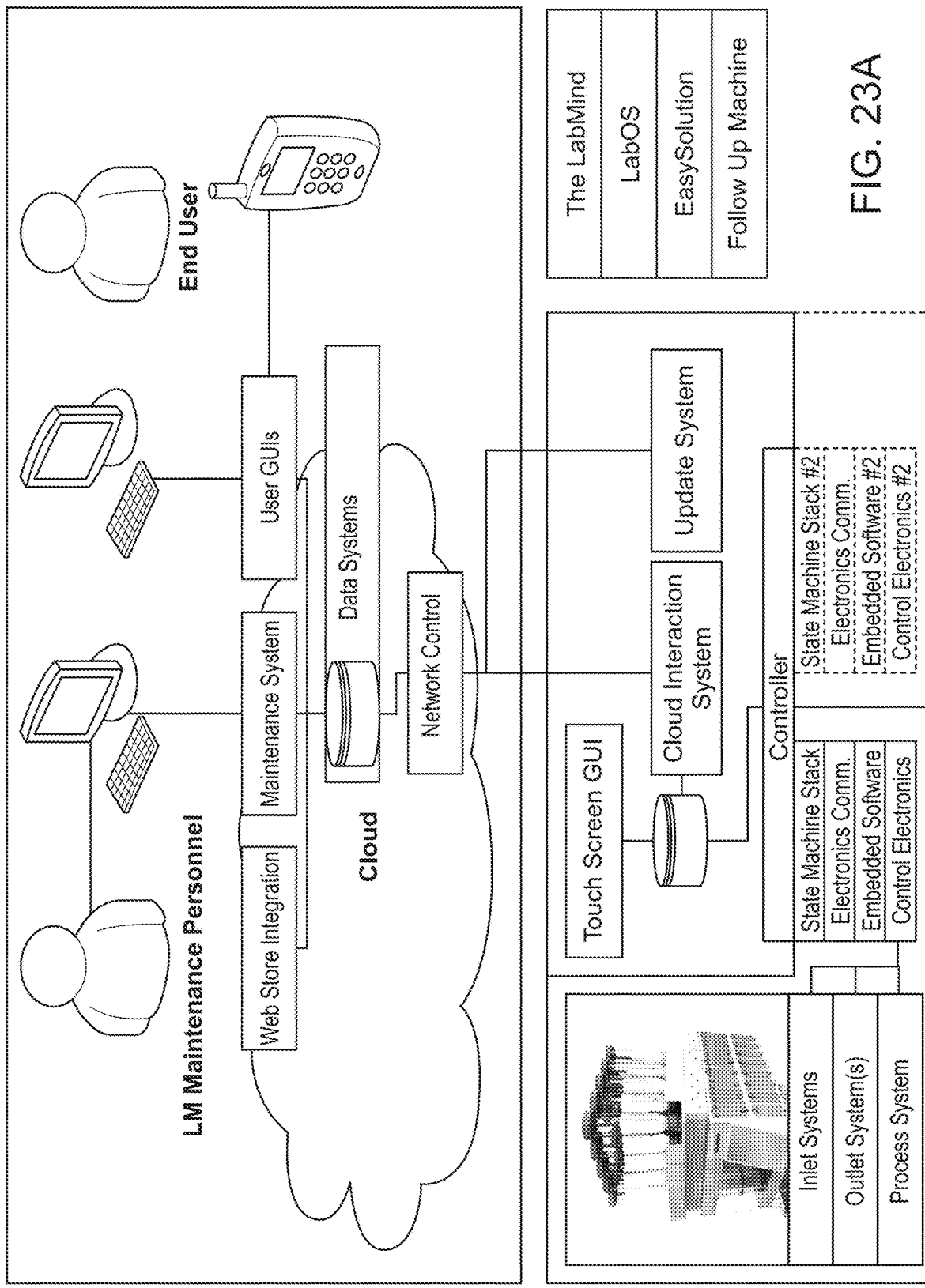
FIG. 23A illustrates a networked system operably linked to an automated solution dispenser according to some embodiments of the present disclosure.
Figure 23B:
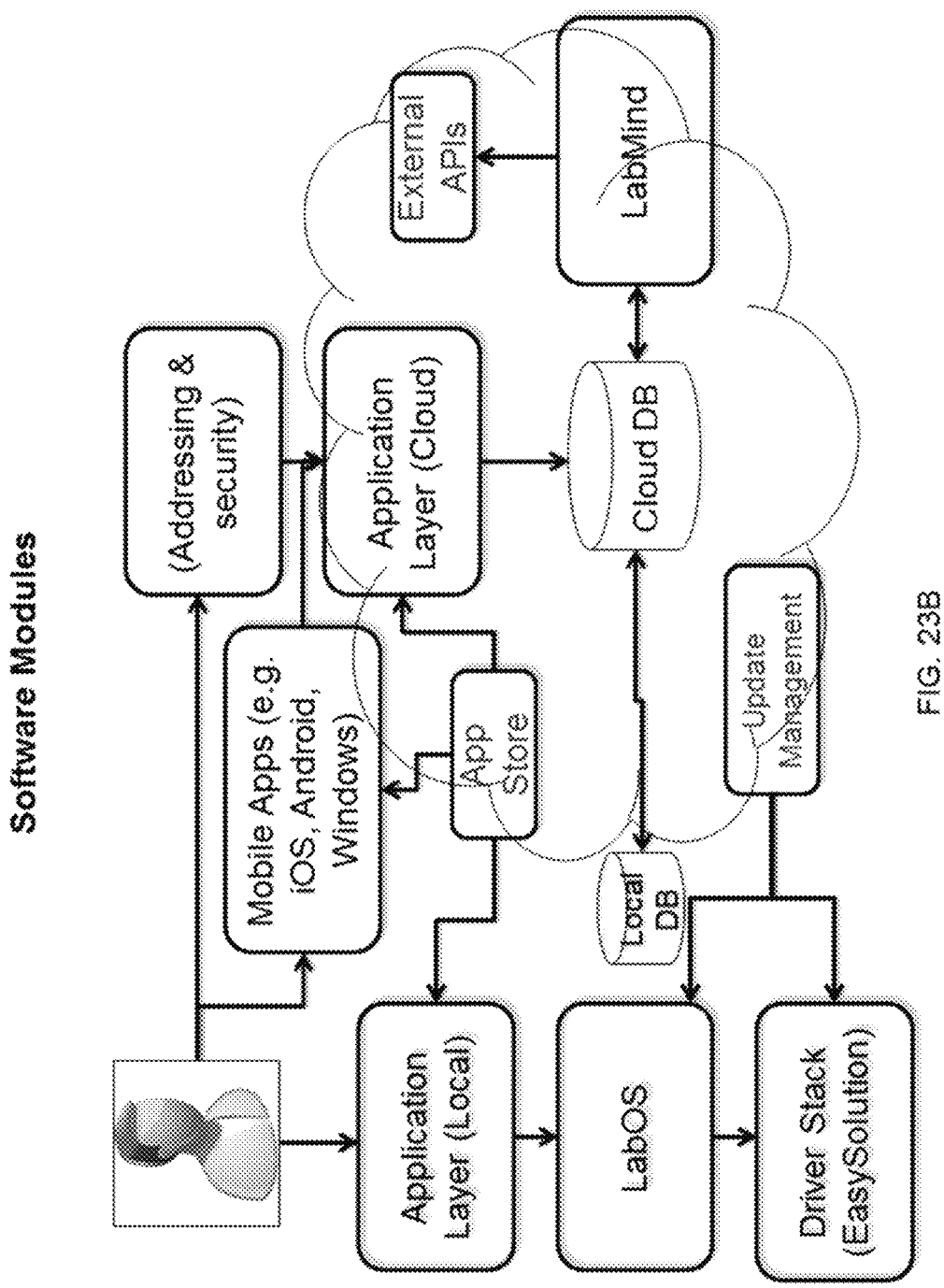
FIG. 23B illustrates an example of a networked cloud system that is designed to work with the automated solution dispenser according to some embodiments of the present disclosure.

The controller of the automated solution dispenser can perform some or all operational tasks locally. In some embodiments, the controller is configured to relay information to a remote location, such as a remote computing center. A remote location, as described herein, may refer to a computer in the next room or one on the other side of the world. A remote computer or computer system, may refer to a computer or computer system at a remote location, to which a user does not have physical access, but which he or she can access or manipulate via some kind of network. A remote location may refer to the physical or network location of a computer that is physically unavailable for access from another computer, computer system or device. In some embodiments, the controller is configured to receive information from a remote computing center. For example, the system can be connected to a network control module of a cloud computing system (FIG. 23A-B). The network control module can relay information between the controller and the data systems in the cloud. In another example, a module from the cloud, such as the network control module, can provide updates to the system. In some embodiments, a component of the cloud can be given permission to install software updates or a new software component to the system.

The systems equipped with the cloud computing systems may generate and contain organizational information creating a hierarchy of multiple automated solution dispenser units. For example, the systems may utilize data for large organizational entities with multiple locations, such as a large corporation, a university with multiple campuses or buildings. Hierarchical information involving multiple locations can be used so that a user, for example a manager, can get information about consumable use/solution preparation information for one or more locations within the organizational entity or the entire organizational entity. The system can act as a queue manager, in a similar fashion to a "printer pool", so that it can optimally distribute requests for solutions to a plurality of automated solution dispenser units. The system may be able take into account proximity and/or specifications from the user submitting the solution request for queue management. The system may propose queue management recommendations to the user for selecting. Further, the systems described herein can link the consumable consumption to the user ordering the solution and not the system used, allowing for appropriate allocation of costs, which can be significant problem in laboratories.

The data systems in the cloud may comprise one or more database structures. The database structure(s) can be designed enabling the storage of operating parameters, user instructions, recipes for different solutions, schedule of solution preparation, past usage, information on the solution components, e.g. label information, material safety datasheets etc., consumption of solution components, current stock of solution components, ordering information for solution components, system maintenance schedules, alert schedules/rules, e.g. for preparation of solutions, consumption/current stock of solution components etc., or priority information for users. In various embodiments, the database structure links the stored information in an operationally advantageous manner. For example, the past usage of one or more solution comprising a particular solution component can be used to generate a rule of consumption rate for the particular solution component. The database structure can link this information with the current stock level of a component to compute future levels of consumption.

In various embodiments, the data systems in the cloud further comprise information relating to the ordering and/or purchasing of solution components and/or system components. Users can be enabled to order such components by interacting with the cloud. The user interaction with the cloud can be via the controller of the automated solution dispenser. The user interaction with the cloud can also be accomplished using a separate system, for example a separate computer, handheld device, or phone. The user interaction with the cloud may comprise a onetime transaction. The user interaction with the cloud can also set up a rule for repeated transactions.

The user may be allowed to interact with the system to schedule a solution preparation on the automated solution dispenser. The user may be enabled to submit other data to the data systems of the cloud, for example the user can review and/or a recipe, leave notes, review a supplier, schedule a maintenance or submit other suitable information for the system.

FIG. 23A-B illustrates the use of a networked cloud system with the automated solution dispenser according to some embodiments of the present disclosure. Accordingly, a controller controls the inlet systems, the outlet systems, the process systems and/or any other suitable components of the automated solution dispenser. The controller may utilize dedicated control electronics for controlling the automated solution dispenser. The controller may additionally comprise a state machine stack, electronics communications subsystem, or embedded software. In some embodiments, the controller comprises a second set or further sets of control electronics, embedded software, electronics communications subsystem, and a state machine stack. The second or further sets can be dedicated to a follow-up machine, for example, a second piece or additional pieces of laboratory equipment, also controlled by the controller.

The controller may be accessed by a user through a graphical user interface (GUI), for example a touch-screen GUI. The controller may be connected to a cloud. System updates may be communicated between the cloud and the controller through the cloud connection. For example, the embedded software, any drivers, and/or any suitable components of the controller may be updated through a system update delivered from the cloud systems. The cloud may also provide optimized sets of parameters for the preparation of solutions. The solution prep parameter sets may be stored and/or optimized in the data systems of the cloud.

The controller may also deliver information to the cloud system, for example, parameters collected from the automated solution dispenser and/or additional follow-up machines including but not limited to laboratory equipment, a log of ordered solutions, a log of usage for various substances making up the solutions by the automated solution dispenser, such as water, solvents, solids, acids, bases, and any other suitable components, a log of usage for various components of the solution dispenser, such as mechanical components or electronic components, or any other suitable information.

Data systems within the cloud can store and maintain any information provided by the controller, maintenance personnel or end users. In some embodiments, the cloud system provides for web store integration for the ordering and/or purchasing of solution components. The controller and/or the networked cloud systems can follow the consumption or stock of a solution ingredient at a particular site, for example the consumption or stock by one or more automated solution dispensers at the site. The web store can provide access to chemical vendors and/or procure the solution components and provide them to end users without or without mark-up. The mark-up can be about 5%, 10%, 15%, 20%, 25%, 40%, 50%, 75%, 100%, 200% or more of the procurement price or the retail price of the solution component, in many cases, commercially available chemicals. Unavailable chemicals can be specially ordered, for example, a synthesis order for a chemical, for example a peptide or oligonucleotide can be sent to a synthesis vendor. The web store can be accessed as the end user demands. Further, the web store can provide alerts for the purchase of solution components based on default or user defined thresholds of consumption rate, total consumption, stock amount, and/or any other suitable parameter.

The web store can further facilitate other transactions including the purchase or ordering of system components/requirements, such as mechanical components of the system, software/drivers, software/driver upgrades, $3^{rd}$ party applications, solution recipes, maintenance fees, maintenance personnel visits or any other necessary components/requirements as needed by the user. The system components can be provided in a similar manner to the solution components or alternative transaction mechanisms can be used. For example, maintenance personnel visits can be recommended on a regular schedule, such as twice or once a year. In some cases, problems may be detected from a distance. In some cases, problems may be resolved remotely without requiring a visit from the maintenance personnel. Purchase of replacement parts can be recommended and their shipment can be scheduled remotely. Local user can be guided for the maintenance and/or repair of the system components remotely, for example by guidance videos. Maintenance fees can be adjusted according the terms and conditions for the purchase or sale of the instrument. Mechanical components can be suggested for renewal based on the specifics of each mechanical component. Software/drivers and related upgrades can be provided by user demand or as they become available.

Maintenance personnel may be given access to the automated solution dispenser and/or the controller through the cloud systems. Maintenance personnel may access log files providing information about the current and past states of the automated solution dispenser and/or the controller. Maintenance personnel may take full and direct control of the system at the lowest levels of the interface, install and/or upgrade software/drivers, boot/reboot the system, perform calibrations, recommend replacement parts and/or perform any suitable task to maintain the automated solution dispenser and/or the controller.

In some embodiments, the cloud provides an access point for end users to access the controller and/or the automated solution dispenser. Secondary access points including desktops, laptops, or mobile devices may network with the automated solution dispenser and/or the controller. Examples of secondary computers and networking systems/methods are described herein. Graphical user interfaces and/or APIs for the software/drivers to be accessed by end users may be provided to secondary computers in the network.

13. Access from Remote Computers/Handheld Devices

In some embodiments, system and methods of the present disclosure relate to accessing the controller of an automated solution dispenser remotely. Additional/secondary computers, such as desktop or laptop computers, mobile devices, for example handheld devices, or mobile phones may access the CS that is operably linked to the automated solution dispenser. Secondary computers may access the CS through a wired or wireless network. In some embodiments, the secondary computers send and/or receive data to or from the CS using an application programming interface (API). In some embodiments, the secondary computers may run the CS environment, for example using a virtual private network (VPN). Data on the CS may be replicated and/or mirrored on the secondary computers as desired or on a regular schedule. In some embodiments, a secondary computer connecting to the CS is operably linked to another instrument, for example a laboratory instrument. The CS and the secondary computer may thus link two laboratory instruments, establishing an environment, wherein the particular usage of one instrument may affect or may be conditional on the usage of the other. For example, the automated solution dispenser may wait for the delivery of containers by a robot before starting solution preparation. For another example, a pump may deliver a prepared solution to another instrument, such as a chromatography device, or electrophoresis device. For another example, the automated solution dispenser may wait for an auxiliary water filter to deliver water to the dispenser. In some embodiments, two or more instruments are be linked using solely the CS that is operably linked to the automated solution dispenser or using the CS in addition to secondary computers, which may be operably linked to one or more laboratory instruments. Various methods of establishing connections between the CS and a secondary computer are described in further detail below and elsewhere in this application.

Network Solutions

Devices, systems and methods of the present disclosure may utilize, or be implemented with the aid of, one or more networks, such as a Local Area Network (LAN), Wireless LAN (WLAN), and in some cases a Storage Area Network (SAN), a Campus Area Network (CAN), Metropolitan Area Network (MAN) or Wide Area Network (WAN), to provide communication between one or more controlling/monitoring stations and the devices that are integrated in the system. Physical computer to computer or computer to device communications can be achieved through any standard commercially available hardware and software. An example of hard-wired networking is the ANSI/IEEE 802.3 (CSMA/CD) standard, utilized as the LAN communication protocol with appropriate networking software and interface cards. In large installations where several individual locations are linked to a central facility, the LANs can subsequently be connected to a user third party WAN. Optical fibers, twisted pair, or coax cable can be used to couple the network computers together. Communication can also be achieved through satellite, telephone lines, TV cable networks, Internet or any other protocols allowing for bi-directional communications. Examples of networked computer/device systems are further described in U.S. Pat. No. 6,055,487, which is herein incorporated by reference in its entirety.

In some embodiments, multiple computers may connect to multiple storage systems through a Storage-Area Network (SAN), a Network-attached storage (NAS), or a hybrid thereof. A storage area network (SAN) is a dedicated, centrally managed, information infrastructure, which enables interconnection of compute nodes and storage nodes. A storage area network facilitates universal access and sharing of storage resources. SANs are often implemented with Fibre Channel technology. Typically, a SAN utilizes block-oriented protocols, such as a small computer system interface (SCSI)-like protocols encapsulated within Fibre Channel frames, for providing storage to compute nodes. However, file systems, known as SAN file systems or shared disk file systems, can be built on top of SANs do provide file-level access. In contrast, general purpose networks (GPNs), including local area networks (LANs), wide area networks (WANs) and the Internet typically implements file-oriented protocols. Some storage area networks may encapsulate block oriented protocols in other protocols, such as an iSCSI protocol.

In some cases, it is possible to find more than one path through a SAN from the computer to one or more of the storage devices. When more than one such path exists, the path over which data is communicated can be controlled and it may become possible or desirable to distribute communications among the multiple paths. Network solutions for integrated controlling/monitoring/device systems are further described in U.S. Pat. No. 6,985,983, which is herein incorporated by reference in its entirety.

In various embodiments, the computer system that is directly connected to a primary piece of laboratory equipment, such as the automated solution dispenser described herein, acts as a hub, for example a WLAN hub, for a network.

Drivers, Applications, and Operating Systems

In various embodiments, the OS of the central/controller computer is equipped with application programming interfaces for easy installation of additional drivers and/or applications. In some embodiments, a separate operating system (OS) driver may be utilized for each operating system, interface adapter and device protocol combination. Any OS can be used, including LINUX, UNIX, MAC OS X, GOOGLE CHROME OS, MICROSOFT WINDOWS, MINIX, SINGULARITY or any other suitable OS.

An OS driver may be installable into the operating system it is designed for by a variety of users, for example when a user supplements the integrated system with a new device. The driver can generate control sequences according to the device protocol for each device supported. These control sequences can be passed from the OS driver, typically through an interface adapter, to the device, for example over any relevant cabling or wireless solution. Data and command response information can be returned from the device through the interface adapter to the OS driver.

In some embodiments, fewer but more complex installable OS drivers may be used. With this approach, a single complex OS driver can be used with a desired operating system and can have the ability to interface OS-specific system-call commands to device-specific commands for each of the device types that may connect to each adapter. Such complex OS drivers may typically contain an OS-interface module for communicating with the OS; command interpreting and translation modules, dedicated to different types of devices in communication with the OS-interface module; redundancy control modules operating in tandem with command interpreting and translation modules for controlling redundant features of various types of devices; an adapter-interface module in communication with the adapter and with the command interpreting and translation modules; and/or a redundancy control module operating in conjunction with the adapter-interface module to control any path redundancy that may exist. Features of such complex drivers are further described in U.S. Pat. No. 6,985,983, which is herein incorporated by reference in its entirety.

Integrated Systems

In some embodiments, the present disclosure relates to an integrated controller which includes a plurality of local and/or remote devices and one or more controlling and monitoring stations. The local and/or remote devices may include a camera, a light detector, a moveable optical system, a radioactivity detector, a light source, a power supply, a voltage regulator, a voltage meter, an ammeter, a thermocoupler, a thermometer, a potentiometer, an oscillator, a heater, a cooler, a pump, a pressure regulator, a chromatography system, an agitator, a shaker, a sonicator, a vacuum source, a scale, a centrifuge, a filtration device, a timer, a monitor, a robotic arm, an automated pipetting system, a positive displacement pump, and/or a printer. The controlling/monitoring stations may include a computer for controlling predetermined functions of the devices in the system. The controller may be in direct communication with an automated solution dispenser.

In some embodiments, a network, such as a LAN, WLAN, CAN, MAN, WAN or SAN, provides communication between the devices and the controlling/monitoring stations and data storage stations. A computer interface may provide bi-directional communication between analytical instruments, robots and peripheral devices and a computer. In various embodiments, the system employs a robot which is responsive to computer commands and capable of performing mechanical functions. Systems incorporating multiple controllers and peripheral devices in a network are exemplified in U.S. Pat. No. 5,366,896, which is herein incorporated by reference in its entirety.

Exemplary embodiments of the present disclosure seek to provide a system and method for the remote control of laboratory equipment from a single central computer/controller or from multiple computers networked into a central computer/controller. In various embodiments, a user interface incorporates features to control an automated solution dispenser as well as any peripheral devices. The user interface may be replicated exactly or in a suitably alternate form in a networked computer. In some embodiments, the user interface is only accessible through a networked computer.

Various features of the user interface may allow for quick, efficient, simple control of the laboratory equipment in the system. Accordingly, collaboration between local and networked users may be facilitated.

Interfaces—Application Programming Interfaces

In some embodiments, network software (e.g., Novell, Banyan, Windows NT, UNIX, etc.) executing on a network server is used to insulate clients (end users) at least somewhat from the profusion of interface command sets. Network software may do so by limiting clients to a series of network-supported operations.

In some embodiments, network software controls the entire network. Network software may interact with and issue interface commands to connected devices through application program interfaces (APIs) designed for that network such as, through software that implements the APIs. In some embodiments, specific APIs for each network software/device combination are utilized. The interface commands may be translated among and through various APIs. In some embodiments, a generalized command set may aid communication among the networked devices.

Systems and methods of the present disclosure may integrate one or more pieces or units of laboratory equipment. In some embodiments, the integration is performed at a Laboratory Information Management System (LIMS) or lower level. A computer system, such as LabOS, may run multiple pieces of laboratory equipment. Software and hardware for laboratory applications may be integrated using methods and systems of the present disclosure. In various embodiments, similar components with shared functions are repeated in multiple pieces of laboratory equipment. Flexible linking of individual components, such as a camera with computer systems that drive and/or obtain data from such components is possible using the methods and systems of the present disclosure. Computer systems may control multiple components in various pieces of equipment, thus creating new combination of available components. For example, a camera may be used as a colony counter, through the use of custom software. In another example, a computer system can control liquid chromatographers, by controlling pumps, sensors, or other components within this piece of laboratory equipment. Software can be provided by anyone, including, for example, the vendor supplying the computer system, the laboratory equipment, an independent laboratory end user or any other suitable user. Computer systems of the present disclosure may be operably linked to a primary piece of laboratory equipment, such as the automated solution dispenser described herein. Computer systems of the present disclosure, such as LabOS, can be provided with sufficient accessibility to programmers enabling integration of devices, software and remote computers with the original computer system.

Uses of lab information management systems (LIMS) in integrated laboratory systems are further described in U.S. Pat. No. 7,991,560, which is herein incorporated by reference in its entirety.

In some embodiments, a common command interface (CCI) provides an interface abstraction allowing network device applications to maintain one set of code for each command regardless of which command interface (e.g., web, CLI, NMS, etc.) initiates the command Network devices including telecommunications and data communications equipment may be administered and/or controlled through a Command Line Interface (CLI) that provides the user (i.e., administrator) with a textual interface through which the administrator may type in commands CLI connections can be made either directly with the device through a console or through a remote connection. Web interfaces may also allow administrators to remotely control network devices through web pages. In some cases, web interfaces may provide easier access with a more visually rich format through Hypertext Markup Language (HTML). For example, commands may be grouped and displayed according to particular categories and hyperlinks may be used to allow the administrator to jump between different web pages accessing a network comprising one or more laboratory instruments.

In some embodiments, the preferences of a large number of users and advantages of various interfaces are accommodated by utilizing a variety of interfaces, for example, a command language interpreter (CLI) interface and a web interface provided to one or more network devices.

In some cases, the applications corresponding to the commands include separate code for each interface. Applications running on a network device may maintain an API for each external interface. In some embodiments, the source of each received command is tracked so that responses can be provided in the appropriate format, for example, HTML for a web interface or American Standard Code for Information Interchange (ASCII) for a CLI.

In some embodiments, a common command interface (CCI) provides an interface abstraction allowing network device applications to maintain one set of code for each command regardless of which command interface (e.g., web, CLI, NMS, etc.) initiates the command Command codes in each application may be shared across multiple command interfaces. The interface abstraction allows new applications including additional commands to be added to a network device and existing applications to be dynamically upgraded to include new and/or modified commands without having to modify the CCI. Thus, the network device may provide the increased flexibility of having multiple command interfaces, while minimizing the complexity required to maintain commands across those interfaces. In addition, a community command interface may be used to connect the common command interfaces of multiple network devices. U.S. Patent Pub. No. 2003/0126195 describes uses of common command interfaces in further detail and is herein incorporated by reference in its entirety.

Connections Within the Network

Various laboratory equipment in the system may be connected to a general purpose computer system via a short-distance connection bus, such as general purpose interface bus (GPIB), small computer system interface (SCSI) and/or universal serial bus (USB). The laboratory equipment may be any set of electronic devices with displays and/or control keys. For example, the laboratory equipment may include a camera, a light detector, a moveable optical system, a radioactivity detector, a light source, a power supply, a voltage regulator, a voltage meter, an ammeter, a thermocoupler, a thermometer, a potentiometer, an oscillator, a heater, a cooler, a pump, a pressure regulator, a chromatography system, an agitator, a shaker, a sonicator, a vacuum source, a scale, a centrifuge, a filtration device, a timer, a monitor, a robotic arm, an automated pipetting system, a positive displacement pump, and/or a printer. Each item of hardware may be connected to the controlling computer. One or more standard personal computers may further be connected to the controlling computer. For example, the computer system may be equipped with a GPIB connector, for example, via a payment card industry (PCI) expansion card.

The connection, such as a short-distance connection, between the laboratory equipment and the controlling computer and any networked computers to it may allow for the sending of control signals to the laboratory equipment and allow for the receiving of output from the laboratory equipment.

One or more computers in the system, such as the controller computer or any computers networked to a controller computer, may be connected to a computer network, for example an intranet or the Internet.

Use of Software, Network Stacks, and Layers

The computer system may execute software for performing one or more functions. The computer system may execute software for communicating with the GPIB. In some embodiments, this software comprises a hardware driver. The computer system may also execute one or more hardware drivers for controlling the functions and interpreting the output of the laboratory equipment. There may be one driver for each piece of equipment or several pieces of equipment may share a common driver. One or more drivers may be utilized to effectively communicate with the laboratory equipment. The computer system may also execute software for communicating over the computer network to another computer. This software may include software for connecting to a virtual private network (VPN) or may include a client application for communicating with a remote server application over a virtualized environment. In some embodiments, the automated solution dispenser is controlled using information originating from a remote computer.

The computer system may be in communication with a remote computer system over a network. The connection may be a direct connection, for example, packets may be routed directly between the computer system and the remote computer system over the network or both the computer system and the remote computer system may execute a client application for contacting a server application that is also connected to the network. In this case, the server application may manage the communication between the two computer systems, for example, using a web service or a virtualized environment.

In some embodiments, the computer system is a general purpose computer system. In some embodiments, the computer system may be a special-purpose digital device designed to manage the direct control of the laboratory equipment by the remote computer over the computer network. A special-purpose digital device may include a network adapter port such as an Ethernet port or wireless network adapter, a port for connecting to the laboratory equipment, for example, a GPIB port, and a microprocessor for executing various software layers. Various software layers may be executed by a special-purpose digital device for connecting laboratory equipment to a computer network. For example, a transmission control protocol/internet protocol (TCP/IP) layer may be used to manage communication over the computer network by the sending and receiving of packets of data. The TCP/IP layer may be able to interpret the packets of data and pass along the interpreted information to a driver layer. The driver layer may then translate the data interpreted by the TCP/IP layer into equipment control and output signals. The driver layer may then send the equipment control and output signals to and from a GPIB layer which manages communication with the laboratory equipment.

In some embodiments, the remote computer system is a general purpose computer system. A remote user may use a remote computer system to interface with the computer system across a network. The remote computer system may execute software for transferring data across the network. The software may include software for connecting to a virtual private network (VPN) or may include a client application for communicating with a remote server application over a virtualized environment.

In some embodiments, the remote computer system is equipped to execute user interface software for presenting a virtual control laboratory equipment control panel to a remote user. In some embodiments, for example where the computer system and the remote computer system communicate via a server over the virtual environment, the user interface software may be executed on the server, rather than, for example on the remote computer system.

In some embodiments, a user interface presents a virtual control laboratory equipment control panel to a remote user. In some embodiments, the computer system presents output from the laboratory equipment to a remote user. In various embodiments, any software, for example software for presenting the laboratory equipment control panel or output to a remote user, drivers, or network stacks, is installed by a user other than the manufacturer or the seller of the computer system linked to a primary laboratory equipment, such as an automated solution dispenser. In some embodiments, multiple pieces of laboratory equipment are controlled by the computer system, including for example, an automated solution dispenser. In various embodiments, one or more pieces of laboratory equipment linked to the computer system are provided by a user other than the manufacturer or the seller of the computer system linked to a primary laboratory equipment, such as an automated solution dispenser. In some embodiments, a remote display may include functionality that is not present on a local display of laboratory equipment.

A panel display for remote computer systems may be generated by a virtual panel application that may be executed either on the remote computer or on a server accessed by the remote computer. The virtual panel application may generate the panel display and ensure proper panel display function.

One or more computer systems or servers connected to the laboratory equipment of the present disclosure may determine whether a remote command, for example a command delivered from a remote server or a virtual panel application, is being executed for the first time. Commands sent from remote locations may be sent multiple times. The execution of a particular command may be checked to avoid duplicate executions. In some embodiments, a duplicate command is only executed, when it has not been previously executed. In this fashion, failures in prompt execution of remote commands, due to, for example, connectivity problems, can be smoothed within the network.

Operating systems and software applications used by general purpose computers may be subject to occasional software crashes and other unexpected terminations. Moreover, the network connection between the computer system and the remote computer system may occasionally fail. Accordingly, the possibility exists that the present state of one or more pieces of laboratory equipment may be lost upon a software crash. Each time a piece of laboratory equipment is turned on, or another critical setting is changed, the status of the laboratory equipment may be recorded to a configuration file. Then, as a remote command, for example, one from a virtual panel application, is executed, it may be determined whether the software has experienced a crash or whether the command has previously been executed. In some embodiments, remote software may have access to a log of experienced crashes. Upon a re-execution attempt, the software access information related to shut down status, for example proper or crash shut-down during a previous execution attempt. Crash recovery protocols may be performed in cases where a crash has occurred. Crash recovery protocols may include reading a log/configuration file to determine status of one or more pieces units of laboratory equipment, for example whether they have been left powered on, left in the middle of an execution step or a longer protocol, for example an event loop, for that piece of laboratory equipment. In some embodiments, a user may be prompted to shut down a laboratory equipment left on or to take any other desired remedial steps.

In some embodiments, the program may enter an event loop. The event loop entry may be contingent on information obtained from a log/configuration file, for example reporting the presence or absence of a recent crash or crash recovery has been performed. In some embodiments, an event comprises a user making a change to one or more of the displayed settings related to a piece of laboratory equipment, for example as displayed on a panel display. The user may use a panel display to turn on a power supply, to start a cleaning cycle, to calibrate a pH meter or send any other suitable commands for operating the piece of laboratory equipment. In some embodiments, an event comprises the occurrence of a read update. In an event loop, a determination may be made whether an event has occurred. When an event has occurred, the event may be parsed. Parsing of an event may include executing the instructions offered by the user. For example, where the event includes the user activating a power toggle for a unit of test equipment, commands for activating the unit of test equipment may be generated and transmitted to the test equipment via the network and the computer system.

In some embodiments, an event is a read request. A read request may comprise a command sent to a piece of laboratory equipment requesting that one or more parameters be measured and sent back, such as for display on a panel display. For example, where the piece of laboratory equipment comprises a power supply, the read request may be to read a present voltage, current and power being drawn from the power supply. In another example, where the piece of laboratory equipment comprises a turbidity sensor, the read request may be to read a present turbidity level. Such an operation may be triggered either manually, for example, with a user selecting a read command, such as by using a read button on a panel display, it may be triggered at preset intervals, or it may be triggered upon execution of a predetermined list of commands Thus, in various embodiments, the event associated with a read request may be triggered by user input, the completion of certain events or the passage of a predetermined length of time.

In some embodiments, a command may be interpreted as belonging to a category "not permitted". Commands of various categories, such as a "not permitted" category, may be automatically aborted. Users may be given different levels of permission. Permission levels may be determined by an administrator and may be stored in the system. In some embodiments, a user may be presented with a dialog box regarding the user's permissions. In some embodiments, a particular command or set of commands may be not permitted if execution of the commands, given the present state of the laboratory equipment, is likely to damage the equipment or cause other problems. Further examples for remote controls of laboratory equipment are discussed in U.S. Pat. No. 8,041,437, which is herein incorporated by reference in its entirety.

Standard Integration—SiLA Integration

In various embodiments, the computer systems of the present disclosure may be configured for rapid Standardization in Lab Automation (SiLA) Integration. In particular, SiLA defined device classes, for the most commonly used device types in the lab automation environment may be targeted. For each device class, a common set of commands, event-, status- and error-classes may be defined. All major device functions can be programmable through common commands. In some embodiments, specific commands, extending the Common Command Set may be provided, for example by the supplier of the device or by an independent user. Specific commands may be designed to comply with the guidelines for command definition standards of SiLA. SiLA compliant devices may be chosen. In various embodiments, devices are capable to provide information about their device class, configuration, Common Command Set, and their specific commands upon request. Standardized formats and structures according to SiLA may be used by devices to provide data. Device setup for applied labware may be supported by standardized labware specifications, for example as provided by labware manufacturers.

Ad-Hoc Systems

Small automation systems can be assembled for a specific task providing laboratory users with tremendous flexibility. These systems may be assembled permanently, semi-permanently or temporarily. In some cases, such ad-hoc systems might consist of only a few instruments, from different providers.

Device Interface Standards

Well established, commonly accepted device interface standards may be used to ease automation and integration of systems. In some embodiments, the SiLA device interface standard may be used. Standards may focus on defining interfaces and protocols to interconnect any lab equipment to any control application, for example a SiLA enabled control application. In some embodiments, devices can be controlled through a common command set, such as the SiLA common command set. Standards may be applied to custom systems. In some cases, standards may be incorporated to commercially available components of a system that can be obtained modularly from one or more suppliers.

In some embodiments, a software wrapper may translate native device drivers into a standard command structure, such as a SiLA compatible command structure. Software wrappers may be implemented without changing the hardware.

In some embodiments, interface converter hardware with specific protocol converter software is be connected to the native hardware interface, to encapsulate the device, providing high compatibility with standards, such as SiLA.

Data Interface and Labware Specification Standards

In some embodiments, standard data interfaces, such as extensible markup language (XML) based formats are implemented.

Properties of labware that are used with the systems of the present disclosure may be specified using a standard parameter set, for example and XML based parameter set such as the set used by SiLA.

The need for the user to enter information on labware may be eliminated by using a standardized parameter set for labware.

Users integrating devices from different suppliers in a laboratory environment may utilize standardized data interfaces, labware specification standards, and device interfaces supporting common command sets, such as the SiLA device interfaces, to ease of integration in singular or networked computer systems. Existing instruments can be assembled into new configurations, often saving expenses on new equipment, drivers, and time. In some embodiments, open data exchange standard formats supported by the data capturing components enable input and output of data with ease.

14. Online Tracking of Reagent Use—Targeted Marketing for Reagent/Supply Orders

Various embodiments of the present disclosure may allow for tracking reagent use and/or stock level locally or at a remote location. Reagents can be supplied according to stock levels. For example, alerts can be created when the stock level of a particular reagent falls below a certain level. The rate of reagent use can be taken into account to determine an estimated time of depletion for a particular reagent. The alert may be sent to a user of the system for purchasing of reagents. Alternatively, preapproved purchasing decisions can be automatically carried out through a connected supplier site. A networked vendor can ship desired reagents automatically or upon user approval with or without a margin above third party suppliers.

In some embodiments, the controller operating the automated solution dispenser may keep a log comprising information regarding prepared solutions, either locally or in a remote location. In some embodiments, the log comprises complete solution descriptions from users, including, for example, volume, ingredients, concentrations, pH, and temperature. In some embodiments, the total used weight or volume of particular ingredients are tracked either locally or remotely. The desired ingredients may be linked to one or more suppliers providing the desired ingredients, for example through a web interface or other ordering system. In some embodiments, users may be enabled to compare prices from various suppliers for a desired ingredient and/or buy the desired ingredient through the system. In some embodiments, the system may require a supplier to register in order to link desired ingredients to the supplier. In some embodiments, supplier registration may be allowed for a fee. In some embodiments, the supplier links arc automatically provided, when the stock level of a desired ingredient is below a specified level. The specified levels may be supplied by a user or may be preset in the system by the manufacturer. The preset values may further be changed according to updates from a networked computer.

The systems of the present disclosure may store billing information for a given user enabling ordering of parts, ingredients, and even servicing or maintenance of an instrument. For example, the automated solution dispenser or a different piece of laboratory equipment may output an error code. The error code may recommend the user to service the instrument. Alternatively, the error code can be sent to centralized maintenance personnel. The centralized maintenance personnel can address the problem and may decide to fix it with or without cost to the user. The computer systems of the present disclosure may be configured such that a user may contact a vendor for service. In some embodiments, a user is enabled to purchase an instrument part or desired ingredient through the system. For example, the level of a stock ingredient may fall below a certain level and a system alert is created. The alert further activates an automated display of a user alert communicating the level of a desired ingredient. Further, links to one or more suppliers offering the desired ingredients are displayed enabling the user to put an order for the desired ingredient. In some embodiments, a desired ingredient is purchased automatically from a predefined supplier without requiring further input and/or approval from a user.

The systems described herein can further be integrated with various Enterprise Resource Planning (ERP) systems. Permissions for the utilization of the systems and/or ordering of services and parts can be managed by various ERPs.

Methods and systems of the present disclosure may allow for automated or user triggered delivery of reagents. In some embodiments, said delivery is initiated by a transaction for reagents that are under a stock alert. An intermediate vendor may set up delivery of the reagent charging a marginal fee or percentage over a primary vendor. In some embodiments, the user is allowed to choose the primary vendor. The user may save purchasing settings for one or more reagents in the system, the settings including, but not limited to primary vendor choice, size of delivery, and stock alert settings, such as threshold amount, and rate of consumption.

A variety of consumables can be tracked with the inventory management systems described herein, either locally or remotely, for example using the cloud systems connected to the controllers of the automated solution dispensers. Consumables, whose consumption and/or ordering are managed, include but are not limited to water purification cartridges, filters, reagents for solution preparation, replacement parts for the automated solution dispenser and any other suitable parts necessary for the operation of the automated solution dispenser for preparing solutions. In some embodiments, the controller and/or the networked computers, for example the cloud systems described herein, recognize scheduled experiments and/or predict upcoming experiments based on the user provided solution orders. Based on scheduled or predicted experiments, orders for necessary or complementary consumables suitable for the experiment can be ordered through the ordering systems described herein. The ordering systems may calculate order processing times, delivery times and/or any buffer times for the timely delivery of consumables.

15. Finetuned Solution Recipes from Tracking Instrument Operation

Systems and methods of the present disclosure may allow for tracking solution-making parameters from one or more automated solution dispensers. Data collected during the preparation of a solution can be compiled to refine the solution making instructions for a given solution recipe, for example 2 M GdnHCl at pH 5.

In some embodiments, instrument specifications to make a specified solution, such as a user ordered solution, may be tracked over time and be optimized according to sensor output. For example, iterative protocols to achieve desired final solution compositions may need to be followed for making a given solution for the first time. Upon preparing the same recipe one or more times, the system may recognize that certain steps can be removed or combined with others. For example, total volumes of acid or base additions to pH a solution may be stored reducing time and the number of steps it takes to reach a desired pH. In another example, temperature and/or pH values sufficiently suitable for solubilizing a solid in a liquid may be stored in the system, based on previous solution preparation data. Over time, stored values for parameters may be optimized when even better results are obtained using different values. In some embodiments, one or more automated solution dispensers may have access to a networked computer to obtain optimized values for various parameters. The optimized values themselves may be created by aggregating data from multiple automated solution dispensers connected to the networked computer.

16. Kits, Reagents and Recipes

In various embodiments, the automated solution dispenser prepares buffered solutions. Such buffered solutions have many uses, including in molecular and cell biology, biochemistry, crystallography and various fields known to one skilled in the art, where a controlled pH is critical. In some embodiments, a buffered solution is prepared at a pH that is within 1, 0.8, 0.7, 0.6, 0.5, 0.4, 0.3, 0.2, 0.1 pH unit or less from the pKa (acid dissociation constant at logarithmic scale) of the buffering agent. For example, a buffered solution can be prepared using MES at pH 5.5-6.7, 2-[Bis (2-hydroxyethyl)amino]-2-(hydroxymethyl)-1,3-propanediol (Bis-Tris) at pH 5.8-7.2, ADA at pH 6.0-7.2, aces at pH 6.1-7.5, PIPES at pH 6.1-7.5, MOPSO at pH 6.2-7.6, Bis-Tris Propane at pH 6.3-9.5, HES at pH 6.4-7.8, MOPS at pH 6.5-7.9, HEPES at pH 6.8-8.2, DIPSO at pH 7.0-8.2, MOBS at pH 6.9-8.3, TAPSO at pH 7.0-8.2, Tris(hydroxymethyl) aminomethane hydrochloride (TRIZMA) at pH 7.0-9.0, 4-(2-Hydroxyethyl)piperazine-1-(2-hydroxypropanesulfonic acid) (HEPPSO) at pH 7.1-8.5, POPSO at pH 7.2-8.5, TEA at pH 7.3-8.3, EPPS at pH 7.3-8.7, N-(2-Hydroxy-1, 1-bis(hydroxymethyl)ethyl)glycine (Tricine) at pH 7.4-8.8, Glycyl-glycine (Gly-Gly) at pH 7.5-8.9, 2-(Bis(2-hydroxyethyl)amino)acetic acid (Bicine) at pH 7.6-9.0, HEPBS at pH 7.6-9.0, TAPS at pH 7.7-9.1, AMPD at pH 7.8-9.7, TABS at pH 8.2-9.6, AMPS° at pH 8.3-9.7, CHES at pH 8.6-10.0, CAPSO at pH 8.9-10.3, AMP at pH 9.0-10.5, CAPS at pH 9.7-11.1, CABS at pH 10.0-11.4, or any other buffering agent at a pH that is within the buffering range of the buffering agent.

In some embodiments, multiple buffering agents with differing $pK_a$, can be used. Such buffering systems, such as citric acid—$Na_2HPO_4$ buffer system, possessing a suitable buffering capacity at a pH range of approximately 2.6-7.61, are known to maintain their buffering capacity beyond more than 1 pH unit of the $pK_a$ of either agent. Additional examples of multi-agent buffering systems include the citric acid—sodium citrate buffer system at a pH between 3.0-6.2, $Na_2HPO_4$—$NaH_2PO_4$ buffer system at a pH between 5.8-8.0, or any other suitable system comprising multiple buffering agents.

Methods and systems of the present disclosure may relate to recipes and instructions to prepare the buffered solutions described herein, instrumentation that is capable of preparing the buffered solutions, and the processes related to the manufacturing of such solutions.

The temperature of buffer solutions may change the final pH of a desired solution. In some embodiments, the temperature of the buffer is controlled. Buffers may be prepared and used at specified temperatures to minimize deviation from desired final pH values for solutions.

In some embodiments, the systems and methods described herein allow for preparation of solutions at a pH value of about 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, or 11.5

Solutions prepared by the automated solution dispenser may use aqueous solvents, non-polar solvents, polar protic solvents, polar aprotic solvents, and/or organic solvents. Examples of solvents include, but are not limited to non-polar solvents, such as pentane cyclopenaten, hexane, cyclohexane, benzene, toluene, 1,4-dioxane, chloroform, and diethyl ether, polar aprotic solvents, such as dichloromethane (DCM), tetrahydrofuran (THF), ethyl acetate, acetone, dimethylformamide (DMF), acetonitrile, dimethyl sulfoxide (DMSO), and propylene carbonate, and polar protic solvents, such as formic acid, n-Butanol, isopropanol (IPA), n-propanol, ethanol, methanol, acetic acid, and water. In some embodiments, a prepared solution may have a dielectric constant or may comprise a solvent with a dielectric constant that is greater that is in a range of 1-2, 2-3, 3-4, 4-5, 5-10, 10-15, 15-20, 20-30, 30-40, 40-50, 50-60, 60-70, 70-80 or any other range having any of the dielectric constant range as end points, for example 1-10, 2-4, 3-20, 15-50, 30-60, or 60-80.

Various embodiments of the present disclosure may relate to the preparation, storing, ordering, generation or improvement of kits reagents or solution recipes. In some embodiments, the automated solution dispenser maybe ordered one or more of the solutions described herein, solutions containing one or more ingredients from one of the solutions described herein, at specified pH and/or concentration or at a pH and/or concentration within a range having any of the related pH and concentration values as end points. Example solution descriptions include:

Group 1: 1.0 M Citric acid pH 3.5; 1.0 M Citric acid pH 3.8; 1.0 M Citric acid pH 4.1; 1.0 M Citric acid pH 4.4; 1.0 M Sodium citrate tribasic dihydrate pH 3.6; 1.0 M Sodium citrate tribasic dihydrate pH 3.9; 1.0 M Sodium citrate tribasic dihydrate pH 4.2; 1.0 M Sodium citrate tribasic dihydrate pH 4.5; 1.0 M Sodium acetate trihydrate pH 3.7; 1.0 M Sodium acetate trihydrate pH 4.0; 1.0 M Sodium acetate trihydrate pH 4.3; 1.0 M Sodium acetate trihydrate pH 4.6; 1.0 M Sodium acetate trihydrate pH 4.9; 1.0 DL-Malic pH 4.7; 1.0 DL-Malic pH 5.0; 1.0 DL-Malic pH 5.3; 1.0 DL-Malic pH 5.6; 1.0 DL-Malic pH 5.9; 1.0 M Succinic acid pH 4.8; 1.0 M Succinic acid pH 5.1; 1.0 M Succinic acid pH 5.4; 1.0 M Succinic acid pH 5.7; 1.0 M Succinic acid pH 6.0; 1.0 M Sodium cacodylate trihydrate pH 5.2; 1.0 M Sodium cacodylate trihydrate pH 5.5; 1.0 M Sodium cacodylate trihydrate pH 5.8; 1.0 M Sodium cacodylate trihydrate pH 6.1; 1.0 M Sodium cacodylate trihydrate pH 6.4; 1.0 MES monohydrate pH 5.3; 1.0 MES monohydrate pH 5.6; 1.0 MES monohydrate pH 5.9; 1.0 MES monohydrate pH 6.2; 1.0 MES monohydrate pH 6.5; 1.0 M BIS-TRIS pH 5.7; 1.0 M BIS-TRIS pH 6.0; 1.0 M BIS-TRIS pH 6.3; 1.0 M BIS-TRIS pH 6.6; 1.0 M BIS-TRIS pH 6.9; 1.0 M ADA pH 5.8; 1.0 M ADA pH 6.1; 1.0 M ADA pH 6.4; 1.0 M ADA pH 6.7; 1.0 M ADA pH 7.0; 1.0 M Imidazole pH 6.2; 1.0 M Imidazole pH 6.5; 1.0 M Imidazole pH 6.8; 1.0 M Imidazole pH 7.1; 1.0 M Imidazole pH 7.4; 1.0 M BIS-TRIS propane pH 6.4; 1.0 M BIS-TRIS propane pH 6.7; 1.0 M BIS-TRIS propane pH 7.0; 1.0 M BIS-TRIS propane pH 7.3; 1.0 M MOPS pH 6.5; 1.0 M MOPS pH 6.8; 1.0 M MOPS pH 7.1; 1.0 M MOPS pH 7.4; 1.0 M MOPS pH 7.7; 1.0 M HEPES sodium pH 6.6; 1.0 M HEPES sodium pH 6.9; 1.0 M HEPES sodium pH 7.2; 1.0 M HEPES sodium pH 7.5; 1.0 M HEPES pH 6.8; 1.0 M HEPES pH 7.1; 1.0 M HEPES pH 7.4; 1.0 M HEPES pH 7.7; 1.0 M TRIS hydrochloride pH 7.2; 1.0 M TRIS hydrochloride pH 7.5; 1.0 M TRIS hydrochloride pH 7.8; 1.0 M TRIS hydrochloride pH 8.1; 1.0 M Tris pH 7.3; 1.0 M Tris pH 7.6; 1.0 M Tris pH 7.9; 1.0 M Tris pH 8.2; 1.0 M Tris pH 8.5; 1.0 M Tricine pH 7.4; 1.0 M Tricine pH 7.7; 1.0 M Tricine pH 8.0; 1.0 M Tricine pH 8.3; 1.0 M Tricine pH 8.6; 1.0 M BICINE pH 7.5; 1.0 M BICINE pH 7.8; 1.0 M BICINE pH 8.1; 1.0 M BICINE pH 8.4; 1.0 M BICINE pH 8.7; 1.0 M BIS-TRIS propane pH 8.5; 1.0 M BIS-TRIS propane pH 8.8; 1.0 M BIS-TRIS propane pH 9.1; 1.0 M BIS-TRIS propane pH 9.4; 1.0 M Glycine pH 8.6; 1.0 M Glycine pH 8.9; 1.0 M Glycine pH 9.2; 1.0 M Glycine pH 9.5; 1.0 M AMPD pH 8.7; 1.0 M AMPD pH 9.0; 1.0 M AMPD pH 9.3; 1.0 M AMPD pH 9.6.

Group 2: 0.1 M Citric acid pH 3.5, 2.0 M Ammonium sulfate; 0.1 M Sodium acetate trihydrate pH 4.5, 2.0 M Ammonium sulfate; 0.1 M BIS-TRIS pH 5.5, 2.0 M Ammonium sulfate; 0.1 M BIS-TRIS pH 6.5, 2.0 M Ammonium sulfate; 0.1 M HEPES pH 7.5, 2.0 M Ammonium sulfate; 0.1 M Tris pH 8.5, 2.0 M Ammonium sulfate; 0.1 M Citric acid pH 3.5, 3.0 M Sodium chloride; 0.1 M Sodium acetate trihydrate pH 4.5, 3.0 M Sodium chloride; 0.1 M BIS-TRIS pH 5.5, 3.0 M Sodium chloride; 0.1 M BIS-TRIS pH 6.5, 3.0 M Sodium chloride; 0.1 M HEPES pH 7.5, 3.0 M Sodium chloride; 0.1 M Tris pH 8.5, 3.0 M Sodium chloride; 0.1 M BIS-TRIS pH 5.5, 0.3 M Magnesium formate dihydrate; 0.1 M BIS-TRIS pH 6.5, 0.5 M Magnesium formate dihydrate; 0.1 M HEPES pH 7.5, 0.5 M Magnesium formate dihydrate; 0.1 M Tris pH 8.5, 0.3 M Magnesium formate dihydrate; 1.4 M Sodium phosphate monobasic monohydrate/Potassium phosphate dibasic pH 5.6; 1.4 M Sodium phosphate monobasic monohydrate/Potassium phosphate dibasic pH 6.9; 1.4 M Sodium phosphate monobasic monohydrate/Potassium phosphate dibasic pH 8.2; 0.1 M HEPES pH 7.5, 1.4 M Sodium citrate tribasic dihydrate; 1.8 M Ammonium citrate tribasic pH 7.0; 0.8 M Succinic acid pH 7.0; 2.1 M DL-Malic acid pH 7.0; 2.8 M Sodium acetate trihydrate pH 7.0; 3.5 M Sodium formate pH 7.0; 1.1 M Ammonium tartrate dibasic pH 7.0; 2.4 M Sodium malonate pH 7.0; 35% v/v Tacsimate pH 7.0; 60% Tacsimate pH 7.0; 0.1 M Sodium chloride, 0.1 M 815-TRIS pH 6.5, 1.5 M Ammonium sulfate; 0.8 M Potassium sodium tartrate tetrahydrate, 0.1 M Tris pH 8.5, 0.5% w/v Polyethylene glycol monomethyl ether 5,000; 1.0 M Ammonium sulfate, 0.1 M BIS-TRIS pH 5.5, 1% w/v Polyethylene glycol 3,350; 1.1 M Sodium malonate pH 7.0, 0.1 M HEPES pH 7.0, 0.5% v/v Jeffamine ED-2001 pH 7.0; 1.0 M Succinic acid pH 7.0, 0.1 M HEPES pH 7.0, 1% w/v Polyethylene glycol monomethyl ether 2,000; 1.0 M Ammonium sulfate, 0.1 M HEPES pH 7.0, 0.5% w/v Polyethylene glycol 8,000; 15% v/v Tacsimate pH 7.0, 0.1 M HEPES pH 7.0, 2% w/v Polyethylene glycol 3,350; 25% w/v Polyethylene glycol 1,500; 0.1 M HEPES pH 7.0, 30% v/v Jeffamine M-600 pH 7.0; 0.1 M HEPES pH 7.0, 30% v/v Jeffamine ED-2001 pH 7.0; 0.1 M Citric acid pH 3.5, 25% w/v Polyethylene glycol 3,350; 0.1 M Sodium acetate trihydrate pH 4.5, 25% w/v Polyethylene glycol 3,350; 0.1 M BIS-TRIS pH 5.5, 25% w/v Polyethylene glycol 3,350; 0.1 M BIS-TRIS pH 6.5, 25% w/v Polyethylene glycol 3,350; 0.1 M HEPES pH 7.5, 25% will Polyethylene glycol 3,350; 0.1 M Tris pH 8.5, 25% w/v Polyethylene glycol 3,350; 0.1 M BIS-TRIS pH 6.5, 20% w/v Polyethylene glycol monomethyl ether 5,000; 0.1 M BIS-TRIS pH 6.5, 28% w/v Polyethylene glycol monomethyl ether 2,000; 0.2 M Calcium chloride dihydrate, 0.1 M BIS-TRIS pH 5.5, 45% v/v (F/-)-2-Methyl-2,4-pentanediol; 0.2 M Calcium chloride dihydrate, 0.1 M STS-TRIS pH 6.5, 45% v/v (+/−)-2-Methyl-2,4-pentanediol; 0.2 M Ammonium acetate, 0.1 M BIS-TRIS pH 5.5, 45% v/v Methyl-2,4-pentanediol; 0.2 M Ammonium acetate, 0.1 M BIS-TRIS pH 6.5, 45% v/v (+/−)-2-Methyl-2,4-pentanediol; 0.2 M Ammonium acetate, 0.1 M HEPES pH 7.5, 45% v/v Methyl-2,4-pentanediol; 0.2 M Ammonium acetate, 0.1 M Tris pH 8.5, 45% v/v (+/−)-2-Methyl-2,4-pentanediol; 0.05 M Calcium chloride dihydrate, 0.1 M BIS-TRIS pH 6.5, 30% v/v Polyethylene glycol monomethyl ether 550; 0.05 M Magnesium chloride hexahydrate, 0.1 M HEPES pH 7.5, 30% v/v Polyethylene glycol monomethyl ether 550; 0.2 M Potassium chloride, 0.05 M HEPES pH 7.5, 35% v/v Pentaerythritol propoxylate (5/4 PO/OH); 0.05 M Ammonium sulfate, 0.05 M BIS-TRIS pH 6.5, 30% v/v Pentaerythritol ethoxylate (15/4 EO/OH); 0.1 M BIS-TRIS pH 6.5, 45% v/v Polypropylene glycol P 400; 0.02 M Magnesium chloride hexahydrate, 0.1 M HEPES pH 7.5, 22% w/v Polyacrylic acid sodium salt 5,100; 0.01 M Cobalt(II) chloride hexahydrate, 0.1 M Tris pH 8.5, 20% w/v Polyvinylpyrrolidone K 15; 0.2 M L-Proline, 0.1 M HEPES pH 7.5, 10% w/v Polyethylene glycol 3,350; 0.2 M Trimethylamine N-oxide dihydrate, 0.1 M Tris pH 8.5, 20% w/v Polyethylene glycol monomethyl ether 2,000; 5% v/v Tacsimate pH 7.0, 0.1 M HEPES pH 7.0, 10% w/v Polyethylene glycol monomethyl ether 5,000; 0.005 M Cobalt(II) chloride hexahydrate, 0.005 M Nickel(II) chloride hexahydrate, 0.005 M Cadmium chloride hydrate, 0.005 M Magnesium chloride hexahydrate, 0.1 M HEPES pH 7.5, 12% w/v Polyethylene glycol 3,350; 0.1 M Ammonium acetate, 0.1 M BIS-TRIS pH 5.5, 17% w/v Polyethylene glycol 10,000; 0.2 M Ammonium sulfate, 0.1 M BIS-TRIS pH 5.5, 25% w/v Polyethylene glycol 3,350; 0.2 M Ammonium sulfate, 0.1 M BIS-TRIS pH 6.5, 25% w/v Polyethylene glycol 3,350; 0.2 M Ammonium sulfate, 0.1 M HEPES pH 7.5, 25% w/v Polyethylene glycol 3,350; 0.2 M Ammonium sulfate, 0.1 M Tris pH 8.5, 25% w/v Polyethylene glycol 3,350; 0.2 M Sodium chloride, 0.1 M BIS-TRIS pH 5.5, 25% w/v Polyethylene glycol 3,350; 0.2 M Sodium chloride, 0.1 M BIS-TRIS pH 6.5, 25% w/v Polyethylene glycol 3,350; 0.2 M Sodium chloride, 0.1 M HEPES pH 7.5, 25% w/v Polyethylene glycol 3,350; 0.2 M Sodium chloride, 0.1 M Tris pH 8.5, 25% w/v Polyethylene glycol 3,350; 0.2 M Lithium sulfate monohydrate, 0.1 M BIS-TRIS pH 5.5, 25% w/v Polyethylene glycol 3,350; 0.2 M Lithium sulfate monohydrate, 0.1 M BIS-TRIS pH 6.5, 25% w/v Polyethylene glycol 3,350; 0.2 M Lithium sulfate monohydrate, 0.1 M HEPES pH 7.5, 25% w/v Polyethylene glycol 3,350; 0.2 M Lithium sulfate monohydrate, 0.1 M Tris pH 8.5, 25% w/v Polyethylene glycol 3,350; 0.2 M Ammonium acetate, 0.1 M BIS-TRIS pH 5.5, 25% w/v Polyethylene glycol 3,350; 0.2 M Ammonium acetate, 0.1 M BIS-TRIS pH 6.5, 25% w/v Polyethylene glycol 3,350; 0.2 M Ammonium acetate, 0.1 M HEPES pH 7.5, 25% w/v Polyethylene glycol 3,350; 0.2 M Ammonium acetate, 0.1 M Tris pH 8.5, 25% w/v Polyethylene glycol 3,350; 0.2 M Magnesium chloride hexahydrate, 0.1 M BIS-TRIS pH 5.5, 25% w/v Polyethylene glycol 3,350; 0.2 M Magnesium chloride hexahydrate, 0.1 M BIS-TRIS pH 6.5, 25% w/v Polyethylene glycol 3,350; 0.2 M Magnesium chloride hexahydrate, 0.1 M HEPES pH 7.5, 25% w/v Polyethylene glycol 3,350; 0.2 M Magnesium chloride hexahydrate, 0.1 M Tris pH 8.5, 25% w/v Polyethylene glycol 3,350; 0.2 M Potassium sodium tartrate tetrahydrate, 20% w/v Polyethylene glycol 3,350; 0.2 M Sodium malonate pH 7.0, 20% w/v Polyethylene glycol 3,350; 0.2 M Ammonium citrate tribasic pH 7.0, 20% w/v Polyethylene glycol 3,350; 0.1 M Succinic acid pH 7.0, 15% w/v Polyethylene glycol 3,350; 0.2 M Sodium formate, 20% w/v Polyethylene glycol 3,350; 0.15 M DL-Malic acid pH 7.0, 20% w/v Polyethylene glycol 3,350; 0.1 M Magnesium formate dihydrate, 15% w/v Polyethylene glycol 3,350; 0.05 M Zinc acetate dihydrate, 20% w/v Polyethylene glycol 3,350; 0.2 M Sodium citrate tribasic dihydrate, 20% w/v Polyethylene glycol 3,350; 0.1 M Potassium thiocyanate, 30% w/v Polyethylene glycol monomethyl ether 2,000; 0.15 M Potassium bromide, 30% w/v Polyethylene glycol monomethyl ether 2,000.

Group 3: 0.1 M Citric acid pH 3.5, 2.0 M Ammonium sulfate; 0.1 M Sodium acetate trihydrate pH 4.5, 2.0 M Ammonium sulfate; 0.1 M BIS-TRIS pH 5.5, 2.0 M Ammonium sulfate; 0.1 M BIS-TRIS pH 6.5, 2.0 M Ammonium sulfate; 0.1 M HEPES pH 7.5, 2.0 M Ammonium sulfate; 0.1 M Tris pH 8.5, 2.0 M Ammonium sulfate; 0.1 M Citric acid pH 3.5, 3.0 M Sodium chloride; 0.1 M Sodium acetate trihydrate pH 4.5, 3.0 M Sodium chloride; 0.1 M BIS-TRIS pH 5.5, 10 M Sodium chloride; 0.1 M BIS-TRIS pH 6.5, 3.0 M Sodium chloride; 0.1 M HEPES pH 7.5, 3.0 M Sodium chloride; 0.1 M Tris pH 8.5, 3.0 M Sodium chloride; 0.1 M BIS-TRIS pH 5.5, 0.3 M Magnesium formate dihydrate; 0.1 M BIS-TRIS pH 6.5, 0.5 M Magnesium formate dihydrate; 0.1 M HEPES pH 7.5, 0.5 M Magnesium formate dihydrate; 0.1 M Tris pH 8.5, 0.3 M Magnesium formate dihydrate; 1.4 M Sodium phosphate monobasic monohydrate/Potassium phosphate dibasic pH 5.6; 1.4 M Sodium phosphate monobasic monohydrate/Potassium phosphate dibasic pH 6.9; 1.4 M Sodium phosphate monobasic monohydrate/Potassium phosphate dibasic pH 8.2; 0.1 M HEPES pH 7.5, 1.4 M Sodium citrate tribasic dihydrate; 1.8 M Ammonium citrate tribasic pH 7.0; 0.8 M Succinic acid pH 7.0; 2.1 M DL-Malic acid pH 7.0; 2.8 M Sodium acetate trihydrate pH 7.0; 3.5 M Sodium formate pH 7.0; 1.1 M Ammonium tartrate dibasic pH 7.0; 2.4 M Sodium malonate pH 7.0; 35% v/v Tacsimate pH 7.0; 60% v/v Tacsimate pH 7.0; 0.1 M Sodium chloride, 0.1 M BIS-TRIS pH 6.5, 1.5 M Ammonium sulfate; 0.8 M Potassium sodium tartrate tetrahydrate, 0.1 M Tris pH 8.5, 0.5% w/v Polyethylene glycol monomethyl ether 5,000; 1.0 M Ammonium sulfate, 0.1 M BIS-TRIS pH 5.5, 1% w/v Polyethylene glycol 3,350; 1.1 M Sodium malonate pH 7.0, 0.1 M HEPES pH 7.0, 0.5% v/v Jeffamine ED-2001 pH 7.0; 1.0 M Succinic acid pH 7.0, 0.1 M HEPES pH 7.0, 1% w/v Polyethylene glycol monomethyl ether 2,000; 1.0 M Ammonium sulfate, 0.1 M HEPES pH 7.0, 0.5% w/v Polyethylene glycol 8,000; 15% v/v Tacsimate pH 7.0, 0.1 M HEPES pH 7.0, 2% w/v Polyethylene glycol 3,350; 25% w/v Polyethylene glycol 1,500; 0.1 M HEPES pH 7.0, 30% v/v Jeffamine M-600 pH 7.0; 0.1 M HEPES pH 7.0, 30% v/v Jeffamine ED-2001 pH 7.0; 0.1 M Citric acid pH 3.5, 25% w/v Polyethylene glycol 3,350; 0.1 M Sodium acetate trihydrate pH 4.5, 25% w/v Polyethylene glycol 3,350; 0.1 M BIS-TRIS pH 5.5, 25% w/v Polyethylene glycol 3,350; 0.1 M BIS-TRIS pH 6.5, 25% w/v Polyethylene glycol 3,350; 0.1 M HEPES pH 7.5, 25% w/v Polyethylene glycol 3,350; 0.1 M Tris pH 8.5, 25% w/v Polyethylene glycol 3,350; 0.1 M BIS-TRIS pH 6.5, 20% w/v Polyethylene glycol monomethyl ether 5,000; 0.1 M BIS-TRIS pH 6.5, 28% w/v Polyethylene glycol monomethyl ether 2,000; 0.2 M Calcium chloride dihydrate, 0.1 M BIS-TRIS pH 5.5, 45% v/v (+/−)-2-Methyl-2,4-pentanediol; 0.2 M Calcium chloride dihydrate, 0.1 M BIS-TRIS pH 6.5, 45% v/v (+/−)-2-Methyl-2,4-pentanediol; 0.2 M Ammonium acetate, 0.1 M BIS-TRIS pH 5.5, 45% v/v (+/−)-2-Methyl-2,4-pentanediol; 0.2 M Ammonium acetate, 0.1 M BIS-TRIS pH 6.5, 45% v/v (+/−)-2-Methyl-2,4-pentanediol; 0.2 M Ammonium acetate, 0.1 M HEPES pH 7.5, 45% v/v (+/−)-2-Methyl-2,4-pentanediol; 0.2 M Ammonium acetate, 0.1 M Tris pH 8.5, 45% v/v (+/−)-2-Methyl-2,4-pentanediol; 0.05 M Calcium chloride dihydrate, 0.1 M BIS-TRIS pH 6.5, 30% v/v Polyethylene glycol monomethyl ether 550; 0.05 M Magnesium chloride hexahydrate, 0.1 M HEPES pH 7.5, 30% v/v Polyethylene glycol monomethyl ether 550; 0.2 M Potassium chloride, 0.05 M HEPES pH 7.5, 35% v/v Pentaerythritol propoxylate (5/4 PO/OH); 0.05 M Ammonium sulfate, 0.05 M BIS-TRIS pH 6.5, 30% v/v Pentaerythritol ethoxylate (15/4 EO/OH); 0.1 M BIS-TRIS pH 6.5, 45% v/v Polypropylene glycol P 400; 0.02 M Magnesium chloride hexahydrate, 0.1 M HEPES pH 7.5, 22% w/v Polyacrylic acid sodium salt 5,100; 0.01 M Cobalt(II) chloride hexahydrate, 0.1 M Tris pH 8.5, 20% w/v Polyvinylpyrrolidone K 15; 0.2 M L-Proline, 0.1 M HEPES pH 7.5, 10% w/v Polyethylene glycol 3,350; 0.2 M Trimethylamine N-oxide dihydrate, 0.1 M Tris pH 8.5, 20% w/v Polyethylene glycol monomethyl ether 2,000; 5% v/v Tacsimate pH 7.0, 0.1 M HEPES pH 7.0, 10% w/v Polyethylene glycol monomethyl ether 5,000; 0.005 M Cobalt(II) chloride hexahydrate, 0.005 M Nickel(II) chloride hexahydrate, 0.005 M Cadmium chloride hydrate, 0.005 M Magnesium chloride hexahydrate, 0.1 M HEPES pH 7.5, 12% w/v Polyethylene glycol 3,350; 0.1 M Ammonium acetate, 0.1 M BIS-TRIS pH 5.5, 17% w/v Polyethylene glycol 10,000; 0.2 M Ammonium sulfate, 0.1 M BIS-TRIS pH 5.5, 25% w/v Polyethylene glycol 3,350; 0.2 M Ammonium sulfate, 0.1 M BIS-TRIS pH 6.5, 25% w/v Polyethylene glycol 3,350; 0.2 M Ammonium sulfate, 0.1 M HEPES pH 7.5, 25% w/v Polyethylene glycol 3,350; 0.2 M Ammonium sulfate, 0.1 M Tris pH 8.5, 25% w/v Polyethylene glycol 3,350; 0.2 M Sodium chloride, 0.1 M BIS-TRIS pH 5.5, 25% w/v Polyethylene glycol 3,350; 0.2 M Sodium chloride, 0.1 M BIS-TRIS pH 6.5, 25% w/v Polyethylene glycol 3,350; 0.2 M Sodium chloride, 0.1 M HEPES pH 7.5, 25% w/v Polyethylene glycol 3,350; 0.2 M Sodium chloride, 0.1 M Tris pH 8.5, 25% w/v Polyethylene glycol 3,350; 0.2 M Lithium sulfate monohydrate, 0.1 M BIS-TRIS pH 5.5, 25% w/v Polyethylene glycol 3,350; 0.2 M Lithium sulfate monohydrate, 0.1 M BIS-TRIS pH 6.5, 25% w/v Polyethylene glycol 3,350; 0.2 M Lithium sulfate monohydrate, 0.1 M HEPES pH 7.5, 25% w/v Polyethylene glycol 3,350; 0.2 M Lithium sulfate monohydrate, 0.1 M Tris pH 8.5, 25% w/v Polyethylene glycol 3,350; 0.2 M Ammonium acetate, 0.1 M BIS-TRIS pH 5.5, 25% w/v Polyethylene glycol 3,350; 0.2 M Ammonium acetate, 0.1 M BIS-TRIS pH 6.5, 25% w/v Polyethylene glycol 3,350; 0.2 M Ammonium acetate, 0.1 M HEPES pH 7.5, 25% w/v Polyethylene glycol 3,350; 0.2 M Ammonium acetate, 0.1 M Tris pH 8.5, 25% w/v Polyethylene glycol 3,350; 0.2 M Magnesium chloride hexahydrate, 0.1 M BIS-TRIS pH 5.5, 25% w/v Polyethylene glycol 3,350; 0.2 M Magnesium chloride hexahydrate, 0.1 M BIS-TRIS pH 6.5, 25% w/v Polyethylene glycol 3,350; 0.2 M Magnesium chloride hexahydrate, 0.1 M HEPES pH 7.5, 25% w/v Polyethylene glycol 3,350; 0.2 M Magnesium chloride hexahydrate, 0.1 M Tris pH 8.5, 25% w/v Polyethylene glycol 3,350; 0.2 M Potassium sodium tartrate tetrahydrate, 20% w/v Polyethylene glycol 3,350; 0.2 M Sodium malonate pH 7.0, 20% w/v Polyethylene glycol 3,350; 0.2 M Ammonium citrate tribasic pH 7.0, 20% w/v Polyethylene glycol 3,350; 0.1 M Succinic acid pH 7.0, 15% w/v Polyethylene glycol 3,350; 0.2 M Sodium formate, 20% w/v Polyethylene glycol 3,350; 0.15 M DL-Malic acid pH 7.0, 20% w/v Polyethylene glycol 3,350; 0.1 M Magnesium formate dihydrate, 15% will Polyethylene glycol 3,350; 0.05 M Zinc acetate dihydrate, 20% w/v Polyethylene glycol 3,350; 0.2 M Sodium citrate tribasic dihydrate, 20% w/v Polyethylene glycol 3,350; 0.1 M Potassium thiocyanate, 30% w/v Polyethylene glycol monomethyl ether 2,000; 0.15 M Potassium bromide, 30% w/v Polyethylene glycol monomethyl ether 2,000.

Group 4: 0.02 M Calcium chloride dihydrate, 0.1 M Sodium acetate trihydrate pH 4.6, 30% v/v (+/−)-2-Methyl-2,4-pentanediol; 0.4 M Potassium sodium tartrate tetrahydrate; 0.4 M Ammonium phosphate monobasic; 0.1 M TRIS hydrochloride pH 8.5, 2.0 M Ammonium sulfate; 0.2 M Sodium citrate tribasic dihydrate, 0.1 M HEPES sodium pH 7.5, 30% v/v (+/−)-2-Methyl-2,4-pentanediol; 0.2 M Magnesium chloride hexahydrate, 0.1 M TRIS hydrochloride pH 8.5, 30% w/v Polyethylene glycol 4,000; 0.1 M Sodium cacodylate trihydrate pH 6.5, 1.4 M Sodium acetate trihydrate; 0.2 M Sodium citrate tribasic dihydrate, 0.1 M Sodium cacodylate trihydrate pH 6.5, 30% v/v 2-Propanol; 0.2 M Ammonium acetate, 0.1 M Sodium citrate tribasic dihydrate pH 5.6, 30% w/v Polyethylene glycol 4,000; 0.2 M Ammonium acetate, 0.1 M Sodium acetate trihydrate pH 4.6, 30% w/v Polyethylene glycol 4,000; 0.1 M Sodium citrate tribasic dihydrate pH 5.6, 1.0 M Ammonium phosphate monobasic; 0.2 M Magnesium chloride hexahydrate, 0.1 M HEPES sodium pH 7.5, 30% v/v 2-Propanol; 0.2 M Sodium citrate tribasic dihydrate, 0.1 M TRIS hydrochloride pH 8.5, 30% v/v Polyethylene glycol 400; 0.2 M Calcium chloride dihydrate, 0.1 M HEPES sodium pH 7.5, 28% v/v Polyethylene glycol 400; 0.2 M Ammonium sulfate, 0.1 M Sodium cacodylate trihydrate pH 6.5, 30% w/v Polyethylene glycol 8,000; 0.1 M HEPES sodium pH 7.5, 1.5 M Lithium sulfate monohydrate; 0.2 M Lithium sulfate monohydrate, 0.1 M TRIS hydrochloride pH 8.5, 30% w/v Polyethylene glycol 4,000; 0.2 M Magnesium acetate tetrahydrate, 0.1 M Sodium cacodylate trihydrate pH 6.5, 20% w/v Polyethylene glycol 8,000; 0.2 M Ammonium acetate, 0.1 M TRIS hydrochloride pH 8.5, 30% v/v 2-Propanol; 0.2 M Ammonium sulfate, 0.1 M Sodium acetate trihydrate pH 4.6, 25% w/v Polyethylene glycol 4,000; 0.2 M Magnesium acetate tetrahydrate, 0.1 M Sodium cacodylate trihydrate pH 6.5, 30% v/v (-1-/-)-2-Methyl-2,4-pentanediol; 0.2 M Sodium acetate trihydrate, 0.1 M TRIS hydrochloride pH 8.5, 30% w/v Polyethylene glycol 4,000; 0.2 M Magnesium chloride hexahydrate, 0.1 M HEPES sodium pH 7.5, 30% v/v Polyethylene glycol 400; 0.2 M Calcium chloride dihydrate, 0.1 M Sodium acetate trihydrate pH 4.6, 20% v/v 2-Propanol; 0.1 M Imidazole pH 6.5, 1.0 M Sodium acetate trihydrate; 0.2 M Ammonium acetate, 0.1 M Sodium citrate tribasic dihydrate pH 5.6, 30% v/v (+/−)-2-Methyl-2,4-pentanediol; 0.2 M Sodium citrate tribasic dihydrate, 0.1 M HEPES sodium pH 7.5, 20% v/v 2-Propanol; 0.2 Sodium acetate trihydrate, 0.1 M Sodium cacodylate trihydrate pH 6.5, 30% w/v Polyethylene glycol 8,000; 0.1 M HEPES sodium pH 7.5, 0.8 M Potassium sodium tartrate tetrahydrate; 0.2 M Ammonium sulfate, 30% w/v Polyethylene glycol 8,000; 0.2 M Ammonium sulfate, 30% w/v Polyethylene glycol 4,000; 2.0 M Ammonium sulfate; 4.0 M Sodium formate; 0.1 M Sodium acetate trihydrate pH 4.6, 2.0 M Sodium formate; 0.1 M HEPES sodium pH 7.5, 0.8 M Sodium phosphate monobasic monohydrate, 0.8 M Potassium phosphate monobasic; 0.1 M TRIS hydrochloride pH 8.5, 8% w/v Polyethylene glycol 8,000; 0.1 M Sodium acetate trihydrate pH 4.6, 8% w/v Polyethylene glycol 4,000; 0.1 M HEPES sodium pH 7.5, 1.4 M Sodium citrate tribasic dihydrate; 0.1 M HEPES sodium pH 7.5, 2% v/v Polyethylene glycol 400, 2.0 M Ammonium sulfate; 0.1 M Sodium citrate tribasic dihydrate pH 5.6, 20% v/v 2-Propanol, 20% w/v Polyethylene glycol 4,000; 0.1 M HEPES sodium pH 7.5, 10% v/v 2-Propanol, 20% w/v Polyethylene glycol 4,000; 0.05 M Potassium phosphate monobasic, 20% w/v Polyethylene glycol 8,000; 30% w/v Polyethylene glycol 1,500; 0.2 M Magnesium formate dihydrate; 0.2 M Zinc acetate dihydrate, 0.1 M Sodium cacodylate trihydrate pH 6.5, 18% w/v Polyethylene glycol 8,000; 0.2 M Calcium acetate hydrate, 0.1 M Sodium cacodylate trihydrate pH 6.5, 18% w/v Polyethylene glycol 8,000; 0.1 M Sodium acetate trihydrate pH 4.6, 2.0 M Ammonium sulfate; 0.1 M TRIS hydrochloride pH 8.5, 2.0 M Ammonium phosphate monobasic; 1.0 M Lithium sulfate monohydrate, 2% w/v Polyethylene glycol 8,000; 0.5 M Lithium sulfate monohydrate, 15% w/v Polyethylene glycol 8,000.

Group 5: 0.02 M Calcium chloride dihydrate, 0.1 M Sodium acetate trihydrate pH 4.6, 30% v/v (+/−)-2-Methyl-2,4-pentanediol; 0.4 M Potassium sodium tartrate tetrahydrate; 0.4 M Ammonium phosphate monobasic; 0.1 M TRIS hydrochloride pH 8.5, 2.0 M Ammonium sulfate; 0.2 M Sodium citrate tribasic dihydrate, 0.1 M HEPES sodium pH 7.5, 30% v/v (+/−)-2-Methyl-2,4-pentanediol; 0.2 M Magnesium chloride hexahydrate, 0.1 M TRIS hydrochloride pH 8.5, 30% w/v Polyethylene glycol 4,000; 0.1 M Sodium cacodylate trihydrate pH 6.5, 1.4 M Sodium acetate trihydrate; 0.2 M Sodium citrate tribasic dihydrate, 0.1 M Sodium cacodylate trihydrate pH 6.5, 30% v/v 2-Propanol; 0.2 M Ammonium acetate, 0.1 M Sodium citrate tribasic dihydrate pH 5.6, 30% w/v Polyethylene glycol 4,000; 0.2 M Ammonium acetate, 0.1 M Sodium acetate trihydrate pH 4.6, 30% w/v Polyethylene glycol 4,000; 0.1 M Sodium citrate tribasic dihydrate pH 5.6, 1.0 M Ammonium phosphate monobasic; 0.2 M Magnesium chloride hexahydrate, 0.1 M HEPES sodium pH 7.5, 30% v/v 2-Propanol; 0.2 M Sodium citrate tribasic dihydrate, 0.1 M TRIS hydrochloride pH 8.5, 30% v/v Polyethylene glycol 400; 0.2 M Calcium chloride dihydrate, 0.1 M HEPES sodium pH 7.5, 28% IA Polyethylene glycol 400; 0.2 M Ammonium sulfate, 0.1 M Sodium cacodylate trihydrate pH 6.5, 30% w/v Polyethylene glycol 8,000; 0.1 M HEPES sodium pH 7.5, 1.5 M Lithium sulfate monohydrate; 0.2 M Lithium sulfate monohydrate, 0.1 M TRIS hydrochloride pH 8.5, 30% w/v Polyethylene glycol 4,000; 0.2 M Magnesium acetate tetrahydrate, 0.1 M Sodium cacodylate trihydrate pH 6.5, 20% w/v Polyethylene glycol 8,000; 0.2 M Ammonium acetate, 0.1 M TRIS hydrochloride pH 8.5, 30% v/v 2-Propanol; 0.2 M Ammonium sulfate, 0.1 M Sodium acetate trihydrate pH 4.6, 25% w/v Polyethylene glycol 4,000; 0.2 M Magnesium acetate tetrahydrate, 0.1 M Sodium cacodylate trihydrate pH 6.5, 30% v/v (+/−)-2-Methyl-2,4-pentanediol; 0.2 M Sodium acetate trihydrate, 0.1 M TRIS hydrochloride pH 8.5, 30% w/v Polyethylene glycol 4,000; 0.2 M Magnesium chloride hexahydrate, 0.1 M HEPES sodium pH 7.5, 30% v/v Polyethylene glycol 400; 0.2 M Calcium chloride dihydrate, 0.1 M Sodium acetate trihydrate pH 4.6, 20% v/v 2-Propanol; 0.1 M Imidazole pH 6.5, 1.0 M Sodium acetate trihydrate; 0.2 M Ammonium acetate, 0.1 M Sodium citrate tribasic dihydrate pH 5.6, 30% v/v (+/−)-2-Methyl-2,4-pentanediol; 0.2 M Sodium citrate tribasic dihydrate, 0.1 M HEPES sodium pH 7.5, 20% v/v 2-Propanol; 0.2 M Sodium acetate trihydrate, 0.1 M Sodium cacodylate trihydrate pH 6.5, 30% w/v Polyethylene glycol 8,000; 0.1 M HEPES sodium pH 7.5, 0.8 M Potassium sodium tartrate tetrahydrate; 0.2 M Ammonium sulfate, 30% w/v Polyethylene glycol 8,000; 0.2 M Ammonium sulfate, 30% w/v Polyethylene glycol 4,000; 2.0 M Ammonium sulfate; 4.0 M Sodium formate; 0.1 M Sodium acetate trihydrate pH 4.6, 2.0 M Sodium formate; 0.1 M HEPES sodium pH 7.5, 0.8 M Sodium phosphate monobasic monohydrate, 0.8 M Potassium phosphate monobasic; 0.1 M TRIS hydrochloride pH 8.5, 8% w/v Polyethylene glycol 8,000; 0.1 M Sodium acetate trihydrate pH 4.6, 8% w/v Polyethylene glycol 4,000; 0.1 M HEPES sodium pH 7.5, 1.4 M Sodium citrate tribasic dihydrate; 0.1 M HEPES sodium pH 7.5, 2% v/v Polyethylene glycol 400, 2.0 M Ammonium sulfate; 0.1 M Sodium citrate tribasic dihydrate pH 5.6, 20% v/v 2-Propanol, 20% w/v Polyethylene glycol 4,000; 0.1 M HEPES sodium pH 7.5, 10% v/v 2-Propanol, 20% w/v Polyethylene glycol 4,000; 0.05 M Potassium phosphate monobasic, 20% w/v Polyethylene glycol 8,000; 30% w/v Polyethylene glycol 1,500; 0.2 M Magnesium formate dihydrate; 0.2 M Zinc acetate dihydrate, 0.1 M Sodium cacodylate trihydrate pH 6.5, 18% w/v Polyethylene glycol 8,000; 0.2 M Calcium acetate hydrate, 0.1 M Sodium cacodylate trihydrate pH 6.5, 18% w/v Polyethylene glycol 8,000; 0.1 M Sodium acetate trihydrate pH 4.6, 2.0 M Ammonium sulfate; 0.1 M TRIS hydrochloride pH 8.5, 2.0 M Ammonium phosphate monobasic; 2.0 M Sodium chloride, 10% w/v Polyethylene glycol 6,000; 0.5 M Sodium chloride, 0.01 M Magnesium chloride hexahydrate, 0.01 M Hexadecyltrimethylammonium bromide; 25% v/v Ethylene glycol; 35% v/v 1,4-Dioxane; 2.0 M Ammonium sulfate, 5% v/v 2-Propanol; 1.0 M Imidazole pH 7.0; 10% w/v Polyethylene glycol 1,000, 10% w/v Polyethylene glycol 8,000; 1.5 M Sodium chloride, 10% v/v Ethanol; 0.1 M Sodium acetate trihydrate pH 4.6, 2.0 M Sodium chloride; 0.2 M Sodium chloride, 0.1 M Sodium acetate trihydrate pH 4.6, 30% v/v (+/−)-2-Methyl-2,4-pentanediol; 0.01 M Cobalt(II) chloride hexahydrate, 0.1 M Sodium acetate trihydrate pH 4.6, 1.0 M 1,6-Hexanediol; 0.1 M Cadmium chloride hydrate, 0.1 M Sodium acetate trihydrate pH 4.6, 30% v/v Polyethylene glycol 400; 0.2 M Ammonium sulfate, 0.1 M Sodium acetate trihydrate pH 4.6, 30% w/v Polyethylene glycol monomethyl ether 2,000; 0.2 M Potassium sodium tartrate tetrahydrate, 0.1 M Sodium citrate tribasic dihydrate pH 5.6, 2.0 M Ammonium sulfate; 0.5 M Ammonium sulfate, 0.1 M Sodium citrate tribasic dihydrate pH 5.6, 1.0 M Lithium sulfate monohydrate; 0.5 M Sodium chloride, 0.1 M Sodium citrate tribasic dihydrate pH 5.6, 2% v/v Ethylene imine polymer; 0.1 M Sodium citrate tribasic dihydrate pH 5.6, 35% v/v tert-Butanol; 0.01 M Iron(III) chloride hexahydrate, 0.1 M Sodium citrate tribasic dihydrate pH 5.6, 10% v/v Jeffamine M-600; 0.1 M Sodium citrate tribasic dihydrate pH 5.6, 2.5 M 1,6-Hexanediol; 0.1 M MES monohydrate pH 6.5, 1.6 M Magnesium sulfate heptahydrate; 0.1 M Sodium phosphate monobasic monohydrate, 0.1 M Potassium phosphate monobasic, 0.1 M MES monohydrate pH 6.5, 2.0 M Sodium chloride; 0.1 M MES monohydrate pH 6.5, 12% w/v Polyethylene glycol 20,000; 1.6 M Ammonium sulfate, 0.1 M MES monohydrate pH 6.5, 10% v/v 1,4-Dioxane; 0.05 M Cesium chloride, 0.1 M MES monohydrate pH 6.5, 30% v/v Jeffamine M-600; 0.01 M Cobalt(II) chloride hexahydrate, 0.1 M MES monohydrate pH 6.5, 1.8 M Ammonium sulfate; 0.2 M Ammonium sulfate, 0.1 M MES monohydrate pH 6.5, 30% w/v Polyethylene glycol monomethyl ether 5,000; 0.01 M Zinc sulfate heptahydrate, 0.1 M MES monohydrate pH 6.5, 25% v/v Polyethylene glycol monomethyl ether 550; 1.6 M Sodium citrate tribasic dihydrate pH 6.5; 0.5 M Ammonium sulfate, 0.1 M HEPES pH 7.5, 30% v/v (+/−)-2-Methyl-2,4-pentanediol; 0.1 M HEPES pH 7.5, 10% w/v Polyethylene glycol 6,000, 5% v/v (+/−)-2-Methyl-2,4-pentanediol; 0.1 M HEPES pH 7.5, 20% v/v Jeffamine M-600; 0.1 M Sodium chloride, 0.1 M HEPES pH 7.5, 1.6 M Ammonium sulfate; 0.1 M HEPES pH 7.5, 2.0 M Ammonium formate; 0.05 M Cadmium sulfate hydrate, 0.1 M HEPES pH 7.5, 1.0 M Sodium acetate trihydrate; 0.1 M HEPES pH 7.5, 70% v/v (+/−)-2-Methyl-2,4-pentanediol; 0.1 M HEPES pH 7.5, 4.3 M Sodium chloride; 0.1 M HEPES pH 7.5, 8% AA Ethylene glycol, 10% w/v Polyethylene glycol 8,000; 0.1 M HEPES pH 7.5, 20% w/v Polyethylene glycol 10,000; 0.2 M Magnesium chloride hexahydrate, 0.1 M Tris pH 8.5, 3.4 M 1,6-Hexanediol; 0.1 M Tris pH 8.5, 25% v/v tert-Butanol; 0.01 M Nickel° chloride hexahydrate, 0.1 M Tris pH 8.5, 1.0 M Lithium sulfate monohydrate; 1.5 M Ammonium sulfate, 0.1 M Tris pH 8.5, 12% v/v Glycerol; 0.2 M Ammonium phosphate monobasic, 0.1 M Tris pH 8.5, 50% v/v (+/−)-2-Methyl-2,4-pentanediol; 0.1 M Tris pH 8.5, 20% v/v Ethanol; 0.01 M Nickel(II) chloride hexahydrate, 0.1 M Tris pH 8.5, 20% w/v Polyethylene glycol monomethyl ether 2,000; 0.1 M Sodium chloride, 0.1 M BICINE pH 9.0, 20% v/v Polyethylene glycol monomethyl ether 550; 0.1 M BICINE pH 9.0, 2.0 M Magnesium chloride hexahydrate; 0.1 M BICINE pH 9.0, 2% v/v 1,4-Dioxane, 10% w/v Polyethylene glycol 20.000.

Group 6: 2.0 M Sodium chloride, 10% w/v Polyethylene glycol 6,000; 0.5 M Sodium chloride, 0.01 M Magnesium chloride hexahydrate, 0.01 M Hexadecyltrimethylammonium bromide; 25% v/v Ethylene glycol; 35% v/v 1,4-Dioxane; 2.0 M Ammonium sulfate, 5% v/v 2-Propanol; 1.0 M Imidazole pH 7.0; 10% w/v Polyethylene glycol 1,000, 10% w/v Polyethylene glycol 8,000; 1.5 M Sodium chloride, 10% v/v Ethanol; 0.1 M Sodium acetate trihydrate pH 4.6, 2.0 M Sodium chloride; 0.2 M Sodium chloride, 0.1 M Sodium acetate trihydrate pH 4.6, 30% v/v (+/−)-2-Methyl-2,4-pentanediol; 0.01 M Cobalt(II) chloride hexahydrate, 0.1 M Sodium acetate trihydrate pH 4.6, 1.0 M 1,6-Hexanediol; 0.1 M Cadmium chloride hydrate, 0.1 M Sodium acetate trihydrate pH 4.6, 30% v/v Polyethylene glycol 400; 0.2 M Ammonium sulfate, 0.1 M Sodium acetate trihydrate pH 4.6, 30% w/v Polyethylene glycol monomethyl ether 2,000; 0.2 M Potassium sodium tartrate tetrahydrate, 0.1 M Sodium citrate tribasic dihydrate pH 5.6, 2.0 M Ammonium sulfate; 0.5 M Ammonium sulfate, 0.1 M Sodium citrate tribasic dihydrate pH 5.6, 1.0 M Lithium sulfate monohydrate; 0.5 M Sodium chloride, 0.1 M Sodium citrate tribasic dihydrate pH 5.6, 2% v/v Ethylene imine polymer; 0.1 M Sodium citrate tribasic dihydrate pH 5.6, 35% v/v tert-Butanol; 0.01 M Iron(III) chloride hexahydrate, 0.1 M Sodium citrate tribasic dihydrate pH 5.6, 10% v/v Jeffamine M-600; 0.1 M Sodium citrate tribasic dihydrate pH 5.6, 2.5 M 1,6-Hexanediol; 0.1 M MES monohydrate pH 6.5, 1.6 M Magnesium sulfate heptahydrate; 0.1 M Sodium phosphate monobasic monohydrate, 0.1 M Potassium phosphate monobasic, 0.1 M MES monohydrate pH 6.5, 2.0 M Sodium chloride; 0.1 M MES monohydrate pH 6.5, 12% w/v Polyethylene glycol 20,000; 1.6 M Ammonium sulfate, 0.1 M MES monohydrate pH 6.5, 10% v/v 1,4-Dioxane; 0.05 M Cesium chloride, 0.1 M MES monohydrate pH 6.5, 30% v/v Jeffamine M-600; 0.01 M Cobalt(10 chloride hexahydrate, 0.1 M MES monohydrate pH 6.5, 1.8 M Ammonium sulfate; 0.2 M Ammonium sulfate, 0.1 M MES monohydrate pH 6.5, 30% w/v Polyethylene glycol monomethyl ether 5,000; 0.01 M Zinc sulfate heptahydrate, 0.1 M MES monohydrate pH 6.5, 25% v/v Polyethylene glycol monomethyl ether 550; 1.6 M Sodium citrate tribasic dihydrate pH 6.5; 0.5 M Ammonium sulfate, 0.1 M HEPES pH 7.5, 30% v/v (+/−)-2-Methyl-2,4-pentanediol; 0.1 M HEPES pH 7.5, 10% w/v Polyethylene glycol 6,000, 5% v/v (+/−)-2-Methyl-2,4-pentanediol; 0.1 M HEPES pH 7.5, 20% v/v Jeffamine M-600; 0.1 M Sodium chloride, 0.1 M HEPES pH 7.5, 1.6 M Ammonium sulfate; 0.1 M HEPES pH 7.5, 2.0 M Ammonium formate; 0.05 M Cadmium sulfate hydrate, 0.1 M HEPES pH 7.5, 1.0 M Sodium acetate trihydrate; 0.1 M HEPES pH 7.5, 70% v/v (+/−)-2-Methyl-2,4-pentanediol; 0.1 M HEPES pH 7.5, 4.3 M Sodium chloride; 0.1 M HEPES pH 7.5, 8% v/v Ethylene glycol, 10% w/v Polyethylene glycol 8,000; 0.1 M HEPES pH 7.5, 20% w/v Polyethylene glycol 10,000; 0.2 M Magnesium chloride hexahydrate, 0.1 M Tris pH 8.5, 3.4 M 1,6-Hexanediol; 0.1 M Tris pH 8.5, 25% v/v tert-Butanol; 0.01 M Nickel(II) chloride hexahydrate, 0.1 M Iris pH 8.5, 1.0 M Lithium sulfate monohydrate; 1.5 M Ammonium sulfate, 0.1 M Tris pH 8.5, 12% v/v Glycerol; 0.2 M Ammonium phosphate monobasic, 0.1 M Tris pH 8.5, 50% v/v (+/−)-2-Methyl-2,4-pentanediol; 0.1 M Tris pH 8.5, 20% v/v Ethanol; 0.01 M Nickel(II) chloride hexahydrate, 0.1 M Tris pH 8.5, 20% w/v Polyethylene glycol monomethyl ether 2,000; 0.1 M Sodium chloride, 0.1 M BICINE pH 9.0, 20% v/v Polyethylene glycol monomethyl ether 550; 0.1 M BICINE pH 9.0, 2.0 M Magnesium chloride hexahydrate; 0.1 M BICINE pH 9.0, 2% v/v 1,4-Dioxane, 10% w/v Polyethylene glycol 20,000.

Group 7: 0.1 M Citric acid pH 3.5, 34% v/v Polyethyelene glycol 200; 0.1 M Sodium citrate tribasic dihydrate pH 5.5, 38% v/v Polyethylene glycol 200; 0.1 M HEPES pH 7.5, 42% v/v Polyethylene glycol 200; 0.1 M Sodium acetate trihydrate pH 4.5, 30% v/v Polyethylene glycol 300; 0.1 M BIS-TRIS pH 6.5, 25% v/v Polyethylene glycol 300; 0.1 M BICINE pH 8.5, 20% v/v Polyethylene glycol 300; 0.1 M Sodium acetate trihydrate pH 4.0, 15% v/v Polyethylene glycol 400; 0.1 M MES monohydrate pH 6.0, 22% v/v Polyethylene glycol 400; 0.1 M Tris pH 8.0, 30% v/v Polyethylene glycol 400; 0.1 M Sodium citrate tribasic dihydrate pH 5.0, 30% v/v Polyethylene glycol monomethyl ether 550; 0.1 M Imidazole pH 7.0, 25% v/v Polyethylene glycol monomethyl ether 550; 0.1 M BIS-TRIS propane pH 9.0, 20% v/v Polyethylene glycol monomethyl ether 550; 0.1 M Sodium acetate trihydrate pH 4.0, 10% v/v Jeffamine® M-600® pH 7.0; 0.1 M MES monohydrate pH 6.0, 20% v/v Jeffamine® M-600® pH 7.0; 0.1 M Tris pH 8.0, 30% v/v Jeffamine® M-600® pH 7.0; 0.1 M Citric acid pH 3.5, 14% w/v Polyethylene glycol 1,000; 0.1 M Sodium citrate tribasic dihydrate pH 5.5, 22% will Polyethylene glycol 1,000; 0.1 M HEPES pH 7.5, 30% w/v Polyethylene glycol 1,000; 0.1 M Sodium acetate trihydrate pH 4.5, 30% w/v Polyethylene glycol 1,500; 0.1 M BIS-TRIS pH 6.5, 20% w/v Polyethylene glycol 1,500; 0.1 M BICINE pH 8.5, 15% w/v Polyethylene glycol 1,500; 0.1 M Sodium acetate trihydrate pH 4.0, 10% w/v Polyethylene glycol monomethyl ether 2,000; 0.1 M MES monohydrate pH 6.0, 20% w/v Polyethylene glycol monomethyl ether 2,000; 0.1 M Tris pH 8.0, 30% w/v Polyethylene glycol monomethyl ether 2,000; 0.1 M Sodium citrate tribasic dihydrate pH 5.0, 30% v/v Jeffamine® ED-2001 pH 7.0; 0.1 M Imidazole pH 7.0, 20% NO/Jeffamine® ED-2001 pH 7.0; 0.1 M BIS-TRIS propane pH 9.0, 10% v/v Jeffamine® ED-2001 pH 7.0; 0.1 M Citric acid pH 3.5, 25% w/v Polyethylene glycol 3,350; 0.1 M Sodium citrate tribasic dihydrate pH 5.5, 18% w/v Polyethylene glycol 3,350; 0.1 M HEPES pH 7.5, 12% w/v Polyethylene glycol 3,350; 0.1 M Sodium acetate trihydrate pH 4.0, 10% w/v Polyethylene glycol 4,000; 0.1 M MES monohydrate pH 6.0, 14% w/v Polyethylene glycol 4,000; 0.1 M Trig pH 8.0, 28% w/v Polyethylene glycol 4,000; 0.1 M Sodium acetate trihydrate pH 4.5, 30% Polyethylene glycol monomethyl ether 5,000; 0.1 M BIS-TRIS pH 6.5, 20% w/v Polyethylene glycol monomethyl ether 5,000; 0.1 M BICINE pH 8.5, 8% w/v Polyethylene glycol monomethyl ether 5,000; 0.1 M Sodium citrate tribasic dihydrate pH 5.0, 10% w/v Polyethylene glycol 6,000; 0.1 M Imidazole pH 7.0, 20% w/v Polyethylene glycol 6,000; 0.1 M BIS-TRIS propane pH 9.0, 30% w/v Polyethylene glycol 6,000; 0.1 M Citric acid pH 3.5, 28% w/v Polyethylene glycol 8,000; 0.1 M Sodium citrate tribasic dihydrate pH 5.5, 16% w/v Polyethylene glycol 8,000; 0.1 M HEPES pH 7.5, 4% w/v Polyethylene glycol 8,000; 0.1 M Sodium acetate trihydrate pH 4.5, 10% w/v Polyethylene glycol 10,000; 0.1 M BIS-TRIS pH 6.5, 16% w/v Polyethylene glycol 10,000; 0.1 M BICINE pH 8.5, 20% w/v Polyethylene glycol 10,000; 0.1 M Sodium citrate tribasic dihydrate pH 5.0, 18% w/v Polyethylene glycol 20,000; 0.1 M Imidazole pH 7.0, 12% w/v Polyethylene glycol 20,000; 0.1 M BIS-TRIS propane pH 9.0, 8% w/v Polyethylene glycol 20,000.

Group 8: 0.8 M Lithium sulfate monohydrate, 0.1 M Sodium acetate trihydrate pH 4.0, 4% v/v Polyethylene glycol 200; 0.2 M Lithium sulfate monohydrate, 0.1 M Sodium citrate tribasic dihydrate pH 5.0, 26% v/v Polyethylene glycol 200; 0.05 M Calcium chloride dihydrate, 0.1 M MES monohydrate pH 6.0, 45% v/v Polyethylene glycol 200; 28% v/v 2-Propanol, 0.1 M BIS-TRIS pH 6.5, 3% v/v Polyethylene glycol 200; 20% v/v Tacsimate pH 7.0, 0.1 M HEPES pH 7.5, 2% v/v Polyethylene glycol 200; 10% v/v 2-Propanol, 0.1 M Sodium citrate tribasic dihydrate pH 5.0, 26% v/v Polyethylene glycol 400; 0.2 M Ammonium acetate, 0.1 M Sodium citrate tribasic dihydrate pH 5.5, 24% v/v Polyethylene glycol 400; 0.2 M Ammonium sulfate, 0.1 M BIS-TRIS pH 6.5, 18% v/v Polyethylene glycol 400; 0.19 mM CYMAL®-7, 0.1 M HEPES pH 7.5, 40% v/v Polyethylene glycol 400; 6% v/v 2-Propanol, 0.1 M Sodium acetate trihydrate pH 4.5, 26% v/v Polyethylene glycol monomethyl ether 550; 1.8 M Ammonium sulfate, 0.1 M BIS-TRIS pH 6.5, 2% v/v Polyethylene glycol monomethyl ether 550; 0.15 M DL-Malic acid pH 7.0, 0.1 M Imidazole pH 7.0, 22% AA Polyethylene glycol monomethyl ether 550; 0.1 M Succinic acid pH 7.0, 0.1 M BICINE pH 8.5, 30% v/v Polyethylene glycol monomethyl ether 550; 0.1 M Lithium sulfate monohydrate, 0.1 M Sodium citrate tribasic dihydrate pH 5.5, 20% w/v Polyethylene glycol 1,000; 0.1 M Sodium malonate pH 8.0, 0.1 M Tris pH 8.0, 30% w/v Polyethylene glycol 1,000; 4% v/v (+/−)-2-Methyl-2,4-pentanediol, 0.1 M Citric acid pH 3.5, 20% w/v Polyethylene glycol 1,500; 0.2 M L-Proline, 0.1 M HEPES pH 7.5, 24% w/v Polyethylene glycol 1,500; 10% v/v 2-Propanol, 0.1 M BICINE pH 8.5, 30% w/v Polyethylene glycol 1,500; 0.1 M Sodium chloride, 0.1 M BIS-TRIS propane pH 9.0, 25% w/v Polyethylene glycol 1,500; 0.02 M Nickel(II) chloride hexahydrate, 0.02 M Magnesium chloride hexahydrate, 0.02 M Cadmium chloride hydrate, 0.1 M Sodium acetate trihydrate pH 4.5, 24% w/v Polyethylene glycol monomethyl ether 2,000; 20% v/v 2-Propanol, 0.1 M MES monohydrate pH 6.0, 20% w/v Polyethylene glycol monomethyl ether 2,000; 0.2 M Ammonium citrate tribasic pH 7.0, 0.1 M Imidazole pH 7.0, 20% w/v Polyethylene glycol monomethyl ether 2,000; 4.0 M Potassium formate, 0.1 M BIS-TRIS propane pH 9.0, 2% w/v Polyethylene glycol monomethyl ether 2,000; 50% v/v Tacsimate pH 4.0, 0.1 M Sodium acetate trihydrate pH 4.5, 1% w/v Polyethylene glycol 3,350; 0.10% w/v n-Octyl-β-D-glucoside, 0.1 M Sodium citrate tribasic dihydrate pH 5.5, 22% w/v Polyethylene glycol 3,350; 2% v/v Tacsimate pH 7.0, 5% v/v 2-Propanol, 0.1 M Imidazole pH 7.0, 8% w/v Polyethylene glycol 3,350; 2% v/v 1,4-Dioxane, 0.1 M Tris pH 8.0, 15% w/v Polyethylene glycol 3,350; 18% v/v 2-Propanol, 0.1 M Sodium citrate tribasic dihydrate pH 5.5, 20% w/v Polyethylene glycol 4,000; 6% v/v Tacsimate pH 6.0, 0.1 M MES monohydrate pH 6.0, 25% w/v Polyethylene glycol 4,000; 0.2 M Magnesium formate dihydrate, 0.1 M Sodium acetate trihydrate pH 4.0, 18% w/v Polyethylene glycol monomethyl ether 5,000; 2% v/v Polyethylene glycol 400, 0.1 M Imidazole pH 7.0, 24% w/v Polyethylene glycol monomethyl ether 5,000; 0.2 M Sodium formate, 0.1 M BICINE pH 8.5, 20% w/v Polyethylene glycol monomethyl ether 5,000; 4% v/v 2-Propanol, 0.1 M BIS-TRIS propane pH 9.0, 20% w/v Polyethylene glycol monomethyl ether 5,000; 6% v/v Ethylene glycol, 0.1 M Citric acid pH 3.5, 10% will Polyethylene glycol 6,000; 0.15 M Lithium sulfate monohydrate, 0.1 M Citric acid pH 3.5, 18% Polyethylene glycol 6,000; 10% v/v 2-Propanol, 0.1 M Sodium acetate trihydrate pH 4.0, 22% w/v Polyethylene glycol 6,000; 0.2 M Sodium chloride, 0.1 M Sodium acetate trihydrate pH 4.0, 22% w/v Polyethylene glycol 8,000; 20% v/v 2-Propanol, 0.1 M Tris pH 8.0, 5% w/v Polyethylene glycol 8,000; 10% v/v Polyethylene glycol 200, 0.1 M BIS-TRIS propane pH 9.0, 18% w/v Polyethylene glycol 8,000; 15% v/v 2-Propanol, 0.1 M Sodium citrate tribasic dihydrate pH 5.0, 10% w/v Polyethylene glycol 10,000; 0.4 M Sodium malonate pH 6.0, 0.1 M MES monohydrate pH 6.0, 0.5% w/v Polyethylene glycol 10,000; 0.2 M Potassium sodium tartrate tetrahydrate, 0.1 M BIS-TRIS pH 6.5, 10% w/v Polyethylene glycol 10,000; 5% v/v (+/−)-2-Methyl-2,4-pentanediol, 0.1 M HEPES pH 7.5, 10% w/v Polyethylene glycol 10,000; 0.2 M Ammonium acetate, 0.1 M Tris pH 8.0, 16% w/v Polyethylene glycol 10,000; 5% v/v 2-Propanol, 0.1 M Citric acid pH 3.5, 6% w/v Polyethylene glycol 20,000; 1.0 M Sodium malonate pH 5.0, 0.1 M Sodium acetate trihydrate pH 4.5, 2% w/v Polyethylene glycol 20,000; 0.2 M Magnesium chloride hexahydrate, 0.1 M Sodium citrate tribasic dihydrate pH 5.0, 10% w/v Polyethylene glycol 20,000; 3% will Dextran sulfate sodium salt, 0.1 M BICINE pH 8.5, 15% w/v Polyethylene glycol 20,000.

Group 9: 0.1 M Citric acid pH 3.5, 34% v/v Polyethylene glycol 200; 0.1 M Sodium citrate tribasic dihydrate pH 5.5, 38% v/v Polyethylene glycol 200; 0.1 M HEPES pH 7.5, 42% v/v Polyethylene glycol 200; 0.1 M Sodium acetate trihydrate pH 4.5, 30% v/v Polyethylene glycol 300; 0.1 M BIS-TRIS pH 6.5, 25% v/v Polyethylene glycol 300; 0.1 M BICINE pH 8.5, 20% v/v Polyethylene glycol 300; 0.1 M Sodium acetate trihydrate pH 4.0, 15% v/v Polyethylene glycol 400; 0.1 M MES monohydrate pH 6.0, 22% v/v Polyethylene glycol 400; 0.1 M Tris pH 8.0, 30% v/v Polyethylene glycol 400; 0.1 M Sodium citrate tribasic dihydrate pH 5.0, 30% v/v Polyethylene glycol monomethyl ether 550; 0.1 M Imidazole pH 7.0, 25% v/v Polyethylene glycol monomethyl ether 550; 0.1 M BIS-TRIS propane pH 9.0, 20% v/v Polyethylene glycol monomethyl ether 550; 0.1 M Sodium acetate trihydrate pH 4.0, 10% v/v Jeffamine® M-600® pH 7.0; 0.1 M MES monohydrate pH 6.0, 20% v/v Jeffamine® M-600® pH 7.0; 0.1 M Tris pH 8.0, 30% v/v Jeffamine® M-6000 pH 7.0; 0.1 M Citric acid pH 3.5, 14% w/v Polyethylene glycol 1,000; 0.1 M Sodium citrate tribasic dihydrate pH 5.5, 22% w/v Polyethylene glycol 1,000; 0.1 M HEPES pH 7.5, 30% w/v Polyethylene glycol 1,000; 0.1 M Sodium acetate trihydrate pH 4.5, 30% w/v Polyethylene glycol 1,500; 0.1 M BIS-TRIS pH 6.5, 20% w/v Polyethylene glycol 1,500; 0.1 M BICINE pH 8.5, 15% w/v Polyethylene glycol 1,500; 0.1 M Sodium acetate trihydrate pH 4.0, 10% w/v Polyethylene glycol monomethyl ether 2,000; 0.1 M MES monohydrate pH 6.0, 20% w/v Polyethylene glycol monomethyl ether 2,000; 0.1 M Tris pH 8.0, 30% w/v Polyethylene glycol monomethyl ether 2,000; 0.1 M Sodium citrate tribasic dihydrate pH 5.0, 30% v/v Jeffamine® ED-2001 pH 7.0; 0.1 M Imidazole pH 7.0, 20% v/v Jeffamine® ED-2001 pH 7.0; 0.1 M BIS-TRIS propane pH 9.0, 10% v/v Jeffamine® ED-2001 pH 7.0; 0.1 M Citric acid pH 3.5, 25% w/v Polyethylene glycol 3,350; 0.1 M Sodium citrate tribasic dihydrate pH 5.5, 18% w/v Polyethylene glycol 3,350; 0.1 M HEPES pH 7.5, 12% w/v Polyethylene glycol 3,350; 0.1 M Sodium acetate trihydrate pH 4.0, 10% w/v Polyethylene glycol 4,000; 0.1 M MES monohydrate pH 6.0, 14% w/v Polyethylene glycol 4,000; 0.1 M Tris pH 8.0, 28% w/v Polyethylene glycol 4,000; 0.1 M Sodium acetate trihydrate pH 4.5, 30% Polyethylene glycol monomethyl ether 5,000; 0.1 M BIS-TRIS pH 6.5, 0% w/v Polyethylene glycol monomethyl ether 5,000; 0.1 M BICINE pH 8.5, 8% w/v Polyethylene glycol monomethyl ether 5,000; 0.1 M Sodium citrate tribasic dihydrate pH 5.0, 10% w/v Polyethylene glycol 6,000; 0.1 M Imidazole pH 7.0, 20% w/v Polyethylene glycol 6,000; 0.1 M BIS-TRIS propane pH 9.0, 30% w/v Polyethylene glycol 6,000; 0.1 M Citric acid pH 3.5, 28% w/v Polyethylene glycol 8,000; 0.1 M Sodium citrate tribasic dihydrate pH 5.5, 16% w/v Polyethylene glycol 8,000; 0.1 M HEPES pH 7.5, 4% w/v Polyethylene glycol 8,000; 0.1 M Sodium acetate trihydrate pH 4.5, 10% w/v Polyethylene glycol 10,000; 0.1 M BIS-TRIS pH 6.5, 16% w/v Polyethylene glycol 10,000; 0.1 M BICINE pH 8.5, 20% w/v Polyethylene glycol 10,000; 0.1 M Sodium citrate tribasic dihydrate pH 5.0, 18% w/v Polyethylene glycol 20,000; 0.1 M Imidazole pH 7.0, 12% w/v Polyethylene glycol 20,000; 0.1 M BIS-TRIS propane pH 9.0, 8% w/v Polyethylene glycol 20,000; 0.8 M Lithium sulfate monohydrate, 0.1 M Sodium acetate trihydrate pH 4.0, 4% v/v Polyethylene glycol 200; 0.2 M Lithium sulfate monohydrate, 0.1 M Sodium citrate tribasic dihydrate pH 5.0, 26% v/v Polyethylene glycol 200; 0.05 M Calcium chloride dihydrate, 0.1 M MES monohydrate pH 6.0, 45% v/v Polyethylene glycol 200; 28% v/v 2-Propanol, 0.1 M BIS-TRIS pH 6.5, 3% v/v Polyethylene glycol 200; 20% v/v Tacsimate pH 7.0, 0.1 M HEPES pH 7.5, 2% v/v Polyethylene glycol 200; 10% v/v 2-Propanol, 0.1 M Sodium citrate tribasic dihydrate pH 5.0, 26% v/v Polyethylene glycol 400; 0.2 M Ammonium acetate, 0.1 M Sodium citrate tribasic dihydrate pH 5.5, 24% v/v Polyethylene glycol 400; 0.2 M Ammonium sulfate, 0.1 M BIS-TRIS pH 6.5, 18% v/v Polyethylene glycol 400; 0.19 mM CYMAL®-7, 0.1 M HEPES pH 7.5, 40% v/v Polyethylene glycol 400; 6% v/v 2-Propanol, 0.1 M Sodium acetate trihydrate pH 4.5, 26% v/v Polyethylene glycol monomethyl ether 550; 1.8 M Ammonium sulfate, 0.1 M BIS-TRIS pH 6.5, 2% v/v Polyethylene glycol monomethyl ether 550; 0.15 M DL-Malic acid pH 7.0, 0.1 M Imidazole pH 7.0, 22% v/v Polyethylene glycol monomethyl ether 550; 0.1 M Succinic acid pH 7.0, 0.1 M BICINE pH 8.5, 30% v/v Polyethylene glycol monomethyl ether 550; 0.1 M Lithium sulfate monohydrate, 0.1 M Sodium citrate tribasic dihydrate pH 5.5, 20% w/v Polyethylene glycol 1,000; 0.1 M Sodium malonate pH 8.0, 0.1 M Tris pH 8.0, 30% w/v Polyethylene glycol 1,000; 4% v/v (+/−)-2-Methyl-2,4-pentanediol, 0.1 M Citric acid pH 3.5, 20% w/v Polyethylene glycol 1,500; 0.2 M L-Proline, 0.1 M HEPES pH 7.5, 24% w/v Polyethylene glycol 1,500; 10% v/v 2-Propanol, 0.1 M BICINE pH 8.5, 30% w/v Polyethylene glycol 1,500; 0.1 M Sodium chloride, 0.1 M BIS-TRIS propane pH 9.0, 25% w/v Polyethylene glycol 1,500; 0.02 M Nickel(II) chloride hexahydrate, 0.02 M Magnesium chloride hexahydrate, 0.02 M Cadmium chloride hydrate, 0.1 M Sodium acetate trihydrate pH 4.5, 24% w/v Polyethylene glycol monomethyl ether 2,000; 20% v/v 2-Propanol, 0.1 M MES monohydrate pH 6.0, 20% w/v Polyethylene glycol monomethyl ether 2,000; 0.2 M Ammonium citrate tribasic pH 7.0, 0.1 M Imidazole pH 7.0, 20% w/v Polyethylene glycol monomethyl ether 2,000; 4.0 M Potassium formate, 0.1 M BIS-TRIS propane pH 9.0, 2% w/v Polyethylene glycol monomethyl ether 2,000; 50% v/v Tacsimate pH 4.0, 0.1 M Sodium acetate trihydrate pH 4.5, 1% w/v Polyethylene glycol 3,350; 0.10% w/v n-Octyl-β-D-glucoside, 0.1 M Sodium citrate tribasic dihydrate pH 5.5, 22% w/v Polyethylene glycol 3,350; 2% v/v Tacsimate pH 7.0, 5% v/v 2-Propanol, 0.1 M Imidazole pH 7.0, 8% w/v Polyethylene glycol 3,350; 2% v/v 1,4-Dioxane, 0.1 M Tris pH 8.0, 15% w/v Polyethylene glycol 3,350; 18% v/v 2-Propanol, 0.1 M Sodium citrate tribasic dihydrate pH 5.5, 20% w/v Polyethylene glycol 4,000; 6% v/v Tacsimate pH 6.0, 0.1 M MES monohydrate pH 6.0, 25% w/v Polyethylene glycol 4,000; 0.2 M Magnesium formate dihydrate, 0.1 M Sodium acetate trihydrate pH 4.0, 18% w/v Polyethylene glycol monomethyl ether 5,000; 2% v/v Polyethylene glycol 400, 0.1 M Imidazole pH 7.0, 24% w/v Polyethylene glycol monomethyl ether 5,000; 0.2 M Sodium formate, 0.1 M BICINE pH 8.5, 20% w/v Polyethylene glycol monomethyl ether 5,000; 4% v/v 2-Propanol, 0.1 M BIS-TRIS propane pH 9.0, 20% w/v Polyethylene glycol monomethyl ether 5,000; 6% v/v Ethylene glycol, 0.1 M Citric acid pH 3.5, 10% w/v Polyethylene glycol 6,000; 0.15 M Lithium sulfate monohydrate, 0.1 M Citric acid pH 3.5, 18% Polyethylene glycol 6,000; 10% v/v 2-Propanol, 0.1 M Sodium acetate trihydrate pH 4.0, 22% w/v Polyethylene glycol 6,000; 0.2 M Sodium chloride, 0.1 M Sodium acetate trihydrate pH 4.0, 22% w/v Polyethylene glycol 8,000; 20% v/v 2-Propanol, 0.1 M Tris pH 8.0, 5% w/v Polyethylene glycol 8,000; 10% v/v Polyethylene glycol 200, 0.1 M BIS-TRIS propane pH 9.0, 18% w/v Polyethylene glycol 8,000; 15% v/v 2-Propanol, 0.1 M Sodium citrate tribasic dihydrate pH 5.0, 10% w/v Polyethylene glycol 10,000; 0.4 M Sodium malonate pH 6.0, 0.1 M MES monohydrate pH 6.0, 0.5% w/v Polyethylene glycol 10,000; 0.2 M Potassium sodium tartrate tetrahydrate, 0.1 M BIS-TRIS pH 6.5, 10% w/v Polyethylene glycol 10,000; 5% v/v (+/−)-2-Methyl-2,4-pentanediol, 0.1 M HEPES pH 7.5, 10% w/v Polyethylene glycol 10,000; 0.2 M Ammonium acetate, 0.1 M Tris pH 8.0, 16% w/v Polyethylene glycol 10,000; 5% v/v 2-Propanol, 0.1 M Citric acid pH 3.5, 6% w/v Polyethylene glycol 20,000; 1.0 M Sodium malonate pH 5.0, 0.1 M Sodium acetate trihydrate pH 4.5, 2% w/v Polyethylene glycol 20,000; 0.2 M Magnesium chloride hexahydrate, 0.1 M Sodium citrate tribasic dihydrate pH 5.0, 10% w/v Polyethylene glycol 20,000; 3% w/v Dextran sulfate sodium salt, 0.1 M BICINE pH 8.5, 15% w/v Polyethylene glycol 20,000.

Group 10: 0.2 M Sodium fluoride, 20% w/v Polyethylene glycol 3,350; 0.2 M Potassium fluoride, 20% w/v Polyethylene glycol 3,350; 0.2 M Ammonium fluoride, 20% w/v Polyethylene glycol 3,350; 0.2 M Lithium chloride, 20% w/v Polyethylene glycol 3,350; 0.2 M Magnesium chloride hexahydrate, 20% w/v Polyethylene glycol 3,350; 0.2 M Sodium chloride, 20% w/v Polyethylene glycol 3,350; 0.2 M Calcium chloride dihydrate, 20% w/v Polyethylene glycol 3,350; 0.2 M Potassium chloride, 20% w/v Polyethylene glycol 3,350; 0.2 M Ammonium chloride, 20% w/v Polyethylene glycol 3,350; 0.2 M Sodium iodide, 20% w/v Polyethylene glycol 3,350; 0.2 M Potassium iodide, 20% w/v Polyethylene glycol 3,350; 0.2 M Ammonium iodide, 20% w/v Polyethylene glycol 3,350; 0.2 M Sodium thiocyanate, 20% w/v Polyethylene glycol 3,350; 0.2 M Potassium thiocyanate, 20% w/v Polyethylene glycol 3,350; 0.2 M Lithium nitrate, 20% w/v Polyethylene glycol 3,350; 0.2 M Magnesium nitrate hexahydrate, 20% w/v Polyethylene glycol 3,350; 0.2 M Sodium nitrate, 20% w/v Polyethylene glycol 3,350; 0.2 M Potassium nitrate, 20% w/v Polyethylene glycol 3,350; 0.2 M Ammonium nitrate, 20% w/v Polyethylene glycol 3,350; 0.2 M Magnesium formate dihydrate, 20% w/v Polyethylene glycol 3,350; 0.2 M Sodium formate, 20% w/v Polyethylene glycol 3,350; 0.2 M Potassium formate, 20% w/v Polyethylene glycol 3,350; 0.2 M Ammonium formate, 20% w/v Polyethylene glycol 3,350; 0.2 M Lithium acetate dihydrate, 20% w/v Polyethylene glycol 3,350; 0.2 M Magnesium acetate tetrahydrate, 20% w/v Polyethylene glycol 3,350; 0.2 M Zinc acetate dihydrate, 20% w/v Polyethylene glycol 3,350; 0.2 M Sodium acetate trihydrate, 20% w/v Polyethylene glycol 3,350; 0.2 M Calcium acetate hydrate, 20% w/v Polyethylene glycol 3,350; 0.2 M Potassium acetate, 20% w/v Polyethylene glycol 3,350; 0.2 M Ammonium acetate, 20% w/v Polyethylene glycol 3,350; 0.2 M Lithium sulfate monohydrate, 20% w/v Polyethylene glycol 3,350; 0.2 M Magnesium sulfate heptahydrate, 20% w/v Polyethylene glycol 3,350; 0.2 M Sodium sulfate decahydrate, 20% w/v Polyethylene glycol 3,350; 0.2 M Potassium sulfate, 20% w/v Polyethylene glycol 3,350; 0.2 M Ammonium sulfate, 20% w/v Polyethylene glycol 3,350; 0.2 M Sodium tartrate dibasic dihydrate, 20% w/v Polyethylene glycol 3,350; 0.2 M Potassium sodium tartrate tetrahydrate, 20% w/v Polyethylene glycol 3,350; 0.2 M Ammonium tartrate dibasic, 20% w/v Polyethylene glycol 3,350; 0.2 M Sodium phosphate monobasic monohydrate, 20% w/v Polyethylene glycol 3,350; 0.2 M Sodium phosphate dibasic dihydrate, 20% w/v Polyethylene glycol 3,350; 0.2 M Potassium phosphate monobasic, 20% w/v Polyethylene glycol 3,350; 0.2 M Potassium phosphate dibasic, 20% w/v Polyethylene glycol 3,350; 0.2 M Ammonium phosphate monobasic, 20% w/v Polyethylene glycol 3,350; 0.2 M Ammonium phosphate dibasic, 20% w/v Polyethylene glycol 3,350; 0.2 M Lithium citrate tribasic tetrahydrate, 20% w/v Polyethylene glycol 3,350; 0.2 M Sodium citrate tribasic dihydrate, 20% w/v Polyethylene glycol 3,350; 0.2 M Potassium citrate tribasic monohydrate, 20% will Polyethylene glycol 3,350; 0.2 M Ammonium citrate dibasic, 20% w/v Polyethylene glycol 3,350.

Group 11: 0.1 M Sodium malonate pH 4.0, 12% w/v Polyethylene glycol 3,350; 0.2 M Sodium malonate pH 4.0, 20% w/v Polyethylene glycol 3,350; 0.1 M Sodium malonate pH 5.0, 12% w/v Polyethylene glycol 3,350; 0.2 M Sodium malonate pH 5.0, 20% w/v Polyethylene glycol 3,350; 0.1 M Sodium malonate pH 6.0, 12% w/v Polyethylene glycol 3,350; 0.2 M Sodium malonate pH 6.0, 20% w/v Polyethylene glycol 3,350; 0.1 M Sodium malonate pH 7.0, 12% w/v Polyethylene glycol 3,350; 0.2 M Sodium malonate pH 7.0, 20% w/v Polyethylene glycol 3,350; 4% v/v Tacsimate pH 4.0, 12% w/v Polyethylene glycol 3,350; 8% v/v Tacsimate pH 4.0, 20% w/v Polyethylene glycol 3,350; 4% v/v Tacsimate pH 5.0, 12% w/v Polyethylene glycol 3,350; 8% v/v Tacsimate pH 5.0, 20% w/v Polyethylene glycol 3,350; 4% v/v Tacsimate pH 6.0, 12% w/v Polyethylene glycol 3,350; 8% v/v Tacsimate pH 6.0, 20% w/v Polyethylene glycol 3,350; 4% v/v Tacsimate pH 7.0, 12% w/v Polyethylene glycol 3,350; 8% v/v Tacsimate pH 7.0, 20% w/v Polyethylene glycol 3,350; 4% v/v Tacsimate pH 8.0, 12% w/v Polyethylene glycol 3,350; 8% v/v Tacsimate pH 8.0, 20% w/v Polyethylene glycol 3,350; 0.1 M Succinic acid pH 7.0, 12% w/v Polyethylene glycol 3,350; 0.2 M Succinic acid pH 7.0, 20% w/v Polyethylene glycol 3,350; 0.1 M Ammonium citrate tribasic pH 7.0, 12% w/v Polyethylene glycol 3,350; 0.2 M Ammonium citrate tribasic pH 7.0, 20% w/v Polyethylene glycol 3,350; 0.1 M DL-Malic acid pH 7.0, 12% w/v Polyethylene glycol 3,350; 0.2 M DL-Malic acid pH 7.0, 20% w/v Polyethylene glycol 3,350; 0.1 M Sodium acetate trihydrate pH 7.0, 12% w/v Polyethylene glycol 3,350; 0.2 M Sodium acetate trihydrate pH 7.0, 20% w/v Polyethylene glycol 3,350; 0.1 M Sodium formate pH 7.0, 12% w/v Polyethylene glycol 3,350; 0.2 M Sodium formate pH 7.0, 20% w/v Polyethylene glycol 3,350; 0.1 M Ammonium tartrate dibasic pH 7.0, 12% w/v Polyethylene glycol 3,350; 0.2 M Ammonium tartrate dibasic pH 7.0, 20% w/v Polyethylene glycol 3,350; 2% v/v Tacsimate pH 4.0, 0.1 M Sodium acetate trihydrate pH 4.6, 16% w/v Polyethylene glycol 3,350; 2% v/v Tacsimate pH 5.0, 0.1 M Sodium citrate tribasic dihydrate pH 5.6, 16% w/v Polyethylene glycol 3,350; 2% v/v Tacsimate pH 6.0, 0.1 M BIS-TRIS pH 6.5, 20% w/v Polyethylene glycol 3,350; 2% v/v Tacsimate pH 7.0, 0.1 M HEPES pH 7.5, 20% w/v Polyethylene glycol 3,350; 2% v/v Tacsimate pH 8.0, 0.1 M Tris pH 8.5, 16% w/v Polyethylene glycol 3,350; (0.07 M Citric acid, 0.03 M BIS-TRIS propane)/pH 3.4, 16% w/v Polyethylene glycol 3,350; (0.06 M Citric acid, 0.04 M BIS-TRIS propane)/pH 4.1, 16% w/v Polyethylene glycol 3,350; (0.05 M Citric acid, 0.05 M BIS-TRIS propane)/pH 5.0, 16% w/v Polyethylene glycol 3,350; (0.04 M Citric acid, 0.06 M BIS-TRIS propane)/pH 6.4, 20% w/v Polyethylene glycol 3,350; (0.03 M Citric acid, 0.07 M BIS-TRIS propane)/pH 7.6, 20% w/v Polyethylene glycol 3,350; (0.02 M Citric acid, 0.08 M BIS-TRIS propane)/pH 8.8, 16% w/v Polyethylene glycol 3,350; 0.02 M Calcium chloride dihydrate, 0.02 M Cadmium chloride hydrate, 0.02 M Cobalt(II) chloride hexahydrate, 20% w/v Polyethylene glycol 3,350; 0.01 M Magnesium chloride hexahydrate, 0.005 M Nickel(II) chloride hexahydrate, 0.1 M HEPES sodium pH 7.0, 15% w/v Polyethylene glycol 3,350; 0.02 M Zinc chloride, 20% w/v Polyethylene glycol 3,350; 0.15 M Cesium chloride, 15% w/v Polyethylene glycol 3,350; 0.2 M Sodium bromide, 20% w/v Polyethylene glycol 3,350; 1% w/v Tryptone, 0.05 M HEPES sodium pH 7.0, 12% w/v Polyethylene glycol 3,350; 1% w/v Tryptone, 0.05 M HEPES sodium pH 7.0, 20% w/v Polyethylene glycol 3,350.

Group 12: 0.2 M Sodium fluoride, 20% w/v Polyethylene glycol 3,350; 0.2 M Potassium fluoride, 20% w/v Polyethylene glycol 3,350; 0.2 M Ammonium fluoride, 20% w/v Polyethylene glycol 3,350; 0.2 M Lithium chloride, 20% w/v Polyethylene glycol 3,350; 0.2 M Magnesium chloride hexahydrate, 20% w/v Polyethylene glycol 3,350; 0.2 M Sodium chloride, 20% w/v Polyethylene glycol 3,350; 0.2 M Calcium chloride dihydrate, 20% w/v Polyethylene glycol 3,350; 0.2 M Potassium chloride, 20% w/v Polyethylene glycol 3,350; 0.2 M Ammonium chloride, 20% w/v Polyethylene glycol 3,350; 0.2 M Sodium iodide, 20% w/v Polyethylene glycol 3,350; 0.2 M Potassium iodide, 20% w/v Polyethylene glycol 3,350; 0.2 M Ammonium iodide, 20% w/v Polyethylene glycol 3,350; 0.2 M Sodium thiocyanate, 20% w/v Polyethylene glycol 3,350; 0.2 M Potassium thiocyanate, 20% w/v Polyethylene glycol 3,350; 0.2 M Lithium nitrate, 20% w/v Polyethylene glycol 3,350; 0.2 M Magnesium nitrate hexahydrate, 20% w/v Polyethylene glycol 3,350; 0.2 M Sodium nitrate, 20% w/v Polyethylene glycol 3,350; 0.2 M Potassium nitrate, 20% w/v Polyethylene glycol 3,350; 0.2 M Ammonium nitrate, 20% w/v Polyethylene glycol 3,350; 0.2 M Magnesium formate dihydrate, 20% w/v Polyethylene glycol 3,350; 0.2 M Sodium formate, 20% w/v Polyethylene glycol 3,350; 0.2 M Potassium formate, 20% w/v Polyethylene glycol 3,350; 0.2 M Ammonium formate, 20% w/v Polyethylene glycol 3,350; 0.2 M Lithium acetate dihydrate, 20% w/v Polyethylene glycol 3,350; 0.2 M Magnesium acetate tetrahydrate, 20% w/v Polyethylene glycol 3,350; 0.2 M Zinc acetate dihydrate, 20% w/v Polyethylene glycol 3,350; 0.2 M Sodium acetate trihydrate, 20% w/v Polyethylene glycol 3,350; 0.2 M Calcium acetate hydrate, 20% w/v Polyethylene glycol 3,350; 0.2 M Potassium acetate, 20% w/v Polyethylene glycol 3,350; 0.2 M Ammonium acetate, 20% w/v Polyethylene glycol 3,350; 0.2 M Lithium sulfate monohydrate, 20% w/v Polyethylene glycol 3,350; 0.2 M Magnesium sulfate heptahydrate, 20% w/v Polyethylene glycol 3,350; 0.2 M Sodium sulfate decahydrate, 20% w/v Polyethylene glycol 3,350; 0.2 M Potassium sulfate, 20% w/v Polyethylene glycol 3,350; 0.2 M Ammonium sulfate, 20% w/v Polyethylene glycol 3,350; 0.2 M Sodium tartrate dibasic dihydrate, 20% w/v Polyethylene glycol 3,350; 0.2 M Potassium sodium tartrate tetrahydrate, 20% w/v Polyethylene glycol 3,350; 0.2 M Ammonium tartrate dibasic, 20% w/v Polyethylene glycol 3,350; 0.2 M Sodium phosphate monobasic monohydrate, 20% w/v Polyethylene glycol 3,350; 0.2 M Sodium phosphate dibasic dihydrate, 20% w/v Polyethylene glycol 3,350; 0.2 M Potassium phosphate monobasic, 20% w/v Polyethylene glycol 3,350; 0.2 M Potassium phosphate dibasic, 20% w/v Polyethylene glycol 3,350; 0.2 M Ammonium phosphate monobasic, 20% w/v Polyethylene glycol 3,350; 0.2 M Ammonium phosphate dibasic, 20% w/v Polyethylene glycol 3,350; 0.2 M Lithium citrate tribasic tetrahydrate, 20% w/v Polyethylene glycol 3,350; 0.2 M Sodium citrate tribasic dihydrate, 20% w/v Polyethylene glycol 3,350; 0.2 M Potassium citrate tribasic monohydrate, 20% w/v Polyethylene glycol 3,350; 0.2 M Ammonium citrate dibasic, 20% w/v Polyethylene glycol 3,350; 0.1 M Sodium malonate pH 4.0, 12% w/v Polyethylene glycol 3,350; 0.2 M Sodium malonate pH 4.0, 20% w/v Polyethylene glycol 3,350; 0.1 M Sodium malonate pH 5.0, 12% w/v Polyethylene glycol 3,350; 0.2 M Sodium malonate pH 5.0, 20% w/v Polyethylene glycol 3,350; 0.1 M Sodium malonate pH 6.0, 12% w/v Polyethylene glycol 3,350; 0.2 M Sodium malonate pH 6.0, 20% w/v Polyethylene glycol 3,350; 0.1 M Sodium malonate pH 7.0, 12% w/v Polyethylene glycol 3,350; 0.2 M Sodium malonate pH 7.0, 20% w/v Polyethylene glycol 3,350; 4% v/v Tacsimate pH 4.0, 12% w/v Polyethylene glycol 3,350; 8% v/v Tacsimate pH 4.0, 20% w/v Polyethylene glycol 3,350; 4% v/v Tacsimate pH 5.0, 12% w/v Polyethylene glycol 3,350; 8% v/v Tacsimate pH 5.0, 20% w/v Polyethylene glycol 3,350; 4% v/v Tacsimate pH 6.0, 12% w/v Polyethylene glycol 3,350; 8% v/v Tacsimate pH 6.0, 20% w/v Polyethylene glycol 3,350; 4% v/v Tacsimate pH 7.0, 12% w/v Polyethylene glycol 3,350; 8% v/v Tacsimate pH 7.0, 20% w/v Polyethylene glycol 3,350; 4% v/v Tacsimate pH 8.0, 12% w/v Polyethylene glycol 3,350; 8% v/v Tacsimate pH 8.0, 20% w/v Polyethylene glycol 3,350; 0.1 M Succinic acid pH 7.0, 12% w/v Polyethylene glycol 3,350; 0.2 M Succinic acid pH 7.0, 20% w/v Polyethylene glycol 3,350; 0.1 M Ammonium citrate tribasic pH 7.0, 12% w/v Polyethylene glycol 3,350; 0.2 M Ammonium citrate tribasic pH 7.0, 20% w/v Polyethylene glycol 3,350; 0.1 M DL-Malic acid pH 7.0, 12% w/v Polyethylene glycol 3,350; 0.2 M DL-Malic acid pH 7.0, 20% w/v Polyethylene glycol 3,350; 0.1 M Sodium acetate trihydrate pH 7.0, 12% w/v Polyethylene glycol 3,350; 0.2 M Sodium acetate trihydrate pH 7.0, 20% w/v Polyethylene glycol 3,350; 0.1 M Sodium formate pH 7.0, 12% w/v Polyethylene glycol 3,350; 0.2 M Sodium formate pH 7.0, 20% w/v Polyethylene glycol 3,350; 0.1 M Ammonium tartrate dibasic pH 7.0, 12% w/v Polyethylene glycol 3,350; 0.2 M Ammonium tartrate dibasic pH 7.0, 20% w/v Polyethylene glycol 3,350; 2% v/v Tacsimate pH 4.0, 0.1 M Sodium acetate trihydrate pH 4.6, 16% w/v Polyethylene glycol 3,350; 2% v/v Tacsimate pH 5.0, 0.1 M Sodium citrate tribasic dihydrate pH 5.6, 16% w/v Polyethylene glycol 3,350; 2% v/v Tacsimate pH 6.0, 0.1 M BIS-TRIS pH 6.5, 20% w/v Polyethylene glycol 3,350; 2% v/v Tacsimate pH 7.0, 0.1 M HEPES pH 7.5, 20% w/v Polyethylene glycol 3,350; 2% v/v Tacsimate pH 8.0, 0.1 M Tris pH 8.5, 16% w/v Polyethylene glycol 3,350; (0.07 M Citric acid, 0.03 M BIS-TRIS propane)/pH 3.4, 16% w/v Polyethylene glycol 3,350; (0.06 M Citric acid, 0.04 M BIS-TRIS propane)/pH 4.1, 16% w/v Polyethylene glycol 3,350; (0.05 M Citric acid, 0.05 M BIS-TRIS propane)/pH 5.0, 16% w/v Polyethylene glycol 3,350; (0.04 M Citric acid, 0.06 M BIS-TRIS propane)/pH 6.4, 20% w/v Polyethylene glycol 3,350; (0.03 M Citric acid, 0.07 M BIS-TRIS propane)/pH 7.6, 20% w/v Polyethylene glycol 3,350; (0.02 M Citric acid, 0.08 M BIS-TRIS propane)/pH 8.8, 16% w/v Polyethylene glycol 3,350; 0.02 M Calcium chloride dihydrate, 0.02 M Cadmium chloride hydrate, 0.02 M Cobalt(II) chloride hexahydrate, 20% w/v Polyethylene glycol 3,350; 0.01 M Magnesium chloride hexahydrate, 0.005 M Nickel(II) chloride hexahydrate, 0.1 M HEPES sodium pH 7.0, 15% w/v Polyethylene glycol 3,350; 0.02 M Zinc chloride, 20% w/v Polyethylene glycol 3,350; 0.15 M Cesium chloride, 15% w/v Polyethylene glycol 3,350; 0.2 M Sodium bromide, 20% w/v Polyethylene glycol 3,350; 1% w/v Tryptone, 0.05 M HEPES sodium pH 7.0, 12% w/v Polyethylene glycol 3,350; 1% w v Tryptone, 0.05 M HEPES sodium pH 7.0, 20% w/v Polyethylene glycol 3,350.

Group 13: 0.1 M Citric acid pH 4.0, 0.8 M Ammonium sulfate; 0.1 M Citric acid pH 5.0, 0.8 M Ammonium sulfate; 0.1 M MES monohydrate pH 6.0, 0.8 M Ammonium sulfate; 0.1 M HEPES pH 7.0, 0.8 M Ammonium sulfate; 0.1 M Tris pH 8.0, 0.8 M Ammonium sulfate; 0.1 M BICINE pH 9.0, 0.8 M Ammonium sulfate; 0.1 M Citric acid pH 4.0, 1.6 M Ammonium sulfate; 0.1 M Citric acid pH 5.0, 1.6 M Ammonium sulfate; 0.1 M MES monohydrate pH 6.0, 1.6 M Ammonium sulfate; 0.1 M HEPES pH 7.0, 1.6 M Ammonium sulfate; 0.1 M Tris pH 8.0, 1.6 M Ammonium sulfate; 0.1 M BICINE pH 9.0, 1.6 M Ammonium sulfate; 0.1 M Citric acid pH 4.0, 2.4 M Ammonium sulfate; 0.1 M Citric acid pH 5.0, 2.4 M Ammonium sulfate; 0.1 M MES monohydrate pH 6.0, 2.4 M Ammonium sulfate; 0.1 M HEPES pH 7.0, 2.4 M Ammonium sulfate; 0.1 M Tris pH 8.0, 2.4 M Ammonium sulfate; 0.1 M BICINE pH 9.0, 2.4 M Ammonium sulfate; 0.1 M Citric acid pH 4.0, 3.0 M Ammonium sulfate; 0.1 M Citric acid pH 5.0, 3.0 M Ammonium sulfate; 0.1 M MES monohydrate pH 6.0, 3.0 M Ammonium sulfate; 0.1 M HEPES pH 7.0, 3.0 M Ammonium sulfate; 0.1 M Tris pH 8.0, 3.0 M Ammonium sulfate; 0.1 M BICINE pH 9.0, 3.0 M Ammonium sulfate.

Group 14: 0.1 M Citric acid pH 4.0, 10% (+/−)-2-Methyl-2,4-pentanediol; 0.1 M Sodium acetate trihydrate pH 5.0, 10% (+/−)-2-Methyl-2,4-pentanediol; 0.1 M MES monohydrate pH 6.0, 10% (+/−)-2-Methyl-2,4-pentanediol; 0.1 M HEPES pH 7.0, 10% (+/−)-2-Methyl-2,4-pentanediol; 0.1 M Tris pH 8.0, 10% (+/−)-2-Methyl-2,4-pentanediol; 0.1 M BICINE pH 9.0, 10% (+/−)-2-Methyl-2,4-pentanediol; 0.1 M Citric acid pH 4.0, 20% (+/−)-2-Methyl-2,4-pentanediol; 0.1 M Sodium acetate trihydrate pH 5.0, 20% (+/−)-2-Methyl-2,4-pentanediol; 0.1 M MES monohydrate pH 6.0, 20% (+/−)-2-Methyl-2,4-pentanediol; 0.1 M HEPES pH 7.0, 20% (+/−)-2-Methyl-2,4-pentanediol; 0.1 M Tris pH 8.0, 20% (+/−)-2-Methyl-2,4-pentanediol; 0.1 M BICINE pH 9.0, 20% (+/−)-2-Methyl-2,4-pentanediol; 0.1 M Citric acid pH 4.0, 40% (+/−)-2-Methyl-2,4-pentanediol; 0.1 M Sodium acetate trihydrate pH 5.0, 40% (+/−)-2-Methyl-2,4-pentanediol; 0.1 M MES monohydrate pH 6.0, 40% (+/−)-2-Methyl-2,4-pentanediol; 0.1 M HEPES pH 7.0, 40% (+42-Methyl-2,4-pentanediol; 0.1 M Tris pH 8.0, 40% (+/−)-2-Methyl-2,4-pentanediol; 0.1 M BICINE pH 9.0, 40% (+/−)-2-Methyl-2,4-pentanediol; 0.1 M Citric acid pH 4.0, 65% (+/−)-2-Methyl-2,4-pentanediol; 0.1 M Sodium acetate trihydrate pH 5.0, 65% (+/−)-2-Methyl-2,4-pentanediol; 0.1 M MES monohydrate pH 6.0, 65% (+/−)-2-Methyl-2,4-pentanediol; 0.1 M HEPES pH 7.0, 65% (+/−)-2-Methyl-2,4-pentanediol; 0.1 M Tris pH 8.0, 65% (+/−)-2-Methyl-2,4-pentanediol; 0.1 M BICINE pH 9.0, 65% (+/−)-2-Methyl-2,4-pentanediol.

Group 15: 0.1 M Citric acid pH 4.0, 5% w/v Polyethylene glycol 6,000; 0.1 M Citric acid pH 5.0, 5% w/v Polyethylene glycol 6,000; 0.1 M MES monohydrate pH 6.0, 5% w/v Polyethylene glycol 6,000; 0.1 M HEPES pH 7.0, 5% w/v Polyethylene glycol 6,000; 0.1 M Tris pH 8.0, 5% w/v Polyethylene glycol 6,000; 0.1 M BICINE pH 9.0, 5% w/v Polyethylene glycol 6,000; 0.1 M Citric acid pH 4.0, 10% w/v Polyethylene glycol 6,000; 0.1 M Citric acid pH 5.0, 10% w/v Polyethylene glycol 6,000; 0.1 M MES monohydrate pH 6.0, 10% w/v Polyethylene glycol 6,000; 0.1 M HEPES pH 7.0, 10% w/v Polyethylene glycol 6,000; 0.1 M Tris pH 8.0, 10% w/v Polyethylene glycol 6,000; 0.1 M BICINE pH 9.0, 10% w/v Polyethylene glycol 6,000; 0.1 M Citric acid pH 4.0, 20% w/v Polyethylene glycol 6,000; 0.1 M Citric acid pH 5.0, 20% w/v Polyethylene glycol 6,000; 0.1 M MES monohydrate pH 6.0, 20% w/v Polyethylene glycol 6,000; 0.1 M HEPES pH 7.0, 20% w/v Polyethylene glycol 6,000; 0.1 M Tris pH 8.0, 20% w/v Polyethylene glycol 6,000; 0.1 M BICINE pH 9.0, 20% w/v Polyethylene glycol 6,000; 0.1 M Citric acid pH 4.0, 30% w/v Polyethylene glycol 6,000; 0.1 M Citric acid pH 5.0, 30% w/v Polyethylene glycol 6,000; 0.1 M MES monohydrate pH 6.0, 30% w/v Polyethylene glycol 6,000; 0.1 M HEPES pH 7.0, 30% w/v Polyethylene glycol 6,000; 0.1 M Tris pH 8.0, 30% w/v Polyethylene glycol 6,000; 0.1 M BICINE pH 9.0, 30% w/v Polyethylene glycol 6,000.

Group 16: 0.1 M Citric acid pH 4.0, 1.0 M Lithium chloride; 0.1 M Citric acid pH 5.0, 1.0 M Lithium chloride; 0.1 M MES monohydrate pH 6.0, 1.0 M Lithium chloride; 0.1 M HEPES pH 7.0, 1.0 M Lithium chloride; 0.1 M Tris pH 8.0, 1.0 M Lithium chloride; 0.1 M BICINE pH 9.0, 1.0 M Lithium chloride; 0.1 M Citric acid pH 4.0, 1.0 M Lithium chloride, 10% w/v Polyethylene glycol 6,000; 0.1 M Citric acid pH 5.0, 1.0 M Lithium chloride, 10% w/v Polyethylene glycol 6,000; 0.1 M MES monohydrate pH 6.0, 1.0 M Lithium chloride, 10% w/v Polyethylene glycol 6,000; 0.1 M HEPES pH 7.0, 1.0 M Lithium chloride, 10% w/v Polyethylene glycol 6,000; 0.1 M Tris pH 8.0, 1.0 M Lithium chloride, 10% w/v Polyethylene glycol 6,000; 0.1 M BICINE pH 9.0, 1.0 M Lithium chloride, 10% w/v Polyethylene glycol 6,000; 0.1 M Citric acid pH 4.0, 1.0 M Lithium chloride, 20% w/v Polyethylene glycol 6,000; 0.1 M Citric acid pH 5.0, 1.0 M Lithium chloride, 20% w/v Polyethylene glycol 6,000; 0.1 M MES monohydrate pH 6.0, 1.0 M Lithium chloride, 20% w/v Polyethylene glycol 6,000; 0.1 M HEPES pH 7.0, 1.0 M Lithium chloride, 20% w/v Polyethylene glycol 6,000; 0.1 M Tris pH 8.0, 1.0 M Lithium chloride, 20% w/v Polyethylene glycol 6,000; 0.1 M BICINE pH 9.0, 1.0 M Lithium chloride, 20% w/v Polyethylene glycol 6,000; 0.1 M Citric acid pH 4.0, 1.0 M Lithium chloride, 30% w/v Polyethylene glycol 6,000; 0.1 M Citric acid pH 5.0, 1.0 M Lithium chloride, 30% w/v Polyethylene glycol 6,000; 0.1 M MES monohydrate pH 6.0, 1.0 M Lithium chloride, 30% w/v Polyethylene glycol 6,000; 0.1 M HEPES pH 7.0, 1.0 M Lithium chloride, 30% w/v Polyethylene glycol 6,000; 0.1 M Tris pH 8.0, 1.0 M Lithium chloride, 30% w/v Polyethylene glycol 6,000; 0.1 M BICINE pH 9.0, 1.0 M Lithium chloride, 30% w/v Polyethylene glycol 6,000.

Group 17: 0.1 M Citric acid pH 4.0, 0.8 M Ammonium sulfate; 0.1 M Citric acid pH 5.0, 0.8 M Ammonium sulfate; 0.1 M MES monohydrate pH 6.0, 0.8 M Ammonium sulfate; 0.1 M HEPES pH 7.0, 0.8 M Ammonium sulfate; 0.1 M Tris pH 8.0, 0.8 M Ammonium sulfate; 0.1 M BICINE pH 9.0, 0.8 M Ammonium sulfate; 0.1 M Citric acid pH 4.0, 1.6 M Ammonium sulfate; 0.1 M Citric acid pH 5.0, 1.6 M Ammonium sulfate; 0.1 M MES monohydrate pH 6.0, 1.6 M Ammonium sulfate; 0.1 M HEPES pH 7.0, 1.6 M Ammonium sulfate; 0.1 M Tris pH 8.0, 1.6 M Ammonium sulfate; 0.1 M BICINE pH 9.0, 1.6 M Ammonium sulfate; 0.1 M Citric acid pH 4.0, 2.4 M Ammonium sulfate; 0.1 M Citric acid pH 5.0, 2.4 M Ammonium sulfate; 0.1 M MES monohydrate pH 6.0, 2.4 M Ammonium sulfate; 0.1 M HEPES pH 7.0, 2.4 M Ammonium sulfate; 0.1 M Tris pH 8.0, 2.4 M Ammonium sulfate; 0.1 M BICINE pH 9.0, 2.4 M Ammonium sulfate; 0.1 M Citric acid pH 4.0, 3 M Ammonium sulfate; 0.1 M Citric acid pH 5.0, 3 M Ammonium sulfate; 0.1 M MES monohydrate pH 6.0, 3 M Ammonium sulfate; 0.1 M HEPES pH 7.0, 3 M Ammonium sulfate; 0.1 M Tris pH 8.0, 3 M Ammonium sulfate; 0.1 M BICINE pH 9.0, 3 M Ammonium sulfate; 1.0 M Sodium malonate pH 4.0; 1.5 M Sodium malonate pH 4.0; 1.9 M Sodium malonate pH 4.0; 2.4 M Sodium malonate pH 4.0; 2.9 M Sodium malonate pH 4.0; 3.4 M Sodium malonate pH 4.0; 1.0 M Sodium malonate pH 5.0; 1.5 M Sodium malonate pH 5.0; 1.9 M Sodium malonate pH 5.0; 2.4 M Sodium malonate pH 5.0; 2.9 M Sodium malonate pH 5.0; 3.4 M Sodium malonate pH 5.0; 1.0 M Sodium malonate pH 6.0; 1.5 M Sodium malonate pH 6.0; 1.9 M Sodium malonate pH 6.0; 2.4 M Sodium malonate pH 6.0; 2.9 M Sodium malonate pH 6.0; 3.4 M Sodium malonate pH 6.0; 1.0 M Sodium malonate pH 7.0; 1.5 M Sodium malonate pH 7.0; 1.9 M Sodium malonate pH 7.0; 2.4 M Sodium malonate pH 7.0; 2.9 M Sodium malonate pH 7.0; 3.4 M Sodium malonate pH 7.0; 0.8 M Sodium phosphate monobasic monohydrate/Potassium phosphate dibasic pH 5.0; 0.8 M Sodium phosphate monobasic monohydrate/Potassium phosphate dibasic pH 5.6; 0.8 M Sodium phosphate monobasic monohydrate/Potassium phosphate dibasic pH 6.3; 0.8 M Sodium phosphate monobasic monohydrate/Potassium phosphate dibasic pH 6.9; 0.8 M Sodium phosphate monobasic monohydrate/Potassium phosphate dibasic pH 7.5; 0.8 M Sodium phosphate monobasic monohydrate/Potassium phosphate dibasic pH 8.2; 1.0 M Sodium phosphate monobasic monohydrate/Potassium phosphate dibasic pH 5.0; 1.0 M Sodium phosphate monobasic monohydrate/Potassium phosphate dibasic pH 5.6; 1.0 M Sodium phosphate monobasic monohydrate/Potassium phosphate dibasic pH 6.3; 1.0 M Sodium phosphate monobasic monohydrate/Potassium phosphate dibasic pH 6.9; 1.0 M Sodium phosphate monobasic monohydrate/Potassium phosphate dibasic pH 7.5; 1.0 M Sodium phosphate monobasic monohydrate/Potassium phosphate dibasic pH 8.2; 1.4 M Sodium phosphate monobasic monohydrate/Potassium phosphate dibasic pH 5.0; 1.4 M Sodium phosphate monobasic monohydrate/Potassium phosphate dibasic pH 5.6; 1.4 M Sodium phosphate monobasic monohydrate/Potassium phosphate dibasic pH 6.3; 1.4 M Sodium phosphate monobasic monohydrate/Potassium phosphate dibasic pH 6.9; 1.4 M Sodium phosphate monobasic monohydrate/Potassium phosphate dibasic pH 7.5; 1.4 M Sodium phosphate monobasic monohydrate/Potassium phosphate dibasic pH 8.2; 1.8 M Sodium phosphate monobasic monohydrate/Potassium phosphate dibasic pH 5.0; 1.8 M Sodium phosphate monobasic monohydrate/Potassium phosphate dibasic pH 5.6; 1.8 M Sodium phosphate monobasic monohydrate/Potassium phosphate dibasic pH 6.3; 1.8 M Sodium phosphate monobasic monohydrate/Potassium phosphate dibasic pH 6.9; 1.8 M Sodium phosphate monobasic monohydrate/Potassium phosphate dibasic pH 7.5; 1.8 M Sodium phosphate monobasic monohydrate/Potassium phosphate dibasic pH 8.2; 0.1 M Citric acid pH 4.0, 1.0 M Sodium chloride; 0.1 M Citric acid pH 5.0, 1.0 M Sodium chloride; 0.1 M MES monohydrate pH 6.0, 1.0 M Sodium chloride; 0.1 M HEPES pH 7.0, 1.0 M Sodium chloride; 0.1 M Tris pH 8.0, 1.0 M Sodium chloride; 0.1 M BICINE pH 9.0, 1.0 M Sodium chloride; 0.1 M Citric acid pH 4.0, 2.0 M Sodium chloride; 0.1 M Citric acid pH 5.0, 2.0 M Sodium chloride; 0.1 M MES monohydrate pH 6.0, 2.0 M Sodium chloride; 0.1 M HEPES pH 7.0, 2.0 M Sodium chloride; 0.1 M Tris pH 8.0, 2.0 M Sodium chloride; 0.1 M BICINE pH 9.0, 2.0 M Sodium chloride; 0.1 M Citric acid pH 4.0, 3.0 M Sodium chloride; 0.1 M Citric acid pH 5.0, 3.0 M Sodium chloride; 0.1 M IVIES monohydrate pH 6.0, 3.0 M Sodium chloride; 0.1 M HEPES pH 7.0, 3.0 M Sodium chloride; 0.1 M Tris pH 8.0, 3.0 M Sodium chloride; 0.1 M BICINE pH 9.0, 3.0 M Sodium chloride; 0.1 M Citric acid pH 4.0, 4.0 M Sodium chloride; 0.1 M Citric acid pH 5.0, 4.0 M Sodium chloride; 0.1 M MES monohydrate pH 6.0, 4.0 M Sodium chloride; 0.1 M HEPES pH 7.0, 4.0 M Sodium chloride; 0.1 M Tris pH 8.0, 4.0 M Sodium chloride; 0.1 M BICINE pH 9.0, 4.0 M Sodium chloride.

Group 18: 0.1 M Citric acid pH 4.0, 1.0 M Sodium chloride; 0.1 M Citric acid pH 5.0, 1.0 M Sodium chloride; 0.1 M MES monohydrate pH 6.0, 1.0 M Sodium chloride; 0.1 M HEPES pH 7.0, 1.0 M Sodium chloride; 0.1 M Tris pH 8.0, 1.0 M Sodium chloride; 0.1 M BICINE pH 9.0, 1.0 M Sodium chloride; 0.1 M Citric acid pH 4.0, 2.0 M Sodium chloride; 0.1 M Citric acid pH 5.0, 2.0 M Sodium chloride; 0.1 M MES monohydrate pH 6.0, 2.0 M Sodium chloride; 0.1 M HEPES pH 7.0, 2.0 M Sodium chloride; 0.1 M Tris pH 8.0, 2.0 M Sodium chloride; 0.1 M BICINE pH 9.0, 2.0 M Sodium chloride; 0.1 M Citric acid pH 4.0, 3.0 M Sodium chloride; 0.1 M Citric acid pH 5.0, 3.0 M Sodium chloride; 0.1 M MES monohydrate pH 6.0, 3.0 M Sodium chloride; 0.1 M HEPES pH 7.0, 3.0 M Sodium chloride; 0.1 M Tris pH 8.0, 3.0 M Sodium chloride; 0.1 M BICINE pH 9.0, 3.0 M Sodium chloride; 0.1 M Citric acid pH 4.0, 4.0 M Sodium chloride; 0.1 M Citric acid pH 5.0, 4.0 M Sodium chloride; 0.1 M MES monohydrate pH 6.0, 4.0 M Sodium chloride;

0.1 M HEPES pH 7.0, 4.0 M Sodium chloride; 0.1 M Tris pH 8.0, 4.0 M Sodium chloride; 0.1 M BICINE pH 9.0, 4.0 M Sodium chloride.

Group 19: 1.0 M Sodium malonate pH 4.0; 1.5 M Sodium malonate pH 4.0; 1.9 M Sodium malonate pH 4.0; 2.4 M Sodium malonate pH 4.0; 2.9 M Sodium malonate pH 4.0; 3.4 M Sodium malonate pH 4.0; 1.0 M Sodium malonate pH 5.0; 1.5 M Sodium malonate pH 5.0; 1.9 M Sodium malonate pH 5.0; 2.4 M Sodium malonate pH 5.0; 2.9 M Sodium malonate pH 5.0; 3.4 M Sodium malonate pH 5.0; 1.0 M Sodium malonate pH 6.0; 1.5 M Sodium malonate pH 6.0; 1.9 M Sodium malonate pH 6.0; 2.4 M Sodium malonate pH 6.0; 2.9 M Sodium malonate pH 6.0; 3.4 M Sodium malonate pH 6.0; 1.0 M Sodium malonate pH 7.0; 1.5 M Sodium malonate pH 7.0; 1.9 M Sodium malonate pH 7.0; 2.4 M Sodium malonate pH 7.0; 2.9 M Sodium malonate pH 7.0; 3.4 M Sodium malonate pH 7.0.

Group 20: 0.8 M Sodium phosphate monobasic monohydrate/Potassium phosphate dibasic pH 5.0; 0.8 M Sodium phosphate monobasic monohydrate/Potassium phosphate dibasic pH 5.6; 0.8 M Sodium phosphate monobasic monohydrate/Potassium phosphate dibasic pH 6.3; 0.8 M Sodium phosphate monobasic monohydrate/Potassium phosphate dibasic pH 6.9; 0.8 M Sodium phosphate monobasic monohydrate/Potassium phosphate dibasic pH 7.5; 0.8 M Sodium phosphate monobasic monohydrate/Potassium phosphate dibasic pH 8.2; 1.0 M Sodium phosphate monobasic monohydrate/Potassium phosphate dibasic pH 5.0; 1.0 M Sodium phosphate monobasic monohydrate/Potassium phosphate dibasic pH 5.6; 1.0 M Sodium phosphate monobasic monohydrate/Potassium phosphate dibasic pH 6.3; 1.0 M Sodium phosphate monobasic monohydrate/Potassium phosphate dibasic pH 6.9; 1.0 M Sodium phosphate monobasic monohydrate/Potassium phosphate dibasic pH 7.5; 1.0 M Sodium phosphate monobasic monohydrate/Potassium phosphate dibasic pH 8.2; 1.4 M Sodium phosphate monobasic monohydrate/Potassium phosphate dibasic pH 5.0; 1.4 M Sodium phosphate monobasic monohydrate/Potassium phosphate dibasic pH 5.6; 1.4 M Sodium phosphate monobasic monohydrate/Potassium phosphate dibasic pH 6.3; 1.4 M Sodium phosphate monobasic monohydrate/Potassium phosphate dibasic pH 6.9; 1.4 M Sodium phosphate monobasic monohydrate/Potassium phosphate dibasic pH 7.5; 1.4 M Sodium phosphate monobasic monohydrate/Potassium phosphate dibasic pH 8.2; 1.8 M Sodium phosphate monobasic monohydrate/Potassium phosphate dibasic pH 5.0; 1.8 M Sodium phosphate monobasic monohydrate/Potassium phosphate dibasic pH 5.6; 1.8 M Sodium phosphate monobasic monohydrate/Potassium phosphate dibasic pH 6.3; 1.8 M Sodium phosphate monobasic monohydrate/Potassium phosphate dibasic pH 6.9; 1.8 M Sodium phosphate monobasic monohydrate/Potassium phosphate dibasic pH 7.5; 1.8 M Sodium phosphate monobasic monohydrate/Potassium phosphate dibasic pH 8.2.

Group 21: 1.8 M Sodium acetate trihydrate pH 7.0, 0.1 M BIS-TRIS propane pH 7.0; 2.8 M Sodium acetate trihydrate pH 7.0, 0.1 M BIS-TRIS propane pH 7.0; 1.5 M Ammonium chloride, 0.1 M Sodium acetate trihydrate pH 4.6; 1.5 M Ammonium chloride, 0.1 M BIS-TRIS propane pH 7.0; 1.5 M Ammonium chloride, 0.1 M Tris pH 8.5; 3.5 M Ammonium chloride, 0.1 M Sodium acetate trihydrate pH 4.6; 3.5 M Ammonium chloride, 0.1 M BIS-TRIS propane pH 7.0; 3.5 M Ammonium chloride, 0.1 M Tris pH 8.5; 2.2 M Sodium chloride, 0.1 M Sodium acetate trihydrate pH 4.6; 2.2 M Sodium chloride, 0.1 M BIS-TRIS propane pH 7.0; 2.2 M Sodium chloride, 0.1 M Tris pH 8.5; 3.2 M Sodium chloride, 0.1 M Sodium acetate trihydrate pH 4.6; 3.2 M Sodium chloride, 0.1 M BIS-TRIS propane pH 7.0; 3.2 M Sodium chloride, 0.1 M Tris pH 8.5; 1.0 M Ammonium citrate dibasic, 0.1 M Sodium acetate trihydrate pH 4.6; 1.8 M Ammonium citrate dibasic, 0.1 M Sodium acetate trihydrate pH 4.6; 1.0 M Ammonium citrate tribasic pH 7.0, 0.1 M BIS-TRIS propane pH 7.0; 2.0 M Ammonium citrate tribasic pH 7.0, 0.1 M BIS-TRIS propane pH 7.0; 0.7 M Sodium citrate tribasic dihydrate, 0.1 M BIS-TRIS propane pH 7.0; 0.7 M Sodium citrate tribasic dihydrate, 0.1 M Tris pH 8.5; 1.2 M Sodium citrate tribasic dihydrate, 0.1 M HIS-TRIS propane pH 7.0; 1.2 M Sodium citrate tribasic dihydrate, 0.1 M Tris pH 8.5; 0.4 M Magnesium formate dihydrate, 0.1 M Sodium acetate trihydrate pH 4.6; 0.4 M Magnesium formate dihydrate, 0.1 M BIS-TRIS propane pH 7.0; 0.4 M Magnesium formate dihydrate, 0.1 M Tris pH 8.5; 0.7 M Magnesium formate dihydrate, 0.1 M BIS-TRIS propane pH 7.0; 2.0 M Sodium formate, 0.1 M Sodium acetate trihydrate pH 4.6; 2.0 M Sodium formate, 0.1 M BIS-TRIS propane pH 7.0; 2.0 M Sodium formate, 0.1 M Tris pH 8.5; 3.5 M Sodium formate, 0.1 M Sodium acetate trihydrate pH 4.6; 3.5 M Sodium formate, 0.1 M BIS-TRIS propane pH 7.0; 3.5 M Sodium formate, 0.1 M Tris pH 8.5; 1.2 M DL-Malic acid pH 7.0, 0.1 M BIS-TRIS propane pH 7.0; 2.2 M DL-Malic acid pH 7.0, 0.1 M BIS-TRIS propane pH 7.0; 1.4 M Sodium malonate pH 7.0, 0.1 M BIS-TRIS propane pH 7.0; 2.4 M Sodium malonate pH 7.0, 0.1 M BIS-TRIS propane pH 7.0; 2.5 M Ammonium nitrate, 0.1 M Sodium acetate trihydrate pH 4.6; 2.5 M Ammonium nitrate, 0.1 M BIS-TRIS propane pH 7.0; 2.5 M Ammonium nitrate, 0.1 M Tris pH 8.5; 6.0 M Ammonium nitrate, 0.1 M Sodium acetate trihydrate pH 4.6; 6.0 M Ammonium nitrate, 0.1 M BIS-TRIS propane pH 7.0; 6.0 M Ammonium nitrate, 0.1 M Tris pH 8.5; 1.5 M Sodium nitrate, 0.1 M Sodium acetate trihydrate pH 4.6; 1.5 M Sodium nitrate, 0.1 M BIS-TRIS propane pH 7.0; 1.5 M Sodium nitrate, 0.1 M Tris pH 8.5; 4.0 M Sodium nitrate, 0.1 M Sodium acetate trihydrate pH 4.6; 4.0 M Sodium nitrate, 0.1 M BIS-TRIS propane pH 7.0; 4.0 M Sodium nitrate, 0.1 M Tris pH 8.5; 1.0 M Ammonium phosphate monobasic, 0.1 M Sodium acetate trihydrate pH 4.6; 1.8 M Ammonium phosphate monobasic, 0.1 M Sodium acetate trihydrate pH 4.6; 1.5 M Ammonium phosphate dibasic, 0.1 M Tris pH 8.5; 2.4 M Ammonium phosphate dibasic, 0.1 M Tris pH 8.5; 1.0 M Sodium phosphate monobasic monohydrate, Potassium phosphate dibasic/pH 5.0; 1.0 M Sodium phosphate monobasic monohydrate, Potassium phosphate dibasic/pH 6.9; 1.0 M Sodium phosphate monobasic monohydrate, Potassium phosphate dibasic/pH 8.2; 1.8 M Sodium phosphate monobasic monohydrate, Potassium phosphate dibasic/pH 5.0; 1.8 M Sodium phosphate monobasic monohydrate, Potassium phosphate dibasic/pH 6.9; 1.8 M Sodium phosphate monobasic monohydrate, Potassium phosphate dibasic/pH 8.2; 0.5 M Succinic acid pH 7.0, 0.1 M BIS-TRIS propane pH 7.0; 1.0 M Succinic acid pH 7.0, 0.1 M BIS-TRIS propane pH 7.0; 1.5 M Ammonium sulfate, 0.1 M Sodium acetate trihydrate pH 4.6; 1.5 M Ammonium sulfate, 0.1 M BIS-TRIS propane pH 7.0; 1.5 M Ammonium sulfate, 0.1 M Tris pH 8.5; 2.5 M Ammonium sulfate, 0.1 M Sodium acetate trihydrate pH 4.6; 2.5 M Ammonium sulfate, 0.1 M BIS-TRIS propane pH 7.0; 2.5 M Ammonium sulfate, 0.1 M Tris pH 8.5; 0.8 M Lithium sulfate monohydrate, 0.1 M Sodium acetate trihydrate pH 4.6; 0.8 M Lithium sulfate monohydrate, 0.1 M BIS-TRIS propane pH 7.0; 0.8 M Lithium sulfate monohydrate, 0.1 M Tris pH 8.5; 1.5 M Lithium sulfate monohydrate, 0.1 M Sodium acetate trihydrate pH 4.6; 1.5 M Lithium sulfate monohydrate, 0.1 M BIS-TRIS propane pH 7.0; 1.5 M Lithium sulfate monohydrate, 0.1 M Tris pH 8.5;

1.0 M Magnesium sulfate hydrate, 0.1 M Sodium acetate trihydrate pH 4.6; 1.0 M Magnesium sulfate hydrate, 0.1 M BIS-TRIS propane pH 7.0; 1.0 M Magnesium sulfate hydrate, 0.1 M Tris pH 8.5; 1.8 M Magnesium sulfate hydrate, 0.1 M Sodium acetate trihydrate pH 4.6; 1.8 M Magnesium sulfate hydrate, 0.1 M BIS-TRIS propane pH 7.0; 1.8 M Magnesium sulfate hydrate, 0.1 M Tris pH 8.5; 0.7 M Ammonium tartrate dibasic, 0.1 M Sodium acetate trihydrate pH 4.6; 0.7 M Ammonium tartrate dibasic, 0.1 M BIS-MS propane pH 7.0; 0.7 M Ammonium tartrate dibasic, 0.1 M Tris pH 8.5; 1.0 M Ammonium tartrate dibasic, 0.1 M Sodium acetate trihydrate pH 4.6; 1.3 M Ammonium tartrate dibasic, 0.1 M BIS-TRIS propane pH 7.0; 1.4 M Ammonium tartrate dibasic, 0.1 M Tris pH 8.5; 0.6 M Potassium sodium tartrate tetrahydrate, 0.1 M BIS-TRIS propane pH 7.0; 1.2 M Potassium sodium tartrate tetrahydrate, 0.1 M BIS-TRIS propane pH 7.0; 0.6 M Potassium sodium tartrate tetrahydrate, 0.1 M Tris pH 8.5; 1.2 M Potassium sodium tartrate tetrahydrate, 0.1 M Tris pH 8.5; 0.5 M Potassium thiocyanate, 0.1 M Sodium acetate trihydrate pH 4.6; 0.5 M Potassium thiocyanate, 0.1 M BIS-TRIS propane pH 7.0; 0.5 M Potassium thiocyanate, 0.1 M Tris pH 8.5; 4.0 M Ammonium acetate, 0.1 M Sodium acetate trihydrate pH 4.6; 4.0 M Ammonium acetate, 0.1 M BIS-TRIS propane pH 7.0; 4.0 M Ammonium acetate, 0.1 M Tris pH 8.5; 35% v/v Tacsimate pH 7.0, 0.1 M BIS-TRIS propane pH 7.0; 60% v/v Tacsimate pH 7.0, 0.1 M BIS-TRIS propane pH 7.0.

Group 22: PBS buffer, pH 6.6-7.6 (10 mM disodium hydrogen phosphate/sodium dihydrogen phosphate, 137 mM sodium chloride, 2.7 mM potassium chloride, pH 6.6-7.6); 10×PBS buffer; 50×PBS buffer; TE buffer (10 mM Tris, 1 mM EDTA, pH 8); 10× TE buffer; 50× TE buffer; TBS buffer (25 mM Tris, 150 mM NaCl, 2 mM KCl, pH 7.4); 10×TBS buffer; 50×TBS buffer; TAE buffer (40 mM tris-acetate, 1 mM EDTA, pH 8.3); 10×TAE buffer; 50×TAE buffer; TBST buffer (0.1% Polysorbate 20 (TWEEN-20) in 1×TBS, pH 7.4); 10×TBST buffer; 50×TBST buffer; TBE buffer (45 mM Tris-borate, 1 mM EDTA, pH 8); 10×TBE buffer; 50×TBE buffer; 10% sodium dodecyl sulfate (SDS); 20% SDS; 30% SDS.

Group 23: 1.8 M Sodium acetate trihydrate pH 7.0, 0.1 M BIS-TRIS propane pH 7.0; 2.8 M Sodium acetate trihydrate pH 7.0, 0.1 M BIS-TRIS propane pH 7.0; 1.5 M Ammonium chloride, 0.1 M Sodium acetate trihydrate pH 4.6; 1.5 M Ammonium chloride, 0.1 M BIS-TRIS propane pH 7.0; 1.5 M Ammonium chloride, 0.1 M Tris pH 8.5; 3.5 M Ammonium chloride, 0.1 M Sodium acetate trihydrate pH 4.6; 3.5 M Ammonium chloride, 0.1 M BIS-TRIS propane pH 7.0; 3.5 M Ammonium chloride, 0.1 M Tris pH 8.5; 2.2 M Sodium chloride, 0.1 M Sodium acetate trihydrate pH 4.6; 2.2 M Sodium chloride, 0.1 M BIS-TRIS propane pH 7.0; 2.2 M Sodium chloride, 0.1 M Tris pH 8.5; 3.2 M Sodium chloride, 0.1 M Sodium acetate trihydrate pH 4.6; 3.2 M Sodium chloride, 0.1 M BIS-TRIS propane pH 7.0; 3.2 M Sodium chloride, 0.1 M Tris pH 8.5; 1.0 M Ammonium citrate dibasic, 0.1 M Sodium acetate trihydrate pH 4.6; 1.8 M Ammonium citrate dibasic, 0.1 M Sodium acetate trihydrate pH 4.6; 1.0 M Ammonium citrate tribasic pH 7.0, 0.1 M BIS-TRIS propane pH 7.0; 2.0 M Ammonium citrate tribasic pH 7.0, 0.1 M BIS-TRIS propane pH 7.0; 0.7 M Sodium citrate tribasic dihydrate, 0.1 M BIS-TRIS propane pH 7.0; 0.7 M Sodium citrate tribasic dihydrate, 0.1 M Tris pH 8.5; 1.2 M Sodium citrate tribasic dihydrate, 0.1 M BIS-TRIS propane pH 7.0; 1.2 M Sodium citrate tribasic dihydrate, 0.1 M Tris pH 8.5; 0.4 M Magnesium formate dihydrate, 0.1 M Sodium acetate trihydrate pH 4.6; 0.4 M Magnesium formate dihydrate, 0.1 M BIS-TRIS propane pH 7.0; 0.4 M Magnesium formate dihydrate, 0.1 M Tris pH 8.5; 0.7 M Magnesium formate dihydrate, 0.1 M BIS-TRIS propane pH 7.0; 2.0 M Sodium formate, 0.1 M Sodium acetate trihydrate pH 4.6; 2.0 M Sodium formate, 0.1 M BIS-TRIS propane pH 7.0; 2.0 M Sodium formate, 0.1 M Tris pH 8.5; 3.5 M Sodium formate, 0.1 M Sodium acetate trihydrate pH 4.6; 3.5 M Sodium formate, 0.1 M BIS-TRIS propane pH 7.0; 3.5 M Sodium formate, 0.1 M Tris pH 8.5; 1.2 M DL-Malic acid pH 7.0, 0.1 M BIS-TRIS propane pH 7.0; 2.2 M DL-Malic acid pH 7.0, 0.1 M BIS-TRIS propane pH 7.0; 1.4 M Sodium malonate pH 7.0, 0.1 M BIS-TRIS propane pH 7.0; 2.4 M Sodium malonate pH 7.0, 0.1 M BIS-TRIS propane pH 7.0; 2.5 M Ammonium nitrate, 0.1 M Sodium acetate trihydrate pH 4.6; 2.5 M Ammonium nitrate, 0.1 M BIS-TRIS propane pH 7.0; 2.5 M Ammonium nitrate, 0.1 M Tris pH 8.5; 6.0 M Ammonium nitrate, 0.1 M Sodium acetate trihydrate pH 4.6; 6.0 M Ammonium nitrate, 0.1 M BIS-TRIS propane pH 7.0; 6.0 M Ammonium nitrate, 0.1 M Tris pH 8.5; 1.5 M Sodium nitrate, 0.1 M Sodium acetate trihydrate pH 4.6; 1.5 M Sodium nitrate, 0.1 M BIS-TRIS propane pH 7.0; 1.5 M Sodium nitrate, 0.1 M Tris pH 8.5; 4.0 M Sodium nitrate, 0.1 M Sodium acetate trihydrate pH 4.6; 4.0 M Sodium nitrate, 0.1 M BIS-TRIS propane pH 7.0; 4.0 M Sodium nitrate, 0.1 M Tris pH 8.5.

Group 24: 1.0 M Ammonium phosphate monobasic, 0.1 M Sodium acetate trihydrate pH 4.6; 1.8 M Ammonium phosphate monobasic, 0.1 M Sodium acetate trihydrate pH 4.6; 1.5 M Ammonium phosphate dibasic, 0.1 M Tris pH 8.5; 2.4 M Ammonium phosphate dibasic, 0.1 M Tris pH 8.5; 1.0 M Sodium phosphate monobasic monohydrate, Potassium phosphate dibasic/pH 5.0; 1.0 M Sodium phosphate monobasic monohydrate, Potassium phosphate dibasic/pH 6.9; 1.0 M Sodium phosphate monobasic monohydrate, Potassium phosphate dibasic/pH 8.2; 1.8 M Sodium phosphate monobasic monohydrate, Potassium phosphate dibasic/pH 5.0; 1.8 M Sodium phosphate monobasic monohydrate, Potassium phosphate dibasic/pH 6.9; 1.8 M Sodium phosphate monobasic monohydrate, Potassium phosphate dibasic/pH 8.2; 0.5 M Succinic acid pH 7.0, 0.1 M BIS-TRIS propane pH 7.0; 1.0 M Succinic acid pH 7.0, 0.1 M BIS-TRIS propane pH 7.0; 1.5 M Ammonium sulfate, 0.1 M Sodium acetate trihydrate pH 4.6; 1.5 M Ammonium sulfate, 0.1 M BIS-TRIS propane pH 7.0; 1.5 M Ammonium sulfate, 0.1 M Tris pH 8.5; 2.5 M Ammonium sulfate, 0.1 M Sodium acetate trihydrate pH 4.6; 2.5 M Ammonium sulfate, 0.1 M BIS-TRIS propane pH 7.0; 2.5 M Ammonium sulfate, 0.1 M Tris pH 8.5; 0.8 M Lithium sulfate monohydrate, 0.1 M Sodium acetate trihydrate pH 4.6; 0.8 M Lithium sulfate monohydrate, 0.1 M BIS-TRIS propane pH 7.0; 0.8 M Lithium sulfate monohydrate, 0.1 M Tris pH 8.5; 1.5 M Lithium sulfate monohydrate, 0.1 M Sodium acetate trihydrate pH 4.6; 1.5 M Lithium sulfate monohydrate, 0.1 M BIS-TRIS propane pH 7.0; 1.5 M Lithium sulfate monohydrate, 0.1 M Tris pH 8.5; 1.0 M Magnesium sulfate hydrate, 0.1 M Sodium acetate trihydrate pH 4.6; 1.0 M Magnesium sulfate hydrate, 0.1 M BIS-TRIS propane pH 7.0; 1.0 M Magnesium sulfate hydrate, 0.1 M Tris pH 8.5; 1.8 M Magnesium sulfate hydrate, 0.1 M Sodium acetate trihydrate pH 4.6; 1.8 M Magnesium sulfate hydrate, 0.1 M BIS-TRIS propane pH 7.0; 1.8 M Magnesium sulfate hydrate, 0.1 M Tris pH 8.5; 0.7 M Ammonium tartrate dibasic, 0.1 M Sodium acetate trihydrate pH 4.6; 0.7 M Ammonium tartrate dibasic, 0.1 M BIS-TRIS propane pH 7.0; 0.7 M Ammonium tartrate dibasic, 0.1 M Tris pH 8.5; 1.0 M Ammonium tartrate dibasic, 0.1 M Sodium acetate trihydrate pH 4.6; 1.3 M Ammonium tartrate dibasic, 0.1 M BIS-TRIS propane pH 7.0; 1.4 M Ammonium tartrate dibasic, 0.1 M Tris pH 8.5;

0.6 M Potassium sodium tartrate tetrahydrate, 0.1 M BIS-TRIS propane pH 7.0; 1.2 M Potassium sodium tartrate tetrahydrate, 0.1 M BIS-TRIS propane pH 7.0; 0.6 M Potassium sodium tartrate tetrahydrate, 0.1 M Tris pH 8.5; 1.2 M Potassium sodium tartrate tetrahydrate, 0.1 M Tris pH 8.5; 0.5 M Potassium thiocyanate, 0.1 M Sodium acetate trihydrate pH 4.6; 0.5 M Potassium thiocyanate, 0.1 M BIS-TRIS propane pH 7.0; 0.5 M Potassium thiocyanate, 0.1 M Tris pH 8.5; 4.0 M Ammonium acetate, 0.1 M Sodium acetate trihydrate pH 4.6; 4.0 M Ammonium acetate, 0.1 M BIS-TR IS propane pH 7.0; 4.0 M Ammonium acetate, 0.1 M Tris pH 8.5; 35% v/v Tacsimate pH 7.0, 0.1 M BIS-TRIS propane pH 7.0; 60% v/v Tacsimate pH 7.0, 0.1 M BIS-TRIS propane pH 7.0.

Group 25: 0.1 M Sodium chloride, 0.1 M Sodium acetate trihydrate pH 4.6, 12% v/v (+/−)-2-Methyl-2,4-pentanediol; 0.1 M Zinc acetate dihydrate, 0.1 M Sodium acetate trihydrate pH 4.6, 12% w/v Polyethylene glycol 4,000; 0.2 M Ammonium sulfate, 0.1 M Sodium acetate trihydrate pH 4.6, 10% w/v Polyethylene glycol 4,000; 0.1 M Sodium chloride, 0.1 M Sodium acetate trihydrate pH 4.6, 12% v/v 2-Propanol; 0.1 M Sodium acetate trihydrate pH 4.6, 12% w/v Polyethylene glycol 4,000; 0.1 M Sodium acetate trihydrate pH 4.6, 1.0 M Ammonium sulfate; 0.1 M Sodium acetate trihydrate pH 4.6, 1.0 M Magnesium sulfate heptahydrate; 0.1 M Magnesium chloride hexahydrate, 0.1 M Sodium acetate trihydrate pH 4.6, 18% v/v Polyethylene glycol 400; 0.1 M Lithium sulfate monohydrate, 0.1 M Sodium acetate trihydrate pH 4.6, 1.0 M Ammonium phosphate monobasic; 0.1 M Sodium chloride, 0.1 M Sodium acetate trihydrate pH 4.6, 12% w/v Polyethylene glycol 6,000; 0.1 M Magnesium chloride hexahydrate, 0.1 M Sodium acetate trihydrate pH 4.6, 12% w/v Polyethylene glycol 6,000; 0.1 M Sodium chloride, 0.1 M Sodium citrate tribasic dihydrate pH 5.6, 18% v/v Polyethylene glycol 400; 0.1 M Lithium sulfate monohydrate, 0.1 M Sodium citrate tribasic dihydrate pH 5.6, 12% w/v Polyethylene glycol 4,000; 0.1 M Sodium citrate tribasic dihydrate, 0.1 M Sodium citrate tribasic dihydrate pH 5.6, 10% v/v 2-Propanol; 0.1 M Sodium chloride, 0.1 M Sodium citrate tribasic dihydrate pH 5.6, 12% v/v (+/−)-2-Methyl-2,4-pentanediol; 0.1 M Sodium citrate tribasic dihydrate pH 5.6, 1.0 M Magnesium sulfate heptahydrate; 0.1 M Sodium chloride, 0.1 M Sodium citrate tribasic dihydrate pH 5.6, 12% will Polyethylene glycol 4,000; 0.1 M Lithium sulfate monohydrate, 0.1 M Sodium citrate tribasic dihydrate pH 5.6, 12% w/v Polyethylene glycol 6,000; 0.1 M Magnesium chloride hexahydrate, 0.1 M Sodium citrate tribasic dihydrate pH 5.6, 4% v/v (+/−)-2-Methyl-2,4-pentanediol; 0.1 M Sodium citrate tribasic dihydrate pH 5.6, 0.1 M Sodium chloride; 0.1 M Lithium sulfate monohydrate, 0.1 M Sodium citrate tribasic dihydrate pH 5.6, 4% v/v Polyethylene glycol 400; 0.1 M ADA pH 6.5, 1.0 M Ammonium sulfate; 0.1 M Lithium sulfate monohydrate, 0.1 M ADA pH 6.5, 12% w/v Polyethylene glycol 4,000, 2% v/v 2-Propanol; 0.1 M ADA pH 6.5, 1.0 M Ammonium phosphate dibasic; 0.1 M Magnesium chloride hexahydrate, 0.1 M ADA pH 6.5, 12% Av/v Polyethylene glycol 6,000; 0.1 M ADA pH 6.5, 12% v/v (+/−)-2-Methyl-2,4-pentanediol; 0.1 M Lithium sulfate monohydrate, 0.1 M ADA pH 6.5, 1.0 M Magnesium sulfate hydrate; 0.3 M Lithium sulfate monohydrate, 0.1 M ADA pH 6.5, 4% v/v Polyethylene glycol 400; 0.1 M Ammonium sulfate, 0.1 M HEPES sodium pH 7.5, 0.5 M Sodium phosphate dibasic dihydrate, 0.5 M Potassium phosphate dibasic; 0.1 M Sodium chloride, 0.1 M HEPES sodium pH 7.5, 10% w/v Polyethylene glycol 4,000; 0.1 M Magnesium chloride hexahydrate, 0.1 M HEPES sodium pH 7.5, 18% v/v Polyethylene glycol 400; 0.1 M HEPES sodium pH 7.5, 1.0 M Potassium sodium tartrate tetrahydrate; 0.1 M Ammonium sulfate, 0.1 M HEPES sodium pH 7.5, 18% v/v Polyethylene glycol 400; 0.1 M Ammonium sulfate, 0.1 M HEPES sodium pH 7.5, 10% w/v Polyethylene glycol 4,000; 0.1 M Sodium citrate tribasic dihydrate, 0.1 M HEPES sodium pH 7.5, 12% v/v (+/−)-2-Methyl-2,4-pentanediol; 0.1 M HEPES sodium pH 7.5, 1.0 M Sodium citrate tribasic dihydrate; 0.6 M Magnesium sulfate hydrate, 0.1 M HEPES sodium pH 7.5, 4% v/v Polyethylene glycol 400; 0.6 M Magnesium sulfate hydrate, 0.1 M HEPES sodium pH 7.5, 4% v/v (+/−)-2-Methyl-2,4-pentanediol; 0.1 M Lithium sulfate monohydrate, 0.1 M HEPES sodium pH 7.5, 0.1 M Potassium sodium tartrate tetrahydrate; 0.1 M Lithium sulfate monohydrate, 0.1 M TRIS hydrochloride pH 8.5, 12% v/v (+/−)-2-Methyl-2,4-pentanediol; 0.1 M Ammonium phosphate dibasic, 0.1 M TRIS hydrochloride pH 8.5, 0.5 M Sodium phosphate dibasic dihydrate, 0.5 M Potassium phosphate dibasic; 0.1 M TRIS hydrochloride pH 8.5, 0.1 M Sodium acetate trihydrate; 0.1 M TRIS hydrochloride pH 8.5, 0.1 M Sodium chloride; 0.1 M Ammonium phosphate dibasic, 0.1 M TRIS hydrochloride pH 8.5, 12% w/v Polyethylene glycol 6,000; 0.1 M Potassium sodium tartrate tetrahydrate, 0.1 M TRIS hydrochloride pH 8.5, 0.4 M Magnesium sulfate hydrate; 0.1 M TRIS hydrochloride pH 8.5, 0.2 M Lithium sulfate monohydrate; 0.1 M TRIS hydrochloride pH 8.5, 0.5 M Ammonium sulfate; 0.1 M Sodium citrate tribasic dihydrate, 0.1 M TRIS hydrochloride pH 8.5, 5% v/v Polyethylene glycol 400.

Group 26: 0.1 M Sodium chloride, 0.1 M Sodium acetate trihydrate pH 4.6, 12% v/v (+/−)-2-Methyl-2,4-pentanediol; 0.1 M Zinc acetate dihydrate, 0.1 M Sodium acetate trihydrate pH 4.6, 12% w/v Polyethylene glycol 4,000; 0.2 M Ammonium sulfate, 0.1 M Sodium acetate trihydrate pH 4.6, 10% w/v Polyethylene glycol 4,000; 0.1 M Sodium chloride, 0.1 M Sodium acetate trihydrate pH 4.6, 12% v/v 2Propanol; 0.1 M Sodium acetate trihydrate pH 4.6, 12% w/v Polyethylene glycol 4,000; 0.1 M Sodium acetate trihydrate pH 4.6, 1.0 M Ammonium sulfate; 0.1 M Sodium acetate trihydrate pH 4.6, 1.0 M Magnesium sulfate heptahydrate; 0.1 M Magnesium chloride hexahydrate, 0.1 M Sodium acetate trihydrate pH 4.6, 18% v/v Polyethylene glycol 400; 0.1 M Lithium sulfate monohydrate, 0.1 M Sodium acetate trihydrate pH 4.6, 1.0 M Ammonium phosphate monobasic; 0.1 M Sodium chloride, 0.1 M Sodium acetate trihydrate pH 4.6, 12% w/v Polyethylene glycol 6,000; 0.1 M Magnesium chloride hexahydrate, 0.1 M Sodium acetate trihydrate pH 4.6, 12% w/v Polyethylene glycol 6,000; 0.1 M Sodium chloride, 0.1 M Sodium citrate tribasic dihydrate pH 5.6, 18% v/v Polyethylene glycol 400; 0.1 M Lithium sulfate monohydrate, 0.1 M Sodium citrate tribasic dihydrate pH 5.6, 12% w/v Polyethylene glycol 4,000; 0.1 M Sodium citrate tribasic dihydrate, 0.1 M Sodium citrate tribasic dihydrate pH 5.6, 10% v/v 2-Propanol; 0.1 M Sodium chloride, 0.1 M Sodium citrate tribasic dihydrate pH 5.6, 12% v/v (+/−)-2-Methyl-2,4-pentanediol; 0.1 M Sodium citrate tribasic dihydrate pH 5.6, 1.0 M Magnesium sulfate heptahydrate; 0.1 M Sodium chloride, 0.1 M Sodium citrate tribasic dihydrate pH 5.6, 12% w/v Polyethylene glycol 4,000; 0.1 M Lithium sulfate monohydrate, 0.1 M Sodium citrate tribasic dihydrate pH 5.6, 12% w/v Polyethylene glycol 6,000; 0.1 M Magnesium chloride hexahydrate, 0.1 M Sodium citrate tribasic dihydrate pH 5.6, 4% v/v (+/−)-2-Methyl-2,4-pentanediol; 0.1 M Sodium citrate tribasic dihydrate pH 5.6, 0.1 M Sodium chloride; 0.1 M Lithium sulfate monohydrate, 0.1 M Sodium citrate tribasic dihydrate pH 5.6, 4% v/v Polyethylene glycol 400; 0.1 M ADA pH 6.5, 1.0 M Ammonium sulfate; 0.1 M Lithium sulfate monohydrate, 0.1 M ADA pH 6.5, 12% w/v Polyethylene glycol 4,000, 2% v/v 2-Propanol; 0.1 M ADA pH 6.5, 1.0 M Ammonium phosphate dibasic; 0.1 M Magnesium chloride hexahydrate, 0.1 M ADA pH 6.5, 12% w/v Polyethylene glycol 6,000; 0.1 M ADA pH 6.5, 12% v/v (+/−)-2-Methyl-2,4-pentanediol; 0.1 M Lithium sulfate monohydrate, 0.1 M ADA pH 6.5, 1.0 M Magnesium sulfate hydrate; 0.3 M Lithium sulfate monohydrate, 0.1 M ADA pH 6.5, 4% v/v Polyethylene glycol 400; 0.1 M Ammonium sulfate, 0.1 M HEPES sodium pH 7.5, 0.5 M Sodium phosphate dibasic dihydrate, 0.5 M Potassium phosphate dibasic; 0.1 M Sodium chloride, 0.1 M HEPES sodium pH 7.5, 10% w/v Polyethylene glycol 4,000; 0.1 M Magnesium chloride hexahydrate, 0.1 M HEPES sodium pH 7.5, 18% v/v Polyethylene glycol 400; 0.1 M HEPES sodium pH 7.5, 1.0 M Potassium sodium tartrate tetrahydrate; 0.1 M Ammonium sulfate, 0.1 M HEPES sodium pH 7.5, 18% v/v Polyethylene glycol 400; 0.1 M Ammonium sulfate, 0.1 M HEPES sodium pH 7.5, 10% w/v Polyethylene glycol 4,000; 0.1 M Sodium citrate tribasic dihydrate, 0.1 M HEPES sodium pH 7.5, 12% v/v (+/−)-2-Methyl-2,4-pentanediol; 0.1 M HEPES sodium pH 7.5, 1.0 M Sodium citrate tribasic dihydrate; 0.6 M Magnesium sulfate hydrate, 0.1 M HEPES sodium pH 7.5, 4% v/v Polyethylene glycol 400; 0.6 M Magnesium sulfate hydrate, 0.1 M HEPES sodium pH 7.5, 4% v/v (+/−)-2-Methyl-2,4-pentanediol; 0.1 M Lithium sulfate monohydrate, 0.1 M HEPES sodium pH 7.5, 0.1 M Potassium sodium tartrate tetrahydrate; 0.1 M Lithium sulfate monohydrate, 0.1 M TRIS hydrochloride pH 8.5, 12% v/v (+/−)-2-Methyl-2,4-pentanediol; 0.1 M Ammonium phosphate dibasic, 0.1 M TRIS hydrochloride pH 8.5, 0.5 M Sodium phosphate dibasic dihydrate, 0.5 M Potassium phosphate dibasic; 0.1 M TRIS hydrochloride pH 8.5, 0.1 M Sodium acetate trihydrate; 0.1 M TRIS hydrochloride pH 8.5, 0.1 M Sodium chloride; 0.1 M Ammonium phosphate dibasic, 0.1 M TRIS hydrochloride pH 8.5, 12% w/v Polyethylene glycol 6,000; 0.1 M Potassium sodium tartrate tetrahydrate, 0.1 M TRIS hydrochloride pH 8.5, 0.4 M Magnesium sulfate hydrate; 0.1 M TRIS hydrochloride pH 8.5, 0.2 M Lithium sulfate monohydrate; 0.1 M TRIS hydrochloride pH 8.5, 0.5 M Ammonium sulfate; 0.1 M Sodium citrate tribasic dihydrate, 0.1 M TRIS hydrochloride pH 8.5, 5% v/v Polyethylene glycol 400; 0.02 M Calcium chloride dihydrate, 0.1 M Sodium acetate trihydrate pH 4.6, 15% v/v (+/−)-2-Methyl-2,4-pentanediol; 0.2 M Potassium sodium tartrate tetrahydrate; 0.2 M Ammonium phosphate monobasic; 0.1 M TRIS hydrochloride pH 8.5, 1.0 M Ammonium sulfate; 0.2 M Sodium citrate tribasic dihydrate, 0.1 M HEPES sodium pH 7.5, 15% v/v (+/−)-2-Methyl-2,4-pentanediol; 0.2 M Magnesium chloride hexahydrate, 0.1 M TRIS hydrochloride pH 8.5, 15% w/v Polyethylene glycol 4,000; 0.1 M Sodium cacodylate trihydrate pH 6.5, 0.7 M Sodium acetate trihydrate; 0.2 M Sodium citrate tribasic dihydrate, 0.1 M Sodium cacodylate trihydrate pH 6.5, 15% v/v 2-Propanol; 0.2 M Ammonium acetate, 0.1 M Sodium citrate tribasic dihydrate pH 5.6, 15% w/v Polyethylene glycol 4,000; 0.2 M Ammonium acetate, 0.1 M Sodium acetate trihydrate pH 4.6, 15% w/v Polyethylene glycol 4,000; 0.1 M Sodium citrate tribasic dihydrate pH 5.6, 0.5 M Ammonium phosphate monobasic; 0.2 M Magnesium chloride hexahydrate, 0.1 M HEPES sodium pH 7.5, 15% v/v 2-Propanol; 0.2 M Sodium citrate tribasic dihydrate, 0.1 M TRIS hydrochloride pH 8.5, 15% v/v Polyethylene glycol 400; 0.2 M Calcium chloride dihydrate, 0.1 M HEPES sodium pH 7.5, 14% v/v Polyethylene glycol 400; 0.2 M Ammonium sulfate, 0.1 M Sodium cacodylate trihydrate pH 6.5, 15% w/v Polyethylene glycol 8,000; 0.1 M HEPES sodium pH 7.5, 0.75 M Lithium sulfate monohydrate; 0.2 M Lithium sulfate monohydrate, 0.1 M TRIS hydrochloride pH 8.5, 15% w/v Polyethylene glycol 4,000; 0.2 M Magnesium acetate tetrahydrate, 0.1 M Sodium cacodylate trihydrate pH 6.5, 10% w/v Polyethylene glycol 8,000; 0.2 M Ammonium acetate, 0.1 M TRIS hydrochloride pH 8.5, 15% v/v 2-Propanol; 0.2 M Ammonium sulfate, 0.1 M Sodium acetate trihydrate pH 4.6, 12.5% w/v Polyethylene glycol 4,000; 0.2 M Magnesium acetate tetrahydrate, 0.1 M Sodium cacodylate trihydrate pH 6.5, 15% v/v (+/−)-2-Methyl-2,4-pentanediol; 0.2 M Sodium acetate trihydrate, 0.1 M TRIS hydrochloride pH 8.5, 15% w/v Polyethylene glycol 4,000; 0.2 M Magnesium chloride hexahydrate, 0.1 M HEPES sodium pH 7.5, 15% v/v Polyethylene glycol 400; 0.2 M Calcium chloride dihydrate, 0.1 M Sodium acetate trihydrate pH 4.6, 10% v/v 2-Propanol; 0.1 M Imidazole pH 6.5, 0.5 M Sodium acetate trihydrate; 0.2 M Ammonium acetate, 0.1 M Sodium citrate tribasic dihydrate pH 5.6, 15% v/v (+/−)-2-Methyl-2,4-pentanediol; 0.2 M Sodium citrate tribasic dihydrate, 0.1 M HEPES sodium pH 7.5, 10% v/v 2-Propanol; 0.2 M Sodium acetate trihydrate, 0.1 M Sodium cacodylate trihydrate pH 6.5, 15% w/v Polyethylene glycol 8,000; 0.1 M HEPES sodium pH 7.5, 0.4 M Potassium sodium tartrate tetrahydrate; 0.2 M Ammonium sulfate, 15% w/v Polyethylene glycol 8,000; 0.2 M Ammonium sulfate, 15% w/v Polyethylene glycol 4,000; 1.0 M Ammonium sulfate; 2.0 M Sodium formate; 0.1 M Sodium acetate trihydrate pH 4.6, 1.0 M Sodium formate; 0.1 M HEPES sodium pH 7.5, 0.4 M Sodium phosphate monobasic monohydrate, 0.4 M Potassium phosphate monobasic; 0.1 M TRIS hydrochloride pH 8.5, 4% w/v Polyethylene glycol 8,000; 0.1 M Sodium acetate trihydrate pH 4.6, 4% will Polyethylene glycol 4,000; 0.1 M HEPES sodium pH 7.5, 0.7 M Sodium citrate tribasic dihydrate; 0.1 M HEPES sodium pH 7.5, 1.0 M Ammonium sulfate, 2% v/v Polyethylene glycol 400; 0.1 M Sodium citrate tribasic dihydrate pH 5.6, 10% v/v 2-Propanol, 10% w/v Polyethylene glycol 4,000; 0.1 M HEPES sodium pH 7.5, 5% v/v 2-Propanol, 10% w/v Polyethylene glycol 4,000; 0.05 M Potassium phosphate monobasic, 10% w/v Polyethylene glycol 8,000; 15% w/v Polyethylene glycol 1,500; 0.1 M Magnesium formate dihydrate; 0.2 M Zinc acetate dihydrate, 0.1 M Sodium cacodylate trihydrate pH 6.5, 9% w/v Polyethylene glycol 8,000; 0.2 M Calcium acetate hydrate, 0.1 M Sodium cacodylate trihydrate pH 6.5, 9% w/v Polyethylene glycol 8,000; 0.1 M Sodium acetate trihydrate pH 4.6, 1.0 M Ammonium sulfate; 0.1 M TRIS hydrochloride pH 8.5, 1.0 M Ammonium phosphate monobasic.

Group 27: 0.02 M Calcium chloride dihydrate, 0.1 M Sodium acetate trihydrate pH 4.6, 15% v/v (+/−)-2-Methyl-2,4-pentanediol; 0.2 M Potassium sodium tartrate tetrahydrate; 0.2 M Ammonium phosphate monobasic; 0.1 M TRIS hydrochloride pH 8.5, 1.0 M Ammonium sulfate; 0.2 M Sodium citrate tribasic dihydrate, 0.1 M HEPES sodium pH 7.5, 15% v/v (+/−)-2-Methyl-2,4-pentanediol; 0.2 M Magnesium chloride hexahydrate, 0.1 M TRIS hydrochloride pH 8.5, 15% w/v Polyethylene glycol 4,000; 0.1 M Sodium cacodylate trihydrate pH 6.5, 0.7 M Sodium acetate trihydrate; 0.2 M Sodium citrate tribasic dihydrate, 0.1 M Sodium cacodylate trihydrate pH 6.5, 15% v/v 2-Propanol; 0.2 M Ammonium acetate, 0.1 M Sodium citrate tribasic dihydrate pH 5.6, 15% w/v Polyethylene glycol 4,000; 0.2 M Ammonium acetate, 0.1 M Sodium acetate trihydrate pH 4.6, 15% w/v Polyethylene glycol 4,000; 0.1 M Sodium citrate tribasic dihydrate pH 5.6, 0.5 M Ammonium phosphate monobasic; 0.2 M Magnesium chloride hexahydrate, 0.1 M HEPES sodium pH 7.5, 15% v/v 2-Propanol; 0.2 M Sodium citrate tribasic dihydrate, 0.1 M TRIS hydrochloride pH 8.5, 15% v/v Polyethylene glycol 400; 0.2 M Calcium chloride dihydrate, 0.1 M HEPES sodium pH 7.5, 14% v/v Polyethylene glycol 400; 0.2 M Ammonium sulfate, 0.1 M Sodium cacodylate trihydrate pH 6.5, 15% w/v Polyethylene glycol 8,000; 0.1 M HEPES sodium pH 7.5, 0.75 M Lithium sulfate monohydrate; 0.2 M Lithium sulfate monohydrate, 0.1 M TRIS hydrochloride pH 8.5, 15% w/v Polyethylene glycol 4,000; 0.2 M Magnesium acetate tetrahydrate, 0.1 M Sodium cacodylate trihydrate pH 6.5, 10% w/v Polyethylene glycol 8,000; 0.2 M Ammonium acetate, 0.1 M TRIS hydrochloride pH 8.5, 15% v/v 2-Propanol; 0.2 M Ammonium sulfate, 0.1 M Sodium acetate trihydrate pH 4.6, 12.5% w/v Polyethylene glycol 4,000; 0.2 M Magnesium acetate tetrahydrate, 0.1 M Sodium cacodylate trihydrate pH 6.5, 15% v/v (-1-0-2-Methyl-2,4-pentanediol; 0.2 M Sodium acetate trihydrate, 0.1 M TRIS hydrochloride pH 8.5, 15% w/v Polyethylene glycol 4,000; 0.2 M Magnesium chloride hexahydrate, 0.1 M HEPES sodium pH 7.5, 15% v/v Polyethylene glycol 400; 0.2 M Calcium chloride dihydrate, 0.1 M Sodium acetate trihydrate pH 4.6, 10% v/v 2-Propanol; 0.1 M Imidazole pH 6.5, 0.5 M Sodium acetate trihydrate; 0.2 M Ammonium acetate, 0.1 M Sodium citrate tribasic dihydrate pH 5.6, 15% v/v (+/−)-2-Methyl-2,4-pentanediol; 0.2 M Sodium citrate tribasic dihydrate, 0.1 M HEPES sodium pH 7.5, 10% v/v 2-Propanol; 0.2 M Sodium acetate trihydrate, 0.1 M Sodium cacodylate trihydrate pH 6.5, 15% w/v Polyethylene glycol 8,000; 0.1 M HEPES sodium pH 7.5, 0.4 M Potassium sodium tartrate tetrahydrate; 0.2 M Ammonium sulfate, 15% w/v Polyethylene glycol 8,000; 0.2 M Ammonium sulfate, 15% w/v Polyethylene glycol 4,000; 1.0 M Ammonium sulfate; 2.0 M Sodium formate; 0.1 M Sodium acetate trihydrate pH 4.6, 1.0 M Sodium formate; 0.1 M HEPES sodium pH 7.5, 0.4 M Sodium phosphate monobasic monohydrate, 0.4 M Potassium phosphate monobasic; 0.1 M TRIS hydrochloride pH 8.5, 4% w/v Polyethylene glycol 8,000; 0.1 M Sodium acetate trihydrate pH 4.6, 4% w/v Polyethylene glycol 4,000; 0.1 M HEPES sodium pH 7.5, 0.7 Sodium citrate tribasic dihydrate; 0.1 M HEPES sodium pH 7.5, 1.0 M Ammonium sulfate, 2% v/v Polyethylene glycol 400; 0.1 M Sodium citrate tribasic dihydrate pH 5.6, 10% v/v 2-Propanol, 10% w/v Polyethylene glycol 4,000; 0.1 M HEPES sodium pH 7.5, 5% v/v 2-Propanol, 10% w/v Polyethylene glycol 4,000; 0.05 M Potassium phosphate monobasic, 10% w/v Polyethylene glycol 8,000; 15% w/v Polyethylene glycol 1,500; 0.1 M Magnesium formate dihydrate; 0.2 M Zinc acetate dihydrate, 0.1 M Sodium cacodylate trihydrate pH 6.5, 9% w/v Polyethylene glycol 8,000; 0.2 M Calcium acetate hydrate, 0.1 M Sodium cacodylate trihydrate pH 6.5, 9% w/v Polyethylene glycol 8,000; 0.1 M Sodium acetate trihydrate pH 4.6, 1.0 M Ammonium sulfate; 0.1 M TRIS hydrochloride pH 8.5, 1.0 M Ammonium phosphate monobasic; 0.5 M Lithium sulfate monohydrate, 2% w/v Polyethylene glycol 8,000; 0.5 M Lithium sulfate monohydrate, 7.5% w/v Polyethylene glycol 8,000.

Group 28: 0.01 M Magnesium chloride hexahydrate, 0.05 M MES monohydrate pH 5.6, 1.8 M Lithium sulfate monohydrate; 0.01 M Magnesium acetate tetrahydrate, 0.05 M MES monohydrate pH 5.6, 2.5 M Ammonium sulfate; 0.1 M Magnesium acetate tetrahydrate, 0.05 M MES monohydrate pH 5.6, 20% v/v (+/−)-2-Methyl-2,4-pentanediol; 0.2 M Potassium chloride, 0.01 M Magnesium sulfate heptahydrate, 0.05 M MES monohydrate pH 5.6, 10% v/v Polyethylene glycol 400; 0.2 M Potassium chloride, 0.01 M Magnesium chloride hexahydrate, 0.05 M MES monohydrate pH 5.6, 5% w/v Polyethylene glycol 8,000; 0.1 M Ammonium sulfate, 0.01 M Magnesium chloride hexahydrate, 0.05 M MES monohydrate pH 5.6, 20% w/v Polyethylene glycol 8,000; 0.02 M Magnesium chloride hexahydrate, 0.05 M MES monohydrate pH 6.0, 15% v/v 2-Propanol; 0.1 M Ammonium acetate, 0.005 M Magnesium sulfate heptahydrate, 0.05 M MES monohydrate pH 6.0, 0.6 M Sodium chloride; 0.1 M Potassium chloride, 0.01 M Magnesium chloride hexahydrate, 0.05 M MES monohydrate pH 6.0, 10% v/v Polyethylene glycol 400; 0.005 M Magnesium sulfate heptahydrate, 0.05 M MES monohydrate pH 6.0, 5% w/v Polyethylene glycol 4,000; 0.01 M Magnesium chloride hexahydrate, 0.05 M Sodium cacodylate trihydrate pH 6.0, 1.0 M Lithium sulfate monohydrate; 0.01 M Magnesium sulfate heptahydrate, 0.05 M Sodium cacodylate trihydrate pH 6.0, 1.8 M Lithium sulfate monohydrate; 0.015 M Magnesium acetate tetrahydrate, 0.05 M Sodium cacodylate trihydrate pH 6.0, 1.7 M Ammonium sulfate; 0.1 M Potassium chloride, 0.025 M Magnesium chloride hexahydrate, 0.05 M Sodium cacodylate trihydrate pH 6.0, 15% v/v 2-Propanol; 0.04 M Magnesium chloride hexahydrate, 0.05 M Sodium cacodylate trihydrate pH 6.0, 5% v/v (+/−)-2-Methyl-2,4-pentanediol; 0.04 M Magnesium acetate tetrahydrate, 0.05 M Sodium cacodylate trihydrate pH 6.0, 30% v/v (+/−)-2-Methyl-2,4-pentanediol; 0.2 M Potassium chloride, 0.01 M Calcium chloride dihydrate, 0.05 M Sodium cacodylate trihydrate pH 6.0, 10% w/v Polyethylene glycol 4,000; 0.01 M Magnesium acetate tetrahydrate, 0.05 M Sodium cacodylate trihydrate pH 6.5, 1.3 M Lithium sulfate monohydrate; 0.01 M Magnesium sulfate heptahydrate, 0.05 M Sodium cacodylate trihydrate pH 6.5, 2.0 M Ammonium sulfate; 0.1 M Ammonium acetate, 0.015 M Magnesium acetate tetrahydrate, 0.05 M Sodium cacodylate trihydrate pH 6.5, 10% v/v 2-Propanol; 0.2 M Potassium chloride, 0.005 M Magnesium chloride hexahydrate, 0.05 M Sodium cacodylate trihydrate pH 6.5, 0.9 M 1,6-Hexanediol; 0.08 M Magnesium acetate tetrahydrate, 0.05 M Sodium cacodylate trihydrate pH 6.5, 15% v/v Polyethylene glycol 400; 0.2 M Potassium chloride, 0.01 M Magnesium chloride hexahydrate, 0.05 M Sodium cacodylate trihydrate pH 6.5, 10% w/v Polyethylene glycol 4,000; 0.2 M Ammonium acetate, 0.01 M Calcium chloride dihydrate, 0.05 M Sodium cacodylate trihydrate pH 6.5, 10% w/v Polyethylene glycol 4,000; 0.08 M Magnesium acetate tetrahydrate, 0.05 M Sodium cacodylate trihydrate pH 6.5, 30% w/v Polyethylene glycol 4,000; 0.2 M Potassium chloride, 0.1 M Magnesium acetate tetrahydrate, 0.05 M Sodium cacodylate trihydrate pH 6.5, 10% w/v Polyethylene glycol 8,000; 0.2 M Ammonium acetate, 0.01 M Magnesium acetate tetrahydrate, 0.05 M Sodium cacodylate trihydrate pH 6.5, 30% w/v Polyethylene glycol 8,000; 0.05 M Magnesium sulfate hydrate, 0.05 M HEPES Sodium pH 7.0, 1.6 M Lithium sulfate monohydrate; 0.01 M Magnesium chloride hexahydrate, 0.05 M HEPES Sodium pH 7.0, 4.0 M Lithium chloride; 0.01 M Magnesium chloride hexahydrate, 0.05 M HEPES Sodium pH 7.0, 1.6 M Ammonium sulfate; 0.005 M Magnesium chloride hexahydrate, 0.05 M HEPES Sodium pH 7.0, 25% v/v Polyethylene glycol monomethyl ether 550; 0.2 M Potassium chloride, 0.01 M Magnesium chloride hexahydrate, 0.05 M HEPES Sodium pH 7.0, 1.7 M 1,6-Hexanediol; 0.2 M Ammonium chloride, 0.01 M Magnesium chloride hexahydrate, 0.05 M HEPES Sodium pH 7.0, 2.5 M 1,6-Hexanediol; 0.1 M Potassium chloride, 0.005 M Magnesium sulfate hydrate, 0.05 M HEPES Sodium pH 7.0, 15% v/v (+/−)-2-Methyl-2,4-pentanediol; 0.1 M Potassium chloride, 0.01 M Magnesium chloride hexahydrate, 0.05 M HEPES Sodium pH 7.0, 5% v/v Polyethylene glycol 400;

0.1 M Potassium chloride, 0.01 M Calcium chloride dihydrate, 0.05 M HEPES Sodium pH 7.0, 10% v/v Polyethylene glycol 400; 0.2 M Potassium chloride, 0.025 M Magnesium sulfate hydrate, 0.05 M HEPES Sodium pH 7.0, 20% v/v Polyethylene glycol 200; 0.2 M Ammonium acetate, 0.15 M Magnesium acetate tetrahydrate, 0.05 M HEPES Sodium pH 7.0, 5% w/v Polyethylene glycol 4,000; 0.1 M Ammonium acetate, 0.02 M Magnesium chloride hexahydrate, 0.05 M HEPES Sodium pH 7.0, 5% w/v Polyethylene glycol 8,000; 0.01 M Magnesium chloride hexahydrate, 0.05 M TRIS hydrochloride pH 7.5, 1.6 M Ammonium sulfate; 0.1 M Potassium chloride, 0.015 M Magnesium chloride hexahydrate, 0.05 M TRIS hydrochloride pH 7.5, 10% v/v Polyethylene glycol monomethyl ether 550; 0.01 M Magnesium chloride hexahydrate, 0.05 M TRIS hydrochloride pH 7.5, 5% v/v 2-Propanol; 0.05 M Ammonium acetate, 0.01 M Magnesium chloride hexahydrate, 0.05 M TRIS hydrochloride pH 7.5, 10% v/v (+/−)-2-Methyl-2,4-pentanediol; 0.2 M Potassium chloride, 0.05 M Magnesium chloride hexahydrate, 0.05 M TRIS hydrochloride pH 7.5, 10% w/v Polyethylene glycol 4,000; 0.025 M Magnesium sulfate hydrate, 0.05 M TRIS hydrochloride pH 8.5, 1.8 M Ammonium sulfate; 0.005 M Magnesium sulfate hydrate, 0.05 M TRIS hydrochloride pH 8.5, 2.9 M 1,6-Hexanediol; 0.1 M Potassium chloride, 0.01 M Magnesium chloride hexahydrate, 0.05 M TRIS hydrochloride pH 8.5, 30% v/v Polyethylene glycol 400; 0.2 M Ammonium chloride, 0.01 M Calcium chloride dihydrate, 0.05 M TRIS hydrochloride pH 8.5, 30% w/v Polyethylene glycol 4,000.

Group 29: 0.04 M Lithium chloride, 0.02 M Magnesium chloride hexahydrate, 0.04 M Sodium cacodylate trihydrate pH 5.5, 30% v/v (+/−)-2-Methyl-2,4-pentanediol, 0.02 M Hexammine cobalt(III) chloride; 0.08 M Sodium chloride, 0.02 M Magnesium chloride hexahydrate, 0.04 M Sodium cacodylate trihydrate pH 5.5, 35% v/v (+/−)-2-Methyl-2,4-pentanediol, 0.02 M Hexammine cobalt(III) chloride; 0.012 M Sodium chloride, 0.08 M Potassium chloride, 0.04 M Sodium cacodylate trihydrate pH 5.5, 45% v/v (+/−)-2-Methyl-2,4-pentanediol, 0.02 M Hexammine cobalt(III) chloride; 0.02 M Magnesium chloride hexahydrate, 0.04 M Sodium cacodylate trihydrate pH 5.5, 40% v/v (+/−)-2-Methyl-2,4-pentanediol, 0.02 M Hexammine cobalt(III) chloride; 0.002 M Calcium chloride dihydrate, 0.05 M Sodium cacodylate trihydrate pH 6.0, 1.8 M Ammonium sulfate, 0.0005 M Spermine; 0.05 M Sodium cacodylate trihydrate pH 6.0, 35% v/v Tacsimate pH 6.0, 0.001 M Spermine; 0.1 M Sodium chloride, 0.05 M Sodium cacodylate trihydrate pH 6.0, 10% w/v Polyethylene glycol 4,000, 0.0005 M Spermine; 0.05 M Potassium chloride, 0.05 M Sodium cacodylate trihydrate pH 6.0, 10% w/v Polyethylene glycol 8,000, 0.0005 M Spermine, 0.0005 M L-Argininamide dihydrochloride; 0.1 M Potassium chloride, 0.05 M Sodium cacodylate trihydrate pH 6.0, 16% w/v Polyethylene glycol 1,000, 0.0005 M Spermine; 0.005 M Magnesium chloride hexahydrate, 0.002 M Calcium chloride dihydrate, 0.05 M Sodium cacodylate trihydrate pH 6.0, 15% v/v 2-Propanol, 0.001 M Spermine; 0.075 M Sodium chloride, 0.002 M Calcium chloride dihydrate, 0.05 M Sodium cacodylate trihydrate pH 6.0, 30% w/v 1,6-Hexanediol, 0.0005 M Spermine; 0.02 M Magnesium sulfate hydrate, 0.002 M Cobalt(II) chloride hexahydrate, 0.05 M Sodium cacodylate trihydrate pH 6.0, 25% v/v (+/−)-2-Methyl-2,4-pentanediol, 0.0005 M Spermine; 0.05 M Sodium cacodylate trihydrate pH 6.0, 30% v/v (+/−)-2-Methyl-2,4-pentanediol; 0.08 M Sodium chloride, 0.012 M Potassium chloride, 0.02 M Magnesium chloride hexahydrate, 0.04 M Sodium cacodylate trihydrate pH 6.0, 30% v/v (+/−)-2-Methyl-2,4-pentanediol, 0.012 M Spermine tetrahydrochloride; 0.08 M Sodium chloride, 0.02 M Magnesium chloride hexahydrate, 0.04 M Sodium cacodylate trihydrate pH 6.0, 35% v/v (+/−)-2-Methyl-2,4-pentanediol, 0.012 M Spermine tetrahydrochloride; 0.08 M Strontium chloride hexahydrate, 0.04 M Sodium cacodylate trihydrate pH 6.0, 35% v/v (+/−)-2-Methyl-2,4-pentanediol, 0.012 M Spermine tetrahydrochloride; 0.08 M Potassium chloride, 0.02 M Barium chloride dihydrate, 0.04 M Sodium cacodylate trihydrate pH 6.0, 40% v/v (+/−)-2-Methyl-2,4-pentanediol, 0.012 M Spermine tetrahydrochloride; 0.08 M Potassium chloride, 0.02 M Magnesium chloride hexahydrate, 0.04 M Sodium cacodylate trihydrate pH 6.0, 45% v/v (+/−)-2-Methyl-2,4-pentanediol, 0.012 M Spermine tetrahydrochloride; 0.08 M Sodium chloride, 0.04 M Sodium cacodylate trihydrate pH 6.0, 45% v/v (+/−)-2-Methyl-2,4-pentanediol, 0.012 M Spermine tetrahydrochloride; 0.08 M Sodium chloride, 0.02 M Barium chloride dihydrate, 0.04 M Sodium cacodylate trihydrate pH 6.0, 45% v/v (+/−)-2-Methyl-2,4-pentanediol, 0.012 M Spermine tetrahydrochloride; 0.012 M Sodium chloride, 0.08 M Potassium chloride, 0.04 M Sodium cacodylate trihydrate pH 6.0, 50% v/v (+/−)-2-Methyl-2,4-pentanediol, 0.012 M Spermine tetrahydrochloride; 0.08 M Potassium chloride, 0.04 M Sodium cacodylate trihydrate pH 6.0, 55% v/v (+/−)-2-Methyl-2,4-pentanediol, 0.012 M Spermine tetrahydrochloride; 0.018 M Magnesium chloride hexahydrate, 0.05 M Sodium cacodylate trihydrate pH 6.5, 10% v/v 2-Propanol, 0.003 M Spermine; 0.02 M Magnesium chloride hexahydrate, 0.05 M MOPS pH 7.0, 2.0 M Ammonium sulfate, 0.0005 M Spermine; 0.05 M HEPES sodium pH 7.0, 40% v/v Tacsimate pH 7.0, 0.002 M Spermine, 0.002 M Hexammine cobalt(III) chloride; 0.02 M Magnesium chloride hexahydrate, 0.05 M MOPS pH 7.0, 55% v/v Tacsimate pH 7.0, 0.005 M Hexammine cobalt(III) chloride; 0.02 M Magnesium chloride hexahydrate, 0.05 M Sodium cacodylate trihydrate pH 7.0, 15% v/v 2-Propanol, 0.001 M Hexammine cobalt(III) chloride, 0.001 M Spermine; 0.005 M Magnesium chloride hexahydrate, 0.05 M MOPS pH 7.0, 25% v/v 1,4-Dioxane, 0.001 M Spermine; 0.01 M Magnesium chloride hexahydrate, 0.002 M Barium chloride dihydrate, 0.05 M MOPS pH 7.0, 30% v/v 1,4-Dioxane; 0.001 M Magnesium chloride hexahydrate, 0.002 M Calcium chloride dihydrate, 0.05 M MOPS pH 7.0, 15% v/v (+/−)-2-Methyl-2,4-pentanediol; 0.08 M Strontium chloride hexahydrate, 0.02 M Magnesium chloride hexahydrate, 0.04 M Sodium cacodylate trihydrate pH 7.0, 20% v/v (+/−)-2-Methyl-2,4-pentanediol, 0.012 M Spermine tetrahydrochloride; 0.08 M Sodium chloride, 0.04 M Sodium cacodylate trihydrate pH 7.0, 30% v/v (+/−)-2-Methyl-2,4-pentanediol, 0.012 M Spermine tetrahydrochloride; 0.04 M Lithium chloride, 0.08 M Strontium chloride hexahydrate, 0.04 M Sodium cacodylate trihydrate pH 7.0, 30% v/v (+/−)-2-Methyl-2,4-pentanediol, 0.012 M Spermine tetrahydrochloride; 0.04 M Lithium chloride, 0.08 M Strontium chloride hexahydrate, 0.02 M Magnesium chloride hexahydrate, 0.04 M Sodium cacodylate trihydrate pH 7.0, 30% v/v (+/−)-2-Methyl-2,4-pentanediol, 0.012 M Spermine tetrahydrochloride; 0.08 M Sodium chloride, 0.012 M Potassium chloride, 0.02 M Magnesium chloride hexahydrate, 0.04 M Sodium cacodylate trihydrate pH 7.0, 35% v/v (+/−)-2-Methyl-2,4-pentanediol, 0.012 M Spermine tetrahydrochloride; 0.012 M Sodium chloride, 0.08 M Potassium chloride, 0.04 M Sodium cacodylate trihydrate pH 7.0, 40% v/v (+/−)-2-Methyl-2,4-pentanediol, 0.012 M Spermine tetrahydrochloride; 0.08 M Sodium chloride, 0.02 M Barium chloride dihydrate, 0.04 M Sodium cacodylate trihydrate pH 7.0, 40% v/v (+/−)-2-Methyl-2,4-pentanediol, 0.012 M Spermine tetrahydrochloride; 0.08 M Sodium chloride, 0.02 M Magnesium chloride hexahydrate, 0.04 M Sodium cacodylate trihydrate pH 7.0, 40% v/v (+/−)-2-Methyl-2,4-pentanediol, 0.012 M Spermine tetrahydrochloride; 0.08 M Potassium chloride, 0.02 M Barium chloride dihydrate, 0.04 M Sodium cacodylate trihydrate pH 7.0, 40% v/v (+/−)-2-Methyl-2,4-pentanediol, 0.012 M Spermine tetrahydrochloride; 0.08 M Potassium chloride, 0.02 M Magnesium chloride hexahydrate, 0.04 M Sodium cacodylate trihydrate pH 7.0, 50% v/v (+/−)-2-Methyl-2,4-pentanediol, 0.012 M Spermine tetrahydrochloride; 0.08 M Potassium chloride, 0.04 M Sodium cacodylate trihydrate pH 7.0, 60% v/v (+/−)-2-Methyl-2,4-pentanediol, 0.012 M Spermine tetrahydrochloride; 0.02 M Magnesium chloride hexahydrate, 0.002 M Cobalt(II) chloride hexahydrate, 0.05 M HEPES sodium pH 7.5, 2.0 M Ammonium sulfate, 0.001 M Spermine; 0.02 M Magnesium chloride hexahydrate, 0.05 M PIPES pH 7.5, 4% w/v Polyethylene glycol 8,000, 0.001 M Spermine; 0.015 M Magnesium chloride hexahydrate, 0.002 M Barium chloride dihydrate, 0.05 M PIPES pH 7.5, 7% v/v 2-Propanol, 0.0005 M Spermine; 0.02 M Magnesium chloride hexahydrate, 0.05 M PIPES pH 7.5, 10% w/v 1,6-Hexanediol, 0.001 M Spermine; 0.01 M Magnesium chloride hexahydrate, 0.05 M HEPES sodium pH 7.5, 15% v/v (+/−)-2-Methyl-2,4-pentanediol, 0.0015 M Spermine; 0.2 M Calcium chloride dihydrate, 0.05 M HEPES sodium pH 7.5, 28% v/v Polyethylene glycol 400, 0.002 M Spermine; 0.002 M Copper(II) chloride dihydrate, 0.05 M TRIS hydrochloride pH 8.5, 1.8 M Lithium sulfate monohydrate, 0.0005 M Spermine.

Group 30: 0.01 M Magnesium chloride hexahydrate, 0.05 M MES monohydrate pH 5.6, 1.8 M Lithium sulfate monohydrate; 0.01 M Magnesium acetate tetrahydrate, 0.05 M MES monohydrate pH 5.6, 2.5 M Ammonium sulfate; 0.1 M Magnesium acetate tetrahydrate, 0.05 M MES monohydrate pH 5.6, 20% v/v (+/−)-2-Methyl-2,4-pentanediol; 0.2 M Potassium chloride, 0.01 M Magnesium sulfate heptahydrate, 0.05 M MES monohydrate pH 5.6, 10% v/v Polyethylene glycol 400; 0.2 M Potassium chloride, 0.01 M Magnesium chloride hexahydrate, 0.05 M MES monohydrate pH 5.6, 5% w/v Polyethylene glycol 8,000; 0.1 M Ammonium sulfate, 0.01 M Magnesium chloride hexahydrate, 0.05 M MES monohydrate pH 5.6, 20% w/v Polyethylene glycol 8,000; 0.02 M Magnesium chloride hexahydrate, 0.05 M MES monohydrate pH 6.0, 15% v/v 2-Propanol; 0.1 M Ammonium acetate, 0.005 M Magnesium sulfate heptahydrate, 0.05 M MES monohydrate pH 6.0, 0.6 M Sodium chloride; 0.1 M Potassium chloride, 0.01 M Magnesium chloride hexahydrate, 0.05 M MES monohydrate pH 6.0, 10% v/v Polyethylene glycol 400; 0.005 M Magnesium sulfate heptahydrate, 0.05 M MES monohydrate pH 6.0, 5% w/v Polyethylene glycol 4,000; 0.01 M Magnesium chloride hexahydrate, 0.05 M Sodium cacodylate trihydrate pH 6.0, 1.0 M Lithium sulfate monohydrate; 0.01 M Magnesium sulfate heptahydrate, 0.05 M Sodium cacodylate trihydrate pH 6.0, 1.8 M Lithium sulfate monohydrate; 0.015 M Magnesium acetate tetrahydrate, 0.05 M Sodium cacodylate trihydrate pH 6.0, 1.7 M Ammonium sulfate; 0.1 M Potassium chloride, 0.025 M Magnesium chloride hexahydrate, 0.05 M Sodium cacodylate trihydrate pH 6.0, 15% v/v 2-Propanol; 0.04 M Magnesium chloride hexahydrate, 0.05 M Sodium cacodylate trihydrate pH 6.0, 5% v/v (+/−)-2-Methyl-2,4-pentanediol; 0.04 M Magnesium acetate tetrahydrate, 0.05 M Sodium cacodylate trihydrate pH 6.0, 30% v/v (+/−)-2-Methyl-2,4-pentanediol; 0.2 M Potassium chloride, 0.01 M Calcium chloride dihydrate, 0.05 M Sodium cacodylate trihydrate pH 6.0, 10% w/v Polyethylene glycol 4,000; 0.01 M Magnesium acetate tetrahydrate, 0.05 M Sodium cacodylate trihydrate pH 6.5, 1.3 M Lithium sulfate monohydrate; 0.01 M Magnesium sulfate heptahydrate, 0.05 M Sodium cacodylate trihydrate pH 6.5, 2.0 M Ammonium sulfate; 0.1 M Ammonium acetate, 0.015 M Magnesium acetate tetrahydrate, 0.05 M Sodium cacodylate trihydrate pH 6.5, 10% v/v 2-Propanol; 0.2 M Potassium chloride, 0.005 M Magnesium chloride hexahydrate, 0.05 M Sodium cacodylate trihydrate pH 6.5, 0.9 M 1,6-Hexanediol; 0.08 M Magnesium acetate tetrahydrate, 0.05 M Sodium cacodylate trihydrate pH 6.5, 15% v/v Polyethylene glycol 400; 0.2 M Potassium chloride, 0.01 M Magnesium chloride hexahydrate, 0.05 M Sodium cacodylate trihydrate pH 6.5, 10% w/v Polyethylene glycol 4,000; 0.2 M Ammonium acetate, 0.01 M Calcium chloride dihydrate, 0.05 M Sodium cacodylate trihydrate pH 6.5, 10% w/v Polyethylene glycol 4,000; 0.08 M Magnesium acetate tetrahydrate, 0.05 M Sodium cacodylate trihydrate pH 6.5, 30% w/v Polyethylene glycol 4,000; 0.2 M Potassium chloride, 0.1 M Magnesium acetate tetrahydrate, 0.05 M Sodium cacodylate trihydrate pH 6.5, 10% w/v Polyethylene glycol 8,000; 0.2 M Ammonium acetate, 0.01 M Magnesium acetate tetrahydrate, 0.05 M Sodium cacodylate trihydrate pH 6.5, 30% w/v Polyethylene glycol 8,000; 0.05 M Magnesium sulfate hydrate, 0.05 M HEPES Sodium pH 7.0, 1.6 M Lithium sulfate monohydrate; 0.01 M Magnesium chloride hexahydrate, 0.05 M HEPES Sodium pH 7.0, 4.0 M Lithium chloride; 0.01 M Magnesium chloride hexahydrate, 0.05 M HEPES Sodium pH 7.0, 1.6 M Ammonium sulfate; 0.005 M Magnesium chloride hexahydrate, 0.05 M HEPES Sodium pH 7.0, 25% v/v Polyethylene glycol monomethyl ether 550; 0.2 M Potassium chloride, 0.01 M Magnesium chloride hexahydrate, 0.05 M HEPES Sodium pH 7.0, 1.7 M 1,6-Hexanediol; 0.2 M Ammonium chloride, 0.01 M Magnesium chloride hexahydrate, 0.05 M HEPES Sodium pH 7.0, 2.5 M 1,6-Hexanediol; 0.1 M Potassium chloride, 0.005 M Magnesium sulfate hydrate, 0.05 M HEPES Sodium pH 7.0, 15% v/v (+/−)-2-Methyl-2,4-pentanediol; 0.1 M Potassium chloride, 0.01 M Magnesium chloride hexahydrate, 0.05 M HEPES Sodium pH 7.0, 5% v/v Polyethylene glycol 400; 0.1 M Potassium chloride, 0.01 M Calcium chloride dihydrate, 0.05 M HEPES Sodium pH 7.0, 10% v/v Polyethylene glycol 400; 0.2 M Potassium chloride, 0.025 M Magnesium sulfate hydrate, 0.05 M HEPES Sodium pH 7.0, 20% v/v Polyethylene glycol 200; 0.2 M Ammonium acetate, 0.15 M Magnesium acetate tetrahydrate, 0.05 M HEPES Sodium pH 7.0, 5% w/v Polyethylene glycol 4,000; 0.1 M Ammonium acetate, 0.02 M Magnesium chloride hexahydrate, 0.05 M HEPES Sodium pH 7.0, 5% w/v Polyethylene glycol 8,000; 0.01 M Magnesium chloride hexahydrate, 0.05 M TRIS hydrochloride pH 7.5, 1.6 M Ammonium sulfate; 0.1 M Potassium chloride, 0.015 M Magnesium chloride hexahydrate, 0.05 M TRIS hydrochloride pH 7.5, 10% v/v Polyethylene glycol monomethyl ether 550; 0.01 M Magnesium chloride hexahydrate, 0.05 M TRIS hydrochloride pH 7.5, 5% v/v 2-Propanol; 0.05 M Ammonium acetate, 0.01 M Magnesium chloride hexahydrate, 0.05 M TRIS hydrochloride pH 7.5, 10% v/v (+/−)-2-Methyl-2,4-pentanediol; 0.2 M Potassium chloride, 0.05 M Magnesium chloride hexahydrate, 0.05 M TRIS hydrochloride pH 7.5, 10% w/v Polyethylene glycol 4,000; 0.025 M Magnesium sulfate hydrate, 0.05 M TRIS hydrochloride pH 8.5, 1.8 M Ammonium sulfate; 0.005 M Magnesium sulfate hydrate, 0.05 M TRIS hydrochloride pH 8.5, 2.9 M 1,6-Hexanediol; 0.1 M Potassium chloride, 0.01 M Magnesium chloride hexahydrate, 0.05 M TRIS hydrochloride pH 8.5, 30% v/v Polyethylene glycol 400; 0.2 M Ammonium chloride, 0.01 M Calcium chloride dihydrate, 0.05 M TRIS hydrochloride pH 8.5, 30% w/v Polyethylene glycol 4,000; 0.04 M Lithium chloride, 0.02 M Magnesium chloride hexahydrate, 0.04 M Sodium cacodylate trihydrate pH 5.5, 30% v/v (+/−)-2-Methyl-2,4-pentanediol, 0.02 M Hexammine cobalt(III) chloride; 0.08 M Sodium chloride, 0.02 M Magnesium chloride hexahydrate, 0.04 M Sodium cacodylate trihydrate pH 5.5, 35% v/v (+/−)-2-Methyl-2,4-pentanediol, 0.02 M Hexammine cobalt (III) chloride; 0.012 M Sodium chloride, 0.08 M Potassium chloride, 0.04 M Sodium cacodylate trihydrate pH 5.5, 45% v/v (+/−)-2-Methyl-2,4-pentanediol, 0.02 M Hexammine cobalt(III) chloride; 0.02 M Magnesium chloride hexahydrate, 0.04 M Sodium cacodylate trihydrate pH 5.5, 40% v/v (+/−)-2-Methyl-2,4-pentanediol, 0.02 M Hexammine cobalt (III) chloride; 0.002 M Calcium chloride dihydrate, 0.05 M Sodium cacodylate trihydrate pH 6.0, 1.8 M Ammonium sulfate, 0.0005 M Spermine; 0.05 M Sodium cacodylate trihydrate pH 6.0, 35% v/v Tacsimate pH 6.0, 0.001 M Spermine; 0.1 M Sodium chloride, 0.05 M Sodium cacodylate trihydrate pH 6.0, 10% w/v Polyethylene glycol 4,000, 0.0005 M Spermine; 0.05 M Potassium chloride, 0.05 M Sodium cacodylate trihydrate pH 6.0, 10% w/v Polyethylene glycol 8,000, 0.0005 M Spermine, 0.0005 M L-Argininamide dihydrochloride; 0.1 M Potassium chloride, 0.05 M Sodium cacodylate trihydrate pH 6.0, 16% w/v Polyethylene glycol 1,000, 0.0005 M Spermine; 0.005 M Magnesium chloride hexahydrate, 0.002 M Calcium chloride dihydrate, 0.05 M Sodium cacodylate trihydrate pH 6.0, 15% v/v 2-Propanol, 0.001 M Spermine; 0.075 M Sodium chloride, 0.002 M Calcium chloride dihydrate, 0.05 M Sodium cacodylate trihydrate pH 6.0, 30% w/v 1,6-Hexanediol, 0.0005 M Spermine; 0.02 M Magnesium sulfate hydrate, 0.002 M Cobalt(II) chloride hexahydrate, 0.05 M Sodium cacodylate trihydrate pH 6.0, 25% v/v (+/−)-2-Methyl-2,4-pentanediol, 0.0005 M Spermine; 0.05 M Sodium cacodylate trihydrate pH 6.0, 30% v/v (+/−)-2-Methyl-2,4-pentanediol; 0.08 M Sodium chloride, 0.012 M Potassium chloride, 0.02 M Magnesium chloride hexahydrate, 0.04 M Sodium cacodylate trihydrate pH 6.0, 30% v/v (+/−)-2-Methyl-2,4-pentanediol, 0.012 M Spermine tetrahydrochloride; 0.08 M Sodium chloride, 0.02 M Magnesium chloride hexahydrate, 0.04 M Sodium cacodylate trihydrate pH 6.0, 35% v/v (+/−)-2-Methyl-2,4-pentanediol, 0.012 M Spermine tetrahydrochloride; 0.08 M Strontium chloride hexahydrate, 0.04 M Sodium cacodylate trihydrate pH 6.0, 35% v/v (+/−)-2-Methyl-2,4-pentanediol, 0.012 M Spermine tetrahydrochloride; 0.08 M Potassium chloride, 0.02 M Barium chloride dihydrate, 0.04 M Sodium cacodylate trihydrate pH 6.0, 40% v/v (+/−)-2-Methyl-2,4-pentanediol, 0.012 M Spermine tetrahydrochloride; 0.08 M Potassium chloride, 0.02 M Magnesium chloride hexahydrate, 0.04 M Sodium cacodylate trihydrate pH 6.0, 45% v/v (+/−)-2-Methyl-2,4-pentanediol, 0.012 M Span-line tetrahydrochloride; 0.08 M Sodium chloride, 0.04 M Sodium cacodylate trihydrate pH 6.0, 45% v/v (+/−)-2-Methyl-2,4-pentanediol, 0.012 M Spermine tetrahydrochloride; 0.08 M Sodium chloride, 0.02 M Barium chloride dihydrate, 0.04 M Sodium cacodylate trihydrate pH 6.0, 45% v/v (+/−)-2-Methyl-2,4-pentanediol, 0.012 M Spermine tetrahydrochloride; 0.012 M Sodium chloride, 0.08 M Potassium chloride, 0.04 M Sodium cacodylate trihydrate pH 6.0, 50% v/v (+/−)-2-Methyl-2,4-pentanediol, 0.012 M Spermine tetrahydrochloride; 0.08 M Potassium chloride, 0.04 M Sodium cacodylate trihydrate pH 6.0, 55% v/v (+/−)-2-Methyl-2,4-pentanediol, 0.012 M Spermine tetrahydrochloride; 0.018 M Magnesium chloride hexahydrate, 0.05 M Sodium cacodylate trihydrate pH 6.5, 10% v/v 2-Propanol, 0.003 M Spermine; 0.02 M Magnesium chloride hexahydrate, 0.05 M MOPS pH 7.0, 2.0 M Ammonium sulfate, 0.0005 M Spermine; 0.05 M HEPES sodium pH 7.0, 40% v/v Tacsimate pH 7.0, 0.002 M Spermine, 0.002 M Hexammine cobalt(III) chloride; 0.02 M Magnesium chloride hexahydrate, 0.05 M MOPS pH 7.0, 55% v/v Tacsimate pH 7.0, 0.005 M Hexammine cobalt(III) chloride; 0.02 M Magnesium chloride hexahydrate, 0.05 M Sodium cacodylate trihydrate pH 7.0, 15% v/v 2-Propanol, 0.001 M Hexammine cobalt(III) chloride, 0.001 M Spermine; 0.005 M Magnesium chloride hexahydrate, 0.05 M MOPS pH 7.0, 25% v/v 1,4-Dioxane, 0.001 M Spermine; 0.01 M Magnesium chloride hexahydrate, 0.002 M Barium chloride dihydrate, 0.05 M MOPS pH 7.0, 30% v/v 1,4-Dioxane; 0.001 M Magnesium chloride hexahydrate, 0.002 M Calcium chloride dihydrate, 0.05 M MOPS pH 7.0, 15% v/v (+/−)-2-Methyl-2,4-pentanediol; 0.08 M Strontium chloride hexahydrate, 0.02 M Magnesium chloride hexahydrate, 0.04 M Sodium cacodylate trihydrate pH 7.0, 20% v/v (+/−)-2-Methyl-2,4-pentanediol, 0.012 M Spermine tetrahydrochloride; 0.08 M Sodium chloride, 0.04 M Sodium cacodylate trihydrate pH 7.0, 30% v/v (+/−)-2-Methyl-2,4-pentanediol, 0.012 M Spermine tetrahydrochloride; 0.04 M Lithium chloride, 0.08 M Strontium chloride hexahydrate, 0.04 M Sodium cacodylate trihydrate pH 7.0, 30% v/v (+/−)-2-Methyl-2,4-pentanediol, 0.012 M Spermine tetrahydrochloride; 0.04 M Lithium chloride, 0.08 M Strontium chloride hexahydrate, 0.02 M Magnesium chloride hexahydrate, 0.04 M Sodium cacodylate trihydrate pH 7.0, 30% v/v (+/−)-2-Methyl-2,4-pentanediol, 0.012 M Spermine tetrahydrochloride; 0.08 M Sodium chloride, 0.012 M Potassium chloride, 0.02 M Magnesium chloride hexahydrate, 0.04 M Sodium cacodylate trihydrate pH 7.0, 35% v/v (+/−)-2-Methyl-2,4-pentanediol, 0.012 M Spermine tetrahydrochloride; 0.012 M Sodium chloride, 0.08 M Potassium chloride, 0.04 M Sodium cacodylate trihydrate pH 7.0, 40% v/v (+/−)-2-Methyl-2,4-pentanediol, 0.012 M Spermine tetrahydrochloride; 0.08 M Sodium chloride, 0.02 M Barium chloride dihydrate, 0.04 M Sodium cacodylate trihydrate pH 7.0, 40% v/v (+/−)-2-Methyl-2,4-pentanediol, 0.012 M Spermine tetrahydrochloride; 0.08 M Sodium chloride, 0.02 M Magnesium chloride hexahydrate, 0.04 M Sodium cacodylate trihydrate pH 7.0, 40% v/v (+/−)-2-Methyl-2,4-pentanediol, 0.012 M Spermine tetrahydrochloride; 0.08 M Potassium chloride, 0.02 M Barium chloride dihydrate, 0.04 M Sodium cacodylate trihydrate pH 7.0, 40% v/v (+/−)-2-Methyl-2,4-pentanediol, 0.012 M Spermine tetrahydrochloride; 0.08 M Potassium chloride, 0.02 M Magnesium chloride hexahydrate, 0.04 M Sodium cacodylate trihydrate pH 7.0, 50% v/v (+/−)-2-Methyl-2,4-pentanediol, 0.012 M Spermine tetrahydrochloride; 0.08 M Potassium chloride, 0.04 M Sodium cacodylate trihydrate pH 7.0, 60% v/v (1-/−)-2-Methyl-2,4-pentanediol, 0.012 M Spermine tetrahydrochloride; 0.02 M Magnesium chloride hexahydrate, 0.002 M Cobalt(II) chloride hexahydrate, 0.05 M HEPES sodium pH 7.5, 2.0 M Ammonium sulfate, 0.001 M Spermine; 0.02 M Magnesium chloride hexahydrate, 0.05 M PIPES pH 7.5, 4% w/v Polyethylene glycol 8,000, 0.001 M Spermine; 0.015 M Magnesium chloride hexahydrate, 0.002 M Barium chloride dihydrate, 0.05 M PIPES pH 7.5, 7% v/v 2-Propanol, 0.0005 M Spermine; 0.02 M Magnesium chloride hexahydrate, 0.05 M PIPES pH 7.5, 10% w/v 1,6-Hexanediol, 0.001 M Sim-mine; 0.01 M Magnesium chloride hexahydrate, 0.05 M HEPES sodium pH 7.5, 15% v/v (+/−)-2-Methyl-2,4-pentanediol, 0.0015 M Spermine; 0.2 M Calcium chloride dihydrate, 0.05 M HEPES sodium pH 7.5, 28% v/v Polyethylene glycol 400, 0.002 M Spermine; 0.002

M Copper(II) chloride dihydrate, 0.05 M TRIS hydrochloride pH 8.5, 1.8 M Lithium sulfate monohydrate, 0.0005 M Spermine.

Group 31: 0.02 M Calcium chloride dihydrate, 0.1 M Sodium acetate trihydrate pH 4.6, 30% v/v (+/−)-2-Methyl-2,4-pentanediol; 0.26 M Potassium sodium tartrate tetrahydrate, 35% v/v Glycerol; 0.26 M Ammonium phosphate monobasic, 35% v/v Glycerol; 0.075 M TRIS hydrochloride pH 8.5, 1.5 M Ammonium sulfate, 25% v/v Glycerol; 0.2 M Sodium citrate tribasic dihydrate, 0.1 M HEPES sodium pH 7.5, 30% v/v (+/−)-2-Methyl-2,4-pentanediol; 0.16 M Magnesium chloride hexahydrate, 0.08 M TRIS hydrochloride pH 8.5, 24% w/v Polyethylene glycol 4,000, 20% v/v Glycerol; 0.07 M Sodium cacodylate trihydrate pH 6.5, 0.98 M Sodium acetate trihydrate, 30% v/v Glycerol; 0.14 M Sodium citrate tribasic dihydrate, 0.07 M Sodium cacodylate trihydrate pH 6.5, 21% v/v 2-Propanol, 30% v/v Glycerol; 0.17 M Ammonium acetate, 0.085 M Sodium citrate tribasic dihydrate pH 5.6, 25.5% w/v Polyethylene glycol 4,000, 15% v/v Glycerol; 0.17 M Ammonium acetate, 0.085 M Sodium acetate trihydrate pH 4.6, 25.5% w/v Polyethylene glycol 4,000, 15% v/v Glycerol; 0.07 M Sodium citrate tribasic dihydrate pH 5.6, 0.7 M Ammonium phosphate monobasic, 30% v/v Glycerol; 0.18 M Magnesium chloride hexahydrate, 0.09 M HEPES sodium pH 7.5, 27% v/v 2-Propanol, 10% v/v Glycerol; 0.2 M Sodium citrate tribasic dihydrate, 0.1 M TRIS hydrochloride pH 8.5, 30% v/v Polyethylene glycol 400; 0.19 M Calcium chloride dihydrate, 0.095 M HEPES sodium pH 7.5, 26.6% v/v Polyethylene glycol 400, 5% v/v Glycerol; 0.17 M Ammonium sulfate, 0.085 M Sodium cacodylate trihydrate pH 6.5, 25.5% w/v Polyethylene glycol 8,000, 15% v/v Glycerol; 0.075 M HEPES sodium pH 7.5, 1.125 M Lithium sulfate monohydrate, 25% v/v Glycerol; 0.17 M Lithium sulfate monohydrate, 0.085 M TRIS hydrochloride pH 8.5, 25.5% w/v Polyethylene glycol 4,000, 15% v/v Glycerol; 0.16 M Magnesium acetate tetrahydrate, 0.08 M Sodium cacodylate trihydrate pH 6.5, 16% w/v Polyethylene glycol 8,000, 20% v/v Glycerol; 0.16 M Ammonium acetate, 0.08 M TRIS hydrochloride pH 8.5, 24% v/v 2-Propanol, 20% v/v Glycerol; 0.16 M Ammonium sulfate, 0.08 M Sodium acetate trihydrate pH 4.6, 20% w/v Polyethylene glycol 4,000, 20% v/v Glycerol; 0.2 M Magnesium acetate tetrahydrate, 0.1 M Sodium cacodylate trihydrate pH 6.5, 30% v/v (+/−)-2-Methyl-2,4-pentanediol; 0.17 M Sodium acetate trihydrate, 0.085 M TRIS hydrochloride pH 8.5, 25.5% w/v Polyethylene glycol 4,000, 15% v/v Glycerol; 0.2 M Magnesium chloride hexahydrate, 0.1 M HEPES sodium pH 7.5, 30% v/v Polyethylene glycol 400; 0.14 M Calcium chloride dihydrate, 0.07 M Sodium acetate trihydrate pH 4.6, 14% v/v 2-Propanol, 30% v/v Glycerol; 0.07 M Imidazole pH 6.5, 0.7 M Sodium acetate trihydrate, 30% v/v Glycerol; 0.2 M Ammonium acetate, 0.1 M Sodium citrate tribasic dihydrate pH 5.6, 30% v/v (+/−)-2-Methyl-2,4-pentanediol; 0.14 M Sodium citrate tribasic dihydrate, 0.07 M HEPES sodium pH 7.5, 14% v/v 2-Propanol, 30% v/v Glycerol; 0.17 M Sodium acetate trihydrate, 0.085 M Sodium cacodylate trihydrate pH 6.5, 25.5% w/v Polyethylene glycol 8,000, 15% v/v Glycerol; 0.065 M HEPES sodium pH 7.5, 0.52 M Potassium sodium tartrate tetrahydrate, 35% v/v Glycerol; 0.17 M Ammonium sulfate, 25.5% w/v Polyethylene glycol 8,000, 15% v/v Glycerol; 0.17 M Ammonium sulfate, 25.5% w/v Polyethylene glycol 4,000, 15% v/v Glycerol; 1.5 M Ammonium sulfate, 25% v/v Glycerol; 3.6 M Sodium formate, 10% v/v Glycerol; 0.07 M Sodium acetate trihydrate pH 4.6, 1.4 M Sodium formate, 30% v/v Glycerol; 0.075 M HEPES sodium pH 7.5, 0.6 M Sodium phosphate monobasic monohydrate, 0.6 M Potassium phosphate monobasic, 25% v/v Glycerol; 0.065 M TRIS hydrochloride pH 8.5, 5.2% w/v Polyethylene glycol 8,000, 35% v/v Glycerol; 0.07 M Sodium acetate trihydrate pH 4.6, 5.6% w/v Polyethylene glycol 4,000, 30% v/v Glycerol; 0.09 M HEPES sodium pH 7.5, 1.26 M Sodium citrate tribasic dihydrate, 10% v/v Glycerol; 0.085 M HEPES sodium pH 7.5, 1.7 M Ammonium sulfate, 1.7% w/v Polyethylene glycol 400, 15% v/v Glycerol; 0.095 M Sodium citrate tribasic dihydrate pH 5.6, 19% w/v Polyethylene glycol 4,000, 19% v/v 2-Propanol, 5% v/v Glycerol; 0.085 M HEPES sodium pH 7.5, 17% w/v Polyethylene glycol 4,000, 8.5% v/v 2-Propanol, 15% v/v Glycerol; 0.04 M Potassium phosphate monobasic, 16% w/v Polyethylene glycol 8,000, 20% v/v Glycerol; 24% w/v Polyethylene glycol 1,500, 20% v/v Glycerol; 0.1 M Magnesium formate dihydrate, 50% v/v Glycerol; 0.16 M Zinc acetate dihydrate, 0.08 M Sodium cacodylate trihydrate pH 6.5, 14.4% w/v Polyethylene glycol 8,000, 20% v/v Glycerol; 0.16 M Calcium acetate hydrate, 0.08 M Sodium cacodylate trihydrate pH 6.5, 14.4% w/v Polyethylene glycol 8,000, 20% v/v Glycerol; 0.08 M Sodium acetate trihydrate pH 4.6, 1.6 M Ammonium sulfate, 20% v/v Glycerol; 0.08 M TRIS hydrochloride pH 8.5, 1.6 M Ammonium phosphate monobasic, 20% v/v Glycerol; 0.8 M Lithium sulfate monohydrate, 1.6% w/v Polyethylene glycol 8,000, 20% v/v Glycerol; 0.4 M Lithium sulfate monohydrate, 12% w/v Polyethylene glycol 8,000, 20% v/v Glycerol.

Group 32: 1.6 M Sodium chloride, 8% w/v Polyethylene glycol 6,000, 20% v/v Glycerol; 0.3 M Sodium chloride, 0.006 M Magnesium chloride hexahydrate, 0.006 M Hexadecyltrimethylammonium bromide, 40% v/v Glycerol; 21.25% v/v Ethylene glycol, 15% v/v Glycerol; 26.25% v/v 1,4-Dioxane, 25% v/v Glycerol; 1.5 M Ammonium sulfate, 3.75% v/v 2-Propanol, 25% v/v Glycerol; 0.65 M Imidazole pH 7.0, 35% v/v Glycerol; 8% w/v Polyethylene glycol 1,000, 8% w/v Polyethylene glycol 8,000, 20% v/v Glycerol; 1.05 M Sodium chloride, 7% v/v Ethanol, 30% v/v Glycerol; 0.075 M Sodium acetate trihydrate pH 4.6, 1.5 M Sodium chloride, 25% v/v Glycerol; 0.2 M Sodium chloride, 0.1 M Sodium acetate trihydrate pH 4.6, 30% v/v (+/−)-2-Methyl-2,4-pentanediol; 0.008 M Cobalt(II) chloride hexahydrate, 0.08 M Sodium acetate trihydrate pH 4.6, 0.8 M 1,6-Hexanediol, 20% v/v Glycerol; 0.095 M Cadmium chloride hydrate, 0.095 M Sodium acetate trihydrate pH 4.6, 28.5% v/v Polyethylene glycol 400, 5% v/v Glycerol; 0.18 M Ammonium sulfate, 0.09 M Sodium acetate trihydrate pH 4.6, 27% w/v Polyethylene glycol monomethyl ether 2,000, 10% v/v Glycerol; 0.15 M Potassium sodium tartrate tetrahydrate, 0.075 M Sodium citrate tribasic dihydrate pH 5.6, 1.5 M Ammonium sulfate, 25% IA Glycerol; 0.375 M Ammonium sulfate, 0.075 M Sodium citrate tribasic dihydrate pH 5.6, 0.75 M Lithium sulfate monohydrate, 25% v/v Glycerol; 0.3 M Sodium chloride, 0.06 M Sodium citrate tribasic dihydrate pH 5.6, 1.2% v/v Ethylene imine polymer, 40% v/v Glycerol; 0.08 M Sodium citrate tribasic dihydrate pH 5.6, 28% v/v tert-Butanol, 20% v/v Glycerol; 0.007 M Iron(III) chloride hexahydrate, 0.07 M Sodium citrate tribasic dihydrate pH 5.6, 7% v/v Jeffamine M-600, 30% v/v Glycerol; 0.095 M Sodium citrate tribasic dihydrate pH 5.6, 2.375 M 1,6-Hexanediol, 5% v/v Glycerol; 0.08 M MES monohydrate pH 6.5, 1.28 M Magnesium sulfate heptahydrate, 20% v/v Glycerol; 0.075 M Sodium phosphate monobasic monohydrate, 0.075 M Potassium phosphate monobasic, 0.075 M MES monohydrate pH 6.5, 1.5 M Sodium chloride, 25% v/v Glycerol; 0.065 M MES monohydrate pH 6.5, 7.8% w/v Polyethylene glycol 20,000, 35% v/v Glycerol; 1.2 M Ammonium sulfate, 0.075 M MES monohydrate pH 6.5, 7.5% v/v 1,4-Dioxane, 25% v/v Glycerol; 0.05 M Cesium chloride, 0.1 M MES monohydrate pH 6.5, 30% v/v Jeffamine M-600; 0.0075 M Cobalt(II) chloride hexahydrate, 0.075 M MES monohydrate pH 6.5, 1.35 M Ammonium sulfate, 25% v/v Glycerol; 0.18 M Ammonium sulfate, 0.09 M MES monohydrate pH 6.5, 27% will Polyethylene glycol monomethyl ether 5,000, 10% v/v Glycerol; 0.009 M Zinc sulfate heptahydrate, 0.09 M MES monohydrate pH 6.5, 22.5% v/v Polyethylene glycol monomethyl ether 550, 10% v/v Glycerol; 1.6 M Sodium citrate tribasic dihydrate pH 6.5; 0.5 M Ammonium sulfate, 0.1 M HEPES pH 7.5, 30% v/v (+/−)-2-Methyl-2,4-pentanediol; 0.08 M HEPES pH 7.5, 8% w/v Polyethylene glycol 6,000, 4% v/v (+/−)-2-Methyl-2,4-pentanediol, 20% v/v Glycerol; 0.085 M HEPES pH 7.5, 17% v/v Jeffamine M-600, 15% v/v Glycerol; 0.075 M Sodium chloride, 0.075 M HEPES pH 7.5, 1.2 M Ammonium sulfate, 25% v/v Glycerol; 0.07 M HEPES pH 7.5, 1.4 M Ammonium formate, 30% v/v Glycerol; 0.0375 M Cadmium sulfate hydrate, 0.075 M HEPES pH 7.5, 0.75 M Sodium acetate trihydrate, 25% v/v Glycerol; 0.1 M HEPES pH 7.5, 70% v/v (+/−)-2-Methyl-2,4-pentanediol; 0.085 M HEPES pH 7.5, 3.655 M Sodium chloride, 15% v/v Glycerol; 0.075 M HEPES pH 7.5, 7.5% w/v Polyethylene glycol 8,000, 6% v/v Ethylene glycol, 25% v/v Glycerol; 0.075 M HEPES pH 7.5, 15% w/v Polyethylene glycol 10,000, 25% v/v Glycerol; 0.2 M Magnesium chloride hexahydrate, 0.1 M Tris pH 8.5, 3.4 M 1,6-Hexanediol; 0.075 M Tris pH 8.5, 18.75% v/v tert-Butanol, 25% v/v Glycerol; 0.0075 M Nickel(II) chloride hexahydrate, 0.075 M Tris pH 8.5, 0.75 M Lithium sulfate monohydrate, 25% v/v Glycerol; 1.275 M Ammonium sulfate, 0.085 M Tris pH 8.5, 25.2% v/v Glycerol; 0.2 M Ammonium phosphate monobasic, 0.1 M Tris pH 8.5, 50% v/v (+/−)-2-Methyl-2,4-pentanediol; 0.075 M Tris pH 8.5, 15% v/v Ethanol, 25% v/v Glycerol; 0.008 M Nickel(II) chloride hexahydrate, 0.08 M Tris pH 8.5, 16% w/v Polyethylene glycol monomethyl ether 2,000, 20% v/v Glycerol; 0.085 M Sodium chloride, 0.085 M BICINE pH 9.0, 17% v/v Polyethylene glycol monomethyl ether 550, 15% v/v Glycerol; 0.095 M WINE pH 9.0, 1.9 M Magnesium chloride hexahydrate, 5% v/v Glycerol; 0.07 M BICINE pH 9.0, 1.4% v/v 1,4-Dioxane, 7% w/v Polyethylene glycol 20,000, 30% v/v Glycerol.

Group 33: 0.02 M Calcium chloride dihydrate, 0.1 M Sodium acetate trihydrate pH 4.6, 30% v/v (+/−)-2-Methyl-2,4-pentanediol; 0.26 M Potassium sodium tartrate tetrahydrate, 35% v/v Glycerol; 0.26 M Ammonium phosphate monobasic, 35% v/v Glycerol; 0.075 M TRIS hydrochloride pH 8.5, 1.5 M Ammonium sulfate, 25% v/v Glycerol; 0.2 M Sodium citrate tribasic dihydrate, 0.1 M HEPES sodium pH 7.5, 30% v/v (+/−)-2-Methyl-2,4-pentanediol; 0.16 M Magnesium chloride hexahydrate, 0.08 M TRIS hydrochloride pH 8.5, 24% w/v Polyethylene glycol 4,000, 20% v/v Glycerol; 0.07 M Sodium cacodylate trihydrate pH 6.5, 0.98 M Sodium acetate trihydrate, 30% v/v Glycerol; 0.14 M Sodium citrate tribasic dihydrate, 0.07 M Sodium cacodylate trihydrate pH 6.5, 21% v/v 2-Propanol, 30% v/v Glycerol; 0.17 M Ammonium acetate, 0.085 M Sodium citrate tribasic dihydrate pH 5.6, 25.5% w/v Polyethylene glycol 4,000, 15% v/v Glycerol; 0.17 M Ammonium acetate, 0.085 M Sodium acetate trihydrate pH 4.6, 25.5% w/v Polyethylene glycol 4,000, 15% v/v Glycerol; 0.07 M Sodium citrate tribasic dihydrate pH 5.6, 0.7 M Ammonium phosphate monobasic, 30% v/v Glycerol; 0.18 M Magnesium chloride hexahydrate, 0.09 M HEPES sodium pH 7.5, 27% v/v 2-Propanol, 10% v/v Glycerol; 0.2 M Sodium citrate tribasic dihydrate, 0.1 M TRIS hydrochloride pH 8.5, 30% v/v Polyethylene glycol 400; 0.19 M Calcium chloride dihydrate, 0.095 M HEPES sodium pH 7.5, 26.6% v/v Polyethylene glycol 400, 5% v/v Glycerol; 0.17 M Ammonium sulfate, 0.085 M Sodium cacodylate trihydrate pH 6.5, 25.5% w/v Polyethylene glycol 8,000, 15% v/v Glycerol; 0.075 M HEPES sodium pH 7.5, 1.125 M Lithium sulfate monohydrate, 25% v/v Glycerol; 0.17 M Lithium sulfate monohydrate, 0.085 M TRIS hydrochloride pH 8.5, 25.5% w/v Polyethylene glycol 4,000, 15% v/v Glycerol; 0.16 M Magnesium acetate tetrahydrate, 0.08 M Sodium cacodylate trihydrate pH 6.5, 16% w/v Polyethylene glycol 8,000, 20% v/v Glycerol; 0.16 M Ammonium acetate, 0.08 M TRIS hydrochloride pH 8.5, 24% v/v 2-Propanol, 20% v/v Glycerol; 0.16 M Ammonium sulfate, 0.08 M Sodium acetate trihydrate pH 4.6, 20% w/v Polyethylene glycol 4,000, 20% v/v Glycerol; 0.2 M Magnesium acetate tetrahydrate, 0.1 M Sodium cacodylate trihydrate pH 6.5, 30% v/v (+/−)-2-Methyl-2,4-pentanediol; 0.17 M Sodium acetate trihydrate, 0.085 M TRIS hydrochloride pH 8.5, 25.5% w/v Polyethylene glycol 4,000, 15% v/v Glycerol; 0.2 M Magnesium chloride hexahydrate, 0.1 M HEPES sodium pH 7.5, 30% v/v Polyethylene glycol 400; 0.14 M Calcium chloride dihydrate, 0.07 M Sodium acetate trihydrate pH 4.6, 14% v/v 2-Propanol, 30% v/v Glycerol; 0.07 M Imidazole pH 6.5, 0.7 M Sodium acetate trihydrate, 30% v/v Glycerol; 0.2 M Ammonium acetate, 0.1 M Sodium citrate tribasic dihydrate pH 5.6, 30% v/v (+/−)-2-Methyl-2,4-pentanediol; 0.14 M Sodium citrate tribasic dihydrate, 0.07 M HEPES sodium pH 7.5, 14% v/v 2-Propanol, 30% v/v Glycerol; 0.17 M Sodium acetate trihydrate, 0.085 M Sodium cacodylate trihydrate pH 6.5, 25.5% w/v Polyethylene glycol 8,000, 15% v/v Glycerol; 0.065 M HEPES sodium pH 7.5, 0.52 M Potassium sodium tartrate tetrahydrate, 35% v/v Glycerol; 0.17 M Ammonium sulfate, 25.5% w/v Polyethylene glycol 8,000, 15% v/v Glycerol; 0.17 M Ammonium sulfate, 25.5% w/v Polyethylene glycol 4,000, 15% v/v Glycerol; 1.5 M Ammonium sulfate, 25% v/v Glycerol; 3.6 M Sodium formate, 10% v/v Glycerol; 0.07 M Sodium acetate trihydrate pH 4.6, 1.4 M Sodium formate, 30% v/v Glycerol; 0.075 M HEPES sodium pH 7.5, 0.6 M Sodium phosphate monobasic monohydrate, 0.6 M Potassium phosphate monobasic, 25% v/v Glycerol; 0.065 M TRIS hydrochloride pH 8.5, 5.2% w/v Polyethylene glycol 8,000, 35% v/v Glycerol; 0.07 M Sodium acetate trihydrate pH 4.6, 5.6% w/v Polyethylene glycol 4,000, 30% v/v Glycerol; 0.09 M HEPES sodium pH 7.5, 1.26 M Sodium citrate tribasic dihydrate, 10% v/v Glycerol; 0.085 M HEPES sodium pH 7.5, 1.7 M Ammonium sulfate, 1.7% w/v Polyethylene glycol 400, 15% v/v Glycerol; 0.095 M Sodium citrate tribasic dihydrate pH 5.6, 19% w/v Polyethylene glycol 4,000, 19% v/v 2-Propanol, 5% v/v Glycerol; 0.085 M HEPES sodium pH 7.5, 17% w/v Polyethylene glycol 4,000, 8.5% v/v 2-Propanol, 15% v/v Glycerol; 0.04 M Potassium phosphate monobasic, 16% w/v Polyethylene glycol 8,000, 20% v/v Glycerol; 24% w/v Polyethylene glycol 1,500, 20% v/v Glycerol; 0.1 M Magnesium formate dihydrate, 50% v/v Glycerol; 0.16 M Zinc acetate dihydrate, 0.08 M Sodium cacodylate trihydrate pH 6.5, 14.4% w/v Polyethylene glycol 8,000, 20% v/v Glycerol; 0.16 M Calcium acetate hydrate, 0.08 M Sodium cacodylate trihydrate pH 6.5, 14.4% w/v Polyethylene glycol 8,000, 20% v/v Glycerol; 0.08 M Sodium acetate trihydrate pH 4.6, 1.6 M Ammonium sulfate, 20% v/v Glycerol; 0.08 M TRIS hydrochloride pH 8.5, 1.6 M Ammonium phosphate monobasic, 20% v/v Glycerol; 1.6 M Sodium chloride, 8% w/v Polyethylene glycol 6,000, 20% v/v Glycerol; 0.3 M Sodium chloride, 0.006 M Magnesium chloride hexahydrate, 0.006 M Hexadecyltrimethylammonium bromide, 40% v/v Glycerol; 21.25% v/v Ethylene glycol, 15% v/v Glycerol; 26.25% v/v 1,4-Dioxane, 25% v/v Glycerol; 1.5 M Ammonium sulfate, 3.75% v/v 2-Propanol, 25% IA Glycerol; 0.65 M Imidazole pH 7.0, 35% v/v Glycerol; 8% w/v Polyethylene glycol 1,000, 8% w/v Polyethylene glycol 8,000, 20% v/v Glycerol; 1.05 M Sodium chloride, 7% v/v Ethanol, 30% v/v Glycerol; 0.075 M Sodium acetate trihydrate pH 4.6, 1.5 M Sodium chloride, 25% v/v Glycerol; 0.2 M Sodium chloride, 0.1 M Sodium acetate trihydrate pH 4.6, 30% v/v (+/−)-2-Methyl-2,4-pentanediol; 0.008 M Cobalt(II) chloride hexahydrate, 0.08 M Sodium acetate trihydrate pH 4.6, 0.8 M 1,6-Hexanediol, 20% v/v Glycerol; 0.095 M Cadmium chloride hydrate, 0.095 M Sodium acetate trihydrate pH 4.6, 28.5% v/v Polyethylene glycol 400, 5% v/v Glycerol; 0.18 M Ammonium sulfate, 0.09 M Sodium acetate trihydrate pH 4.6, 27% w/v Polyethylene glycol monomethyl ether 2,000, 10% v/v Glycerol; 0.15 M Potassium sodium tartrate tetrahydrate, 0.075 M Sodium citrate tribasic dihydrate pH 5.6, 1.5 M Ammonium sulfate, 25% v/v Glycerol; 0.375 M Ammonium sulfate, 0.075 M Sodium citrate tribasic dihydrate pH 5.6, 0.75 M Lithium sulfate monohydrate, 25% v/v Glycerol; 0.3 M Sodium chloride, 0.06 M Sodium citrate tribasic dihydrate pH 5.6, 1.2% v/v Ethylene imine polymer, 40% v/v Glycerol; 0.08 M Sodium citrate tribasic dihydrate pH 5.6, 28% v/v tert-Butanol, 20% v/v Glycerol; 0.007 M Iron(III) chloride hexahydrate, 0.07 M Sodium citrate tribasic dihydrate pH 5.6, 7% v/v Jeffamine M-600, 30% v/v Glycerol; 0.095 M Sodium citrate tribasic dihydrate pH 5.6, 2.375 M 1,6-Hexanediol, 5% v/v Glycerol; 0.08 M MES monohydrate pH 6.5, 1.28 M Magnesium sulfate heptahydrate, 20% v/v Glycerol; 0.075 M Sodium phosphate monobasic monohydrate, 0.075 M Potassium phosphate monobasic, 0.075 M MES monohydrate pH 6.5, 1.5 M Sodium chloride, 25% v/v Glycerol; 0.065 M MES monohydrate pH 6.5, 7.8% w/v Polyethylene glycol 20,000, 35% v/v Glycerol; 1.2 M Ammonium sulfate, 0.075 M MES monohydrate pH 6.5, 7.5% v/v 1,4-Dioxane, 25% v/v Glycerol; 0.05 M Cesium chloride, 0.1 M MES monohydrate pH 6.5, 30% v/v Jeffamine M-600; 0.0075 M Cobalt(10 chloride hexahydrate, 0.075 M MES monohydrate pH 6.5, 1.35 M Ammonium sulfate, 25% v/v Glycerol; 0.18 M Ammonium sulfate, 0.09 M MES monohydrate pH 6.5, 27% w/v Polyethylene glycol monomethyl ether 5,000, 10% v/v Glycerol; 0.009 M Zinc sulfate heptahydrate, 0.09 M IVIES monohydrate pH 6.5, 22.5% v/v Polyethylene glycol monomethyl ether 550, 10% v/v Glycerol; 1.6 M Sodium citrate tribasic dihydrate pH 6.5; 0.5 M Ammonium sulfate, 0.1 M HEPES pH 7.5, 30% v/v (+/−)-2-Methyl-2,4-pentanediol; 0.08 M HEPES pH 7.5, 8% w/v Polyethylene glycol 6,000, 4% v/v (+/−)-2-Methyl-2,4-pentanediol, 20% v/v Glycerol; 0.085 M HEPES pH 7.5, 17% v/v Jeffamine M-600, 15% v/v Glycerol; 0.075 M Sodium chloride, 0.075 M HEPES pH 7.5, 1.2 M Ammonium sulfate, 25% v/v Glycerol; 0.07 M HEPES pH 7.5, 1.4 M Ammonium formate, 30% v/v Glycerol; 0.0375 M Cadmium sulfate hydrate, 0.075 M HEPES pH 7.5, 0.75 M Sodium acetate trihydrate, 25% v/v Glycerol; 0.1 M HEPES pH 7.5, 70% v/v (+/−)-2-Methyl-2,4-pentanediol; 0.085 M HEPES pH 7.5, 3.655 M Sodium chloride, 15% v/v Glycerol; 0.075 M HEPES pH 7.5, 7.5% w/v Polyethylene glycol 8,000, 6% v/v Ethylene glycol, 25% v/v Glycerol; 0.075 M HEPES pH 7.5, 15% w/v Polyethylene glycol 10,000, 25% v/v Glycerol; 0.2 M Magnesium chloride hexahydrate, 0.1 M Tris pH 8.5, 3.4 M 1,6-Hexanediol; 0.075 M Tris pH 8.5, 18.75% v/v tert-Butanol, 25% v/v Glycerol; 0.0075 M Nickel(II) chloride hexahydrate, 0.075 M Tris pH 8.5, 0.75 M Lithium sulfate monohydrate, 25% v/v Glycerol; 1.275 M Ammonium sulfate, 0.085 M Tris pH 8.5, 25.2% v/v Glycerol; 0.2 M Ammonium phosphate monobasic, 0.1 M Tris pH 8.5, 50% v/v (+/−)-2-Methyl-2,4-pentanediol; 0.075 M Tris pH 8.5, 15% v/v Ethanol, 25% v/v Glycerol; 0.008 M Nickel(II) chloride hexahydrate, 0.08 M Tris pH 8.5, 16% w/v Polyethylene glycol monomethyl ether 2,000, 20% v/v Glycerol; 0.085 M Sodium chloride, 0.085 M BICINE pH 9.0, 17% v/v Polyethylene glycol monomethyl ether 550, 15% v/v Glycerol; 0.095 M BICINE pH 9.0, 1.9 M Magnesium chloride hexahydrate, 5% IA Glycerol; 0.07 M BICINE pH 9.0, 1.4% v/v 1,4-Dioxane, 7% w/v Polyethylene glycol 20,000, 30% v/v Glycerol.

Group 34: 10% v/v (+42-Methyl-2,4-pentanediol, 40 mM Sodium cacodylate trihydrate pH 5.5, 20 mM Hexammine cobalt(III) chloride, 20 mM Magnesium chloride hexahydrate; 10% v/v (+/−)-2-Methyl-2,4-pentanediol, 40 mM Sodium cacodylate trihydrate pH 5.5, 20 mM Hexammine cobalt(III) chloride, 80 mM Sodium chloride, 20 mM Magnesium chloride hexahydrate; 10% v/v (+/−)-2-Methyl-2,4-pentanediol, 40 mM Sodium cacodylate trihydrate pH 5.5, 20 mM Hexammine cobalt(III) chloride, 12 mM Sodium chloride, 80 mM Potassium chloride; 10% v/v (+/−)-2-Methyl-2,4-pentanediol, 40 mM Sodium cacodylate trihydrate pH 5.5, 20 mM Hexammine cobalt(III) chloride, 40 mM Lithium chloride, 20 mM Magnesium chloride hexahydrate; 10% v/v (+/−)-2-Methyl-2,4-pentanediol, 40 mM Sodium cacodylate trihydrate pH 6.0, 12 mM Spermine tetrahydrochloride, 80 mM Potassium chloride, 20 mM Magnesium chloride hexahydrate; 10% v/v (+/−)-2-Methyl-2,4-pentanediol, 40 mM Sodium cacodylate trihydrate pH 6.0, 12 mM Spermine tetrahydrochloride, 80 mM Potassium chloride; 10% v/v (+/−)-2-Methyl-2,4-pentanediol, 40 mM Sodium cacodylate trihydrate pH 6.0, 12 mM Spermine tetrahydrochloride, 80 mM Sodium chloride, 20 mM Magnesium chloride hexahydrate; 10% v/v (+/−)-2-Methyl-2,4-pentanediol, 40 mM Sodium cacodylate trihydrate pH 6.0, 12 mM Spermine tetrahydrochloride, 80 mM Sodium chloride; 10% v/v (+/−)-2-Methyl-2,4-pentanediol, 40 mM Sodium cacodylate trihydrate pH 6.0, 12 mM Spermine tetrahydrochloride, 80 mM Sodium chloride, 12 mM Potassium chloride, 20 mM Magnesium chloride hexahydrate; 10% v/v (+/−)-2-Methyl-2,4-pentanediol, 40 mM Sodium cacodylate trihydrate pH 6.0, 12 mM Spermine tetrahydrochloride, 12 mM Sodium chloride, 80 mM Potassium chloride; 10% v/v (+/−)-2-Methyl-2,4-pentanediol, 40 mM Sodium cacodylate trihydrate pH 6.0, 12 mM Spermine tetrahydrochloride, 80 mM Sodium chloride, 20 mM Barium chloride; 10% v/v (+/−)-2-Methyl-2,4-pentanediol, 40 mM Sodium cacodylate trihydrate pH 6.0, 12 mM Spermine tetrahydrochloride, 80 mM Potassium chloride, 20 mM Barium chloride; 10% v/v (+/−)-2-Methyl-2,4-pentanediol, 40 mM Sodium cacodylate trihydrate pH 6.0, 12 mM Spermine tetrahydrochloride, 80 mM Strontium chloride; 10% v/v (+/−)-2-Methyl-2,4-pentanediol, 40 mM Sodium cacodylate trihydrate pH 7.0, 12 mM Spermine tetrahydrochloride, 80 mM Potassium chloride, 20 mM Magnesium chloride hexahydrate; 10% v/v (+/−)-2-Methyl-2,4-pentanediol, 40 mM Sodium cacodylate trihydrate pH 7.0, 12 mM Spermine tetrahydrochloride, 80 mM Potassium chloride; 10% v/v (+/−)-2-Methyl-2,4-pentanediol, 40 mM Sodium cacodylate trihydrate pH 7.0, 12 mM Spermine tetrahydrochloride, 80 mM Sodium chloride, 20 mM Magnesium chloride hexahydrate; 10% v/v (+/−)-2-Methyl-2,4-pentanediol, 40 mM Sodium cacodylate trihydrate pH 7.0, 12 mM Spermine tetrahydrochloride, 80 mM Sodium chloride; 10% v/v (+/−)-2-Methyl-2,4-pentanediol, 40 mM Sodium cacodylate trihydrate pH 7.0, 12 mM Spermine tetrahydrochloride, 80 mM Sodium chloride, 12 mM Potassium chloride, 20 mM Magnesium chloride hexahydrate; 10% v/v (+/−)-2-Methyl-2,4-pentanediol, 40 mM Sodium cacodylate trihydrate pH 7.0, 12 mM Spermine tetrahydrochloride, 12 mM Sodium chloride, 80 mM Potassium chloride; 10% v/v (+/−)-2-Methyl-2,4-pentanediol, 40 mM Sodium cacodylate trihydrate pH 7.0, 12 mM Spermine tetrahydrochloride, 80 mM Sodium chloride, 20 mM Barium chloride; 10% v/v (+/−)-2-Methyl-2,4-pentanediol, 40 mM Sodium cacodylate trihydrate pH 7.0, 12 mM Spermine tetrahydrochloride, 80 mM Potassium chloride, 20 mM Barium chloride; 10% v/v (+/−)-2-Methyl-2,4-pentanediol, 40 mM Sodium cacodylate trihydrate pH 7.0, 12 mM Spermine tetrahydrochloride, 40 mM Lithium chloride, 80 mM Strontium chloride, 20 mM Magnesium chloride hexahydrate; 10% v/v (+/−)-2-Methyl-2,4-pentanediol, 40 mM Sodium cacodylate trihydrate pH 7.0, 12 mM Spermine tetrahydrochloride, 40 mM Lithium chloride, 80 mM Strontium chloride; 10% v/v (+/−)-2-Methyl-2,4-pentanediol, 40 mM Sodium cacodylate trihydrate pH 7.0, 12 mM Spermine tetrahydrochloride, 80 mM Strontium chloride, 20 mM Magnesium chloride hexahydrate.

Group 35: 0.1 M Barium chloride dihydrate; 0.1 M Cadmium chloride hydrate; 0.1 M Calcium chloride dihydrate; 0.1 M Cobalt(II) chloride hexahydrate; 0.1 M Copper (II) chloride dihydrate; 0.1 M Magnesium chloride hexahydrate; 0.1 M Manganese(II) chloride tetrahydrate; 0.1 M Strontium chloride hexahydrate; 0.1 M Yttrium(III) chloride hexahydrate; 0.1 M Zinc chloride; 0.1 M Iron(III) chloride hexahydrate; 0.1 M Nickel(II) chloride hexahydrate; 0.1 M Chromium(III) chloride hexahydrate; 0.1 M Praseodymium (III) acetate hydrate; 1.0 M Ammonium sulfate; 1.0 M Potassium chloride; 1.0 M Lithium chloride; 2.0 M Sodium chloride; 0.5 M Sodium fluoride; 1.0 M Sodium iodide; 2.0 M Sodium thiocyanate; 1.0 M Potassium sodium tartrate tetrahydrate; 1.0 M Sodium citrate tribasic dihydrate; 1.0 M Cesium chloride; 1.0 M Sodium malonate pH 7.0; 0.1 M L-Proline; 0.1 M Phenol; 30% v/v Dimethyl sulfoxide; 0.1 M Sodium bromide; 30% w/v 6-Aminohexanoic acid; 30% w/v 1,5-Diaminopentane dihydrochloride; 30% w/v 1,6-Diaminohexane; 30% w/v 1,8-Diaminooctane; 1.0 M Glycine; 0.3 M Glycyl-glycyl-glycine; 0.1 M Taurine; 0.1 M Betaine hydrochloride; 0.1 M Spermidine; 0.1 M Spun-line tetrahydrochloride; 0.1 M Hexammine cobalt(III) chloride; 0.1 M Sarcosine; 0.1 M Trimethylamine hydrochloride; 1.0 M Guanidine hydrochloride; 0.1 M Urea; 0.1 M β-Nicotinamide adenine dinucleotide hydrate; 0.1 M Adenosine-5'-triphosphate disodium salt hydrate; 0.1 M TCEP hydrochloride; 0.01 M GSH (L-Glutathione reduced), 0.01 M GSSG (L-Glutathione oxidized); 0.1M Ethylenediaminetetraacetic acid disodium salt dihydrate; 5% w/v Polyvinylpyrrolidone K15; 30% w/v Dextran sulfate sodium salt; 40% v/v Pentaerythritol ethoxylate (3/4 EO/OH); 10% w/v Polyethylene glycol 3,350; 30% w/v D-(+)-Glucose monohydrate; 30% w/v Sucrose; 30% w/v Xylitol; 30% w/v D-Sorbitol; 12% w/v myo-Inositol; 30% w/v D-(+)-Trehalose dihydrate; 30% w/v D-(+)-Galactose; 30% v/v Ethylene glycol; 30% v/v Glycerol; 3.0 M NDSB-195; 2.0 M NDSB-201; 2.0 M NDSB-211; 2.0 M NDSB-221; 1.0 M NDSB-256; 0.15 mM CYMAL®-7; 20% w/v Benzamidine hydrochloride; 5% w/v n-Dodecyl-N,N-dimethylamine-N-oxide; 5% w/v n-Octyl-β-D-glucoside; 5% w/v n-Dodecyl-β-D-maltoside; 30% w/v Trimethylamine N-oxide dihydrate; 30% w/v 1,6-Hexanediol; 30% v/v (+/−)-2-Methyl-2,4-pentanediol; 50% v/v Polyethylene glycol 400; 50% v/v Jeffamine M-600 pH 7.0; 40% v/v 2,5-Hexanediol; 40% v/v (±)-1,3-Butanediol; 40% v/v Polypropylene glycol P 400; 30% v/v 1,4-Dioxane; 30% v/v Ethanol; 30% v/v 2-Propanol; 30% v/v Methanol; 10% v/v 1,2-Butanediol; 40% v/v tert-Butanol; 40% v/v 1,3-Propanediol; 40% v/v Acetonitrile; 40% v/v Formamide; 40% v/v 1-Propanol; 5% v/v Ethyl acetate; 40% v/v Acetone; 0.25% v/v Dichloromethane; 7% v/v 1-Butanol; 40% v/v 2,2,2-Trifluoroethanol; 40% v/v 1,1,1,3,3,3-Hexafluoro-2-propanol.

Group 36: 50% w/v Tetraethylammonium bromide; 50% w/v Benzyltriethylammonium chloride; 50% w/v 2-Hydroxyethylammonium formate; 50% w/v Ethylammonium nitrate; 50% w/v Cholin acetate; 50% w/v Choline dihydrogen phosphate; 50% w/v 1-Ethyl-3-methylimidazolium acetate; 50% w/v 1-Butyl-3-methylimidazolium chloride; 50% w/v 1-Ethyl-3-methylimidazolium chloride; 50% w/v 1-Hexyl-3-methylimidazolium chloride; 50% w/v 1-Butyl-3-methylimidazolium dicyanamide; 50% w/v 1,3-Dimethylimidazolium dimethyl phosphate; 50% w/v 1,3-Dimethylimidazolium methyl sulfate; 50% w/v 1-Butyl-3-methylimidazolium methyl sulfate; 50% w/v 1-n-Butyl-3-methylimidazolium n-octylsulfate; 50% w/v 1-Ethyl-3-methylimidazolium thiocyanate; 50% w/v 1-Ethyl-3-methylimidazolium tetrafluoroborate; 50% w/v 1-Butyl-2,3-dimethylimidazolium tetrafluoroborate; 50% w/v 1-Butyl-3-methylimidazolium tetrafluoroborate; 50% w/v 1-Butyl-3-methylimidazolium trifluoroacetate; 50% w/v 1-Ethyl-3-methylimidazolium trifluoromethanesulfonate; 50% w/v Tetrabutylphosphonium bromide; 50% w/v Trisobutylmethylphosphoniumtosylate; 50% w/v 1-Butylpyridinium chloride.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:
1. A system for preparing a solution, comprising:
   a. a mixing chamber;
   b. an automated solution dispenser that directs at least one solid selected from a plurality of solids and at least one liquid selected from a plurality of liquids in the mixing chamber to form the solution having a target volume;
   c. a bottle handling sub-system, wherein the bottle handling sub-system is configured to manipulate one or more containers between a storage position and a dispensing position, wherein said one or more containers are selected from a plurality of containers having different volumes based on said target volume, wherein said one or more containers are configured to receive at least a portion of said solution from said mixing chamber;

d. a sensor configured to detect a volume of said one or more containers; and e. a controller that is operably coupled to the automated solution dispenser, the sensor, and the bottle handling sub-system, wherein the controller is programmed to (i) direct mixing of the at least one solid and the at least one liquid in the mixing chamber to form the solution, (ii) direct the bottle handling sub-system to manipulate at least a subset of the one or more containers from the storage position to the dispensing position, and (iii) dispense at least the portion of the solution from the mixing chamber into the one or more containers based on said volume of said one or more containers detected by said sensor when the one or more containers are at the dispensing position.

2. The system of claim 1, wherein the controller is operably coupled to a user interface that is programmed to receive an input from a user at a remote location, and wherein at least part of the solution is dispensed into the one or more containers according to the input.

3. The system of claim 1, wherein the controller is programmed to (i) receive one or more inputs from the sensor and (ii) compare the one or more inputs to a safety value associated with a safety regulation.

4. The system of claim 3, wherein the controller receives the safety value, the safety regulation, or a combination thereof from a user via a user interface operably coupled to the controller.

5. The system of claim 3, wherein the controller is programmed to present an alarm when the one or more inputs i) exceeds the safety value, ii) is within about 20% of the safety value, iii) violates the safety regulation, or iv) any combination thereof.

6. The system of claim 5, wherein the controller is programmed to present the alarm when the one or more inputs is within about 10% of the safety value.

7. The system of claim 5, wherein the alarm is a visual alert, an audible alert, a tactile alert, or any combination thereof.

8. The system of claim 3, wherein the controller is programmed to discontinue preparing the solution when the one or more inputs i) exceeds the safety value, ii) is within about 20% of the safety value, iii) violates the safety regulation, or iv) any combination thereof.

9. The system of claim 3, wherein the one or more inputs is a solution volume.

10. The system of claim 1, wherein the controller directs the automated solution dispenser to dispense at least a portion of the solution into the one or more containers at the dispensing position not to exceed 100% of the volume detected.

11. The system of claim 1, wherein the sensor is a weight sensor, a pressure sensor, an optical sensor, an ultrasonic sensor, an infrared sensor, a barcode sensor, an apriltag sensor, a material composition sensor, or any combination thereof.

12. The system of claim 1, wherein the sensor detects an emission of light, a reflection of light, an absorption of light, a sound emission, or any combination thereof.

13. The system of claim 1, wherein the sensor identifies said volume independent of an external container shape of the one or more containers.

14. The system of claim 1, wherein at least a portion of the solution is dispensed into a first container of said one or more containers until the sensor detects that a dispensed solution volume is within about 10% of a volume of the first container, after which at least a portion of the solution is then dispensed into a second container of said one or more containers.

15. The system of claim 1, wherein the controller is programmed to receive one or more inputs from the sensor, wherein the one or more inputs comprise (a) an amount of dispensed solution, (b) an amount of solution remaining to be dispensed, (c) a portion of the volume of the one or more containers that is filled with the dispensed solution, (d) a portion of the volume of the one or more containers that is unfilled, or (e) any combination thereof, and wherein the solution is dispensed into the one or more containers according to the one or more inputs.

16. The system of claim 1, wherein the sensor is positioned within the one or more containers.

17. The system of claim 1, wherein the sensor is positioned adjacent an opening of the one or more containers.

18. The system of claim 1, wherein the sensor is two sensors.

19. The system of claim 1, wherein the one or more containers include two or more containers, and wherein at least two of the two or more containers have a different external container shape.

20. The system of claim 1, wherein during use, the bottle handling sub-system selects a number of the one or more containers to receive the solution.

21. The system of claim 20, wherein a selection of the number is based on an input received by the controller from a user via a user interface operably coupled to the controller.

* * * * *